US008796324B2

(12) United States Patent
Brüggemeier et al.

(10) Patent No.: US 8,796,324 B2
(45) Date of Patent: *Aug. 5, 2014

(54) SUBSTITUTED 2-ACETAMIDO-5-ARYL-1,2,4-TRIAZOLONES AND USE THEREOF

(75) Inventors: Ulf Brüggemeier, Leichlingen (DE); Chantal Fürstner, Mülheim an der Ruhr (DE); Volker Geiss, Ratingen (DE); Jörg Keldenich, Wuppertal (DE); Armin Kern, Wuppertal (DE); Martina Delbeck, Heiligenhaus (DE); Peter Kolkhof, Wuppertal (DE); Axel Kretschmer, Wuppertal (DE); Elisabeth Pook, Wuppertal (DE); Carsten Schmeck, Mülheim an der Ruhr (DE); Hubert Trübel, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,444

(22) Filed: Mar. 21, 2012

(65) Prior Publication Data

US 2012/0238607 A1    Sep. 20, 2012

Related U.S. Application Data

(63) Continuation of application No. 12/727,044, filed on Mar. 18, 2010, now Pat. No. 8,202,895.

(30) Foreign Application Priority Data

Mar. 18, 2009  (DE) .......................... 10 2009 013 640
Jan. 20, 2010  (DE) .......................... 10 2010 001 064

(51) Int. Cl.
*A61K 31/4178*  (2006.01)
*A61K 31/4196*  (2006.01)
*C07D 405/04*  (2006.01)
*C07D 409/04*  (2006.01)

(52) U.S. Cl.
USPC ..... 514/384; 514/397; 548/311.4; 548/315.1; 548/315.4; 548/263.2

(58) Field of Classification Search
None
See application file for complete search history.

(56) References Cited

U.S. PATENT DOCUMENTS

| 5,281,614 | A  | 1/1994  | Ashton et al. |
| 5,326,776 | A  | 7/1994  | Winn et al. |
| 6,693,102 | B2 | 2/2004  | Stasch et al. |
| 6,743,798 | B1 | 6/2004  | Straub et al. |
| 6,762,152 | B1 | 7/2004  | Müller et al. |
| 6,833,364 | B1 | 12/2004 | Straub et al. |
| 6,864,287 | B1 | 3/2005  | Alonso-Alija et al. |
| 6,924,251 | B1 | 8/2005  | Schwarz et al. |
| 6,969,697 | B2 | 11/2005 | Muller et al. |
| 7,080,644 | B2 | 7/2006  | Gumaste et al. |
| 7,173,037 | B2 | 2/2007  | Alonso-Alija et al. |
| 7,279,444 | B2 | 10/2007 | Muller et al. |
| 7,674,825 | B2 | 3/2010  | Alonso-Alija et al. |
| 8,202,895 | B2 * | 6/2012 | Bruggemeier et al. ....... 514/376 |
| 2001/0020100 | A1 | 9/2001 | Manning et al. |
| 2004/0082798 | A1 | 4/2004 | Alonso-Alija et al. |
| 2004/0176446 | A1 | 9/2004 | Alonso-Alija et al. |

FOREIGN PATENT DOCUMENTS

WO    0119355    3/2001

OTHER PUBLICATIONS

Hassan et al., "Aryl-Aryl Bond Formation One Century after the Discovery of the Ulmann Reaction," Chem Rev 2002, 102:1359-1469.
Arnswald, et al., "Unconventional Regiospecific Synthesis of Aromatic Carbonamides and Thiocarbonamides by Means of Tin-Mediated Friedel-Crafts Reactions." J. Org. Chem., 1993 58(25): 7022-7028.
Papadopoulos et al.,"Friedel-Crafts Thioacylation with Ethoxycarbonyl Isothiocyanate: a One-Step Synthesis of Aromatic Thioamides," J. Org. Chem 1976, 41(6): 962-965.
U.S. Appl. No. 13/818,337, filed Feb. 22, 2013.
U.S. Appl. No. 13/819,885, filed Feb. 28, 2013.
Schrier, Robert W., The sea within us: Disorders of body water homeostasis, Current Opinion in Investigational Drugs, 2007, 8(4):304-311.
Finley, et al., "Arginine Vasopressin Antagonists for the Treatment of Heart Failure and Hyponatremia," Circulation 2008, 118:410-421, p. 412, col. 2.
Sanghi, et al. "Vasopressin antagonism: a future treatment option in heart failure," European Heart Journal, 2005, 26:538-543.
Goldsmith, et al., "Current treatments and novel pharmacologic treatments for hyponatremia in congestive heart failure," Am. J. Cardiol, 2005, 95(suppl): 14B-23B.
Gines , P. et al., "Effects of stavaptan, a selective vasopressin V2 receptor antagonist, on ascites and serum sodium cirrhosis with hyponatremia," Hepatology, 2008, 48(1):204-212.
Chang et al., Triazolinones as Nonpeptide Angiotensin II Antagonists. 1. Synthesis and Evaluation of Potent 2, 4, 5-Trisubstituted Triazoloinones, J. Med. Chem. 1993, vol. 36, Nr. 17, 2558-2568.
Dobosz et al., "Synthesis and Some Pharmacological Properties of 3-(4-phenyl-5-oxo-1,2,4-triazolin-1-ylmethyl)-1,2,-triazolin-5-thione Derivatives," Acta Polomiae Pharmaceutica 2002, vol. 59, No. 4, 281-290.
Verbalis, J.G., "AVP receptor antagonists as aquaretics: Review and assessment of clinical data," Cleveland Clinic Journal of Medicine, Sep. 2009, 73, S24-S33.

* cited by examiner

*Primary Examiner* — Michael Barker
(74) *Attorney, Agent, or Firm* — Karen B. King

(57) ABSTRACT

The present application relates to new, substituted 2-acetamido-5-aryl-1,2,4-triazolones, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

8 Claims, No Drawings

SUBSTITUTED 2-ACETAMIDO-5-ARYL-1,2,4-TRIAZOLONES AND USE THEREOF

The present application relates to new, substituted 2-acetamido-5-aryl-1,2,4-triazolones, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

The liquid content of the human body is subject to various physiological control mechanisms the purpose whereof is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centres in the brain regulate drinking behaviour and control fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurones in the *Nucleus supraopticus* and *N. paraventricularis* in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatraemia (sodium concentration <135 mmol/L); it is the most important electrolyte abnormality in hospital patients, with an incidence of ca. 5% or 250 000 cases per year in the USA alone. If the plasma sodium concentration falls below 115 mmol/L, comatose states and death are imminent.

Depending on the underlying cause, a distinction is made between hypovolaemic, euvolaemic and hypervolaemic hyponatraemia. The forms of hypervolaemia with oedema formation are clinically significant. Typical examples of this are syndrome of inappropriate ADH/vasopressin secretion (SIAD) (e.g. after craniocerebral trauma or as paraneoplasia in carcinomas) and hypervolaemic hyponatraemia in liver cirrhosis, various renal diseases and cardiac insufficiency [De Luca L. et al., *Am. J. Cardiol.* 96 (suppl.), 19L-23L (2005)]. In particular, patients with cardiac insufficiency, in spite of their relative hyponatraemia and hypervolaemia, often display elevated vasopressin levels, which is seen as the consequence of generally disturbed neurohumoral regulation in cardiac insufficiency [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta receptor blockers on the one hand and by ACE inhibitors or angiotensin receptor blockers on the other is now an inherent part of the pharmacological treatment of cardiac insufficiency, the inappropriate elevation of vasopressin secretion in advanced cardiac insufficiency is at present still not adequately treatable. Apart from the retention of water mediated by V2 receptors and the unfavourable haemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of cardiac insufficiency. In particular, compounds with combined activity on both vasopressin receptors (V1a and V2) should both have desirable renal and also haemodynamic effects and thus offer an especially ideal profile for the treatment of patients with cardiac insufficiency. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle hypertrophy, could be further intensified [Saghi P. et al., *Europ. Heart J.* 26, 538-543 (2005)].

WO 99/54315 discloses substituted triazolones with neuroprotective activity, and WO 2006/117657 describes triazolone derivatives as anti-inflammatory agents. Furthermore, EP 503 548-A1 and EP 587 134-A2 claim cyclic urea derivatives and their use for the treatment of thromboses. Substituted triazole thiones as ion channel modulators are disclosed in WO 2005/097112. WO 2007/134862 describes substituted imidazol-2-ones and 1,2,4-triazolones as vasopressin receptor antagonists for the treatment of cardiovascular disorders.

It is an object of the present invention to provide new compounds which act as potent, selective dual V1a/V2 receptor antagonists and are such as suitable for the treatment and/or prevention of diseases, more particularly for the treatment and/or prevention of cardiovascular disorders.

The present invention provides compounds of the general formula (I)

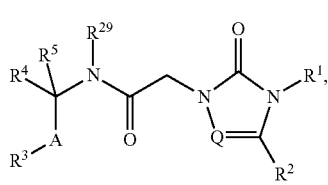

(I)

in which

A is —C($R^{6A}R^{6B}$)—* or —C($R^{6A}R^{6B}$)—C($R^{7A}R^{7B}$)—*, where
* is the attachment site to $R^3$,
$R^{6A}$ is hydrogen, ($C_1$-$C_4$) alkyl or trifluoromethyl,
$R^{6B}$ is hydrogen or ($C_1$-$C_4$) alkyl,
$R^{7A}$ is hydrogen, ($C_1$-$C_4$) alkyl or trifluoromethyl,
$R^{7B}$ is hydrogen or ($C_1$-$C_4$) alkyl, Q is CH or N, $R^1$ is ($C_1$-$C_6$) alkyl, ($C_2$-$C_6$) alkenyl, ($C_2$-$C_6$) alkynyl or ($C_3$-$C_7$) cycloalkyl,
where ($C_1$-$C_6$) alkyl, ($C_2$-$C_6$) alkenyl and ($C_2$-$C_6$) alkynyl may be substituted by 1 to 3 substituents independently of one another selected from the group consisting of deuterium, halogen, cyano, oxo, hydroxyl, trifluoromethyl, ($C_3$-$C_7$) cycloalkyl, ($C_1$-$C_6$) alkoxy, trifluoromethoxy and phenyl,
in which ($C_3$-$C_7$) cycloalkyl may be substituted by 1 or 2 substituents independently of one another selected from the group consisting of ($C_1$-$C_4$) alkyl, oxo, hydroxyl, ($C_1$-$C_4$) alkoxy and amino, and
in which ($C_1$-$C_6$) alkoxy may be substituted by 1 or 2 substituents independently of one another selected from the group consisting of amino, hydroxyl, ($C_1$-$C_4$) alkoxy, hydroxycarbonyl and ($C_1$-$C_4$) alkoxycarbonyl, and
in which phenyl may be substituted by 1 to 3 substituents independently of one another selected from the group consisting of halogen, cyano, nitro, ($C_1$-$C_4$) alkyl, trifluoromethyl, hydroxyl, hydroxymethyl, ($C_1$-$C_4$) alkoxy, trifluoromethoxy, ($C_1$-$C_4$) alkoxymethyl, hydroxycarbonyl, ($C_1$-$C_4$) alkoxycarbonyl, aminocarbonyl, mono-($C_1$-$C_4$) alkylaminocarbonyl and di-($C_1$-$C_4$) alkylaminocarbonyl, and
where ($C_3$-$C_7$) cycloalkyl may be substituted by 1 or 2 substituents independently of one another selected from the group consisting of fluorine, ($C_1$-$C_4$) alkyl, ($C_1$-$C_4$) alkoxy, hydroxy, amino and oxo, $R^2$ is benzothienyl, phenyl, thienyl or furyl, where benzothienyl, phenyl, thienyl and furyl may be substituted by 1 to 3 substituents independently of one another selected from the group consisting of halogen, cyano, nitro, ($C_1$-$C_4$) alkyl, trifluoromethyl, hydroxyl, ($C_1$-$C_4$) alkoxy and trifluoromethoxy, $R^3$ is trifluoromethyl, hydroxyl, trifluoromethoxy, ($C_1$-$C_4$) alkoxy, ($C_3$-$C_7$) cycloalkoxy, nitro, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$, —S(=O)$_n$$R^{21}$, —O—$SO_2$—$NR^{24}R^{25}$, —$NR^{26}$—$SO_2$—$NR^{27}R^{28}$ or —$NR^{30}R^{31}$, where $R^8$ is hydrogen or ($C_1$-$C_4$) alkyl,
$R^9$ is hydrogen, ($C_1$-$C_4$) alkyl or ($C_3$-$C_7$) cycloalkyl, or
$R^8$ and $R^9$ together with the atoms to which they are attached form a 5- to 7-membered heterocycle,
where the 5- to 7-membered heterocycle may be substituted by 1 or 2 substituents independently of one another selected from the group consisting of fluorine, ($C_1$-$C_4$) alkyl and trifluoromethyl, $R^{10}$ is hydrogen or ($C_1$-$C_4$) alkyl,
$R^{11}$ is ($C_1$-$C_4$) alkyl or ($C_3$-$C_7$) cycloalkyl, or
$R^{10}$ and $R^{11}$ together with the atoms to which they are attached form a 5- to 7-membered heterocycle,
where the 5- to 7-membered heterocycle may be substituted by 1 or 2 substituents independently of one another selected from the group consisting of fluorine, ($C_1$-$C_4$) alkyl and trifluoromethyl, $R^{12}$ is hydrogen, ($C_1$-$C_4$) alkyl or ($C_3$-$C_7$) cycloalkyl,
$R^{13}$ is hydrogen, ($C_1$-$C_4$) alkyl or ($C_3$-$C_7$) cycloalkyl, or
$R^{12}$ and $R^{13}$ together with the nitrogen atom to which they are attached form a 4- to 7-membered heterocycle,
where the 4- to 7-membered heterocycle may be substituted by 1 or 2 substituents independently of one another selected from the group consisting of fluorine, oxo, hydroxyl, ($C_1$-$C_4$) alkyl and trifluoromethyl, $R^{14}$ is hydrogen, ($C_1$-$C_4$) alkyl or ($C_3$-$C_7$) cycloalkyl,
$R^{15}$ is hydrogen, ($C_1$-$C_4$) alkyl or ($C_3$-$C_7$) cycloalkyl, or
$R^{14}$ and $R^{15}$ together with the nitrogen atom to which they are attached form a 4- to 7-membered heterocycle,
where the 4- to 7-membered heterocycle may be substituted by 1 or 2 substituents independently of one another selected from the group consisting of fluorine, oxo, hydroxyl, ($C_1$-$C_4$) alkyl and trifluoromethyl, $R^{16}$ is hydrogen or ($C_1$-$C_4$) alkyl,
$R^{17}$ is hydrogen, ($C_1$-$C_4$) alkyl or ($C_3$-$C_7$) cycloalkyl,
$R^{18}$ is hydrogen, ($C_1$-$C_4$) alkyl or ($C_3$-$C_7$) cycloalkyl, or
$R^{16}$ and $R^{17}$ together with the nitrogen atoms to which they are attached form a 5- to 7-membered heterocycle,
where the 5- to 7-membered heterocycle may be substituted by 1 or 2 substituents independently of one another selected from the group consisting of fluorine, trifluoromethyl and ($C_1$-$C_4$) alkyl, or
$R^{17}$ and $R^{18}$ together with the nitrogen atom to which they are attached form a 4- to 7-membered heterocycle,
where the 4- to 7-membered heterocycle may be substituted by 1 or 2 substituents independently of one another selected from the group consisting of fluorine, oxo, hydroxyl, ($C_1$-$C_4$) alkyl and trifluoromethyl, $R^{19}$ is hydrogen or ($C_1$-$C_4$) alkyl,
$R^{20}$ is ($C_1$-$C_4$) alkyl or ($C_3$-$C_7$) cycloalkyl, or
$R^{19}$ and $R^{20}$ together with the atoms to which they are attached form a 5- to 7-membered heterocycle, where the 5- to 7-membered heterocycle may be substituted by 1 or 2 substituents independently of one another selected from the group consisting of fluorine, $(C_1-C_4)$ alkyl and trifluoromethyl, n is a number 0, 1 or 2, $R^{21}$ is hydrogen, $(C_1-C_4)$ alkyl or $(C_3-C_7)$ cycloalkyl, $R^{24}$ is hydrogen, $(C_1-C_4)$ alkyl or $(C_3-C_7)$ cycloalkyl, $R^{25}$ is hydrogen, $(C_1-C_4)$ alkyl or $(C_3-C_7)$ cycloalkyl, or $R^{24}$ and $R^{25}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl, $(C_1-C_4)$ alkyl and trifluoromethyl, $R^{26}$ is hydrogen or $(C_1-C_4)$ alkyl, $R^{27}$ is hydrogen, $(C_1-C_4)$ alkyl or $(C_3-C_7)$ cycloalkyl, $R^{28}$ is hydrogen, $(C_1-C_4)$ alkyl or $(C_3-C_7)$ cycloalkyl, or $R^{26}$ and $R^{27}$ together with the nitrogen atoms to which they are attached form a 5- to 7-membered heterocycle, where the 5- to 7-membered heterocycle may be substituted by 1 or 2 substituents independently of one another selected from the group consisting of fluorine, trifluoromethyl and $(C_1-C_4)$ alkyl, or $R^{27}$ and $R^{28}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl and $(C_1-C_4)$ alkyl, $R^{30}$ is hydrogen, $(C_1-C_4)$ alkyl or $(C_3-C_7)$ cycloalkyl, $R^{31}$ is $(C_1-C_4)$ alkyl or $(C_3-C_7)$ cycloalkyl, or $R^{30}$ and $R^{31}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl, $(C_1-C_4)$ alkyl and trifluoromethyl, $R^4$ is phenyl, naphthyl or 5- to 10-membered heteroaryl, where phenyl, naphthyl and 5- to 10-membered heteroaryl may be substituted by 1 to 3 substituents independently of one another selected from the group consisting of halogen, cyano, nitro, $(C_1-C_4)$ alkyl, difluoromethyl, trifluoromethyl, hydroxyl, $(C_1-C_4)$ alkoxy, difluoromethoxy and trifluoromethoxy, $R^5$ is hydrogen, deuterium, trifluoromethyl or $(C_1-C_4)$ alkyl, $R^{29}$ is hydrogen or $(C_1-C_4)$ alkyl, and also their salts, solvates, and solvates of the salts.

Compounds according to the invention are the compounds of the formula (I) and their salts, solvates, and solvates of the salts; the compounds of the below-specified formulae embraced by formula (I), and their salts, solvates, and solvates of the salts; and also the compounds specified below as working examples and embraced by formula (I), and their salts, solvates, and solvates of the salts; in so far as the below-specified compounds embraced by formula (I) are not already salts, solvates, and solvates of the salts.

Depending on their structure, the compounds according to the invention may exist in stereoisomeric forms (enantiomers, diastereomers). The present invention therefore embraces the enantiomers or diastereomers and their respective mixtures. From such mixtures of enantiomers and/or diastereomers it is possible to isolate the stereoisomerically uniform constituents in a known way.

Where the compounds according to the invention are able to occur in tautomeric forms, the present invention embraces all of the tautomeric forms.

Salts preferred in the context of the present invention are physiologically unobjectionable salts of the compounds of the invention. Also embraced are salts which, while not themselves suitable for pharmaceutical applications, may nevertheless be used, for example, for the isolation or purification of the compounds of the invention.

Physiologically unobjectionable salts of the compounds of the invention embrace acid addition salts of mineral acids, carboxylic acids and sulphonic acids, examples being salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, maleic acid, citric acid, fumaric acid, maleic acid and benzoic acid.

Physiologically unobjectionable salts of the compounds of the invention also embrace salts with customary bases, such as—by way of example and preferably—alkali metal salts (e.g. sodium and potassium salts), alkaline earth metal salts (e.g. calcium and magnesium salts) and ammonium salts, derived from ammonia or from organic amines having 1 to 16 C atoms, such as—by way of example and preferably-ethylamine, diethylamine, triethylamine, ethyldiisopropylamine, monoethanolamine, diethanolamine, trisethanolamine, dicyclohexylamine, dimethylaminoethanol, procaine, dibenzylamine, N-methylmorpholine, arginine, lysine, ethylenediamine and N-methylpiperidine.

Solvates in the context of the invention are those forms of the compounds of the invention that form a complex in solid or liquid state by coordination with solvent molecules. Hydrates are one specific form of solvates, where the coordination is with water. Preferred solvates in the context of the present invention are hydrates.

Furthermore, the present invention also embraces prodrugs of the compounds of the invention. The term "prodrugs" embraces compounds which may themselves be biologically active or inactive but which during their residence time in the body are converted (metabolically or by hydrolysis, for example) into compounds of the invention.

In the context of the present invention, the substituents, unless otherwise specified, have the following definitions:

Alkyl in the context of the invention is a linear or branched alkyl radical having 1 to 6 or 1 to 4 carbon atoms. By way of example and for preference it includes the following: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl in the context of the invention is a monocyclic saturated alkyl radical having 3 to 7 or 3 to 6 carbon atoms. By way of example and for preference it includes the following: cyclopropyl, cyclobutyl, cyclopentyl, cyclohexyl and cycloheptyl.

Alkenyl in the context of the invention is a linear or a branched alkenyl radical having 2 to 6 carbon atoms and one or two double bonds. Preference is given to a straight-chain or branched alkenyl radical having 2 to 4 carbon atoms and one double bond. By way of example and for preference it includes the following: vinyl, allyl, isopropenyl and n-but-2-en-1-yl.

Alkynyl in the context of the invention is a linear or branched alkynyl radical having 2 to 6 carbon atoms and one triple bond. By way of example and for preference it includes the following: ethynyl, n-prop-1-yn-1-yl, n-prop-2-yn-1-yl, n-but-2-yn-1-yl and n-but-3-yn-1-yl.

Alkoxy in the context of the invention is a linear or branched alkoxy radical having 1 to 6 or 1 to 4 carbon atoms. By way of example and for preference it includes the following: methoxy, ethoxy, n-propoxy, isopropoxy, 1-methylpropoxy, n-butoxy, isobutoxy and tert-butoxy.

Cycloalkoxy in the context of the invention is a monocyclic saturated cycloalkyl radical having 3 to 7 carbon atoms which is attached via an oxygen atom. By way of example and for preference it includes the following: cyclopropyloxy, cyclobutyloxy, cyclopentyloxy, cyclohexyloxy and cycloheptyloxy.

Alkoxycarbonyl in the context of the invention is a linear or branched alkoxy radical having 1 to 6 carbon atoms and a carbonyl group attached to the oxygen. By way of example and for preference it includes the following: methoxycarbonyl, ethoxycarbonyl, n-propoxycarbonyl, isopropoxycarbonyl and tert-butoxycarbonyl.

Mono-alkylaminocarbonyl in the context of the invention is an amino group which is linked via a carbonyl group and which has a linear or branched alkyl substituent having 1 to 4 carbon atoms. By way of example and for preference it includes the following: methylaminocarbonyl, ethylaminocarbonyl, n-propylaminocarbonyl, isopropylaminocarbonyl, n-butylaminocarbonyl and tert-butylaminocarbonyl.

Di-alkylaminocarbonyl in the context of the invention is an amino group which is linked via a carbonyl group and which has two identical or different linear or branched alkyl substituents each having 1 to 4 carbon atoms. By way of example and for preference it includes the following: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Heterocycle in the context of the invention is a saturated or partially unsaturated heterocycle having a total of 4 to 7 ring atoms, which comprises one to three ring heteroatoms from the series N, O and/or S, and is linked via a ring carbon atom or possibly a ring nitrogen atom. By way of example it includes the following: azetidinyl, pyrrolidinyl, piperidinyl, azepanyl, pyrazolidinyl, imidazolidinyl, piperazinyl, tetrahydropyrimidinyl, oxazolidinyl, morpholinyl, thiomorpholinyl, diazepanyl, tetrahydrofuranyl, tetrahydropyranyl, oxazinanyl, oxazepanyl, 2-oxopyrrolidin-1-yl, 2-oxopiperidin-1-yl, 2-oxoazepan-1-yl, 2-oxoimidazolidin-1-yl, 2-oxo-1,3-oxazolidin-3-yl, 2-oxotetrahydropyrimidin-1(2H)-yl, 2-oxo-1,3-oxazinan-3-yl, 2-oxo-1,3-diazepan-1-yl, 2-oxo-1,3-oxazepan-3-yl, 2,3-dihydro-1H-pyrrol-1-yl, 2-oxo-2,3-dihydro-1H-pyrrol-1-yl, 2-oxo-2,5-dihydro-1H-pyrrol-1-yl, 2-oxo-1,3-oxazolidinyl-3-yl, 2-oxo-1,3-oxazol-3(2H)-yl, 2-oxoimidazolidin-1-yl, 2-oxo-2,3-dihydro-1H-imidazol-1-yl, 1,1-dioxido-1,2-thiazolidin-2-yl, 1,1-dioxido-1,2-thiazinan-2-yl, 1,1-dioxido-1,2-thiazepan-2-yl, 1,1-dioxido-1,2,5-thiadiazolidin-2-yl, 1,1-dioxido-1,2,6-thiadiazinan-2-yl and 1,1-dioxido-1,2,7-thiadiazepan-2-yl. Preference is given to azetidinyl, pyrrolidinyl, piperidinyl, piperazinyl, morpholinyl, diazepanyl, oxazepanyl, 2-oxoimidazolidin-1-yl, 2-oxo-2,3-dihydro-1H-pyrrol-1-yl, 2-oxo-2,5-dihydro-1H-pyrrol-1-yl, 2-oxo-1,3-oxazolidin-3-yl, 1,1-dioxido-1,2,5-thiadiazolidin-2-yl, 2-oxotetrahydropyrimidin-1(2H)-yl, 2-oxo-1,3-oxazinan-3-yl, 2-oxo-1,3-diazepan-1-yl and 2-oxo-1,3-oxazepan-3-yl.

Heteroaryl in the context of the invention is a monocyclic or possibly bicyclic aromatic heterocycle (heteroaromatic) having a total of 5 to 10 ring atoms, which comprises up to three identical or different ring heteroatoms from the series N, O and/or S, and is linked via a ring carbon atom or possibly via a ring nitrogen atom. By way of example it includes the following: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to three ring heteroatoms from the series N, O and/or S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

Halogen the context of the invention includes fluorine, chlorine, bromine and iodine. Preference is given to chlorine or fluorine.

An oxo group in the context of the invention is an oxygen atom attached via a double bond to a carbon atom.

If radicals in the compounds of the invention are substituted, the radicals, unless otherwise specified, may be substituted one or more times. In the context of the present invention it is the case that, for all radicals which occur more than once, their definitions are independent of one another. Substitution by one, two or three identical or different substituents is preferred. Very particular preference is given to substitution by one substituent.

Preference in the context of the present invention is given to compounds of the general formula (I-B)

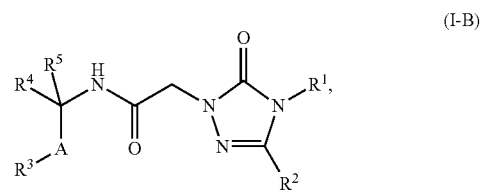

(I-B)

in which
A is —C($R^{6A}R^{6B}$)—* or —C($R^{6A}R^{6B}$)—C($R^{7A}R^{7B}$)—*,
  where
  * is the attachment site to $R^3$,
  $R^{6A}$ is hydrogen, ($C_1$-$C_4$) alkyl or trifluoromethyl,
  $R^{6B}$ is hydrogen or ($C_1$-$C_4$) alkyl,
  $R^{7A}$ is hydrogen, ($C_1$-$C_4$) alkyl or trifluoromethyl,
  $R^{7B}$ is hydrogen or ($C_1$-$C_4$) alkyl,
$R^1$ is ($C_1$-$C_6$) alkyl, ($C_2$-$C_6$) alkenyl, ($C_2$-$C_6$) alkynyl or ($C_3$-$C_7$) cycloalkyl,
  where ($C_1$-$C_6$) alkyl, ($C_2$-$C_6$) alkenyl and ($C_2$-$C_6$) alkynyl may be substituted by 1 to 3 substituents independently of one another selected from the group consisting of halogen, cyano, oxo, hydroxyl, trifluoromethyl, ($C_3$-$C_7$) cycloalkyl, ($C_1$-$C_6$) alkoxy, trifluoromethoxy and phenyl,
    in which ($C_3$-$C_7$) cycloalkyl may be substituted by 1 or 2 substituents independently of one another selected from the group consisting of ($C_1$-$C_4$) alkyl, oxo, hydroxyl, ($C_1$-$C_4$) alkoxy and amino, and
    in which ($C_1$-$C_6$) alkoxy may be substituted by 1 or 2 substituents independently of one another selected from the group consisting of amino, hydroxyl, ($C_1$-$C_4$) alkoxy, hydroxycarbonyl and ($C_1$-$C_4$) alkoxycarbonyl, and in which phenyl may be substituted by 1 to 3 substituents independently of one another selected from the group consisting of halogen, cyano, nitro, ($C_1$-$C_4$) alkyl, trifluoromethyl, hydroxyl, hydroxymethyl, ($C_1$-$C_4$) alkoxy, trifluoromethoxy, ($C_1$-$C_4$) alkoxymethyl, hydroxycarbonyl, ($C_1$-$C_4$) alkoxycarbonyl, aminocarbonyl, mono-($C_1$-$C_4$) alkylaminocarbonyl and di-($C_1$-$C_4$) alkylaminocarbonyl, and where ($C_3$-$C_7$) cycloalkyl may be substituted by 1 or 2 substituents independently of one another selected from the group consisting of fluorine, ($C_1$-$C_4$) alkyl, ($C_1$-$C_4$) alkoxy, hydroxy, amino and oxo, $R^2$ is phenyl, thienyl or furyl, where phenyl, thienyl and furyl may be substituted by 1 to 3 substituents independently of one another selected from the group consisting of halogen, cyano, nitro, ($C_1$-$C_4$) alkyl, trifluoromethyl, hydroxyl, ($C_1$-$C_4$) alkoxy and trifluoromethoxy, $R^3$ is trifluoromethyl, hydroxyl, nitro, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$ or —S(=O)$_n$$R^{21}$, where $R^8$ is hydrogen or ($C_1$-$C_4$) alkyl, $R^9$ is hydrogen, ($C_1$-$C_4$) alkyl or ($C_3$-$C_7$) cycloalkyl, $R^{10}$ is hydrogen or ($C_1$-$C_4$) alkyl, $R^{11}$ is ($C_1$-$C_4$) alkyl or ($C_3$-$C_7$) cycloalkyl, $R^{12}$ is hydrogen, ($C_1$-$C_4$) alkyl or ($C_3$-$C_7$) cycloalkyl, $R^{13}$ is hydrogen, ($C_1$-$C_4$) alkyl or ($C_3$-$C_7$) cycloalkyl, or $R^{12}$ and $R^{13}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl and ($C_1$-$C_4$) alkyl, $R^{14}$ is hydrogen, ($C_1$-$C_4$) alkyl or ($C_3$-$C_7$) cycloalkyl, $R^{15}$ is hydrogen, ($C_1$-$C_4$) alkyl or ($C_3$-$C_7$) cycloalkyl, or $R^{14}$ and $R^{15}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl and ($C_1$-$C_4$) alkyl, $R^{16}$ is hydrogen or ($C_1$-$C_4$) alkyl, $R^{17}$ is hydrogen, ($C_1$-$C_4$) alkyl or ($C_3$-$C_7$) cycloalkyl, $R^{18}$ is hydrogen, ($C_1$-$C_4$) alkyl or ($C_3$-$C_7$) cycloalkyl, or $R^{16}$ and $R^{17}$ together with the nitrogen atoms to which they are attached form a 5- to 7-membered heterocycle, where the 5- to 7-membered heterocycle may be substituted by 1 or 2 substituents independently of one another selected from the group consisting of fluorine and ($C_1$-$C_4$) alkyl, or $R^{17}$ and $R^{18}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl and ($C_1$-$C_4$) alkyl, $R^{19}$ is hydrogen or ($C_1$-$C_4$) alkyl, $R^{20}$ is ($C_1$-$C_4$) alkyl or ($C_3$-$C_7$) cycloalkyl, or $R^{19}$ and $R^{20}$ together with the atoms to which they are attached form a 5- to 7-membered heterocycle, where the 5- to 7-membered heterocycle may be substituted by 1 or 2 substituents independently of one another selected from the group consisting of fluorine and ($C_1$-$C_4$) alkyl, n is a number 0, 1 or 2, $R^{21}$ is hydrogen, ($C_1$-$C_4$) alkyl or ($C_3$-$C_7$) cycloalkyl, $R^4$ is phenyl, naphthyl or 5- to 10-membered heteroaryl, where phenyl, naphthyl and 5- to 10-membered heteroaryl may be substituted by 1 to 3 substituents independently of one another selected from the group consisting of halogen, cyano, nitro, ($C_1$-$C_4$) alkyl, difluoromethyl, trifluoromethyl, hydroxyl, ($C_1$-$C_4$) alkoxy, difluoromethoxy and trifluoromethoxy, $R^5$ is hydrogen, trifluoromethyl or ($C_1$-$C_4$) alkyl, and also their salts, solvates, and solvates of the salts.

Preference is given in the context of the present invention to compounds of the formula (I) in which A is —C($R^{6A}R^{6B}$)—* or —C($R^{6A}R^{6B}$)—C($R^{7A}R^{7B}$)—*, where

* is the attachment site to $R^3$, $R^{6A}$ is hydrogen, methyl or trifluoromethyl, $R^{6B}$ is hydrogen or methyl, $R^{7A}$ is hydrogen, methyl or trifluoromethyl, $R^{7B}$ is hydrogen or methyl, Q is CH or N, $R^1$ is ($C_1$-$C_6$) alkyl, ($C_2$-$C_6$) alkenyl or ($C_3$-$C_6$) cycloalkyl, where ($C_1$-$C_6$) alkyl and ($C_2$-$C_6$) alkenyl may be substituted by 1 to 3 substituents independently of one another selected from the group consisting of fluorine, chlorine, cyano, oxo, hydroxyl, trifluoromethyl, ($C_3$-$C_6$) cycloalkyl, ($C_1$-$C_4$) alkoxy, trifluoromethoxy and phenyl, in which ($C_3$-$C_6$) cycloalkyl may be substituted by 1 or 2 substituents independently of one another selected from the group consisting of methyl, ethyl, oxo, hydroxyl, methoxy, ethoxy and amino, and in which phenyl may be substituted by a substituent selected from the group consisting of fluorine, chlorine, cyano, methyl, ethyl, trifluoromethyl, methoxy, ethoxy, trifluoromethoxy, methoxymethyl, ethoxymethyl, hydroxycarbonyl, methoxycarbonyl, ethoxycarbonyl and aminocarbonyl, and where ($C_3$-$C_6$) cycloalkyl may be substituted by 1 or 2 substituents independently of one another selected from the group consisting of fluorine, methyl, ethyl, methoxy, ethoxy, hydroxyl, amino and oxo, $R^2$ is benzothien-2-yl, phenyl or thienyl, where benzothien-2-yl, phenyl and thienyl may be substituted by 1 or 2 substituents independently of one another selected from the group consisting of fluorine, chlorine, bromine, methyl, ethyl, trifluoromethyl, hydroxyl, methoxy, ethoxy and trifluoromethoxy, $R^3$ is trifluoromethyl, hydroxyl, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$, —S(=O)$_n$$R^{21}$, —O—$SO_2$—$NR^{24}R^{25}$ or —$NR^{26}$—$SO_2$—$NR^{27}R^{28}$—, where $R^8$ is hydrogen or methyl, $R^9$ is ($C_1$-$C_4$) alkyl, or $R^8$ and $R^9$ together with the atoms to which they are attached form a 5- to 7-membered heterocycle, $R^{10}$ is hydrogen or methyl, $R^{11}$ is ($C_1$-$C_4$) alkyl, or $R^{10}$ and $R^{11}$ together with the atoms to which they are attached form a 5- to 7-membered heterocycle, $R^{12}$ is ($C_1$-$C_4$) alkyl, $R^{13}$ is ($C_1$-$C_4$) alkyl, $R^{14}$ is hydrogen or ($C_1$-$C_4$) alkyl, $R^{15}$ is hydrogen, ($C_1$-$C_4$) alkyl or ($C_3$-$C_7$) cycloalkyl, or $R^{14}$ and $R^{15}$ together with the nitrogen atom to which they are attached form a 4- to 7-membered heterocycle, $R^{16}$ is hydrogen or $(C_1-C_4)$ alkyl,
$R^{17}$ is hydrogen or $(C_1-C_4)$ alkyl,
$R^{18}$ is hydrogen, $(C_1-C_4)$ alkyl or $(C_3-C_7)$ cycloalkyl, or
$R^{16}$ and $R^{17}$ together with the nitrogen atoms to which they are attached form a 5- to 7-membered heterocycle,
$R^{19}$ is hydrogen or methyl,
$R^{20}$ is $(C_1-C_4)$ alkyl, or
$R^{19}$ and $R^{20}$ together with the atoms to which they are attached form a 5- to 7-membered heterocycle,
n is a number 0, 1 or 2,
$R^{21}$ is $(C_1-C_4)$ alkyl,
$R^{24}$ is hydrogen or methyl,
$R^{25}$ is hydrogen or methyl,
$R^{26}$ is hydrogen or methyl,
$R^{27}$ is hydrogen or $(C_1-C_4)$ alkyl,
$R^{28}$ is hydrogen or $(C_1-C_4)$ alkyl, or
$R^{26}$ and $R^{27}$ together with the nitrogen atoms to which they are attached form a 5- to 7-membered heterocycle,
$R^4$ is phenyl,
where phenyl may be substituted by 1 to 3 substituents independently of one another selected from the group consisting of fluorine, chlorine, cyano, methyl, ethyl, difluoromethyl, trifluoromethyl, hydroxyl, methoxy, ethoxy, difluoromethoxy and trifluoromethoxy,
$R^5$ is hydrogen, deuterium, trifluoromethyl, methyl or ethyl,
$R^{29}$ is hydrogen or methyl,
and also their salts, solvates, and solvates of the salts.

Preference is given in the context of the present invention to compounds of the formula (I-B) in which
A is —C($R^{6A}R^{6B}$)—* or —C($R^{6A}R^{6B}$)—C($R^{7A}R^{7B}$)—*,
where
* is the attachment site to $R^3$,
$R^{6A}$ is hydrogen, methyl or trifluoromethyl,
$R^{6B}$ is hydrogen or methyl,
$R^{7A}$ is hydrogen, methyl or trifluoromethyl,
$R^{7B}$ is hydrogen or methyl,
$R^1$ is $(C_1-C_6)$ alkyl, $(C_2-C_6)$ alkenyl or $(C_3-C_6)$ cycloalkyl,
where $(C_1-C_6)$ alkyl and $(C_2-C_6)$ alkenyl may be substituted by 1 to 3 substituents independently of one another selected from the group consisting of fluorine, chlorine, cyano, oxo, hydroxyl, trifluoromethyl, $(C_3-C_6)$ cycloalkyl, $(C_1-C_4)$ alkoxy, trifluoromethoxy and phenyl,
in which $(C_3-C_6)$ cycloalkyl may be substituted by 1 or 2 substituents independently of one another selected from the group consisting of methyl, ethyl, oxo, hydroxyl, methoxy, ethoxy and amino, and
in which phenyl may be substituted by a substituent selected from the group consisting of fluorine, chlorine, cyano, methyl, ethyl, trifluoromethyl, methoxy, ethoxy, trifluoromethoxy, methoxymethyl, ethoxymethyl, hydroxycarbonyl, methoxycarbonyl, ethoxycarbonyl and aminocarbonyl, and
where $(C_3-C_6)$ cycloalkyl may be substituted by 1 or 2 substituents independently of one another selected from the group consisting of fluorine, methyl, ethyl, methoxy, ethoxy, hydroxyl, amino and oxo,
$R^2$ is phenyl or thienyl,
where phenyl and thienyl may be substituted by 1 or 2 substituents independently of one another selected from the group consisting of fluorine, chlorine, methyl, ethyl, trifluoromethyl, hydroxyl, methoxy, ethoxy and trifluoromethoxy,
$R^3$ is trifluoromethyl, hydroxyl, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$ or —$NR^{19}$—C(=O)—$OR^{20}$, where
$R^8$ is hydrogen or methyl,
$R^9$ is $(C_1-C_4)$ alkyl,
$R^{10}$ is hydrogen or methyl,
$R^{11}$ is $(C_1-C_4)$ alkyl,
$R^{12}$ is $(C_1-C_4)$ alkyl,
$R^{13}$ is $(C_1-C_4)$ alkyl,
$R^{14}$ is hydrogen or $(C_1-C_4)$ alkyl,
$R^{15}$ is hydrogen, $(C_1-C_4)$ alkyl or $(C_3-C_7)$ cycloalkyl, or
$R^{14}$ and $R^{15}$ together with the nitrogen atom to which they are attached form a 4- to 6-membered heterocycle,
$R^{16}$ is hydrogen or $(C_1-C_4)$ alkyl,
$R^{17}$ is hydrogen or $(C_1-C_4)$ alkyl,
$R^{18}$ is hydrogen, $(C_1-C_4)$ alkyl or $(C_3-C_7)$ cycloalkyl, or
$R^{17}$ and $R^{18}$ together with the nitrogen atom to which they are attached form a 4- to 6-membered heterocycle,
$R^{19}$ is hydrogen or methyl,
$R^{20}$ is $(C_1-C_4)$ alkyl, or
$R^{19}$ and $R^{20}$ together with the atoms to which they are attached form a 5- or 6-membered heterocycle,
$R^4$ is phenyl,
where phenyl may be substituted by 1 to 3 substituents independently of one another selected from the group consisting of fluorine, chlorine, cyano, methyl, ethyl, difluoromethyl, trifluoromethyl, hydroxyl, methoxy, ethoxy, difluoromethoxy and trifluoromethoxy,
$R^5$ is hydrogen, trifluoromethyl, methyl or ethyl,
and also their salts, solvates, and solvates of the salts.

Particular preference is given in the context of the present invention to compounds of the formula (I) in which
A is —C($R^{6A}R^{6B}$)—* or —C($R^{6A}R^{6B}$)—C($R^{7A}R^{7B}$)—*,
where
* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen,
Q is N,
$R^1$ is $(C_2-C_4)$ alkyl, $(C_2-C_4)$ alkenyl or cyclopropyl,
where $(C_2-C_4)$ alkyl and $(C_2-C_4)$ alkenyl may be substituted by 1 or 2 substituents independently of one another selected from the group consisting of fluorine, oxo, hydroxyl and trifluoromethyl,
$R^2$ is phenyl,
where phenyl may be substituted by a substituent selected from the group consisting of fluorine or chlorine,
$R^3$ is hydroxyl, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$, —S(=O)$_n R^{21}$ or —$NR^{26}$—$SO_2$—$NR^{27}R^{28}$—,
where
$R^8$ is hydrogen,
$R^9$ is methyl,
$R^{10}$ is hydrogen,
$R^{11}$ is methyl or ethyl,
$R^{12}$ is methyl,
$R^{13}$ is methyl,
$R^{14}$ is hydrogen or methyl,
$R^{15}$ is hydrogen, methyl or ethyl,
$R^{16}$ is hydrogen,
$R^{17}$ is hydrogen or methyl,
$R^{18}$ is hydrogen, methyl or ethyl, or
$R^{16}$ and $R^{17}$ together with the nitrogen atoms to which they are attached form a 2-oxoimidazolidin-1-yl or a 2-oxotetrahydropyrimidin-1(2H)-yl ring,
$R^{19}$ is hydrogen,
$R^{20}$ is methyl or ethyl, or $R^{19}$ and $R^{20}$ together with the atoms to which they are attached form a 2-oxo-1,3-oxazolidin-3-yl or 2-oxo-1,3-oxazinan-3-yl ring,
n is a number 0 or 2,
$R^{21}$ is methyl,
$R^{26}$ is hydrogen,
$R^{27}$ is hydrogen,
$R^{28}$ is hydrogen,
$R^4$ is a group of the formula

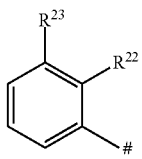

where
# is the attachment site to —$C(R^5)(AR^3)N$—,
$R^{22}$ is hydrogen, cyano, methyl, trifluoromethoxy, fluorine, chlorine, trifluoromethyl and methoxy,
$R^{23}$ is hydrogen, cyano, methyl, trifluoromethoxy, fluorine, chlorine, trifluoromethyl and methoxy,
where at least one of the radicals $R^{22}$ and $R^{23}$ is other than hydrogen,
$R^5$ is hydrogen or methyl,
$R^{29}$ is hydrogen,
and also their salts, solvates, and solvates of the salts.

Particular preference is additionally given in the context of the present invention to compounds of the formula (I) in which
A is —$C(R^{6A}R^{6B})$—* or —$C(R^{6A}R^{6B})$—$C(R^{7A}R^{7B})$—*,
where
* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen,
Q is N,
$R^1$ is ($C_2$-$C_4$) alkyl, ($C_2$-$C_4$) alkenyl or cyclopropyl, where ($C_2$-$C_4$) alkyl and ($C_2$-$C_4$) alkenyl may be substituted by 1 or 2 substituents independently of one another selected from the group consisting of fluorine, oxo, hydroxyl and trifluoromethyl,
$R^2$ is phenyl,
where phenyl may be substituted by a substituent selected from the group consisting of fluorine or chlorine,
$R^3$ is trifluoromethyl, hydroxyl, amino, —$NR^8$—$C(=O)$—$R^9$, —$NR^{10}$—$SO_2$—$R^{11}$, —$SO_2$—$NR^{12}R^{13}$, —O—C(=O)—$NR^{14}R^{15}$, —$NR^{16}$—$C(=O)$—$NR^{17}R^{18}$, —$NR^{19}$—$C(=O)$—$OR^{20}$, —$S(=O)_nR^{21}$ or —$NR^{26}$—$SO_2$—$NR^{27}R^{28}$—,
where
$R^8$ is hydrogen,
$R^9$ is methyl,
$R^{10}$ is hydrogen,
$R^{11}$ is methyl or ethyl,
$R^{12}$ is methyl,
$R^{13}$ is methyl,
$R^{14}$ is hydrogen or methyl,
$R^{15}$ is hydrogen, methyl or ethyl,
$R^{16}$ is hydrogen,
$R^{17}$ is hydrogen or methyl,
$R^{18}$ is hydrogen, methyl or ethyl, or $R^{16}$ and $R^{17}$ together with the nitrogen atoms to which they are attached form a 2-oxoimidazolidin-1-yl or a 2-oxotetrahydropyrimidin-1(2H)-yl ring,
$R^{19}$ is hydrogen,
$R^{20}$ is methyl or ethyl, or
$R^{19}$ and $R^{20}$ together with the atoms to which they are attached form a 2-oxo-1,3-oxazolidin-3-yl or 2-oxo-1,3-oxazinan-3-yl ring,
n is a number 0 or 2,
$R^{21}$ is methyl,
$R^{26}$ is hydrogen,
$R^{27}$ is hydrogen,
$R^{28}$ is hydrogen,
$R^4$ is a group of the formula

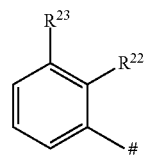

where
# is the attachment site to —$C(R^5)(AR^3)N$—,
$R^{22}$ is hydrogen, fluorine, chlorine, trifluoromethyl and methoxy,
$R^{23}$ is hydrogen, fluorine, chlorine, trifluoromethyl and methoxy,
where at least one of the radicals $R^{22}$ and $R^{23}$ is other than hydrogen,
$R^5$ is hydrogen or methyl,
$R^{29}$ is hydrogen,
and also their salts, solvates, and solvates of the salts.

More particular preference is given in the context of the present invention to compounds of the formula (I) in which
A is —$C(R^{6A}R^{6B})$—* or —$C(R^{6A}R^{6B})$—$C(R^{7A}R^{7B})$—*,
where
* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen,
Q is N,
$R^1$ is 3,3,3-trifluoroprop-1-en-1-yl, 3,3,3-trifluoropropyl or 1,1,1-trifluoropropan-2-ol-3-yl,
$R^2$ is phenyl,
where phenyl may be substituted by a substituent selected from the group consisting of fluorine or chlorine,
$R^3$ is hydroxyl, amino, —$NR^8$—$C(=O)$—$R^9$, —$NR^{10}$—$SO_2$—$R^{11}$, —$SO_2$—$NR^{12}R^{13}$, —O—$C(=O)$—$NR^{14}R^{15}$, —$NR^{16}$—$C(=O)$—$NR^{17}R^{18}$, —$NR^{19}$—$C(=O)$—$OR^{20}$, —$S(=O)_nR^{21}$ or —$NR^{26}$—$SO_2$—$NR^{27}R^{28}$—,
where
$R^8$ is hydrogen,
$R^9$ is methyl,
$R^{10}$ is hydrogen,
$R^{11}$ is methyl or ethyl,
$R^{12}$ is methyl,
$R^{13}$ is methyl,
$R^{14}$ is hydrogen or methyl,
$R^{15}$ is hydrogen, methyl or ethyl,
$R^{16}$ is hydrogen,
$R^{17}$ is hydrogen or methyl,
$R^{18}$ is hydrogen, methyl or ethyl, or $R^{16}$ and $R^{17}$ together with the nitrogen atoms to which they are attached form a 2-oxoimidazolidin-1-yl or a 2-oxotetrahydropyrimidin-1(2H)-yl ring,
$R^{19}$ is hydrogen,
$R^{20}$ is methyl or ethyl, or
$R^{19}$ and $R^{20}$ together with the atoms to which they are attached form a 2-oxo-1,3-oxazolidin-3-yl or 2-oxo-1,3-oxazinan-3-yl ring,
n is a number 0 or 2,
$R^{21}$ is methyl,
$R^{26}$ is hydrogen,
$R^{27}$ is hydrogen,
$R^{28}$ is hydrogen,
$R^4$ is a group of the formula

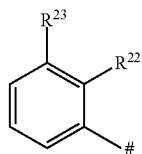

where
\# is the attachment site to —C($R^5$)(A$R^3$)N—,
$R^{22}$ is hydrogen, fluorine, chlorine and trifluoromethyl,
$R^{23}$ is hydrogen, fluorine, chlorine and trifluoromethyl,
where at least one of the radicals $R^{22}$ and $R^{23}$ is other than hydrogen,
$R^5$ is hydrogen or methyl,
$R^{29}$ is hydrogen,
and also their salts, solvates, and solvates of the salts.

Particular preference is given in the context of the present invention to compounds of the formula (I-B) in which
A is —C($R^{6A}R^{6B}$)—* or —C($R^{6A}R^{6B}$)—C($R^{7A}R^{7B}$)—*,
where
* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen,
$R^1$ is ($C_2$-$C_4$) alkyl, ($C_2$-$C_4$) alkenyl or cyclopropyl,
where ($C_2$-$C_4$) alkyl and ($C_2$-$C_4$) alkenyl are substituted by 1 or 2 substituents independently of one another selected from the group consisting of fluorine, hydroxyl, oxo and trifluoromethyl,
$R^2$ is phenyl,
where phenyl is substituted by a substituent selected from the group consisting of fluorine and chlorine,
$R^3$ is trifluoromethyl, hydroxyl, amino, —$NR^8$—C(=O)—$R^9$, —$NR^{13}$—$SO_2$—$R^{11}$, —O—C(=O)—$NR^{14}R^{15}$ or —$NR^{16}$—C(=O)—$NR^{17}R^{18}$,
where
$R^8$ is hydrogen,
$R^9$ is methyl,
$R^{10}$ is hydrogen,
$R^{11}$ is methyl or ethyl,
$R^{14}$ is hydrogen or methyl,
$R^{15}$ is hydrogen, methyl or ethyl,
$R^{16}$ is hydrogen,
$R^{17}$ is hydrogen or methyl,
$R^{18}$ is hydrogen, methyl or ethyl, $R^4$ is a group of the formula

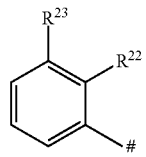

where
\# is the attachment site to —C($R^5$)(A$R^3$)N—,
$R^{22}$ is hydrogen, cyano, methyl, trifluoromethoxy, fluorine, chlorine, trifluoromethyl and methoxy,
$R^{23}$ is hydrogen, cyano, methyl, trifluoromethoxy, fluorine, chlorine, trifluoromethyl and methoxy,
where at least one of the radicals $R^{22}$ and $R^{23}$ is other than hydrogen,
$R^5$ is hydrogen or methyl,
and also their salts, solvates, and solvates of the salts.

Particular preference is additionally given in the context of the present invention to compounds of the formula (I-B) in which
A is —C($R^{6A}R^{6B}$)—* or —C($R^{6A}R^{6B}$)—C($R^{7A}R^{7B}$)—*,
where
* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen,
$R^1$ is ($C_2$-$C_4$) alkyl, ($C_2$-$C_4$) alkenyl or cyclopropyl,
where ($C_2$-$C_4$) alkyl and ($C_2$-$C_4$) alkenyl are substituted by 1 or 2 substituents independently of one another selected from the group consisting of fluorine, hydroxyl, oxo and trifluoromethyl,
$R^2$ is phenyl,
where phenyl is substituted by a substituent selected from the group consisting of fluorine and chlorine,
$R^3$ is trifluoromethyl, hydroxyl, amino, —$NR^8$—C(=O)—$R^9$, —$NR^{10}$—$SO_2$—$R^{11}$, —O—C(=O)—$NR^{14}R^{15}$ or —$NR^{16}$—C(=O)—$NR^{17}R^{18}$,
where
$R^8$ is hydrogen,
$R^9$ is methyl,
$R^{10}$ is hydrogen,
$R^{11}$ is methyl or ethyl,
$R^{14}$ is hydrogen or methyl,
$R^{15}$ is hydrogen, methyl or ethyl,
$R^{16}$ is hydrogen,
$R^{17}$ is hydrogen or methyl,
$R^{18}$ is hydrogen, methyl or ethyl,
$R^4$ is a group of the formula

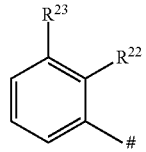

where
\# is the attachment site to —C($R^5$)(A$R^3$)N—,
$R^{22}$ is hydrogen, fluorine, chlorine, trifluoromethyl and methoxy,
$R^{23}$ is hydrogen, fluorine, chlorine, trifluoromethyl and methoxy, where at least one of the radicals $R^{22}$ and $R^{23}$ is other than hydrogen,
$R^5$ is hydrogen or methyl,
and also their salts, solvates, and solvates of the salts.

More particular preference is given in the context of the present invention to compounds of the formula (I-B) in which
A is —C($R^{6A}R^{6B}$)—* or —C($R^{6A}R^{6B}$)—C($R^{7A}R^{7B}$)—*,
  where
    * is the attachment site to $R^3$,
    $R^{6A}$ is hydrogen or trifluoromethyl,
    $R^{6B}$ is hydrogen,
    $R^{7A}$ is hydrogen,
    $R^{7B}$ is hydrogen,
$R^1$ is 3,3,3-trifluoroprop-1-en-1-yl, 3,3,3-trifluoropropyl or 1,1,1-trifluoropropan-2-ol-3-yl,
$R^2$ is phenyl,
  where phenyl is substituted by a substituent selected from the group consisting of fluorine and chlorine,
$R^3$ is hydroxyl, amino, —$NR^8$—C(=O)—$R^9$, —$NR^{10}$—$SO_2$—$R^{11}$, —O—C(=O)—$NR^{14}R^{15}$ or —$NR^{16}$—C(=O)—$NR^{17}R^{18}$,
  where
    $R^8$ is hydrogen,
    $R^9$ is methyl,
    $R^{10}$ is hydrogen,
    $R^{11}$ is methyl or ethyl,
    $R^{14}$ is hydrogen or methyl,
    $R^{15}$ is hydrogen, methyl or ethyl,
    $R^{16}$ is hydrogen,
    $R^{17}$ is hydrogen or methyl,
    $R^{18}$ is hydrogen, methyl or ethyl,
$R^4$ is a group of the formula

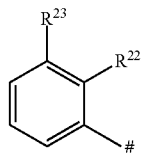

where
    # is the attachment site to —C($R^5$)($AR^3$)N—,
    $R^{22}$ is hydrogen, fluorine, chlorine or trifluoromethyl,
    $R^{23}$ is hydrogen, fluorine, chlorine or trifluoromethyl,
    where at least one of the radicals $R^{22}$ and $R^{23}$ is other than hydrogen,
$R^5$ is hydrogen or methyl,
and also their salts, solvates, and solvates of the salts.

Preference is given in the context of the present invention as well to compounds of the formula (I) in which $R^2$ is p-chlorophenyl.

Preference is given in the context of the present invention as well to compounds of the formula (I) in which
$R^2$ is phenyl or thienyl,
  where phenyl and thienyl may be substituted by a substituent selected from the group consisting of fluorine, chlorine, methyl, ethyl, trifluoromethyl, hydroxy, methoxy, ethoxy and trifluoromethoxy.

Preference is given in the context of the present invention as well to compounds of the formula (I) in which $R^1$ is 3,3,3-trifluoroprop-1-en-1-yl.

Preference is given in the context of the present invention as well to compounds of the formula (I) in which $R^1$ is 3,3,3-trifluoropropyl.

Preference is given in the context of the present invention as well to compounds of the formula (I) in which $R^1$ is 1,1,1-trifluoropropan-2-ol-3-yl.

Preference is given in the context of the present invention as well to compounds of the formula (I) in which
$R^1$ is ($C_2$-$C_4$) alkyl or ($C_2$-$C_4$) alkenyl,
  where ($C_2$-$C_4$) alkyl and ($C_2$-$C_4$) alkenyl are substituted by 1 or 2 substituents independently of one another selected from the group consisting of fluorine, hydroxyl, oxo and trifluoromethyl.

Preference is given in the context of the present invention as well to compounds of the formula (I) in which $R^1$ is cyclopropyl.

Preference is given in the context of the present invention as well to compounds of the formula (I) in which
$R^3$ is —O—C(=O)—$NR^{14}R^{15}$ or —$NR^{16}$—C(=O)—$NR^{17}R^{18}$,
  where
    $R^{14}$ is hydrogen or methyl,
    $R^{15}$ is hydrogen, methyl or ethyl,
    $R^{16}$ is hydrogen,
    $R^{17}$ is hydrogen or methyl,
    $R^{18}$ is hydrogen, methyl or ethyl.

Preference is given in the context of the present invention as well to compounds of the formula (I) in which
$R^3$ is —$NR^{10}$—$SO_2$—$R^{11}$,
  where
    $R^{10}$ is hydrogen and
    $R^{11}$ is methyl or ethyl.

Preference is given in the context of the present invention as well to compounds of the formula (I) in which
$R^3$ is hydroxyl or amino.

Preference is given in the context of the present invention as well to compounds of the formula (I) in which
$R^3$ is —$NR^{16}$—C(=O)—$NR^{17}R^{18}$ or —$NR^{19}$—C(=O)—$OR^{20}$,
  where
    $R^{16}$ and $R^{17}$ together with the nitrogen atoms to which they are attached form a 2-oxoimidazolidin-1-yl or a 2-oxotetrahydropyrimidin-1(2H)-yl ring,
    $R^{19}$ and $R^{20}$ together with the atoms to which they are attached form a 2-oxo-1,3-oxazolidin-3-yl or 2-oxo-1,3-oxazinan-3-yl ring.

Preference is given in the context of the present invention as well to compounds of the formula (I) in which
$R^3$ is —$NR^{16}$—C(=O)—$NR^{17}R^{18}$ or —$NR^{19}$—C(=O)—$OR^{20}$,
  where
    $R^{16}$ and $R^{17}$ together with the nitrogen atoms to which they are attached form a 2-oxo-imidazolidin-1-yl ring,
    $R^{19}$ and $R^{20}$ together with the atoms to which they are attached form a 2-oxo-1,3-oxazolidin-3-yl ring.

Preference is given in the context of the present invention as well to compounds of the formula (I) in which A is —$CH_2$—$CH_2$—.

Preference is given in the context of the present invention as well to compounds of the formula (I) in which A is —$CH_2$—.

Preference is given in the context of the present invention as well to compounds of the formula (I) in which Q is N.

Preference is given in the context of the present invention as well to compounds of the formula (I) in which Q is CH.

Preference is given in the context of the present invention as well to compounds of the formula (I) in which $R^5$ is hydrogen, trifluoromethyl, methyl or ethyl.

Preference is given in the context of the present invention as well to compounds of the formula (I) in which $R^5$ is hydrogen.

Preference is given in the context of the present invention as well to compounds of the formula (I) in which $R^5$ is methyl.

Preference is given in the context of the present invention as well to compounds of the formula (I) in which $R^5$ is trifluoromethyl, methyl or ethyl.

Preference is given in the context of the present invention as well to compounds of the formula (I) in which $R^{29}$ is hydrogen.

Preference is given in the context of the present invention as well to compounds of the formula (I) in which $R^{29}$ is methyl.

The radical definitions given individually in the respective combinations and preferred combinations of radicals are also replaced arbitrarily, independently of the particular radical combinations specified, by radical definitions from other combinations.

Very particular preference is given to combinations from two or more of the above-mentioned ranges of preference.

The invention further provides a process for preparing the compounds of the formula (I) according to the invention, characterized in that

[A] a compound of the formula (II)

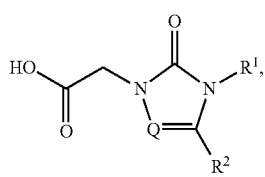

(II)

in which Q, $R^1$ and $R^2$ are each as defined above is coupled in an inert solvent, with activation of the carboxylic acid function, to a compound of the formula (III)

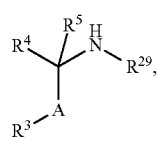

(III)

in which A, $R^3$, $R^4$, $R^5$ and $R^{29}$ are each as defined above, or

[B] a compound of the formula (IV)

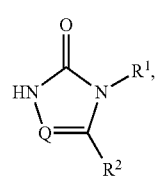

(IV)

in which Q, $R^1$ and $R^2$ are each as defined above is reacted in an inert solvent, in the presence of a base, with a compound of the formula (V)

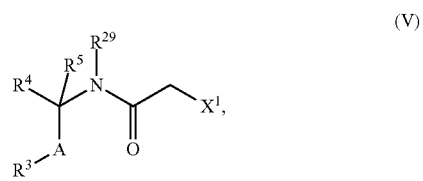

(V)

in which A, $R^3$, $R^4$, $R^5$ and $R^{29}$ are each as defined above and

X' is a leaving group, such as halogen, mesylate or tosylate, for example, and the resulting compounds of the formula (I) are converted optionally with the corresponding (i) solvents and/or (ii) bases or acids into their solvates, salts and/or solvates of the salts.

Inert solvents for the process step (II)+(III)→(I) are for example ethers such as diethyl ether, dioxan, tetrahydrofuran, glycol dimethyl ether or diethylene glycol dimethyl ether, hydrocarbons such as benzene, toluene, xylene, hexane, cyclohexane or petroleum fractions, halogenated hydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N'-dimethylpropyleneurea (DMPU) or N-methylpyrrolidone (NMP). Likewise it is possible to use mixtures of the said solvents. Dichloro-methane, tetrahydrofuran, dimethylformamide or mixtures of these solvents are preferred.

Suitable condensation agents for the amidation in the process step (II)+(III)→(I) include, for example, carbodiimides such as N,N'-diethyl-, N,N'-dipropyl-, N,N'-diisopropyl- or N,N'-dicyclo-hexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3 sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)phosphoryl chloride, benzotriazol-1-yloxy-tris(dimethylamino)phosphonium hexa-fluorophosphate, benzotriazol-1-yloxy-tris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with other additives such as 1-hydroxybenzotriazole (HOBt) or N-hydroxysuccinimide (HOSu), and, as bases, alkali metal carbonates, e.g. sodium or potassium carbonate or hydrogen carbonate, or organic bases such as trialkylamines, e.g. triethylamine, N-methylmorpholine, N-methylpiperidine or N,N-diisopropylethylamine. Preferably EDC in combination with HOBt or TBTU in the presence of N,N-diisopropylethylamine is used.

The condensation (II)+(III)→(I) is generally performed in a temperature range from −20° C. to +60° C., preferably at 0° C. to +40° C. The reaction can take place under standard atmospheric, increased or reduced pressure (e.g. from 0.5 to 5 bar). The operation is generally carried out under atmospheric pressure.

Inert solvents for the process step (IV)+(V)→(I) are for example halogenated hydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as acetone, methyl ethyl ketone, ethyl acetate, acetonitrile, N,N-dimethylformamide, dimethyl sulphoxide, N,N'-dimethylpropyleneurea (DMPU), N-methylpyrrolidone (NMP) or pyridine. Likewise it is possible to use mixtures of the said solvents. Preferably, acetonitrile, acetone or dimethylformamide is used.

As bases for the process step (IV)+(V)→(I), the usual inorganic or organic bases are suitable. These preferably include alkali metal hydroxides such as for example lithium, sodium or potassium hydroxide, alkali metal or alkaline earth metal carbonates such as lithium, sodium, potassium, calcium or caesium carbonate, alkali metal alcoholates such as sodium or potassium methanolate, sodium or potassium ethanolate or sodium or potassium tert-butylate, alkali metal hydrides such as sodium or potassium hydride, amides such as sodamide, lithium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo-[4.3.0]non-5-ene (DBN), 1,8-diazabicyclo[5.4.0]undec-7-ene (DBU) or 1,4-diazabicyclo[2.2.2]-octane (DABCO®). Preferably, potassium carbonate or caesium carbonate is used.

In this step, the base is used in an amount of 1 to 5 mol, preferably in an amount of 1 to 2.5 mol, based on 1 mol of the compound of the formula (IV). The reaction generally takes place in a temperature range from 0° C. to +100° C., preferably at +20° C. to +80° C. The reaction can take place under standard atmospheric, increased or reduced pressure (e.g. from 0.5 to 5 bar). The operation is generally carried out under atmospheric pressure.

The preparation of the compounds of the invention can be illustrated by the following synthesis scheme:

Alternatively, compounds of the formula (I) in which A is —$CH_2$— or —$CH_2$—$CH_2$— can also be prepared by reducing a compound of the formula (XV)

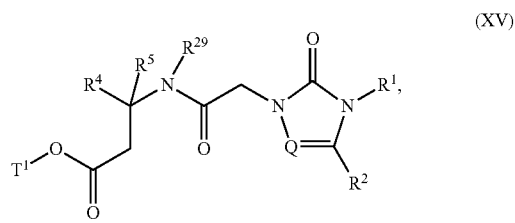

in which Q, $R^1$, $R^2$, $R^4$, $R^5$ and $R^{29}$ are each as defined above and $T^1$ is hydrogen or ($C_1$-$C_4$)-alkyl, in an inert solvent in the presence of a suitable reducing agent, to give a compound of the formula (I-A)

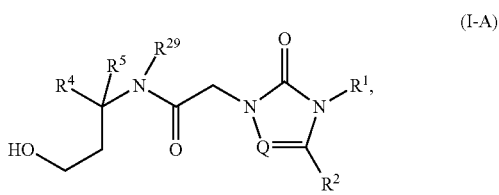

in which Q, $R^1$, $R^2$, $R^4$, $R^5$ and $R^{29}$ are each as defined above, and subjecting the compound (I-A), if desired, to further modification in accordance with the reactions and methods known to a person skilled in the art, such as, for example, nucleophilic and electrophilic substitutions, oxidations, reductions, hydrogenations, transition metal-catalysed coupling reactions, eliminations, alkylation, amination, esterification, ester cleavage, etherification, ether cleavage, and also introduction and removal of temporary protecting groups.

Suitable inert solvents for the process step (XV)→(I-A) here are alcohols such as methanol, ethanol, n-propanol or isopropanol, or ethers such as diethyl ether, dioxane, tetrahydrofuran, glycol dimethyl ether, dimethoxyethane or diethyl- Scheme 1

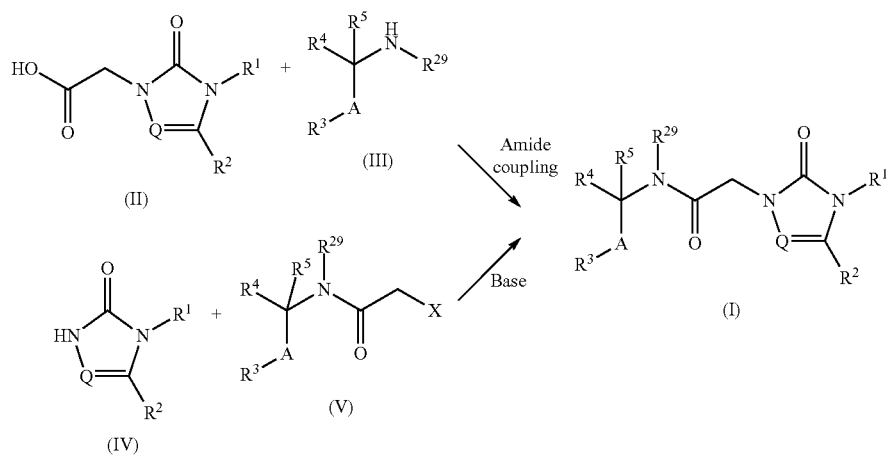

ene glycol dimethyl ether, or halogenated hydrocarbons such as dichloromethane, trichloromethane, carbon tetrachloride or 1,2-dichloroethane, or other solvents such as dimethylformamide. It is likewise possible to use mixtures of the said solvents. Preference is given to using dimethoxyethane and tetrahydrofuran.

Suitable reducing agents for the process step (XV)→(I-A) include borohydrides, such as, for example, sodium borohydride, sodium triacetoxyborohydride, lithium borohydride or sodium cyanoborohydride, aluminium hydrides such as, for example, lithium aluminium hydride, sodium bis(2-methoxyethoxy)aluminium hydride or diisobutylaluminium hydride, diborane or borane-tetrahydrofuran complex.

The reaction (XV)→(I-A) takes place in general in a temperature range from 0° C. to +60° C., preferably from 0° C. to +40° C.

The compounds of the formula (II) can be obtained by base-induced alkylation of compounds of the formula (IV) to give the $N^2$-substituted compounds (VII) and subsequent ester hydrolysis (see Scheme 2):

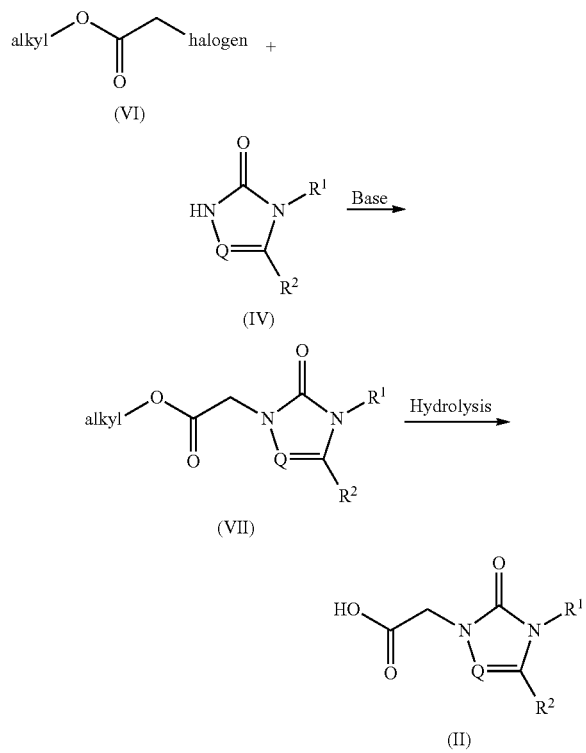

The compounds of the formula (VII) in which Q is N may alternatively also be prepared from N-(alkoxycarbonyl) arylthioamides of the formula (IX), which are known from the literature [see, for example, M. Arnswald, W. P. Neumann, J. Org. Chem. 58 (25), 7022-7028 (1993); E. P. Papadopoulos, J. Org. Chem. 41 (6), 962-965 (1976)], by reaction with hydrazino esters of the formula (VIII) and subsequent alkylation at N-4 of the triazolone (X) (Scheme 3):

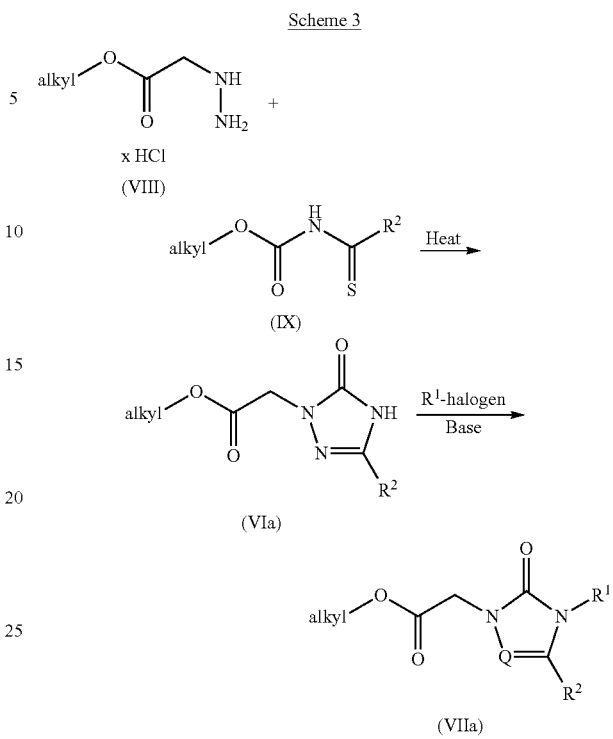

The compounds of the formula (IV) in which Q is N may be prepared starting from carboxylic hydrazides of the formula (XI) by reaction with isocyanates of the formula (XII) or nitrophenyl carbamates of the formula (XIII) and subsequent base-induced cyclisation of the intermediate hydrazinecarboxamides (XIV) (Scheme 4):

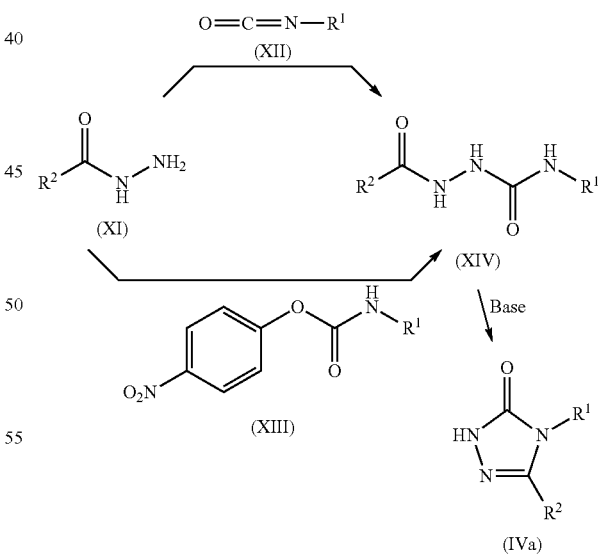

The compound in which $R^1$ corresponds to the substituent $CH_2CH(OH)CF_3$ is reacted, initially following Scheme 4, from alkyl isocyanatoacetate (XIIa) and (XI) to give (XIVa). Subsequent basic cyclisation leads to the triazolone (IVa). Introduction of the $CF_3$ group is accomplished by reaction of (IVa) with trifluoroacetic anhydride in pyridine. The resulting ketone (IVb) can then be converted by reduction to (IVc) (Scheme 5):

Scheme 5

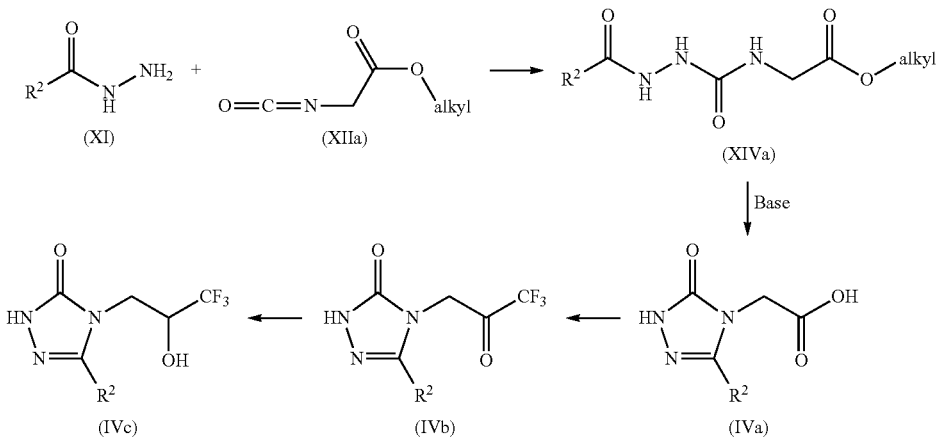

The compounds of the formula (II) in which Q is CH are accessible through reaction of α-amino ketones of the formula (XVI) with isocyanates of the formula (XVII) and subsequent ester hydrolysis (Scheme 6). The compounds of the formula (XVI), for their part, can be synthesized in a way which is known from the literature, from α-bromo ketones of the formula (XVIII) and amino esters of the formula (XIX) (Scheme 7):

Scheme 6

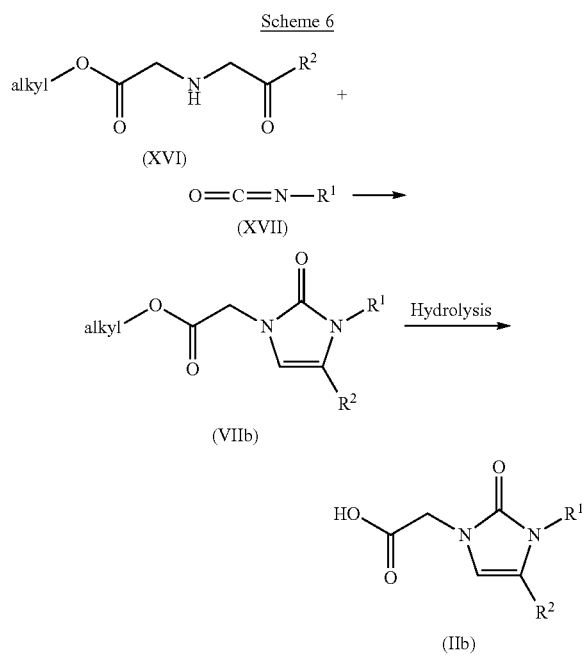

Scheme 7

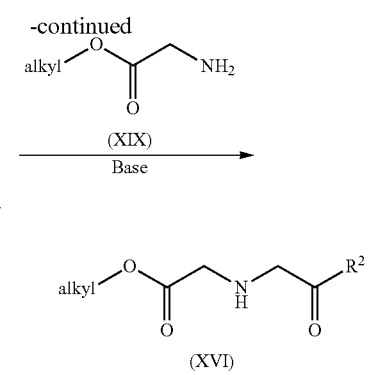

The compounds of the formulae (III), (V), (VI), (VIII), (IX), (XI), (XII), (XIIa), (XIII), (XVII), (XIX) and (XX) are variously available commercially, known from the literature, or can be prepared in analogy to processes known from the literature, or as described in the present experimental section.

Further compounds of the invention may also be prepared, if desired, by conversions of functional groups of individual substituents, particularly those listed under $R^1$ and $R^3$, starting from the compounds of the formula (I) obtained in accordance with processes above. These conversions are carried out in accordance with customary methods known to a person skilled in the art, and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, especially formation of carboxamides, and also introduction and removal of temporary protecting groups.

The present invention further encompasses compounds of the formula (III)

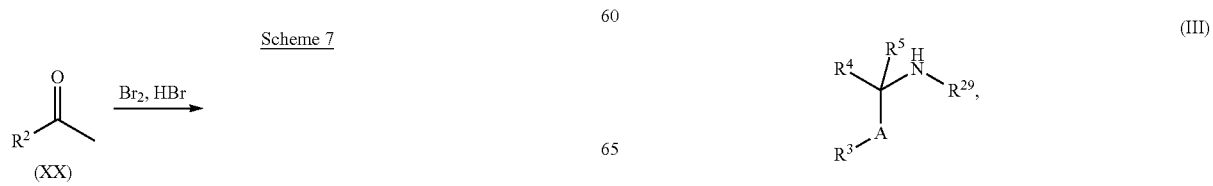

in which

A is —C($R^{6A}R^{6B}$)—* or —C($R^{6A}R^{6B}$)—C($R^{7A}R^{7B}$)—*,
  where
  * is the attachment site to $R^3$,
  $R^{6A}$ is hydrogen or trifluoromethyl,
  $R^{6B}$ is hydrogen,
  $R^{7A}$ is hydrogen,
  $R^{7B}$ is hydrogen, Q is N, $R^3$ is hydroxyl, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$, —S(=O)$_n$$R^{21}$ or —$NR^{26}$—$SO_2$—$NR^{27}R^{28}$—,
  where
  $R^8$ is hydrogen,
  $R^9$ is methyl,
  $R^{10}$ is hydrogen,
  $R^{11}$ is methyl or ethyl,
  $R^{12}$ is methyl,
  $R^{13}$ is methyl,
  $R^{14}$ is hydrogen or methyl,
  $R^{15}$ is hydrogen, methyl or ethyl,
  $R^{16}$ is hydrogen,
  $R^{17}$ is hydrogen or methyl,
  $R^{18}$ is hydrogen, methyl or ethyl, or
  $R^{16}$ and $R^{17}$ together with the nitrogen atoms to which they are attached form a 2-oxoimidazolidin-1-yl or a 2-oxotetrahydropyrimidin-1(2H)-yl ring,
  $R^{19}$ is hydrogen,
  $R^{20}$ is methyl or ethyl, or
  $R^{19}$ and $R^{20}$ together with the atoms to which they are attached form a 2-oxo-1,3-oxazolidin-3-yl or 2-oxo-1,3-oxazinan-3-yl ring,
  n is a number 0 or 2,
  $R^{21}$ is methyl,
  $R^{26}$ is hydrogen,
  $R^{27}$ is hydrogen,
  $R^{28}$ is hydrogen, $R^4$ is a group of the formula

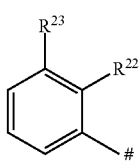

where
  # is the attachment site to —C($R^5$)(A$R^3$)N—,
  $R^{22}$ is hydrogen, fluorine, chlorine and trifluoromethyl,
  $R^{23}$ is hydrogen, fluorine, chlorine and trifluoromethyl,
  where at least one of the radicals $R^{22}$ and $R^{23}$ is other than hydrogen, $R^5$ is hydrogen or methyl, $R^{29}$ is hydrogen.

The present invention further encompasses compounds of the formula (V)

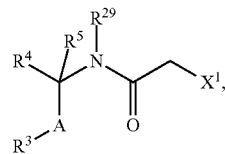

(V)

in which

A is —C($R^{6A}R^{6B}$)—* or —C($R^{6A}R^{6B}$)—C($R^{7A}R^{7B}$)—*,
  where
  * is the attachment site to $R^3$,
  $R^{6A}$ is hydrogen or trifluoromethyl,
  $R^{6B}$ is hydrogen,
  $R^{7A}$ is hydrogen,
  $R^{7B}$ is hydrogen, Q is N, $R^3$ is hydroxyl, amino, —$NR^8$—C(=O)—$R^9$, —$NR^{10}$—$SO_2$—$R^{11}$, —$SO_2$—$NR^{12}R^{13}$, —O—C(=O)—$NR^{14}R^{15}$, —$NR^{16}$—C(=O)—$NR^{17}R^{18}$, —$NR^{19}$—C(=O)—$OR^{20}$, —S(=O)$_n$$R^{21}$ or —$NR^{26}$—$SO_2$—$NR^{27}R^{28}$—,
  where
  $R^8$ is hydrogen,
  $R^9$ is methyl,
  $R^{10}$ is hydrogen,
  $R^{11}$ is methyl or ethyl,
  $R^{12}$ is methyl,
  $R^{13}$ is methyl,
  $R^{14}$ is hydrogen or methyl,
  $R^{15}$ is hydrogen, methyl or ethyl,
  $R^{16}$ is hydrogen,
  $R^{17}$ is hydrogen or methyl,
  $R^{18}$ is hydrogen, methyl or ethyl, or
  $R^{16}$ and $R^{17}$ together with the nitrogen atoms to which they are attached form a 2-oxoimidazolidin-1-yl or a 2-oxotetrahydropyrimidin-1(2H)-yl ring,
  $R^{19}$ is hydrogen,
  $R^{20}$ is methyl or ethyl, or
  $R^{19}$ and $R^{20}$ together with the atoms to which they are attached form a 2-oxo-1,3-oxazolidin-3-yl or 2-oxo-1,3-oxazinan-3-yl ring,
  n is a number 0 or 2,
  $R^{21}$ is methyl,
  $R^{26}$ is hydrogen,
  $R^{27}$ is hydrogen,
  $R^{28}$ is hydrogen, $R^4$ is a group of the formula

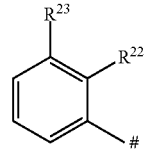

where
  # is the attachment site to —C($R^5$)(A$R^3$)N—,
  $R^{22}$ is hydrogen, fluorine, chlorine and trifluoromethyl,
  $R^{23}$ is hydrogen, fluorine, chlorine and trifluoromethyl,
  where at least one of the radicals $R^{22}$ and $R^{23}$ is other than hydrogen, $R^5$ is hydrogen or methyl, $R^{29}$ is hydrogen.

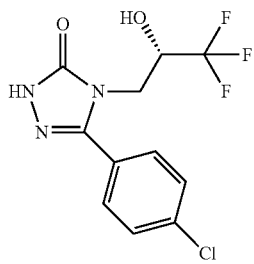 [SMILES: O=c1[nH]nc(-c2ccc(Cl)cc2)n1C[C@H](O)C(F)(F)F]

5-(4-chlorophenyl)-4-[(2S)-3,3,3-trifluoro-2-hydroxypropyl]-2,4-dihydro-3H-1,2,4-triazol-3-one.

The compounds according to the invention possess valuable pharmacological properties and can be used for the prevention and/or treatment of various diseases and disease-induced states in humans and animals.

The compounds according to the invention are potent selective dual V1a/V2 receptor antagonists, which inhibit vasopressin activity in vitro and in vivo.

The compounds according to the invention are particularly suitable for the prophylaxis and/or treatment of cardiovascular diseases. In this connection, the following may for example and preferably be mentioned as target indications: acute and chronic cardiac insufficiency, arterial hypertension, coronary heart disease, stable and unstable angina pectoris, myocardial ischaemia, myocardial infarction, shock, arteriosclerosis, atrial and ventricular arrhythmias, transitory and ischaemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, oedema formation such as for example pulmonary oedema, cerebral oedema, renal oedema or cardiac insufficiency-related oedema, and restenoses for example after thrombolysis treatments, percutaneous-transluminal angioplasties (PTA), transluminal coronary angioplasties (PTCA), heart transplants and bypass operations.

In the sense of the present invention, the term cardiac insufficiency also includes more specific or related disease forms such as right cardiac insufficiency, left cardiac insufficiency, global insufficiency, ischaemic cardiomyopathy, dilatative cardiomyopathy, congenital heart defects, heart valve defects, cardiac insufficiency with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic cardiac insufficiency, alcohol-toxic cardiomyopathy, cardiac storage diseases, diastolic cardiac insufficiency and systolic cardiac insufficiency.

Furthermore, the compounds according to the invention are suitable for use as a diuretic for the treatment of oedemas and in electrolyte disorders, in particular in hypervolaemic and euvolaemic hyponatraemia.

The compounds according to the invention are also suitable for the prophylaxis and/or treatment of polycystic kidney disease (PCKD) and syndrome of inappropriate ADH secretion (SIADH).

In addition, the compounds according to the invention can be used for the prophylaxis and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prophylaxis and/or treatment of central nervous disorders such as anxiety states and depression, of glaucoma and of cancer, in particular of pulmonary tumours.

Furthermore, the compounds according to the invention can be used for the prophylaxis and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example phaeochromocytoma and adrenal apoplexy, diseases of the intestine such as for example Crohn's disease and diarrhoea, or of menstrual disorders such as for example dysmenorrhoea, or endometriosis.

A further object of the present invention is the use of the compounds according to the invention for the treatment and/or prophylaxis of diseases, in particular of the diseases mentioned above.

A further object of the present invention are the compounds according to the invention for use in a method for the treatment and/or prophylaxis of acute and chronic cardiac insufficiency, hypervolaemic and envolaemic hyponatraemia, liver cirrhosis, ascites, oedemas, and the syndrome of inadequate ADH secretion (SIADH).

A further object of the present invention is the use of the compounds according to the invention for the production of a medicament for the treatment and/or prophylaxis of diseases, in particular of the diseases mentioned above.

A further object of the present invention is a method for the treatment and/or prophylaxis of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prophylaxis of the diseases mentioned above. As combination active substances suitable for this, the following may for example and preferably be mentioned:

organic nitrates and NO donors, such as for example sodium nitroprusside, nitroglycerine, isosorbide mononitrate, isosorbide dinitrate, molsidomine or SIN-1, and inhalational NO;

diuretics, in particular loop diuretics and thiazides and thiazide-like diuretics;

positive-inotropically active compounds, such as for example cardiac glycosides (digoxin), and beta-adrenergic and dopaminergic agonists such as isoproterenol, adrenalin, noradrenalin, dopamine and dobutamine;

compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as aminone and milrinone;

natriuretic peptides such as for example "atrial natriuretic peptide" (ANP, anaritide), "B-type natriuretic peptide"

or "brain natriuretic peptide" (BNP, nesiritide), "C-type natriuretic peptide" (CNP) and urodilatin;

calcium sensitisers, such as for example and preferably levosimendan;

NO- and haem-independent activators of guanylate cyclase, such as in particular the compounds described in WO 01/19355, WO 01/19776, WO 01/19778, WO 01/19780, WO 02/070462 and WO 02/070510;

NO-independent, but haem-dependent stimulators of guanylate cyclase, such as in particular riociguat and the compounds described in WO 00/06568, WO 00/06569, WO 02/42301 and WO 03/095451;

inhibitors of human neutrophil elastase (HNE), such as for example sivelestat or DX-890 (reltran);

compounds inhibiting the signal transduction cascade, such as for example tyrosine kinase inhibitors, in particular sorafenib, imatinib, gefitinib and erlotinib;

compounds influencing the energy metabolism of the heart, such as for example and preferably etomoxir, dichloracetate, ranolazine or trimetazidine;

agents with antithrombotic action, for example and preferably from the group of the thrombocyte aggregation inhibitors, anticoagulants or profibrinolytic substances;

blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists and rho-kinase inhibitors; and/or active substances modifying fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric gallic acid adsorbers, gallic acid reabsorption inhibitors and lipoprotein (a) antagonists.

In a preferred embodiment of the invention, the compounds according to the invention are administered in combination with a diuretic, such as for example and preferably furosemid, bumetanid, torsemid, bendroflumethiazid, chlorthiazid, hydrochlorthiazid, hydroflumethiazid, methyclothiazid, polythiazid, trichlormethiazid, chlorthalidon, indapamid, metolazon, quinethazon, acetazolamid, dichlorophenamid, methazolamid, glycerine, isosorbide, mannitol, amilorid or triamteren.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamol.

In a preferred embodiment of the invention, the compounds according to the invention are administered in combination with a thrombin inhibitor, such as for example and preferably ximela-gatran, melagatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably riva-roxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists, rho-kinase inhibitors and diuretics.

In a preferred embodiment of the invention, the compounds according to the invention are administered in combination with a calcium antagonist, such as for example and preferably nife-dipin, amlodipin, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP).

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta receptor blocker, such as for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenon, canrenon or potassium canrenoate.

In a preferred embodiment of the invention, the compounds according to the invention are administered in combination with a rho-kinase inhibitor, such as for example and preferably fasu-dil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha, PPAR-gamma and/or PPAR-delta agonists, cholesterol absorption inhibitors, polymeric gallic acid adsorbers, gallic acid reabsorption inhibitors, lipase inhibitors and lipoprotein (a) antagonists.

In a preferred embodiment of the invention, the compounds according to the invention are administered in combination with a CETP inhibitor, such as for example and preferably dalcetrapib, BAY 60-5521, anacetrapib or CETP-vaccine (CETi-1).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasimibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pio-glitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric gallic acid adsorber, such as for example and preferably cholestyramine, colestipol, colesolvam, cholestagel or colestimid.

In a preferred embodiment of the invention, the compounds according to the invention are administered in combination with a gallic acid reabsorption inhibitor, such as for example and preferably ASBT(=IBAT) inhibitors such as for example AZD-7806, S-8921, AK-105, BARI-1741, SC-435 or SC-635.

In a preferred embodiment of the invention, the compounds according to the invention are administered in combination with a lipoprotein (a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable additives, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or aural routes or as an implant or stent.

For these administration routes, the compounds according to the invention can be administered in suitable administration forms.

For oral administration, administration forms which function according to the state of the art, releasing the compounds according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilisates, capsules (for example hard or soft gelatine capsules), dragees, granules, pellets, powders, emulsions, suspensions, aerosols or solutions are suitable.

Parenteral administration can be effected omitting an absorption step (e.g. intravenous, intra-arterial, intracardial, intraspinal or intralumbar administration) or involving absorption (e.g. intra-muscular, subcutaneous, intracutaneous, percutaneous or intraperitoneal administration). Suitable administration forms for parenteral administration include injection and infusion preparations in the form of solutions, suspensions, emulsions, lyophilisates or sterile powders.

For the other administration routes, for example inhalation formulations (including powder inhalers and nebulisers), nasal drops, solutions or sprays, tablets for lingual, sublingual or buccal administration, tablets, films/wafers or capsules, suppositories, oral or ophthalmic preparations, vaginal capsules, aqueous suspensions (lotions, shakable mixtures), lipophilic suspensions, ointments, creams, transdermal therapeutic systems (e.g. plasters), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable additives. These additives include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as for example ascorbic acid), colourants (e.g. inorganic pigments such as for example iron oxides) and flavour or odour correctors.

In general, to achieve effective results in parenteral administration it has been found advantageous to administer quantities of about 0.001 to 10 mg/kg, preferably about 0.01 to 1 mg/kg body weight. In oral administration, the dosage is about 0.01 bis 100 mg/kg, preferably about 0.01 to 20 mg/kg and quite especially preferably 0.1 to 10 mg/kg body weight.

Nonetheless it can sometimes be necessary to deviate from the said quantities, namely depending on body weight, administration route, individual response to the active substance, nature of the preparation and time or interval at which administration takes place. Thus in some cases it can be sufficient to manage with less than the aforesaid minimum quantity, while in other cases the stated upper limit must be exceeded. In the event of administration of larger quantities, it may be advisable to divide these into several individual administrations through the day.

The following practical examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

A. EXAMPLES

Abbreviations

BOC tert-butoxycarbonyl
CI chemical ionization (in MS)
DCI direct chemical ionization (in MS)
DME 1,2-dimethoxyethane
DMF dimethylformamide
DMSO dimethyl sulphoxide
EDC N'-(3-dimethylaminopropyl)-N-ethylcarbodiimide hydrochloride
eq. equivalent(s)
ESI electrospray ionization (in MS)
GC/MS gas chromatography-coupled mass spectrometry
sat. saturated
h hour(s)
HOBt 1-hydroxy-1H-benzotriazole hydrate
HPLC high pressure, high performance liquid chromatography
HV high vacuum
LC/MS liquid chromatography-coupled mass spectrometry
LDA lithium diisopropylamide
LiHMDS lithium hexamethyldisilazane min(s) minute(s)
MS mass spectrometry
MTBE methyl tert-butyl ether
NMR nuclear magnetic resonance spectrometry rac racemic/racemate
$R_f$ retention factor (in thin layer chromatography on silica gel)
RT room temperature
$R_t$ retention time (in HPLC)
THF tetrahydrofuran
TMOF trimethyl orthoformate
UV ultraviolet spectrometry
v/v volume to volume ratio (of a solution)
LC/MS, HPLC and GC/MS Methods:

Method 1: MS instrument type: Micromass ZQ; HPLC instrument type: Waters Alliance 2795; column: Phenomenex Synergi 2.5μ MAX-RP 100A Mercury 20 mm×4 mm; eluent A: 1 l water+0.5 ml 50% formic acid, eluent B: 1 l acetonitrile+0.5 ml 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 2: MS instrument type: Waters (Micromass) Quattro Micro; HPLC instrument type: Agilent 1100 series; column: Thermo Hypersil GOLD 3μ 20×4 mm; eluent A: 1 l water+0.5 ml 50% formic acid; eluent B: 1 l acetonitrile+0.5 ml 50% formic acid; gradient: 0.0 min 100% A→3.0 min 10% A→4.0 min 10% A→4.01 min 100% A (flow 2.5 ml)→5.00 min 100% A; oven: 50° C.; flow rate: 2 ml/min; UV detection: 210 nm.

Method 3: Instrument: Micromass Quattro Premier with Waters HPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 90% A→0.1 min 90% A→15 min 10% A→2.2 min 10% A; oven: 50° C.; flow rate: 0.33 ml/min; UV detection: 210 nm.

Method 4: Instrument: Waters ACQUITY SQD HPLC System; column: Waters Acquity HPLC HSS T3 1.8μ 50×1 mm; eluent A: 1 l water+0.25 ml 99% formic acid; eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 5: Instrument: Waters ACQUITY SQD HPLC System; column: Waters Acquity HPLC HSS T3 1.8μ 50×1 mm; eluent A: 1 l water+0.25 ml 99% formic acid; eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 6: MS instrument type: Micromass ZQ; HPLC instrument type: HP 1100 Series; UV DAD; column: Phenomenex Gemini 3μ 30 mm×3.00 mm; eluent A: 1 l water+0.5 ml 50% formic acid; eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 7: MS instrument type: Waters ZQ; HPLC instrument type: Agilent 1100 Series; UV DAD; column: Thermo Hypersil GOLD 3μ 20 mm×4 mm; eluent A: 1 l water+0.5 ml 50% formic acid; eluent B: 1 l acetonitrile+0.5 ml 50% formic acid; gradient: 0.0 min 100% A→3.0 min 10% A→4.0 min 10% A→4.1 min 100% flow rate: 2.5 ml/min; oven: 55° C.; flow rate 2 ml/min; UV detection: 210 nm.

Method 8 (chiral preparative HPLC): Chiral stationary silica gel phase based on the selector poly-(N-methacryloyl-D-leucine-dicyclopropylmethylamide); column: 670 mm×40 mm, flow rate: 80 ml/min, temperature: 24° C.; UV detector 260 nm. Eluent: isohexane/ethyl acetate 30:70.

Method 8a: Eluent: isohexane/ethyl acetate 10:90 (v/v); flow rate: 50 ml/min

Method 9 (chiral analytical HPLC): Chiral stationary silica gel phase based on the selector poly(N-methacryloyl-D-leucine-dicyclopropylmethylamide); column: 250 mm×4.6 mm, eluent ethyl acetate 100%, flow rate: 1 ml/min, temperature: 24° C.; UV detector 265 nm.

Method 10 (preparative HPLC): column: Grom-Sil 1200DS-4HE, 10 μm, SNo. 3331, 250 mm×30 mm Eluent A: formic acid 0.1% in water, eluent B: acetonitrile; flow rate: 50 ml/min programme: 0-3 min: 10% B; 3-27 min: gradient to 95% B; 27-34 min: 95% B; 34.01-38 min: 10% B.

Method 11 (chiral preparative HPLC): Stationary phase Daicel Chiralcel OD-H, 5 μm, column: 250 mm×20 mm; temperature: RT; UV detection: 230 nm. Various eluents:

Method 11a: Eluent: isohexane/isopropanol 70:30 (v/v); flow rate: 20 ml/min

Method 11b: Eluent: isohexane/isopropanol 50:50 (v/v); flow rate: 18 ml/min

Method 11c: Eluent: isohexane/methanol/ethanol 70:15:15; (v/v/v); flow rate 20 ml/min Method 11d: Eluent: isohexane/isopropanol 75:25 (v/v); flow rate 15 ml/min Method 12 (chiral analytical HPLC): Stationary phase Daicel Chiralcel OD-H, column: 250 mm×4 mm; flow rate: 1 ml/min; temperature: RT; UV detection: 230 nm. Various eluents:

Method 12a: Eluent: isohexane/isopropanol 1:1 (v/v);

Method 12b: Eluent: isohexane/methanol/ethanol 70:15:15 (v/v/v)

Method 12c: Eluent: isohexane/isopropanol 75:25 (v/v);

Method 13 (chiral preparative HPLC): Chiral stationary silica gel phase based on the selector poly-(N-methacryloyl-D-leucine-dicyclopropylmethylamide); column: 600 mm×30 mm, eluent: step gradient ethyl acetate/methanol 1:1 (0-17 min) ethyl acetate (17.01 min to 21 min) ethyl acetate/methanol 1:1 (21.01 min to 25 min); flow rate: 80 ml/min, temperature: 24° C.; UV detector 265 nm.

Method 13a: as Method 13, but eluent: 0-5.08 min isohexane/ethyl acetate 10:90, then ethyl acetate 100%

Method 13b: Eluent: 100% ethyl acetate

Method 14 (chiral analytical HPLC): as Method 9 but flow rate 2 ml/min.

Method 15 (chiral preparative HPLC): Chiral stationary silica gel phase based on the selector poly(N-methacryloyl-L-isoleucine-3-pentylamide); column: 430 mm×40 mm, flow rate: 80 ml/min, temperature: 24° C.; UV detector 265 nm. Various eluents:

Method 15a: 100% ethyl acetate

Method 15b: isohexane/ethyl acetate 10:90

Method 16 (chiral analytical HPLC): Chiral stationary silica gel phase based on the selector poly(N-methacryloyl-L-isoleucine-3-pentylamide); column: 250 mm×4.6 mm, eluent 100% ethyl acetate, flow rate: 2 ml/min, temperature: 24° C.; UV detector 265 nm.

Method 17 (chiral preparative HPLC): Chiral stationary silica gel phase based on the selector poly(N-methacryloyl-L-leucine-(+)-3-pinanemethylamide); column: 600 mm×30 mm, flow rate: 80 ml/min, temperature: 24° C.; UV detector 265 nm. Various eluents:

Method 17a: isohexane/ethyl acetate 20:80

Method 17b: isohexane/ethyl acetate 30:70

Method 17c: isohexane/ethyl acetate 50:50

Method 17d: 100% ethyl acetate

Method 17e: isohexane/ethyl acetate 40:60

Method 17f: isohexane/ethyl acetate 10:90

Method 18 (chiral analytical HPLC): Chiral stationary silica gel phase based on the selector poly(N-methacryloyl-L-leucine-(+)-3-pinanemethylamide); column: 250 mm×4.6 mm, temperature: 24° C.; UV detector 265 nm.

Method 18a: Eluent: isohexane/ethyl acetate 50:50, flow rate: 2 ml/min.

Method 18b: Eluent: 100% ethyl acetate, flow rate: 2 ml/min.

Method 18c: Eluent: 100% ethyl acetate, flow rate: 1 ml/min.

Method 19 (preparative HPLC): column Grom-Sil 1200DS-4HE 10 μm, 250 mm×30 mm; eluent: A=water, B=acetonitrile; gradient: 0.0 min 10% B, 3 min 10% B, 30 min 95% B, 42 min 95% B, 42.01 min 10% B, 45 min 10% B; flow rate: 50 ml/min; column temperature: RT; UV detection: 210 nm.

Method 20 (preparative HPLC): column: Reprosil C18, 10 μm, 250 mm×30 mm Eluent A: formic acid 0.1% in water, eluent B: methanol; flow rate: 50 ml/min Programme: 0 to 4.25 min: 90% A/10% B; 4.26-4.5 min: Gradient to 60% B; 4.5-11.5 min: gradient to 80% B; 11.51-17 min gradient to 100% B; 17.01 to 19.5 min 100% B; 19.51-19.75 gradient to 40% B; 19.76 to 20.51 min: 60% A/40% B.

Method 21 chiral preparative HPLC): Stationary phase Daicel Chiralpak AS-H, 5 μm, column: 250 mm×20 mm; temperature: RT; UV detection: 230 nm; flow rate: 20 ml/min; various eluents:

Method 21a: Eluent: isohexane/isopropanol 65:35

Method 21b: Eluent: isohexane/isopropanol 50:50; flow rate 20 ml/min

Method 22 (chiral analytical HPLC): Stationary phase Daicel Chiralpak AD-H 5 μm, column: 250 mm×4 mm; UV detection: 220 nm. Flow rate: 1 ml/min. Eluent: isohexane/isopropanol 50:50.

Method 23 (preparative HPLC): column: YMC ODS C18, 10 μm, 250 mm×30 mm Eluent A: formic acid 0.1% in water, eluent B: methanol; flow rate: 50 ml/min. Programme: 0 to 4.25 min: 90% A/10% B; 4.26-4.5 min: gradient to 60% B; 4.5-11.5 min: gradient to 80% B; 11.51-17 min gradient to 100% B; 17.01 to 19.5 min 100% B; 19.51-19.75 gradient to 40% B; 19.76 to 20.51 min: 60% A/40% B.

Method 24 (chiral preparative HPLC): Chiral stationary phase based on the selector poly(N-methacryloyl-L-leucine-tert-butylamide) on irregular (fractionated) vinyl silica gel column: 250 mm×20 mm, flow rate: 45 ml/min, temperature: RT; UV detector 260 nm. Various eluents:

Method 24a: isohexane/ethyl acetate 10:90

Method 24b: isohexane/ethyl acetate 20:80

Method 25 (chiral analytical HPLC): Chiral stationary phase based on the selector poly(N-methacryloyl-L-leucine-tert-butylamide) on irregular (fractionated) vinyl silica gel column: 250 mm×4 mm, flow rate: 1.5 ml/min, temperature: RT; UV detector 260 nm. Various eluents:

Method 25a: isohexane/ethyl acetate 20:80

Method 25b: isohexane/ethyl acetate 30:70

Method 26 (chiral preparative HPLC): Stationary phase Daicel Chiralpak AD-H, 5 μm, column: 250 mm×20 mm; temperature: RT; UV detection: 230 nm; flow rate: 20 ml/min; various eluents.

Method 26a: isohexane/isopropanol 65:35 (v/v)

Method 26b: isohexane/isopropanol 80:20 (v/v)

Method 26c: isohexane/isopropanol 50:50 (v/v)

Method 26d: isohexane/ethanol 65:35 (v/v)

Method 26e: isohexane/ethanol 50:50 (v/v)

Method 27 (chiral analytical HPLC): Stationary phase Daicel Chiralpak AD-H, 5 μm, column: 250 mm×4 mm; temperature: 30° C.; UV detection: 230 nm; flow rate: 1 ml/min; various eluents.

Method 27a: isohexane/isopropanol 50:50 (v/v)

Method 27b: isohexane/isopropanol 60:40 (v/v)

Method 27c: isohexane/isopropanol/20% trifluoroacetic acid 75:24:1 (v/v/v)

Method 27d: isohexane/ethanol 50:50 (v/v)

Method 28 chiral preparative HPLC): Chiral stationary silica gel phase based on the selector poly(N-methacryloyl-L-leucine-(+)-3-pinanemethylamide); column: 600 mm×40 mm; temperature: RT; UV detector 265 nm; eluent: isohexane/isopropanol 80:20 (v/v); flow rate: 50 ml/min.

Method 29 (chiral preparative HPLC): Chiral stationary phase based on the selector poly(N-methacryloyl-D-valine-3-pentylamide) on spherical mercapto silica gel; column: 250 mm×20 mm; temperature: RT; UV detector 260 nm; eluent: isohexane/isopropanol 60:40 (v/v); flow rate: 20 ml/min.

Method 30 (chiral preparative HPLC): Chiral stationary phase based on the selector poly(N-methacryloyl-D-valine-3-pentylamide) on spherical mercapto silica gel; column: 250 mm×4 mm; temperature: RT; UV detector 260 nm; eluent: isohexane/isopropanol 60:40 (v/v); flow rate: 1.5 ml/min.

Method 31 (LC-MS): MS instrument type: Waters ZQ; HPLC instrument type: Agilent 1100 Series; UV DAD; column: Thermo Hypersil GOLD 3μ 20 mm×4 mm; eluent A: 1 l water+0.5 ml 50% formic acid; eluent B: 1 l acetonitrile+0.5 ml 50% formic acid; gradient: 0.0 min 100% A→3.0 min 10% A→4.0 min 10% A→4.1 min 100% flow rate: 2.5 ml/min; oven: 55° C.; flow rate 2 ml/min; UV detection: 210 nm.

Method 32 (preparative HPLC): column: Reprosil C18, 10 μm, 250 mm×40 mm Eluent A: formic acid 0.1% in water, eluent B: acetonitrile; flow rate: 50 ml/min Programme: 0-6 min: 90% A/10% B; 6-40 min: Gradient to 95% B; 40-53 min: 5% A/95% B; 53.01-54 min: gradient to 10% B; 54.01-57 min: 90% A/10% B.

Method 33 (chiral preparative HPLC): Chiral stationary phase based on the selector poly(N-methacryloyl-D-leucine-dicyclopropylmethylamide) on spherical vinyl silica gel; column: 670 mm×40 mm, flow rate: 80 ml/min, temperature: 24° C.; UV detector 265 nm. Eluent: 0 to 7.75 min: 100% ethyl acetate; 7.76 min to 12.00 min: 100% methanol; 12.01 min to 16.9 min: 100% ethyl acetate.

Method 34: chiral analytical HPLC under SFC (Supercritical Fluid Chromatography) conditions: chiral stationary phase based on the selector poly(N-methacryloyl-D-leucine-dicyclopropylmethylamide) on spherical vinyl silica gel; column: 250 mm×4.6 mm, temperature: 35° C., eluent: $CO_2$/methanol 67:33. Pressure: 120 bar, flow rate: 4 ml/min, UV detector 250 nm.

Starting Compounds and Intermediates

Example 1A

Ethyl N-({2-[(4-chlorophenyl)carbonyl]hydrazinyl}carbonyl)glycinate

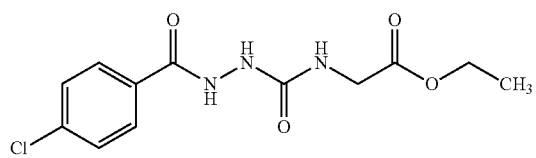 [SMILES: CCOC(=O)CNC(=O)NNC(=O)c1ccc(Cl)cc1]

A suspension of 12.95 g (75.9 mmol) of 4-chlorobenzhydrazide in 50 ml of dry THF was introduced at 50° C. and admixed dropwise with a solution of 10.0 g (77.5 mmol) of ethyl 2-isocyanatoacetate in 100 ml of dry THF. First of all a solution formed, and then a precipitate was produced. After the end of the addition, the mixture was stirred at 50° C. for 2 h more, then left to stand overnight at RT. The crystals were isolated by filtration, washed with a little diethyl ether and dried in an HV. This gave 21.43 g (89% of theory) of the title compound.

LC/MS [Method 1]: $R_t$=1.13 min; m/z=300 (M+H)$^+$ $^1$H NMR (DMSO-$d_6$, 400 MHz): δ=10.29 (s, 1H), 8.21 (s, 1H), 7.91 (d, 2H), 7.57 (d, 2H), 6.88 (br.s, 1H), 4.09 (q, 2H), 3.77 (d, 2H), 1.19 (t, 3H)

Example 2A

[3-(4-Chlorophenyl)-5-oxo-1,5-dihydro-4H-1,2,4-triazol-4-yl]acetic acid

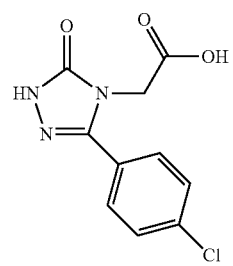 [SMILES: O=C(O)Cn1c(-c2ccc(Cl)cc2)n[nH]c1=O]

Of the compound from Example 1A, 21.43 g (67.93 mmol) were admixed with 91 ml of a 3N aqueous sodium hydroxide solution and heated at reflux overnight. After cooling to RT, the mixture was adjusted to a pH of 1 by slow addition of approximately 20% strength hydrochloric acid. The precipitated solid was isolated by filtration, washed with water and dried at 60° C. under reduced pressure. Yield: 17.55 g (90% of theory, approximately 88% purity).

LC/MS [Method 1]: $R_t$=0.94 min; m/z=254 (M+H)$^+$ $^1$H NMR (DMSO-$d_6$, 400 MHz): δ=13.25 (br.s, 1H), 12.09 (s, 1H), 7.65-7.56 (m, 4H), 4.45 (s, 2H).

Example 3A 5-(4-Chlorophenyl)-4-(3,3,3-trifluoro-2-oxopropyl)-2,4-dihydro-3H-1,2,4-triazol-3-one (or, in hydrate form: 5-(4-chlorophenyl)-4-(3,3,3-trifluoro-2,2-dihydroxypropyl)-2,4-dihydro-3H-1,2,4-triazol-3-one)

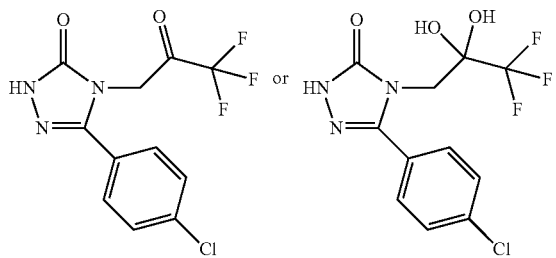 [SMILES: O=C(Cn1c(-c2ccc(Cl)cc2)n[nH]c1=O)C(F)(F)F ; "or" ; O=c1[nH]nc(-c2ccc(Cl)cc2)n1CC(O)(O)C(F)(F)F]

Of the compound from Example 2A, 5 g (16.36 mmol) were dissolved under argon in 200 ml of pyridine and then admixed with 17.18 g (81.8 mmol) of trifluoroacetic anhydride. The temperature rose to about 35° C. After 30 min, the pyridine was removed on a rotary evaporator and the residue was diluted with 1.5 l of 0.5N hydrochloric acid. This mixture was heated to 70° C. and then filtered while hot. The solid was washed with a little water. The entire filtrate was extracted three times with ethyl acetate. The combined organic phases were washed with water, then with a saturated aqueous sodium hydrogen carbonate solution, then with a saturated aqueous sodium chloride solution, dried over sodium sulphate and freed from the solvent on a rotary evaporator. The residue was dried under HV. Yield: 3.56 g (68% of theory) of the title compound in hydrate form.

LC/MS [Method 1]: $R_t$=1.51 min; m/z=306 (M+H)$^+$ and 324 (M+H)$^+$(ketone and hydrate)

$^1$H NMR (DMSO-d$_6$, 400 MHz): δ=12.44 (s, 1H), 7.72 (d, 2H), 7.68 (br.s, 2H), 7.61 (d, 2H), 3.98 (s, 2H).

Example 4A 5-(4-Chlorophenyl)-4-(3,3,3-trifluoro-2-hydroxypropyl)-2,4-dihydro-3H-1,2,4-triazol-3-one

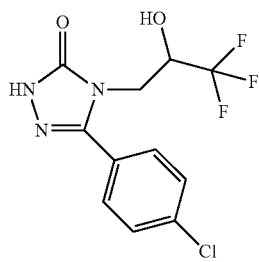 [SMILES: O=c1[nH]nc(-c2ccc(Cl)cc2)n1CC(O)C(F)(F)F]

Of the compound from Example 3A, 3.56 g (11 mmol) were dissolved in 100 ml of methanol and admixed, with ice cooling, with 3.75 g (99 mmol) of sodium borohydride (gas evolution). After 1.5 h, 200 ml of 1M hydrochloric acid were slowly added. The methanol was removed on a rotary evaporator and the residue was diluted with 500 ml of water and extracted three times with ethyl acetate. The combined organic phases were washed with saturated aqueous sodium hydrogen carbonate solution, then with saturated aqueous sodium chloride solution, dried over sodium sulphate and freed from the solvent on a rotary evaporator. The residue was dried under an HV. This gave 3.04 g (90% of theory) of the title compound.

LC/MS [Method 2]: R$_t$=1.80 min; m/z=308 (M+H)$^+$.

$^1$H NMR (DMSO-d$_6$, 400 MHz): δ=12.11 (s, 1H), 7.75 (d, 2H), 7.62 (d, 2H), 6.85 (d, 1H), 4.34-4.23 (m, 1H), 3.92 (dd, 1H), 3.77 (dd, 1H).

Example 5A

Methyl [3-(4-chlorophenyl)-5-oxo-4-(3,3,3-trifluoro-2-hydroxypropyl)-4,5-dihydro-1H-1,2,4-triazol-1-yl]acetate

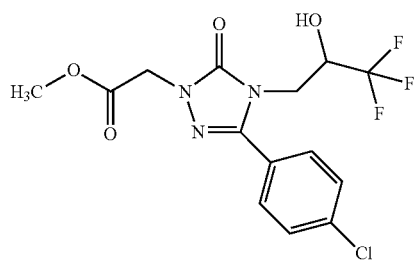 [SMILES: COC(=O)Cn1nc(-c2ccc(Cl)cc2)n(CC(O)C(F)(F)F)c1=O]

Of the compound from Example 4A, 3.04 g (9.9 mmol) were dissolved in 100 ml of acetonitrile and admixed with 1.07 g (9.9 mmol) of methyl chloroacetate, 2.73 g (19.8 mmol) of potassium carbonate and a small spatula-tipful of potassium iodide. The reaction mixture was heated at reflux for 1 h, left to cool to RT and filtered. The filtrate was freed from the volatile components on a rotary evaporator and the residue was dried in an HV. Yield: 3.70 g (89% of theory) of the title compound in approximately 90% purity.

LC/MS [Method 3]: R$_t$=1.10 min; m/z=380 (M+H)$^+$.

$^1$H NMR (DMSO-d$_6$, 400 MHz): δ=7.78 (d, 2H), 7.64 (d, 2H), 6.91 (d, 1H), 4.72 (s, 2H), 4.16-4.35 (m, 1H), 3.99 (dd, 1H), 3.84 (dd, 1H), 3.70 (s, 3H).

The racemic compound from Example 5A was resolved by preparative HPLC on a chiral phase into its enantiomers Example 6A and Example 7A, as already described in WO 2007/134862.

Column: chiral silica gel phase based on the selector poly (N-methacryloyl-L-isoleucine-3-pentylamide), 430 mm×40 mm; eluent: step gradient isohexane/ethyl acetate 1:1→ethyl acetate→isohexane/ethyl acetate 1:1; flow rate: 50 ml/min; temperature: 24° C.; UV detection: 260 nm.

This gives, from 3.6 g of racemic compound from Example 5A (dissolved in 27 ml of ethyl acetate and 27 ml of isohexane and separated into three portions by the column), 1.6 g of the enantiomer 1 which elutes first (Example 6A), and 1.6 g of the enantiomer 2 which elutes subsequently (Example 7A).

Example 6A

Methyl {3-(4-chlorophenyl)-5-oxo-4-[(2S)-3,3,3-trifluoro-2-hydroxypropyl]-4,5-dihydro-1H-1,2,4-triazol-1-yl}acetate (Enantiomer I)

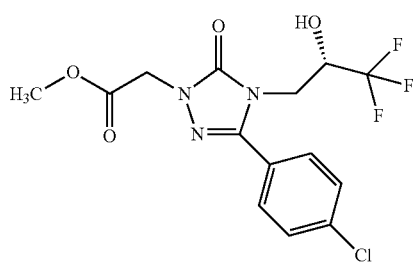 [SMILES: COC(=O)Cn1nc(-c2ccc(Cl)cc2)n(C[C@H](O)C(F)(F)F)c1=O]

First-eluting enantiomer from the racemate resolution of Example 5A.

R$_t$=3.21 min [column: chiral silica gel phase based on the selector poly(N-methacryloyl-L-isoleucine-3-pentylamide), 250 mm×4.6 mm; eluent: isohexane/ethyl acetate 1:1; flow rate: 1 ml/min; UV detection: 260 nm].

Example 7A

Methyl {3-(4-chlorophenyl)-5-oxo-4-[(2R)-3,3,3-trifluoro-2-hydroxypropyl]-4,5-dihydro-1H-1,2,4-triazol-1-yl}acetate (Enantiomer II)

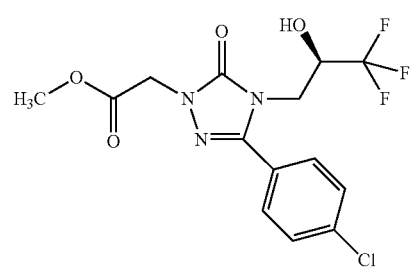 [SMILES: COC(=O)Cn1nc(-c2ccc(Cl)cc2)n(C[C@@H](O)C(F)(F)F)c1=O]

Last-eluting enantiomer from the racemate resolution of Example 5A.

R$_t$=4.48 min [column: chiral silica gel phase based on the selector poly(N-methacryloyl-L-isoleucine-3-pentylamide), 250 mm×4.6 mm; eluent: isohexane/ethyl acetate 1:1; flow rate: 1 ml/min; UV detection: 260 nm].

Example 8A

{3-(4-Chlorophenyl)-5-oxo-4-[(2S)-3,3,3-trifluoro-2-hydroxypropyl]-4,5-dihydro-1H-1,2,4-triazol-1-yl}acetic acid

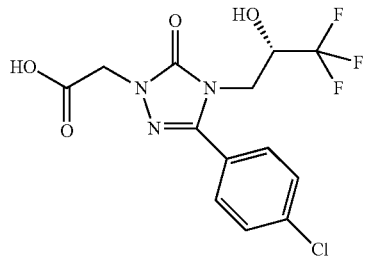 [SMILES: O=C(O)Cn1nc(-c2ccc(Cl)cc2)n(C[C@H](O)C(F)(F)F)c1=O]

The enantiomerically pure ester from Example 6A (1.6 g, 4.21 mmol) was dissolved in 77 ml of methanol and admixed with 17 ml of a 1M solution of lithium hydroxide in water. The mixture was stirred at RT for 1 h and then concentrated on a rotary evaporator. The residue was diluted with 100 ml of water and acidified to a pH of 1-2 using 1N hydrochloric acid. The precipitated product was isolated by filtration, washed in succession with water and cyclohexane and sucked dry. After further drying in an HV, the title compound (1.1 g, 71% of theory) was obtained.

[α]$_D^{20}$=+3.4° (methanol, c=0.37 g/100 ml)
LC/MS [Method 1]: R$_t$=1.51 min; m/z=366 (M+H)$^+$
$^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 9A

{3-(4-Chlorophenyl)-5-oxo-4-[(2R)-3,3,3-trifluoro-2-hydroxypropyl]-4,5-dihydro-1H-1,2,4-triazol-1-yl}acetic acid

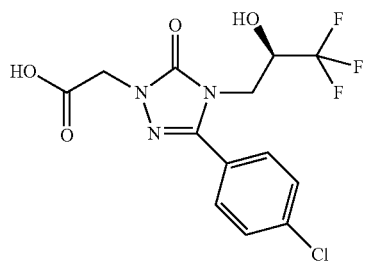 [SMILES: O=C(O)Cn1nc(-c2ccc(Cl)cc2)n(C[C@@H](O)C(F)(F)F)c1=O]

In the same way as for Example 8A, the title compound was obtained from Example 7A.
[α]$_D^{20}$=−4.6° (methanol, c=0.44 g/100 ml)
LC/MS [Method 1]: R$_t$=1.53 min; m/z=366 (M+H)$^+$
$^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 10A tert-Butyl {(phenylsulphonyl)[3-(trifluoromethyl)phenyl]methyl}carbamate

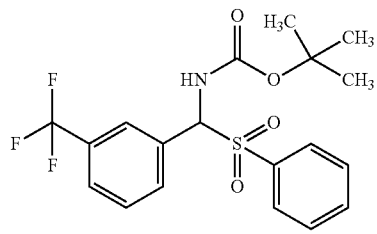 [SMILES: CC(C)(C)OC(=O)NC(c1cccc(C(F)(F)F)c1)S(=O)(=O)c1ccccc1]

A quantity of 4.49 g (38.29 mmol) of tert-butyl carbamate and 12.57 g (76.57 mmol) of sodium benzenesulphinate were introduced in 110 ml of methanol/water 1:2 and admixed in succession with 10 g (57.43 mmol) of 3-(trifluoromethyl)benzenecarbaldehyde and 2.87 ml (76.09 mmol) of formic acid. The mixture was stirred at RT for 30 h. The precipitated product was isolated by filtration, washed in succession with water and diethyl ether and sucked dry. Further drying in an HV gave 11.2 g (47% of theory) of the title compound.

$^1$H-NMR (400 MHz, DMSO-d$_6$): δ=8.86 (d, 1H), 8.14 (s, 1H), 7.99 (d, 1H), 7.88 (d, 2H), 7.80 (d, 1H), 7.71-7.77 (m, 1H), 7.59-7.70 (m, 3H), 6.25 (d, 1H), 1.18 (s, 9H).

Example 11A tert-Butyl {(E)-[3-(trifluoromethyl)phenyl]methylidene}carbamate

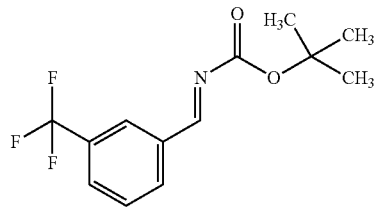 [SMILES: CC(C)(C)OC(=O)/N=C/c1cccc(C(F)(F)F)c1]

A quantity of 10.88 g (78.73 mmol) of potassium carbonate was dried hot in an HV, left to cool under argon to RT and admixed with 127 ml of THF and also with 5.45 g (13.12 mmol) of the sulphonyl compound from Example 10A. The mixture was stirred at reflux for 16 h under argon. The mixture was cooled to RT and then filtered through Celite. The latter was rinsed with THF. The entire filtrate was freed from the volatile components on a rotary evaporator and then in an HV, to give 3.63 g (100% of theory) of the title compound.

MS [DCI]: m/z=274 (M+H)$^+$
$^1$H-NMR (400 MHz, DMSO-d$_6$): δ=8.95 (s, 1H), 8.26 (s, 1H), 8.23 (d, 1H), 8.01 (d, 1H), 7.80 (t, 1H), 1.52 (s, 9H).

Example 12A tert-Butyl {2-nitro-1-[3-(trifluoromethyl)phenyl]ethyl}carbamate

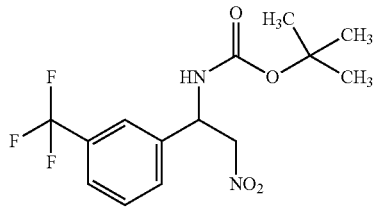 [SMILES: CC(C)(C)OC(=O)NC(C[N+](=O)[O-])c1cccc(C(F)(F)F)c1]

Of the compound from Example 11A, 3.6 g (13.17 mmol) were introduced in 26 ml of nitromethane and admixed with 0.69 ml (3.95 mmol) of N,N-diisopropylethylamine. The mixture was stirred at RT for 2 h. The reaction mixture was diluted with ethyl acetate and washed in succession twice each with 1N hydrochloric acid and saturated aqueous sodium hydrogen carbonate solution, and then with saturated aqueous sodium chloride solution, dried over sodium sulphate and concentrated on a rotary evaporator. The residue (about 5 g) was dissolved in 15 ml of isopropanol at reflux. After cooling, the precipitated product was isolated by filtration, washed with a little isopropanol and sucked dry. After further drying in an HV, the title compound was obtained: 2.26 g (51% of theory).

LC/MS [Method 3]: $R_t$=1.33 min; ES⁻: m/z=333 (M−H)⁻

¹H-NMR (400 MHz, DMSO-d₆): δ=7.88 (d, 1H), 7.78 (s, 1H), 7.70 (t, 2H), 7.59-7.65 (m, 1H), 5.31-5.44 (m, 1H), 4.97 (dd, 1H), 4.72-4.82 (m, 1H), 1.36 (s, 9H).

Example 13A

2-Nitro-1-[3-(trifluoromethyl)phenyl]ethanamine hydrochloride

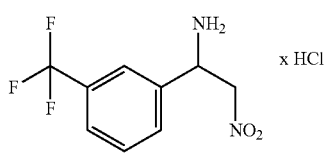 [SMILES: NC(C[N+](=O)[O-])c1cccc(C(F)(F)F)c1]

Of the compound from Example 12A, 340 mg (1.02 mmol) were admixed at RT with 6.8 ml of a 4N solution of hydrogen chloride in dioxane, and stirred for 1 h. The reaction mixture was concentrated under reduced pressure and dried in an HV. This gave 274 mg (99% of theory) of the title compound.

LC/MS [Method 4]: $R_t$=0.54 min; m/z=235 (M+H)⁺

¹H-NMR (400 MHz, DMSO-d₆): δ=8.98 (br.s, 3H), 8.05 (s, 1H), 7.92 (d, 1H), 7.83 (d, 1H), 7.72 (t, 1H), 5.17-5.36 (m, 3H).

Example 14A tert-Butyl {(phenylsulphonyl)[2-(trifluoromethyl)phenyl]methyl}carbamate

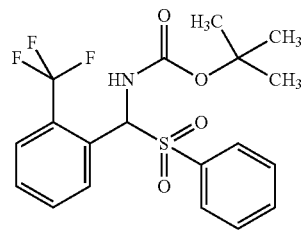 [SMILES: CC(C)(C)OC(=O)NC(c1ccccc1C(F)(F)F)S(=O)(=O)c1ccccc1]

In the same way as for Example 10A, the title compound (4.09 g, 34% of theory) was obtained from 5.00 g (28.7 mmol) of 2-(trifluoromethyl)benzenecarbaldehyde.

¹H-NMR (400 MHz, DMSO-d₆): δ=8.88 (d, 1H), 8.20 (d, 1H), 7.79-7.88 (m, 5H), 7.68 (q, 3H), 6.32 (d, 1H), 1.19 (s, 9H).

Example 15A tert-Butyl {(E)-[2-(trifluoromethyl)phenyl]methylidene}carbamate

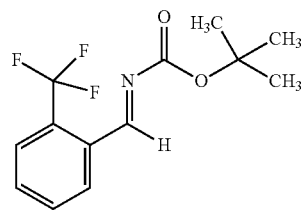 [SMILES: CC(C)(C)OC(=O)/N=C/c1ccccc1C(F)(F)F]

In the same way as for Example 11A, the title compound —2.61 g (97% of theory)—was obtained from 4.09 g (9.85 mmol) of the compound from Example 14A.

MS [DCI]: m/z=274 (M+H)⁺

¹H-NMR (400 MHz, DMSO-d₆): δ=9.02 (br.s, 1H), 8.25 (br.s, 1H), 7.90-7.97 (m, 1H), 7.85 (dd, 2H), 1.52 (s, 9H).

Example 16A tert-Butyl {2-nitro-1-[2-(trifluoromethyl)phenyl]ethyl}carbamate

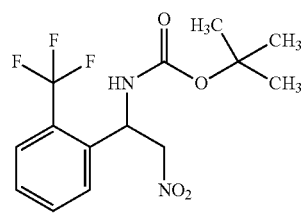

In the same way as for Example 12A, the title compound —1.54 g (84% of theory)—was obtained from 1.50 g (5.49 mmol) of the compound from Example 15A.

LC/MS [Method 5]: $R_t$=1.13 min; ES$^-$: m/z=333 (M−H)$^-$ $^1$H-NMR (400 MHz, DMSO-d$_6$): δ=8.04 (d, 1H), 7.80 (d, 1H), 7.70-7.77 (m, 2H), 7.55 (t, 1H), 5.72 (t, 1H), 4.77 (dd, 1H), 4.62-4.71 (m, 1H), 1.33 (s, 9H).

Example 17A

2-Nitro-1-[2-(trifluoromethyl)phenyl]ethanamine hydrochloride

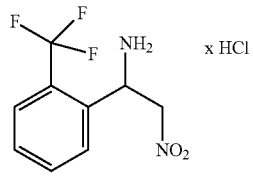 [SMILES: NC(C[N+](=O)[O-])c1ccccc1C(F)(F)F]

In the same way as for Example 13A, from 770 mg (2.30 mmol) of the compound from Example 16A, the title compound was obtained: 656 mg (quant., slightly contaminated).

LC/MS [Method 2]: $R_t$=0.99 min; m/z=235 (M+H)$^+$ $^1$H-NMR (400 MHz, DMSO-d$_6$): δ=9.22 (br.s, 3H), 8.11 (d, 1H), 7.83-7.91 (m, 2H), 7.70 (t, 1H), 5.32-5.41 (m, 1H), 5.14-5.21 (m, 2H).

Example 18A tert-Butyl [(2,3-dichlorophenyl)(phenylsulphonyl)methyl]carbamate

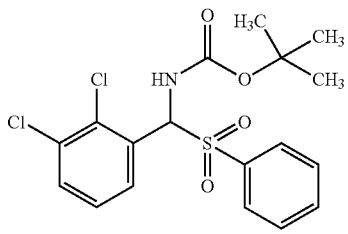 [SMILES: CC(C)(C)OC(=O)NC(c1cccc(Cl)c1Cl)S(=O)(=O)c1ccccc1]

In the same way as for Example 10A, from 5.00 g (28.6 mmol) of 2,3-dichlorobenzenecarbaldehyde, the title compound was obtained: 2.22 g (19% of theory)

$^1$H-NMR (400 MHz, DMSO-d$_6$): δ=8.93 (d, 1H), 7.96 (d, 1H), 7.84 (d, 2H), 7.76 (d, 2H), 7.63-7.71 (m, 2H), 7.51 (t, 1H), 6.60 (d, 1H), 1.21 (s, 9H).

Example 19A tert-Butyl [(E)-(2,3-dichlorophenyl)methylidene]carbamate

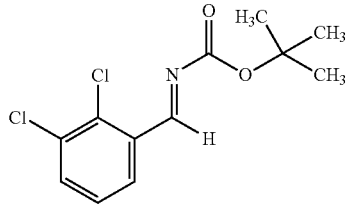 [SMILES: CC(C)(C)OC(=O)/N=C/c1cccc(Cl)c1Cl]

In the same way as for Example 11A, from 2.22 g (5.33 mmol) of the compound from Example 18A, the title compound was obtained: 1.38 g (94% of theory).

MS [DCI]: m/z=274 (M+H)$^+$ $^1$H-NMR (400 MHz, DMSO-d$_6$): δ=9.11 (s, 1H), 8.01 (d, 1H), 7.92 (d, 1H), 7.52 (t, 1H), 1.52 (s, 9H).

Example 20A tert-Butyl {2-nitro-1-[2-(trifluoromethyl)phenyl]ethyl}carbamate

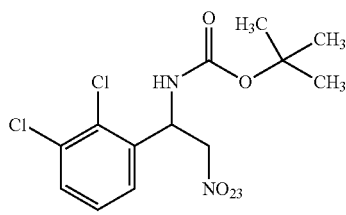

In the same way as for Example 12A, from 1.38 g (5.03 mmol) of the compound from Example 19A, the title compound was obtained: 865 mg (51% of theory).

LC/MS [Method 5]: $R_t$=1.17 min; m/z=333 (M−H)$^-$ $^1$H-NMR (400 MHz, DMSO-d$_6$): δ=8.07 (d, 1H), 7.64 (d, 1H), 7.50 (d, 1H), 7.44 (t, 1H), 5.74 (t, 1H), 4.87 (d, 1H), 4.62 (t, 1H), 1.34 (s, 9H).

Example 21A 1-(2,3-Dichlorophenyl)-2-nitroethanamine hydrochloride

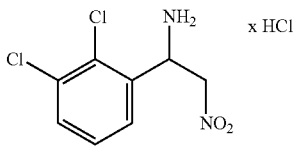 [SMILES: NC(C[N+](=O)[O-])c1cccc(Cl)c1Cl]

In the same way as for Example 13A, from 430 mg (1.28 mmol) of the compound from Example 20A, the title compound was obtained: 363 mg (quant., 90% purity).

LC/MS [Method 6]: $R_t$=0.54/0.61 min; m/z=234 (M+H)$^+$ $^1$H-NMR (400 MHz, DMSO-d$_6$): δ=9.03 (br.s, 3H), 7.81 (d, 1H), 7.78 (dd, 1H), 7.54 (t, 1H), 5.45 (dd, 1H), 5.22-5.28 (m, 2H).

Example 22A tert-Butyl {2-amino-1-[3-(trifluoromethyl)phenyl]ethyl}carbamate

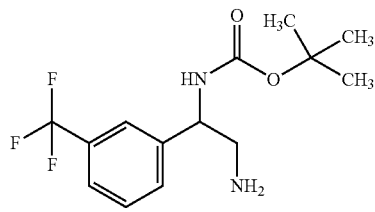 [SMILES: CC(C)(C)OC(=O)NC(CN)c1cccc(C(F)(F)F)c1]

Of the compound from Example 12A, 248 mg (1.04 mmol) were introduced in methanol and admixed with 20 mg of palladium (10% on activated carbon). Hydrogenation took place under atmospheric pressure at RT overnight. The reaction mixture was filtered and the filtrate concentrated under reduced pressure. This gave 300 mg (88% of theory) of the title compound.

LC/MS [Method 5]: $R_t$=0.74 min; m/z=305 (M+H)$^+$ $^1$H-NMR (400 MHz, DMSO-d$_6$) (principal rotamer): δ=7.51-7.72 (m, 4H), 7.44 (d, 1H), 4.50 (d, 1H), 2.63-2.77 (m, 2H), 1.63 (br. s, 2H), 1.36 (s, 9H).

Example 23A tert-Butyl {2-(formylamino)-1-[3-(trifluoromethyl)phenyl]ethyl}carbamate

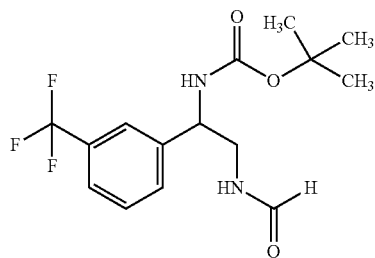 [SMILES: CC(C)(C)OC(=O)NC(CNC=O)c1cccc(C(F)(F)F)c1]

Of the compound from Example 22A, 75 mg (0.25 mmol) were introduced in 1.5 ml of THF and admixed at 0° C. in small portions with 43.25 mg (0.26 mmol) of 4-nitrophenyl formate. The mixture was stirred at 0° C. for 2 h and then at RT overnight. The solvent was removed on a rotary evaporator and the residue was taken up in DMSO and purified by preparative HPLC (method 10). This gave 66 mg (81% of theory) of the title compound.

LC/MS [Method 2]: $R_t$=2.01 min; m/z=333 (M+H)$^+$ $^1$H-NMR (400 MHz, DMSO-d$_6$): δ=8.08 (br.s, 1H), 7.97 (s, 1H), 7.51-7.66 (m, 5H), 4.71 (d, 1H), 3.40 (dt, 1H), 3.22-3.29 (m, 1H), 1.36 (s, 9H).

Example 24A

N-{2-Amino-2-[3-(trifluoromethyl)phenyl]ethyl}formamide hydrochloride

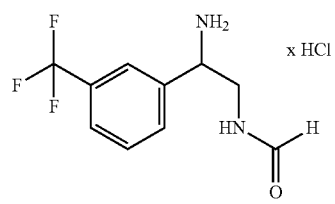 [SMILES: NC(CNC=O)c1cccc(C(F)(F)F)c1]

Of the compound from Example 23A, 66 mg (0.2 mmol) were introduced in 1.5 ml of dichloromethane and admixed at RT with 1.56 ml of a 4N solution of hydrogen chloride in dioxane. The reaction mixture was stirred at RT for 1 h. The reaction mixture was freed from the volatile components on a rotary evaporator and dried in an HV. This gave 50 mg (94% of theory) of the title compound.

LC/MS [Method 2]: $R_t$=0.90 min; m/z=233 (M+H)$^+$ $^1$H-NMR (400 MHz, DMSO-d$_6$): δ=8.56 (br.s, 3H), 8.19 (br.s, 1H), 8.01 (s, 1H), 7.91 (s, 1H), 7.76-7.81 (m, 2H), 7.70 (d, 1H), 4.51 (t, 1H), 3.50-3.71 (m, 2H).

Example 25A tert-Butyl {2-(acetylamino)-1-[3-(trifluoromethyl)phenyl]ethyl}carbamate

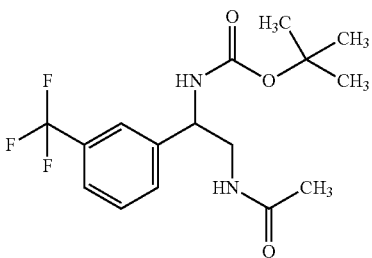 [SMILES: CC(=O)NCC(NC(=O)OC(C)(C)C)c1cccc(C(F)(F)F)c1]

Of the compound from Example 22A, 75 mg (0.25 mmol) were introduced in 2.5 ml of dichloromethane together with 60 µl (0.35 mmol) of N,N-diisopropylethylamine and admixed at RT with 21 µl (0.30 mmol) of acetyl chloride. The mixture was stirred at RT for 1 h. The reaction mixture was diluted with ethyl acetate and washed in succession twice each with 1N hydrochloric acid, saturated aqueous sodium hydrogen carbonate solution, and then with saturated aqueous sodium chloride solution, dried over sodium sulphate and freed from the solvent on a rotary evaporator. Further drying in an HV gave 88 mg of the title compound (100% of theory).

LC/MS [Method 4]: $R_t$=0.98 min; m/z=347 (M+H)$^+$

Example 26A

N-{2-Amino-2-[3-(trifluoromethyl)phenyl]ethyl}acetamide hydrochloride

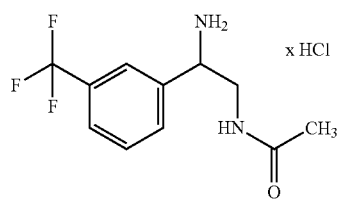 [SMILES: CC(=O)NCC(N)c1cccc(C(F)(F)F)c1]

In the same way as for Example 13A, 70 mg (72% of theory) of the title compound were obtained from Example 25A.

LC/MS [Method 5]: $R_t$=0.46 min; m/z=247 (M+H)$^+$ $^1$H-NMR (400 MHz, DMSO-d$_6$): δ=8.59 (br.s, 3H), 8.11 (t, 1H), 7.90 (s, 1H), 7.75-7.80 (m, 2H), 7.70 (d, 1H), 4.48 (d, 1H), 3.54-3.63 (m, 1H), 3.43-3.51 (m, 1H), 1.78 (s, 3H).

Example 27A tert-Butyl {2-[(ethylsulphonyl)amino]-1-[3-(trifluoromethyl)phenyl]ethyl}carbamate (racemate)

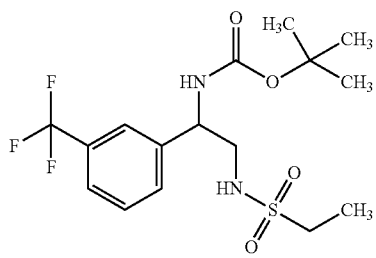 [SMILES: CCS(=O)(=O)NCC(NC(=O)OC(C)(C)C)c1cccc(C(F)(F)F)c1]

A solution of the compound from Example 22A (100 mg, 0.33 mmol) in 2 ml of pyridine was admixed at RT with 62 μl of ethanesulphonyl chloride (0.66 mmol) and the resulting mixture was stirred for 1 h. Then a further 16 μl (0.17 mmol) of ethanesulphonyl chloride were added. The mixture was stirred for 1 h more, diluted with ethyl acetate and extracted by shaking in succession twice each with 1M hydrochloric acid, saturated aqueous sodium hydrogen carbonate solution and saturated aqueous sodium chloride solution. The organic phase was dried over sodium sulphate and concentrated on a rotary evaporator and the residue was dried in an HV. This gave 114 mg (88% of theory) of the title compound.

LC/MS [Method 3]: $R_t$=1.24 min; m/z=297 (M+H-BOC)$^+$ $^1$H-NMR (400 MHz, DMSO-d$_6$): δ=7.69 (br.s, 1H), 7.55-7.66 (m, 3H), 7.49 (br.d, 1H), 7.16 (br. t, 1H), 4.67-4.75 (m, 1H), 3.12-3.38 (m, 2H), 2.81-2.99 (m, 2H), 1.38 (s, 9H), 1.10 (t, 3H).

The title compound was resolved into its two enantiomers—see Examples 28A and 29A—by chromatography on chiral phase (Method 15a).

Example 28A tert-Butyl {2-[(ethylsulphonyl)amino]-1-[3-(trifluoromethyl)phenyl]ethyl}carbamate (enantiomer I)

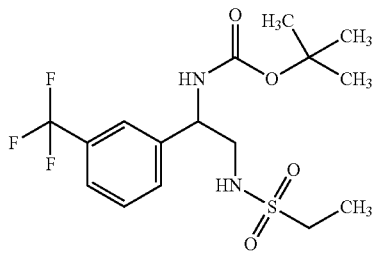

First-eluting enantiomer from the chromatographic enantiomer resolution of Example 27A by Method 15a.
Chiral analytical HPLC [Method 16]: $R_t$=1.35 min.

Example 29A tert-Butyl {2-[(ethyl sulphonyl)amino]-1-[3-(trifluoromethyl)phenyl]ethyl}carbamate (enantiomer II)

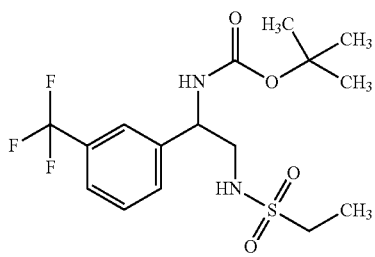

Last-eluting enantiomer from the chromatographic enantiomer resolution of Example 27A by Method 15a.
Chiral analytical HPLC [Method 16]: $R_t$=4.02 min.

Example 30A tert-Butyl {2-[(methyl sulphonyl)amino]-1-[3-(trifluoromethyl)phenyl]ethyl}carbamate (racemate)

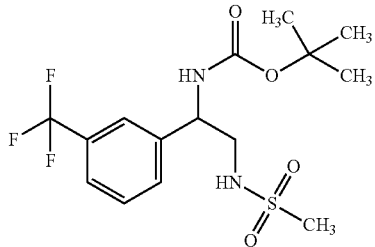 [SMILES: CC(C)(C)OC(=O)NC(CNS(C)(=O)=O)c1cccc(C(F)(F)F)c1]

A solution of the compound from Example 22A (100 mg, 0.33 mmol) in 2 ml of pyridine was admixed at RT with 66 μl (0.66 mmol) of methanesulphonyl chloride and stirred for 1 h. The mixture was diluted with ethyl acetate and extracted by shaking in succession twice each with 1M hydrochloric acid, saturated aqueous sodium hydrogen carbonate solution and saturated aqueous sodium chloride solution. The organic phase was dried over sodium sulphate and concentrated on a rotary evaporator and the residue was dried in an HV. This gave 121 mg (96% of theory) of the title compound.

LC/MS [Method 5]: $R_t$=1.04 min; ESI pos.: m/z=297 (M+H-BOC)$^+$, ESI neg.: m/z=381 (M-H)$^-$, $^1$H-NMR (400 MHz, DMSO-d$_6$): δ=7.68 (br.s, 1H), 7.55-7.66 (m, 3H), 7.50 (br.d, 1H), 7.15 (br. t, 1H), 4.67-4.75 (m, 1H), 3.13-3.27 (m, 2H), 2.80 (s, 3H), 1.36 (s, 9H).

The title compound was resolved into its two enantiomers—see Examples 31A and 32A—by chromatography on chiral phase (Method 15a).

Example 31A tert-Butyl {2-[(methylsulphonyl)amino]-1-[3-(trifluoromethyl)phenyl]ethyl}carbamate (enantiomer I)

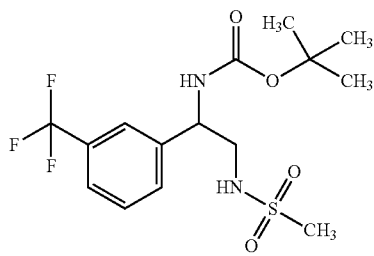 [SMILES: CC(C)(C)OC(=O)NC(CNS(C)(=O)=O)c1cccc(C(F)(F)F)c1]

First-eluting enantiomer from the chromatographic enantiomer resolution of Example 30A by Method 15a.

Chiral analytical HPLC [Method 16]: $R_t$=1.74 min.

Example 32A tert-Butyl {2-[(methylsulphonyl)amino]-1-[3-(trifluoromethyl)phenyl]ethyl}carbamate (enantiomer II)

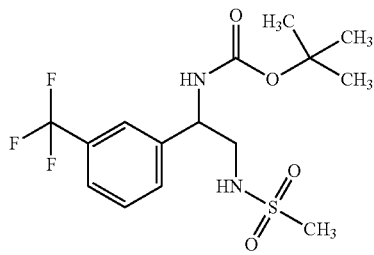 [SMILES: CC(C)(C)OC(=O)NC(CNS(C)(=O)=O)c1cccc(C(F)(F)F)c1]

Last-eluting enantiomer from the chromatographic enantiomer resolution of Example 30A by Method 15a.

Chiral analytical HPLC [Method 16]: $R_t$=3.47 min.

Example 33A tert-Butyl {2-amino-1-[2-(trifluoromethyl)phenyl]ethyl}carbamate

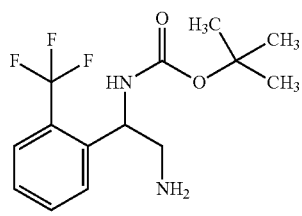 [SMILES: CC(C)(C)OC(=O)NC(CN)c1ccccc1C(F)(F)F]

In a continuous-flow hydrogenation apparatus (H-Cube from Thales Nano, Budapest, Model HC-2-SS) a solution of 770 mg (2.30 mmol) of the compound from Example 16A in 135 ml of methanol was hydrogenated (conditions: Raney nickel cartridge, flow rate of 1 ml/min, 45° C., standard hydrogen pressure). The resulting solution was concentrated on a rotary evaporator and the residue was dried briefly in an HV. This gave 669 mg (95% of theory) of the title compound.

LC/MS [Method 2]: $R_t$=1.39 min; m/z=305(M+H)$^+$ $^1$H-NMR (400 MHz, DMSO-d$_6$) (principal rotamer): δ=7.57-7.68 (m, 3H), 7.51 (br.d, 1H), 7.43 (t, 1H), 4.77 (br.s, 1H), 2.66 (dd, 1H), 2.58 (m, 1H), 1.51 (br. s, 2H), 1.35 (s, 9H).

Example 34A tert-Butyl {2-[(ethylsulphonyl)amino]-1-[2-(trifluoromethyl)phenyl]ethyl}carbamate (racemate)

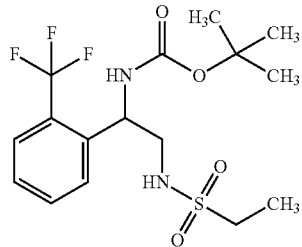 [SMILES: CCS(=O)(=O)NCC(NC(=O)OC(C)(C)C)c1ccccc1C(F)(F)F]

A solution of the compound from Example 33A (100 mg, 0.33 mmol) in 2 ml of pyridine was admixed at RT with 62 μl of ethanesulphonyl chloride (0.66 mmol) and the resulting mixture was stirred for 1 h. Then a further 16 μl (0.66 mmol) of ethanesulphonyl chloride were added. The mixture was stirred for 1 h more, diluted with ethyl acetate and extracted by shaking in succession twice each with 1M hydrochloric acid, saturated aqueous sodium hydrogen carbonate solution and saturated aqueous sodium chloride solution. The organic phase was dried over sodium sulphate and concentrated on a rotary evaporator and the residue was dried in an HV. This gave 113 mg (87% of theory) of the title compound.

LC/MS [Method 3]: $R_t$=1.24 min; m/z=297 (M+H-BOC)$^+$ $^1$H-NMR (400 MHz, DMSO-d$_6$): δ=7.75 (d, 1H), 7.65-7.71 (m, 2H), 7.44-7.50 (m, 2H), 7.31 (br. t, 1H), 4.95-5.05 (m, 1H), 3.03-3.18 (m, 2H), 2.84-3.03 (m, 2H), 1.35 (s, 9H), 1.12 (t, 3H).

The title compound was resolved into its two enantiomers—see Examples 35A and 36A—by chromatography on chiral phase (Method 15a).

Example 35A tert-Butyl {2-[(ethylsulphonyl)amino]-1-[2-(trifluoromethyl)phenyl]ethyl}carbamate (enantiomer I)

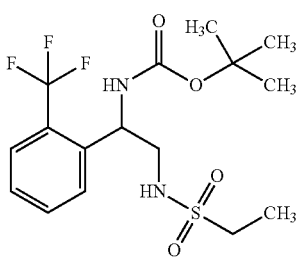

First-eluting enantiomer from the chromatographic enantiomer resolution of Example 34A by Method 15a.
Chiral analytical HPLC [Method 16]: $R_t$=1.65 min.

Example 36A tert-Butyl {2-[(ethyl sulphonyl)amino]-1-[2-(trifluoromethyl)phenyl]ethyl}carbamate (enantiomer II)

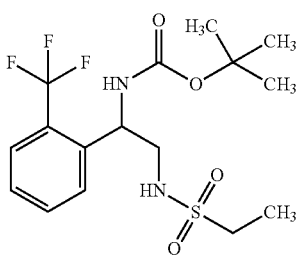 [SMILES: CCS(=O)(=O)NCC(NC(=O)OC(C)(C)C)c1ccccc1C(F)(F)F]

Last-eluting enantiomer from the chromatographic enantiomer resolution of Example 34A by Method 15a.
Chiral analytical HPLC [Method 16]: $R_t$=2.86 min.

Example 37A tert-Butyl {2-[(methylsulphonyl)amino]-1-[2-(trifluoromethyl)phenyl]ethyl}carbamate (racemate)

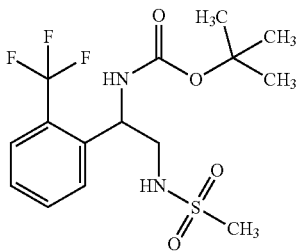 [SMILES: CC(C)(C)OC(=O)NC(CNS(C)(=O)=O)c1ccccc1C(F)(F)F]

In the same way as for the preparation of Example 30A, from the compound of Example 33A (100 mg, 0.33 mmol), 119 mg (95% of theory) of the title compound were obtained.
LC/MS [Method 5]: $R_t$=1.01 min; ESI pos: m/z=283 (M+H−BOC)$^+$, ESI neg: m/z=381 (M−H)$^-$ $^1$H-NMR (400 MHz, DMSO-d$_6$): δ=7.73 (d., 1H), 7.65-7.73 (m, 2H), 7.44-7.53 (m, 2H), 7.27 (br. t, 1H), 4.98-5.08 (m, 1H), 3.04-3.18 (m, 2H), 2.84 (s, 3H), 1.35 (s, 9H).

The title compound was resolved into its two enantiomers—see Examples 38A and 39A—by chromatography on chiral phase (Method 15a).

Example 38A tert-Butyl {2-[(methylsulphonyl)amino]-1-[2-(trifluoromethyl)phenyl]ethyl}carbamate (enantiomer I)

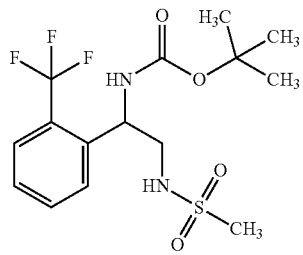 [SMILES: CC(C)(C)OC(=O)NC(CNS(C)(=O)=O)c1ccccc1C(F)(F)F]

First-eluting enantiomer from the chromatographic enantiomer resolution of Example 37A by Method 15a.
Chiral analytical HPLC [Method 16]: $R_t$=2.04 min.

Example 39A tert-Butyl {2-[(methylsulphonyl)amino]-1-[2-(trifluoromethyl)phenyl]ethyl}carbamate (enantiomer II)

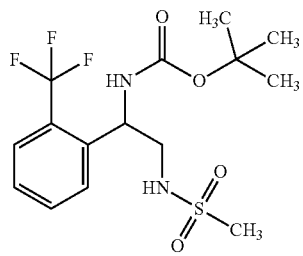 [SMILES: CC(C)(C)OC(=O)NC(CNS(C)(=O)=O)c1ccccc1C(F)(F)F]

Last-eluting enantiomer from the chromatographic enantiomer resolution of Example 37A by Method 15a.
Chiral analytical HPLC [Method 16]: $R_t$=7.41 min.

Example 40A tert-Butyl [2-amino-1-(2,3-dichlorophenyl)ethyl]carbamate

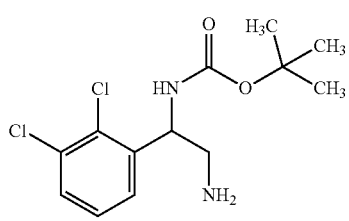 [SMILES: CC(C)(C)OC(=O)NC(CN)c1cccc(Cl)c1Cl]

In a continuous-flow hydrogenation apparatus (H-Cube from Thales Nano, Budapest, Model HC-2-SS) a solution of 440 mg (1.31 mmol) of the compound from Example 20A in 100 ml of methanol was hydrogenated (conditions: Raney nickel cartridge, flow rate of 1 ml/min, 40° C., standard hydrogen pressure). The resulting solution was concentrated on a rotary evaporator and the residue was briefly dried in an HV. This gave 370 mg (91% of theory) of the title compound.

LC/MS [Method 5]: $R_t$=0.76 min; m/z=305 (M+H)$^+$ $^1$H-NMR (400 MHz, DMSO-d$_6$): δ=7.55 (br.d, 1H) 7.51 (dd, 1H), 7.31-7.39 (m, 2H), 4.81-4.89 (m, 1H), 2.72 (dd, 1H), 2.59 (d, 1H), 1.66 (br. s, 2H), 1.36 (s, 9H).

Example 41A tert-Butyl {1-(2,3-dichlorophenyl)-2-[(ethylsulphonyl)amino]ethyl}carbamate (racemate)

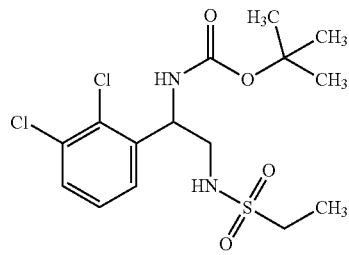 [SMILES: CCS(=O)(=O)NCC(NC(=O)OC(C)(C)C)c1cccc(Cl)c1Cl]

Using the same process as for Example 27A, from 100 mg of the compound from Example 40A (0.33 mmol), 101 mg (78% of theory) of the title compound were obtained.

LC/MS [Method 3]: $R_t$=1.21 min; ESI pos: m/z=297 (M+H−BOC)$^+$; ESI neg: m/z=395 (M−H)$^-$ $^1$H-NMR (400 MHz, DMSO-d$_6$): δ=7.56 (dd, 1H), 7.52 (br.d, 1H), 7.46 (dd, 1H), 7.39 (t, 1H), 7.29 (br. t, 1H), 5.02-5.11 (m, 1H), 3.04-3.22 (m, 2H), 2.86-3.02 (m, 2H), 1.36 (s, 9H), 1.14 (t, 3H).

The title compound was resolved into its two enantiomers—see Examples 42A and 43A—by chromatography on chiral phase (Method 15a).

Example 42A tert-Butyl {1-(2,3-dichlorophenyl)-2-[(ethylsulphonyl)amino]ethyl}carbamate (enantiomer I)

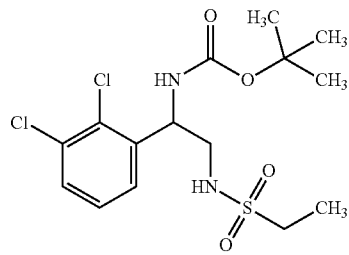 [SMILES: CCS(=O)(=O)NCC(NC(=O)OC(C)(C)C)c1cccc(Cl)c1Cl]

First-eluting enantiomer from the chromatographic enantiomer resolution of Example 41A by Method 15a.

Chiral analytical HPLC [Method 16]: $R_t$=1.94 min.

Example 43A tert-Butyl {1-(2,3-dichlorophenyl)-2-[(ethylsulphonyl)amino]ethyl}carbamate (enantiomer II)

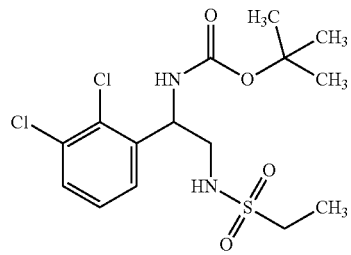 [SMILES: CCS(=O)(=O)NCC(NC(=O)OC(C)(C)C)c1cccc(Cl)c1Cl]

Last-eluting enantiomer from the chromatographic enantiomer resolution of Example 41A by Method 15a.

Chiral analytical HPLC [Method 16]: $R_t$=3.67 min.

Example 44A tert-Butyl {1-(2,3-dichlorophenyl)-2-[(methylsulphonyl)amino]ethyl}carbamate (racemate)

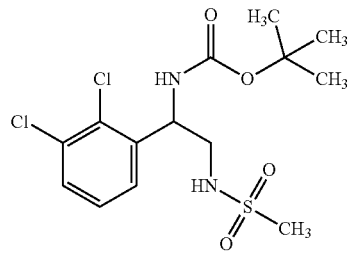 [SMILES: CC(C)(C)OC(=O)NC(CNS(C)(=O)=O)c1cccc(Cl)c1Cl]

In the same way as for the preparation of Example 30A, from the compound of Example 40A (100 mg, 0.33 mmol), 113 mg (90% of theory) of the title compound were obtained.

LC/MS [Method 5]: $R_t$=1.05 min; ESI pos: m/z=283 (M+H−BOC)$^+$, ESI neg: m/z=381 (M−H)$^-$ $^1$H-NMR (400 MHz, DMSO-d$_6$): δ=7.56 (dd, 1H), 7.53 (br.d, 1H), 7.47 (dd, 1H), 7.39 (t, 1H), 7.24 (t, 1H), 5.05-5.15 (m, 1H), 3.05-3.23 (m, 2H), 2.85 (s, 3H), 1.38 (s, 9H).

The title compound was resolved into its two enantiomers—see Examples 45A and 46A—by chromatography on chiral phase (Method 15a).

Example 45A tert-Butyl {1-(2,3-dichlorophenyl)-2-[(methylsulphonyl)amino]ethyl}carbamate (enantiomer I)

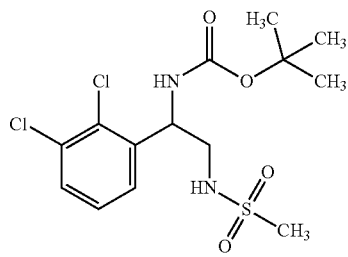

First-eluting enantiomer from the chromatographic enantiomer resolution of Example 44A by Method 15a.
Chiral analytical HPLC [Method 16]: $R_t$=1.88 min.

Example 46A tert-Butyl {1-(2,3-dichlorophenyl)-2-[(methylsulphonyl)amino]ethyl}carbamate (enantiomer II)

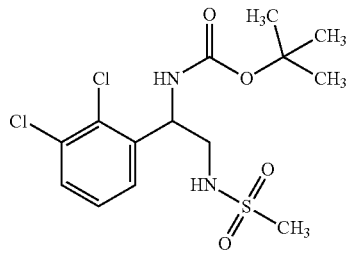 [SMILES: CC(C)(C)OC(=O)NC(CNS(C)(=O)=O)c1cccc(Cl)c1Cl]

Last-eluting enantiomer from the chromatographic enantiomer resolution of Example 44A by Method 15a.
Chiral analytical HPLC [Method 16]: $R_t$=10.30 min.

Example 47A

N-{2-Amino-2-[3-(trifluoromethyl)phenyl]ethyl}methanesulphonamide hydrochloride (enantiomer II)

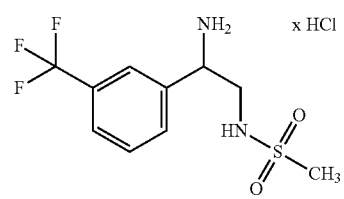 [SMILES: CS(=O)(=O)NCC(N)c1cccc(C(F)(F)F)c1 ; "x HCl"]

A solution of 57 mg (0.15 mmol) of the compound from Example 32A in 2 ml of dichloromethane was admixed with 2 ml of a 4N solution of hydrogen chloride in dioxane, and left with stirring at RT for 2 h. The volatile components were removed on a rotary evaporator. The residue was admixed with 5 ml of dichloromethane, the components were stirred together, and the mixture was concentrated again on a rotary evaporator and dried in an HV. This gave 52 mg (quant.) of the title compound in 85% purity.

LC/MS [Method 3]: $R_t$=0.55 min; ESI pos.: m/z=283 (M+H)$^+$

The same process was used to prepare Examples 48A to 58A:

| Example No. | Name | Structure | Reactant Ex. No. | Analysis LC-MS |
|---|---|---|---|---|
| 48A | N-{2-Amino-2-[3-(trifluoromethyl)phenyl]ethyl}ethanesulphonamide hydrochloride (Enantiomer I) | 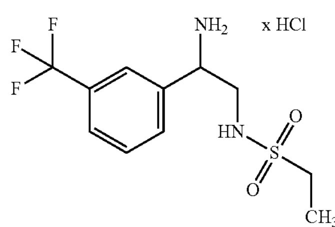 [SMILES: CCS(=O)(=O)NCC(N)c1cccc(C(F)(F)F)c1] | 28A | [Method 4] $R_t$ = 0.55 min; m/z = 297 (M + H)$^+$ |
| 49A | N-{2-Amino-2-[3-(trifluoromethyl)phenyl]ethyl}ethanesulphonamide hydrochloride (Enantiomer II) | 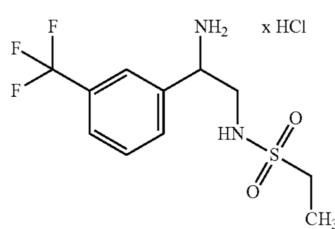 [SMILES: CCS(=O)(=O)NCC(N)c1cccc(C(F)(F)F)c1] | 29A | [Method 4] $R_t$ = 0.56 min; m/z = 297 (M + H)$^+$ |

-continued

| Example No. | Name | Structure | Reactant Ex. No. | Analysis LC-MS |
|---|---|---|---|---|
| 50A | N-{2-Amino-2-[3-(trifluoromethyl)phenyl]-ethyl}methanesulphon-amide hydrochloride (Enantiomer I) | 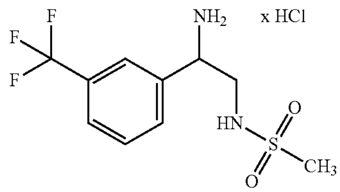 [SMILES: CS(=O)(=O)NCC(N)c1cccc(C(F)(F)F)c1] | 31A | [Method 4] $R_t$ = 0.46 min; m/z = 283 $(M + H)^+$ |
| 51A | N-{2-Amino-2-[2-(trifluoromethyl)phenyl]-ethyl}ethanesulphon-amide hydrochloride (Enantiomer I) | 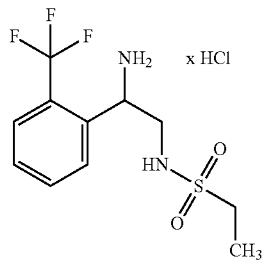 [SMILES: CCS(=O)(=O)NCC(N)c1ccccc1C(F)(F)F] | 35A | [Method 4] $R_t$ = 0.50 min; m/z = 297 $(M + H)^+$ |
| 52A | N-{2-Amino-2-[2-(trifluoromethyl)phenyl]-ethyl}ethanesulphon-amide hydrochloride (Enantiomer II) | 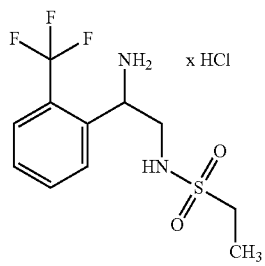 [SMILES: CCS(=O)(=O)NCC(N)c1ccccc1C(F)(F)F] | 36A | [Method 4] $R_t$ = 0.49 min; m/z = 297 $(M + H)^+$ |
| 53A | N-{2-Amino-2-[2-(trifluoromethyl)phenyl]-ethyl}methanesulphon-amide hydrochloride (Enantiomer I) | 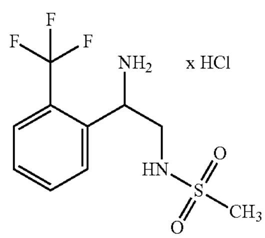 [SMILES: CS(=O)(=O)NCC(N)c1ccccc1C(F)(F)F] | 38A | [Method 4] $R_t$ = 0.40 min; m/z = 283 $(M + H)^+$ |
| 54A | N-{2-Amino-2-[2-(trifluoromethyl)phenyl]-ethyl}methanesulphon-amide hydrochloride (Enantiomer II) | 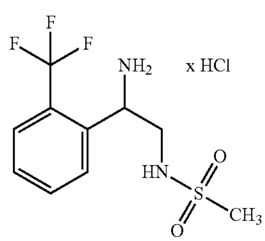 [SMILES: CS(=O)(=O)NCC(N)c1ccccc1C(F)(F)F] | 39A | [Method 4] $R_t$ = 0.38 min; m/z = 283 $(M + H)^+$ |
| 55A | N-{2-Amino-2-(2,3-dichlorophenyl)ethyl}-ethanesulphonamide hydrochloride (Enantiomer I) | 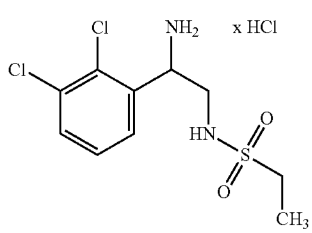 [SMILES: CCS(=O)(=O)NCC(N)c1cccc(Cl)c1Cl] | 42A | [Method 4] $R_t$ = 0.54 min; m/z = 297 $(M + H)^+$ |

| Example No. | Name | Structure | Reactant Ex. No. | Analysis LC-MS |
|---|---|---|---|---|
| 56A | N-{2-Amino-2-(2,3-dichlorophenyl)ethyl}-ethanesulphonamide hydrochloride (Enantiomer II) | 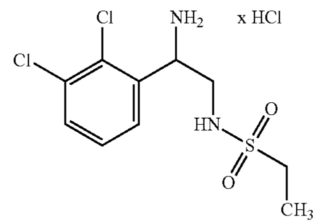 [SMILES: CCS(=O)(=O)NCC(N)c1cccc(Cl)c1Cl] | 43A | [Method 4] $R_t = 0.55$ min; m/z = 297 $(M + H)^+$ |
| 57A | N-{2-Amino-2-(2,3-dichlorophenyl)ethyl}-methanesulphonamide hydrochloride (Enantiomer I) | 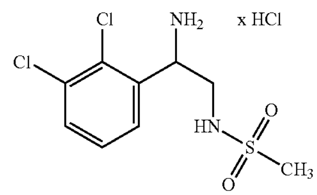 [SMILES: CS(=O)(=O)NCC(N)c1cccc(Cl)c1Cl] | 45A | [Method 4] $R_t = 0.45$ min; m/z = 283 $(M + H)^+$ |
| 58A | N-{2-Amino-2-(2,3-dichlorophenyl)ethyl}-methanesulphonamide hydrochloride (Enantiomer II) | 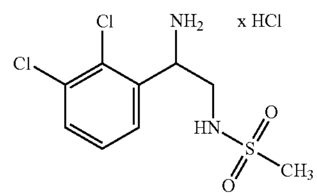 | 46A | [Method 4] $R_t = 0.44$ min; m/z = 297 $(M + H)^+$ |

Example 59A tert-Butyl {2-hydroxy-1-[3-(trifluoromethyl)phenyl]ethyl}carbamate

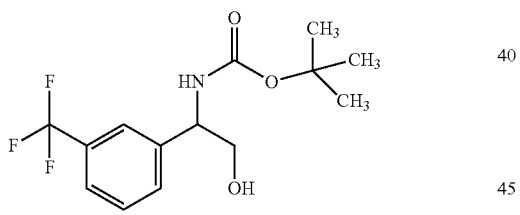

A solution of 4.00 g (12.5 mmol) of N-tert-butoxycarbonyl-2-(3-trifluoromethylphenyl)-DL-glycine and 2.1 ml (15 mmol) of triethylamine in 50 ml of THF was cooled at 0° C. and admixed dropwise with 1.79 ml (13.8 mmol) of isobutyl chloroformate. The resulting thick suspension was stirred at 0° C. for 1 h more, then filtered into a cooled flask. The solid was washed with a little THF and the entire filtrate was added slowly dropwise to an ice-cooled suspension of sodium borohydride (1.42 g, 37.6 mmol) in 6 ml of water (strong gas evolution). The mixture was stirred vigorously at 0° C. for 1 h more, then admixed with 5 ml of 1N hydrochloric acid and extracted three times with ethyl acetate. The organic phase was washed with 1N aqueous sodium hydroxide solution and then twice with saturated aqueous sodium hydrogen carbonate solution, dried over sodium sulphate and concentrated on a rotary evaporator. The residue was purified by preparative HPLC (Method 10). This gave 2.00 g of the title compound (52% of theory).

LC/MS [Method 5]: $R_t=1.02$ min; m/z=328 $(M+Na)^+$, 206 $(M+H-BOC)^+$.

$^1$H NMR (DMSO-$d_6$, 00 MHz): δ=7.65 (s, 1H), 7.51-7.62 (m, 3H), 7.37 (br. d, 1H), 4.86 (t, 1H), 4.57-4.66 (m, 1H), 3.46-3.58 (m, 2H), 1.37 (s, 9H).

Example 60A

2-Amino-2-[3-(trifluoromethyl)phenyl]ethyl carbamate hydrochloride

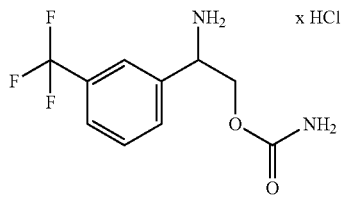 [SMILES: NC(=O)OCC(N)c1cccc(C(F)(F)F)c1 ; "x HCl"]

A solution of 1.00 g (3.28 mmol) of a compound from Example 59A in 20 ml of acetonitrile was cooled to −15° C. and admixed with 399 µl (4.59 mmol) of chlorosulphonyl isocyanate. After 10 min, 18 ml of water were added and the mixture was heated at 60° C. for 2 h. After cooling to RT, the solution was rendered alkaline (pH 9-10) by addition of saturated aqueous sodium hydrogen carbonate solution and extracted three times with ethyl acetate. The combined organic phases were dried over sodium sulphate and freed from the solvents on a rotary evaporator. For complete deprotection of the amino group, the residue was admixed with 15 ml of a 4M solution of hydrogen chloride in dioxane, and this mixture was stirred at RT for 5 min and concentrated on a rotary evaporator. Drying of the residue in an HV gave 785 mg (84% of theory) of the title compound.

LC/MS [Method 4]: $R_t=0.44$ min; m/z=249 $(M+H)^+$

¹H-NMR (400 MHz, DMSO-d₆): δ=8.80 (br.s, 3H), 7.97 (s, 1H), 7.88 (d, 1H), 7.80 (d, 1H), 7.70 (t, 1H), 6.61 (br. s, 2H), 4.63-4.73 (m, 1H), 4.26-4.38 (m, 2H).

Example 61A

2-Amino-2-[2-(trifluoromethyl)phenyl]ethanol hydrochloride

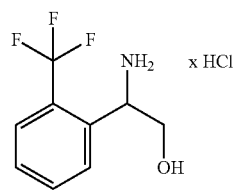 [SMILES: NC(CO)c1ccccc1C(F)(F)F ; "x HCl"]

A quantity of 500 mg (2.28 mmol) of (2-trifluoromethylphenyl)-DL-glycine was added in portions under argon to a 1M borane-THF complex solution in THF (9.13 ml, 9.13 mmol) which was cooled with ice water. After 10 min, the cooling bath was removed and the mixture was stirred at RT for 4 h. For work-up, the pH was made acidic by addition of 1N hydrochloric acid, the THF was removed on a rotary evaporator, and the aqueous solution remaining was neutralized with 1N aqueous sodium hydroxide solution and then rendered alkaline with saturated aqueous sodium hydrogen carbonate solution. It was extracted three times with ethyl acetate. The combined organic phases were dried over sodium sulphate and freed from the solvent on a rotary evaporator. The resulting crude amino alcohol was admixed with 15 ml of a 4M solution of hydrogen chloride in dioxane, and stirred for 5 minutes. The solution was then concentrated on a rotary evaporator. Drying of the residue in an HV gave the title compound (550 mg, quant.) which was reacted further without purification.

LC/MS [Method 2]: $R_t$=0.78 min; m/z=206 (M+H)⁺

¹H NMR (DMSO-d₆, 400 MHz): δ=8.71 (br.s, 3H), 7.92 (d, 1H), 7.78-7.86 (m, 2H), 7.64 (t, 1H), 5.75 (t, 1H), 4.42 (dd, 1H), 3.64-3.77 (m, 2H).

Example 62A tert-Butyl {2-hydroxy-1-[2-(trifluoromethyl)phenyl]ethyl}carbamate

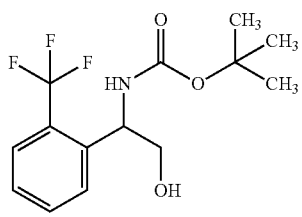 [SMILES: CC(C)(C)OC(=O)NC(CO)c1ccccc1C(F)(F)F]

Of the compound from Example 61A, 367 mg (1.52 mmol) were dissolved in 20 ml of dioxane and 20 ml of 5% strength aqueous sodium hydrogen carbonate solution, the solution was admixed with 356 µl (1.55 mmol) of di-tert-butyl dicarbonate, and the mixture was stirred at RT overnight. It was extracted five times with ethyl acetate. The combined organic phases were dried over sodium sulphate and concentrated on a rotary evaporator. The residue corresponded to the title compound (338 mg, 73% of theory).

LC/MS [Method 2]: $R_t$=2.01 min; m/z=306 (M+H)⁺

¹H NMR (DMSO-d₆, 400 MHz) (rotamers): δ=7.61-7.71 (m, 3H), 7.37-7.48 (m, 2H), 4.90-5.01 (m, 2H), 3.35-3.50 (m, 2H), 1.35 (br.s about 7.5H)⁺1.10 (br.s, 1.5H).

Example 63A

2-Amino-2-[2-(trifluoromethyl)phenyl]ethyl carbamate hydrochloride

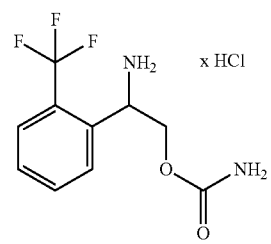 [SMILES: NC(=O)OCC(N)c1ccccc1C(F)(F)F]

A solution of 570 mg (1.87 mmol) of the compound from Example 62A in 100 ml of acetonitrile was cooled to −15° C. and admixed with 325 µl (3.73 mmol) of chlorosulphonyl isocyanate. After 10 min, 50 ml of water were added and the mixture was heated at 60° C. for 4 h. After cooling to RT, the solution was rendered alkaline (pH 9-10) by addition of saturated aqueous sodium hydrogen carbonate solution and extracted three times with ethyl acetate. The combined organic phases were dried over sodium sulphate and freed from the solvents on a rotary evaporator. For complete deprotection of the amino group, the residue was admixed with 15 ml of a 4M solution of hydrogen chloride in dioxane, and the mixture was stirred at RT for 5 min and the volatile components were removed on a rotary evaporator. The residue corresponded to the title compound (630 mg, quant.).

LC/MS [Method 4]: $R_t$=0.34 min; m/z=249 (M+H)⁺

¹H NMR (DMSO-d₆, 400 MHz): δ=8.97 (br.s, 3H), 8.06 (d, 1H), 7.80-7.87 (m, 2H), 7.66 (t, 1H), 6.64 (br.s, 2H), 4.64 (br.s, 1H), 4.37 (dd, 1H), 4.27 (dd, 1H).

Example 64A tert-Butyl [(1R)-1-(3-chlorophenyl)-2-hydroxyethyl]carbamate

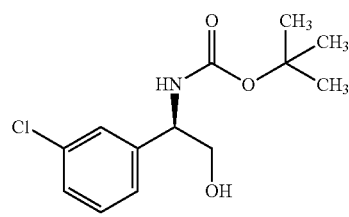 [SMILES: CC(C)(C)OC(=O)N[C@@H](CO)c1cccc(Cl)c1]

In the same way as for Example 62A, from 134 mg (0.644 mmol) of (2R)-2-amino-2-(3-chlorophenyl)ethan-1-ol, 166 mg (95% of theory) of the title compound were obtained.

LC/MS [Method 1]: $R_t$=1.10 min; m/z=272 (M+H-BOC)⁺

Example 65A

2-Amino-2-(3-chlorophenyl)ethyl carbamate hydrochloride

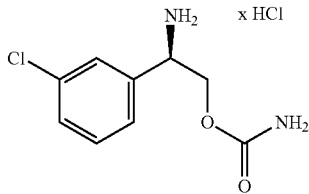 [SMILES: NC(=O)OC[C@H](N)c1cccc(Cl)c1]

In the same way as for Example 60A, from 166 mg (0.61 mmol) of the compound from Example 64A, 200 mg of the title compound were obtained and were used further as a crude product.

LC/MS [Method 4]: $R_t$=0.30 min; m/z=215 (M+H)$^+$
$^1$H-NMR (400 MHz, DMSO-d$_6$): δ=8.71 (br.s, 3H), 7.66 (s, 1H), 7.46-7.54 (m, 3H), 6.62 (br. s, 2H), 4.52-4.62 (m, 1H), 4.22-4.32 (m, 2H).

Example 66A

2-Amino-2-(2-chlorophenyl)ethanol

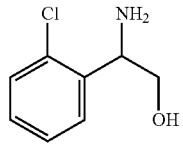

A quantity of 4.00 g (21.6 mmol) of (2-chlorophenyl)-DL-glycine was added in portions under argon to a 1M boran-THF complex solution in THF (64.7 ml, 64.7 mmol) which was cooled with ice water. After 10 min, the cooling bath was removed and the mixture was stirred at RT for 4 h. For work-up, pieces of ice were added slowly until the evolution of gas came to an end. The mixture was rendered alkaline by addition of 1N aqueous sodium hydroxide solution and extracted three times with MTBE. The combined organic phases were dried over sodium sulphate and concentrated on a rotary evaporator. The resulting crude title compound (3.00 g, 77% of theory) was reacted further without additional purification.

LC/MS [Method 4]: $R_t$=0.22 min; m/z=172 (M+H)$^+$
$^1$H NMR (DMSO-d$_6$, 400 MHz): δ=7.64 (d, 1H), 7.37 (d, 1H), 7.32 (t, 1H), 7.24 (t, 1H), 4.87 (br.s, 1H), 4.26-4.32 (m, 1H), 3.53 (dd, 1H), 3.20 (dd, 1H), 2.08 (br. s, 2H).

Example 67A tert-Butyl [1-(2-chlorophenyl)-2-hydroxyethyl]carbamate

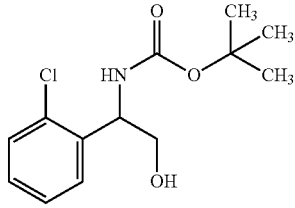 [SMILES: CC(C)(C)OC(=O)NC(CO)c1ccccc1Cl]

Of the compound from Example 66A, 2.3 g (13.4 mmol) were stirred in 100 ml of acetonitrile with 3.69 ml (16 mmol) of di-tert-butyl dicarbonate overnight. Then ethyl acetate and saturated aqueous sodium hydrogen carbonate solution were added. The phases were separated and the aqueous phase was extracted twice more with ethyl acetate. The combined organic phases were washed in succession with water (2×) and saturated aqueous sodium chloride solution, dried over sodium sulphate and concentrated on a rotary evaporator. The residue was dried in an HV. The resulting crude title compound (4.2 g) was reacted without further purification in Example 68A.

LC/MS [Method 6]: $R_t$=2.02 min; m/z=272 (M+H)$^+$
$^1$H NMR (DMSO-d$_6$, 400 MHz) (rotamers): δ=7.43 (dd, 1H), 7.39 (dd, 1H), 7.36 (br.d, 1H), 7.32 (td, 1H), 7.25 (td, 1H), 4.94-5.02 (m, 1H), 4.91 (t, 1H), 3.46-3.54 (m, 1H), 3.35-3.43 (m, 1H), 1.36 (br. s, 7.5H)+1.16 (br. s, 1.5H).

Example 68A

2-Amino-2-(2-chlorophenyl)ethyl carbamate hydrochloride

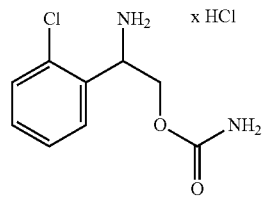 [SMILES: NC(=O)OCC(N)c1ccccc1Cl]

In the same way as for Example 63A, from 2.00 g (7.36 mmol) of the compound from Example 67A, the title compound was obtained (1.10 g, 69% of theory over 2 stages).

LC/MS [Method 4]: $R_t$=0.28 min; m/z=215 (M+H)$^+$
$^1$H NMR (DMSO-d$_6$, 400 MHz): δ=8.76 (br.s, 3H), 7.75 (d, 1H), 7.57 (dd, 1H), 7.41-7.53 (m, 2H), 6.64 (br.s, 2H), 4.82-4.92 (m, 1H), 4.27 (qd [ABX], 2H).

Example 69A (2R)-2-Amino-2-[3-(trifluoromethyl)phenyl]propan-1-ol hydrochloride

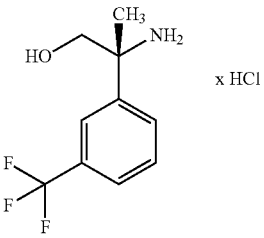

A 1M solution of the borane-tetrahydrofuran complex in THF (37.1 ml, 37.1 mmol) was cooled to 0° C. under argon. Added thereto were 2.5 g (9.27 mmol) of (2R)-2-amino-2-[3-(trifluoromethyl)phenyl]propanoic acid, and, following removal of the cooling bath, the mixture was stirred at RT for 4 h. For work-up, it was cautiously acidified with 1N hydrochloric acid. The THF was removed on a rotary evaporator. The aqueous phase was rendered basic with saturated aqueous sodium hydrogen carbonate solution and extracted three times with ethyl acetate. The combined organic phases were dried over sodium sulphate and concentrated on a rotary evaporator. The resulting crude product (2.4 g) was reacted further without purification.

LC/MS [Method 2]: $R_t$=0.93 min; m/z=218 (M+H)$^+$

Example 70A tert-Butyl {(2R)-1-hydroxy-2-[3-(trifluoromethyl)phenyl]propan-2-yl}carbamate

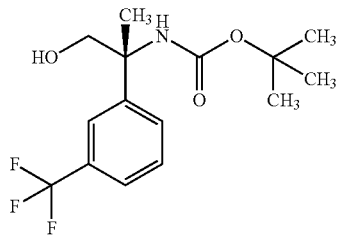 [SMILES: CC(C)(C)OC(=O)N[C@@](C)(CO)c1cccc(C(F)(F)F)c1]

Of the compound from Example 69A, 2.032 g (9.27 mmol) were dissolved in 50 ml of dichloromethane and 10 ml of dioxane, and the solution was admixed with 2.17 ml (9.45 mmol) of di-tert-butyl dicarbonate. The mixture was stirred at RT overnight, then freed from the volatile components on a rotary evaporator. The residue was dried in an HV and then purified by preparative HPLC (Method 10). This gave 2.69 g (91% over theory of 2 stages) of the title compound.

LC/MS [Method 5]: $R_t$=1.09 min; m/z=342 (M+Na)$^+$.

$^1$H NMR (DMSO-$d_6$, 400 MHz) (rotamers): δ=7.50-7.64 (m, 5H), 6.92 (br. s, 1H), 4.97 (br. t, 1H), 3.43-3.54 (m [AB], 3H), 1.58 (s, 3H), 1.34+1.00 (2 br.s, in total 9H).

Example 71A (2R)-2-Amino-2-[3-(trifluoromethyl)phenyl]propyl carbamate hydrochloride

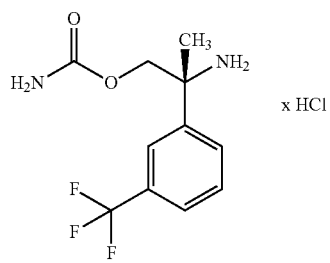 [SMILES: C[C@](N)(COC(N)=O)c1cccc(C(F)(F)F)c1]

A solution of 520 mg (1.63 mmol) of the compound from Example 70A in 10 ml of acetonitrile was cooled to −15° C. and admixed with 198 μl (2.28 mmol) of chlorosulphonyl isocyanate. After 10 min, 18 ml of water were added and the mixture was heated at 60° C. overnight. After cooling to RT, the solution was rendered alkaline by addition of saturated aqueous sodium hydrogen carbonate solution and extracted three times with ethyl acetate. The combined organic phases were dried over sodium sulphate and freed from the solvents on a rotary evaporator. For complete deprotection of the amino group, the residue was admixed with 5 ml of a 4M solution of hydrogen chloride in dioxane, and this mixture was stirred at RT for 5 min and concentrated on a rotary evaporator. Drying of the residue in an HV gave the title compound (440 mg, 90% of theory).

LC/MS [Method 4]: $R_t$=0.47 min; m/z=263 (M+H)$^+$ $^1$H-NMR (400 MHz, DMSO-$d_6$): δ=8.80 (br.s, 3H), 7.97 (s, 1H), 7.88 (d, 1H), 7.80 (d, 1H), 7.70 (t, 1H), 6.61 (br. s, 2H), 4.63-4.73 (m, 1H), 4.26-4.38 (m, 2H).

Example 72A (2R)-2-[(tert-Butoxycarbonyl)amino]-2-(2-chlorophenyl)propanoic acid

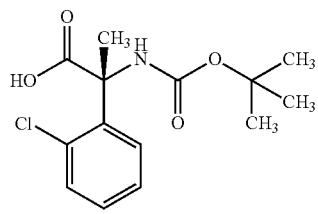 [SMILES: CC(C)(C)OC(=O)N[C@@](C)(C(=O)O)c1ccccc1Cl]

A quantity of 500 mg (2.11 mmol) of (2R)-2-amino-2-[2-(chloromethyl)phenyl]propionoic acid was dissolved in 10 ml of 5% strength sodium hydrogen carbonate solution and admixed with 10 ml of dioxane and then with 511 μl (2.22 mmol) of di-tert-butyl dicarbonate. The mixture was stirred overnight, adjusted cautiously with 1N hydrochloric acid to a pH of 2, and extracted three times with ethyl acetate. The combined organic phases were dried over sodium sulphate and concentrated on a rotary evaporator. The residue (322 mg, 51% of theory) corresponded to the title compound and was reacted further as such.

LC/MS [Method 3]: $R_t$=1.08 min; m/z=322 (M+Na)$^+$

Example 73A tert-Butyl [(2R)-2-(2-chlorophenyl)-1-hydroxypropan-2-yl]carbamate

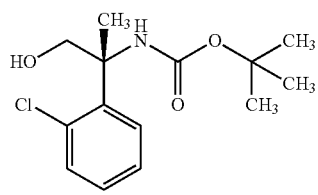 [SMILES: CC(C)(C)OC(=O)N[C@@](C)(CO)c1ccccc1Cl]

In the same way as for Example 59A, from 150 mg (0.5 mmol) of the compound from Example 72A, 110 mg of the title compound were obtained (77% of theory).

LC/MS [Method 4]: $R_t$=0.98 min; m/z=286 (M+H)$^+$ $^1$H NMR (DMSO-$d_6$, 400 MHz): δ=7.44 (d, 1H), 7.32 (d, 1H), 7.17-7.29 (m, 2H), 6.79 (br. s, 1H), 4.96 (br. t, 1H), 3.60-3.82 (m, 2H), 1.64 (s, 3H), 1.33 (s, 9H).

Example 74A (2R)-2-Amino-2-(2-chlorophenyl)propan-1-ol hydrochloride

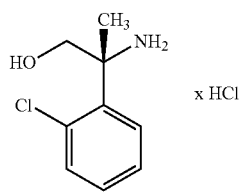

x HCl

In the same way as for Example 47A, from 55 mg (0.19 mmol) of the compound from Example 73A, by treatment with a 4N solution of hydrogen chloride in dioxane, 49 mg (approximately 85% purity) of the title compound were obtained. It was reacted without purification.

LC/MS [Method 5]: $R_t$=0.28 min; m/z=186 (M+H)$^+$ $^1$H NMR (DMSO-$d_6$, 400 MHz): δ=8.63 (br.s, 3H), 7.52 (d, 1H), 7.34-7.49 (m, 3H), 5.69 (br.s, 1H), 4.11 (dd, 1H), 3.83 (dd, 1H), 1.70 (s, 3H).

Example 75A (2R)-2-Amino-2-(2-chlorophenyl)propyl carbamate

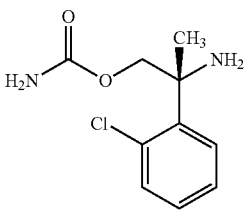

A solution of 55 mg (0.19 mmol) of the compound from Example 73A in 2 ml of acetonitrile was admixed at RT in 3 portions over the course of 20 min with 39 μl (0.42 mmol) of chlorosulphonyl isocyanate. After a further 10 min, 2 ml of water were added and the mixture was heated at 60° C. for 2 h. After cooling to RT, the solution was rendered alkaline by addition of 2N aqueous sodium hydrogen carbonate solution and extracted three times with ethyl acetate. The combined organic phases were dried over sodium sulphate and concentrated on a rotary evaporator. Drying of the residue in an HV gave the slightly contaminated title compound (34 mg, 77% of theory, 90% purity), which was reacted further as such.

$^1$H NMR (DMSO-$d_6$, 400 MHz): δ=7.76 (dd, 1H), 7.38 (dd, 1H), 7.32 (td, 1H), 7.26 (td, 1H), 6.27-6.51 (br. s, 2H), 4.36 (d, 1H), 4.24 (d, 1H), 2.11-2.42 (br.s, 2H), 1.48 (s, 3H).

Example 76A

Methyl {3-(4-chlorophenyl)-5-oxo-4-[(1E)-3,3,3-trifluoroprop-1-en-1-yl]-4,5-dihydro-1H-1,2,4-triazol-1-yl}acetate

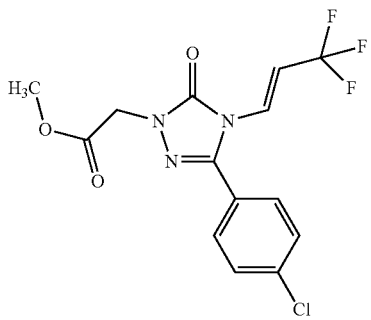 [SMILES: COC(=O)Cn1nc(-c2ccc(Cl)cc2)n(/C=C/C(F)(F)F)c1=O]

280 mg (0.74 mmol) of the compound from Example 7A were introduced at RT together with 108.1 mg (0.89 mmol) of 4-dimethylaminopyridine in 5.3 ml of pyridine, admixed with portions of 0.31 ml (1.84 mmol) of trifluoromethanesulphonic anhydride and stirred for 12 h. The pyridine was removed on a rotary evaporator and the residue was taken up in acetonitrile and 1N hydrochloric acid. The product was purified by preparative HPLC (Method 10). This gave 230 mg (86% of theory) of the title compound.

LC/MS [Method 4]: $R_t$=1.14 min; m/z=362 (M+H)$^+$ $^1$H-NMR (400 MHz, DMSO-$d_6$): δ=7.68 (s, 4H), 7.18 (d, 1H), 6.85 (dd, 1H), 4.78 (s, 2H), 3.72 (s, 3H).

Example 77A

{3-(4-Chlorophenyl)-5-oxo-4-[(1E)-3,3,3-trifluoroprop-1-en-1-yl]-4,5-dihydro-1H-1,2,4-triazol-1-yl}acetic acid

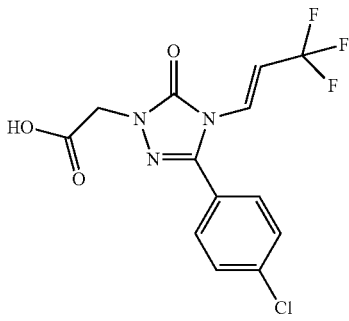 [SMILES: O=C(O)Cn1nc(-c2ccc(Cl)cc2)n(/C=C/C(F)(F)F)c1=O]

Of the compound from Example 76A, 260 mg (0.72 mmol) were dissolved in 5 ml of methanol and admixed with 2.87 ml (2.87 mmol) of a 1M solution of lithium hydroxide in water. The mixture was stirred at RT for 1 h, then acidified with 1N hydrochloric acid and diluted with DMSO. The entire solution was purified by preparative HPLC (Method 10). This gave 215 mg (86% of theory) of the title compound.

LC/MS [Method 4]: $R_t$=1.03 min; m/z=348 (M+H)$^+$ $^1$H-NMR (400 MHz, DMSO-$d_6$): δ=13.31 (br. s, 1H), 7.68 (s, 4H), 7.19 (dd, 1H), 6.79-6.92 (m, 1H), 4.64 (s, 2H).

Example 78A

3-Amino-3-[3-(trifluoromethyl)phenyl]propan-1-ol hydrochloride

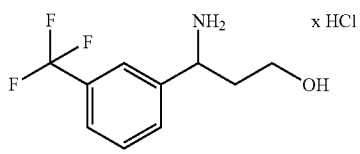 [SMILES: NC(CCO)c1cccc(C(F)(F)F)c1 ; "x HCl"]

With ice cooling and under argon, 2.57 ml (2.57 mmol) of 1M borane-THF complex solution were introduced and were admixed with 150 mg (0.64 mmol) of 3-amino-3-[3-(trifluoromethyl)phenyl]propanoic acid. After 10 min, the cooling bath was removed and the mixture was stirred at RT for 4 h. With ice cooling, 1 ml of 3N aqueous sodium hydroxide solution was added dropwise and the mixture was stirred overnight. The reaction solution was acidified using 1N hydrochloric acid. The THF was removed on a rotary evaporator and the aqueous solution obtained was purified by preparative HPLC (Method 10). This gave 160 mg (97% of theory) of the title compound.

LC/MS [Method 1]: $R_t$=1.08 min; m/z=220 (M+H)$^+$ $^1$H NMR (DMSO-d$_6$, 400 MHz): δ=8.19 (s, 1H), 7.90 (s, 1H), 7.80 (d, 1H), 7.74 (d, 1H), 7.66 (t, 1H), 4.42 (dd, 1H), 3.40 (dt, 1H), 3.25 (ddd, 1H), 2.04-2.16 (m, 1H), 1.87-1.97 (m, 1H).

Example 79A tert-Butyl {(1S)-3-hydroxy-1-[2-(trifluoromethyl)phenyl]propyl}carbamate

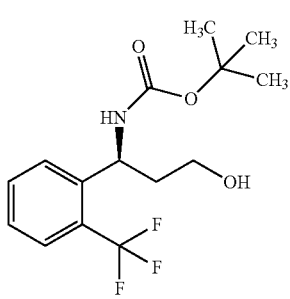 [SMILES: CC(C)(C)OC(=O)N[C@@H](CCO)c1ccccc1C(F)(F)F]

With ice cooling and under argon, 6 ml (6 mmol) of a 1M borane-THF complex solution were introduced and were admixed with (S)-Boc-2-(trifluoromethyl)-β-phenylalanine (500 mg, 1.50 mmol). The mixture was stirred at 0° C. for 1 h. To remove the excess borane, pieces of ice were added. At the end of the evolution of gas, saturated aqueous sodium hydrogen carbonate solution was added and this mixture was extracted with ethyl acetate. The aqueous phase was acidified with 1N hydrochloric acid and extracted twice with ethyl acetate. These combined organic phases were washed with 1N hydrochloric acid and then with saturated aqueous sodium chloride solution, dried over sodium sulphate and concentrated on a rotary evaporator. The residue was dried in an HV and corresponded to the title compound (340 mg, 71% of theory).

LC/MS [Method 3]: $R_t$=1.15 min; m/z=220 (M+H-BOC)$^+$

Example 80A (3S)-3-Amino-3-[2-(trifluoromethyl)phenyl]propan-1-ol hydrochloride

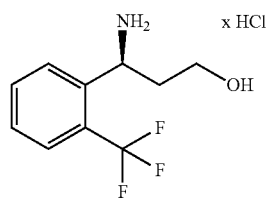 [SMILES: N[C@@H](CCO)c1ccccc1C(F)(F)F ; "x HCl"]

Of the compound from Example 79A, 150 mg (0.47 mmol) were stirred for 20 min in 3 ml of a 4N solution of hydrogen chloride in dioxane. The volatile components were removed on a rotary evaporator and the residue was dried in an HV. This gave 140 mg (87% purity) of the title compound.

LC/MS [Method 3]: $R_t$=1.15 min; m/z=220 (M+H)$^+$ $^1$H NMR (DMSO-d$_6$, 400 MHz): δ=8.69 (br.s, 3H), 7.98 (d, 1H), 7.73-7.89 (m, 2H), 7.62 (t, 1H), 4.59 (br.s, 1H), 3.61-3.81 (m, 1H), 3.40-3.48 (m, 2H), 2.10-2.22 (m, 1H), 1.92-2.02 (m, 1H).

Example 81A (3S)-3-Amino-3-[2-(trifluoromethyl)phenyl]propyl carbamate hydrochloride

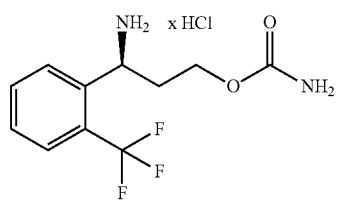 [SMILES: NC(=O)OCC[C@H](N)c1ccccc1C(F)(F)F ; "x HCl"]

In the same way as for Example 63A, from 180 mg (0.70 mmol) of the compound from Example 79A, 190 mg (90% of theory) of the title compound were obtained.

LC/MS [Method 2]: $R_t$=0.97 min; m/z=263 (M+H)$^+$ $^1$H NMR (DMSO-d$_6$, 400 MHz): δ=8.72 (br.s, 3H), 7.99 (d, 1H), 7.80-7.87 (m, 2H), 7.65 (t, 1H), 6.50 (br.s, 2H), 4.48-4.60 (m, 1H), 3.77-3.93 (m, 2H), 2.29-2.39 (m, 1H), 2.12-2.23 (m, 1H).

Example 82A

3-[(tert-Butoxycarbonyl)amino]-3-(2,3-dichlorophenyl)propanoic acid

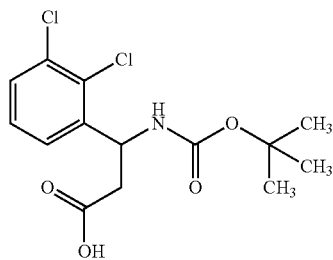 [SMILES: CC(C)(C)OC(=O)NC(CC(=O)O)c1cccc(Cl)c1Cl]

A quantity of 1.50 g (6.41 mmol) of 3-amino-3-(2,3-dichlorophenyl)propanoic acid was suspended in 45 ml of dioxane and 45 ml of 5% strength aqueous sodium hydrogen carbonate solution and the suspension was admixed at room temperature with 1.40 g (6.41 mmol) of di-tert-butyl dicarbonate. The mixture was stirred at room temperature for 16 h. For work-up, the suspension was admixed with about 50 ml of ethyl acetate, with stirring. The precipitate was filtered off with suction. Following phase separation of the mother liquor, the aqueous phase was adjusted cautiously to a pH of 1 using 1N hydrochloric acid and extracted once with about 50 ml of ethyl acetate. The combined organic phases were dried over sodium sulphate, filtered and concentrated under reduced pressure. This gave 1.68 g (79% of theory) of the target compound.

LC-MS [Method 3] $R_t$=1.18 min; MS [ESIneg]: m/z=332 (M−H)⁻

The following compounds were obtained similarly:

Example 85A tert-Butyl [1-(2,3-dichlorophenyl)-3-hydroxypropyl]carbamate

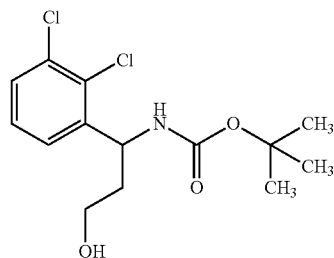

Of the compound from Example 82A, 430 mg (1.29 mmol) were suspended in 5 ml of THF and cooled to 0° C., and the suspension was admixed with 179 μl (1.29 mmol) of triethylamine and also with 184 μl (1.42 mmol) of isobutyl chloroformate and stirred at 0° C. for 1 hour. The suspension was then filtered through a Seitz frit into a cooled flask, and the retained solid was washed with a little THF. The filtrate was added slowly dropwise, with ice cooling, to a solution of 146 mg (3.86 mmol) of sodium borohydride in 0.5 ml of water and stirred at 0° C. for 1 h. For work-up, the reaction mixture was admixed with about 10 ml of saturated aqueous sodium hydrogen carbonate solution and extracted with 50 ml of ethyl acetate. The organic phases were washed once with saturated aqueous sodium hydrogen carbonate solution and once with saturated aqueous sodium chloride solution. They were then dried over sodium sulphate, filtered and concentrated on a rotary evaporator. This gave 419 mg (95% of theory) of the target compound.

LC-MS [Method 3] $R_t$=1.20 min; MS [ESIpos]: m/z=342 (M+Na)⁺

| Example No. | Name | Structure | Analysis LC-MS |
|---|---|---|---|
| 83A | [(tert-Butoxycarbonyl)amino](2,3-difluorophenyl)acetic acid | 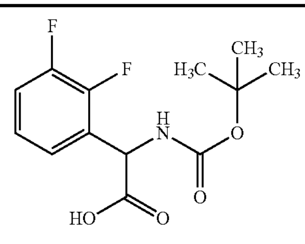 | [Method 2]<br>$R_t$ = 2.97 min;<br>MS [ESIpos]: m/z = 288 (M + H)⁺ |
| 84A | Methyl 3-[(tert-butoxycarbonyl)amino]-3-(2-fluorophenyl)propanoate | 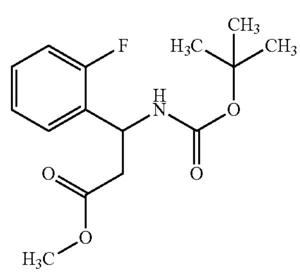 [SMILES: COC(=O)CC(NC(=O)OC(C)(C)C)c1ccccc1F] | [Method 3]<br>$R_t$ = 1.20 min;<br>MS [ESIpos]: m/z = 320 (M + Na)⁺ |

The following compound was obtained similarly:

| Example No. | Name | Structure | Reactant Ex. No. | Analysis LC-MS |
|---|---|---|---|---|
| 86A | tert-Butyl [1-(2,3-difluorophenyl)-2-hydroxyethyl]carbamate | 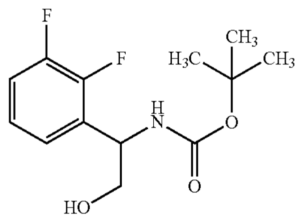 [SMILES: CC(C)(C)OC(=O)NC(CO)c1cccc(F)c1F] | 83A | [Method 2] $R_t$ = 1.94 min; MS [ESIpos]: m/z = 274 (M + H)$^+$ |

Example 87A tert-Butyl [1-(2-fluorophenyl)-3-hydroxypropyl]carbamate

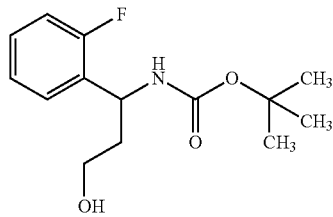 [SMILES: CC(C)(C)OC(=O)NC(CCO)c1ccccc1F]

Of the compound from Example 84A, 580 mg (1.95 mmol) were dissolved in 5 ml of 1,2-dimethoxyethane and the solution was admixed in succession at room temperature with 110.7 mg (2.93 mmol) of sodium borohydride and 16.5 mg (0.39 mmol) of lithium chloride. The mixture was then stirred at 85° C. for 16 h. For work-up, it was admixed with 15 ml of saturated aqueous sodium potassium tartrate solution and extracted three times in each case with 10 ml of ethyl acetate. The combined organic phases were dried over magnesium sulphate, filtered and concentrated on a rotary evaporator. The crude product was purified by chromatography on silica gel (elution: cyclohexane/ethyl acetate 1:1). This gave 383 mg (73% of theory) of the target compound.

LC-MS [Method 4] $R_t$=0.91 min; MS [ESIpos]: m/z=270 (M+H)$^+$ $^1$H-NMR (400 MHz, CDCl$_3$): δ=1.44 (s, 9H), 1.83-2.06 (m, 2H), 3.01 (br.s, 1H), 3.68 (br.s, 2H), 4.98-5.14 (m, 1H), 5.20-5.37 (m, 1H), 7.00-7.09 (m, 1H), 7.09-7.16 (m, 1H), 7.22-7.34 (m, 2H).

Example 88A

3-Amino-3-(2,3-dichlorophenyl)propyl carbamate

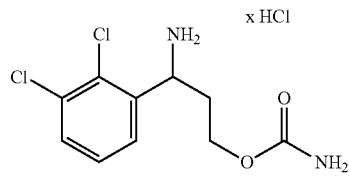 [SMILES: "x HCl" ; NC(=O)OCCC(N)c1cccc(Cl)c1Cl]

In the same way as for Example 63A, from 612 mg of the compound from Example 85A, 572 mg (quant.) of the title compound were obtained as a crude product.

$^1$H NMR (DMSO-d$_6$, 400 MHz): δ=8.58 (br.s, 3H), 7.72 (dd, 2H), 7.53 (t, 1H), 6.53 (br.s, 2H), 4.75-4.87 (m, 1H), 3.92 (dt, 1H), 3.73-3.80 (m, 1H), 2.22-2.32 (m, 1H), 2.07-2.19 (m, 1H).

Example 89A

3-Amino-3-(2-fluorophenyl)propyl carbamate hydrochloride

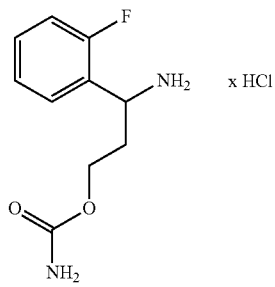 [SMILES: NC(=O)OCCC(N)c1ccccc1F ; "x HCl"]

Starting from 380 mg of the compound from Example 87A, in the same way as in Example 63A, 268 mg (76% of theory) of the target compound were obtained.

$^1$H-NMR (400 MHz, DMSO-d$_6$): δ=2.05-2.21 (m, 1H), 2.25-2.40 (m, 1H), 3.62-3.75 (m, 1H), 3.81-3.93 (m, 1H), 4.50-4.66 (m, 1H), 6.53 (br.s, 2H), 7.23-7.37 (m, 2H), 7.41-7.52 (m, 1H), 7.62-7.75 (m, 1H), 8.64 (br.s, 3H).

Example 90A

3-Amino-3-(2,3-dichlorophenyl)propan-1-ol

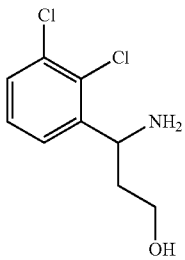 [SMILES: NC(CCO)c1cccc(Cl)c1Cl]

Of the compound from Example 85A, 800 mg (2.50 mmol) were dissolved in 20 ml of dichloromethane and admixed at 0° C. with 1.92 ml (25.0 mmol) of trifluoroacetic acid, then stirred at room temperature for 1 hour. The mixture was freed from the solvent and from the trifluoroacetic acid on a rotary evaporator. The crude product was taken up in 20 ml of toluene and again concentrated on a rotary evaporator under reduced pressure. Purification took place by chromatography on silica gel. By elution with ethyl acetate it was possible to separate off apolar impurities. Elution with dichloromethane/methanol/26% strength ammonia solution (10:1:0.1) gave 673 mg (79% of theory) of the target compound.

LC-MS [Method 3] $R_t$=0.50 min; MS [ESIpos]: m/z=220 $(M+H)^+$

Example 91A

2-Amino-2-[3-(trifluoromethyl)phenyl]ethanol trifluoroacetate

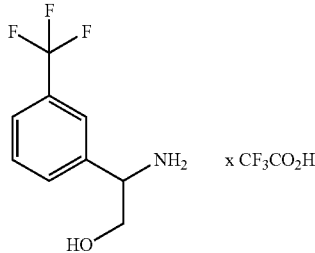

Of the compound from Example 59A, 277 mg (0.91 mmol) were dissolved in 10 ml of dichloromethane and admixed at 0° C. with 0.7 ml (0.91 mmol) of trifluoroacetic acid, then stirred at room temperature for 1 hour. The mixture was concentrated on a rotary evaporator. The crude product was taken up in 20 ml of toluene and again concentrated on a rotary evaporator under reduced pressure. The crude product was purified by preparative HPLC [Method 19]. This gave 124 mg (43% of theory) of the target compound.

LC-MS [Method 5] $R_t$=0.40 min; MS [ESIpos]: m/z=206 $(M+H)^{+(free\ base)}$

1H-NMR (400 MHz, MeOD): δ=3.82 (dd, 2H), 3.94 (dd, 1H), 4.49 (dd, 1H), 7.64-7.71 (m, 1H), 7.71-7.79 (m, 2H), 7.84 (s, 1H).

Example 92A

2-Amino-2-(2,3-difluorophenyl)ethanol hydrochloride

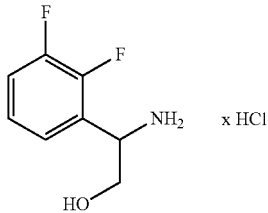 [SMILES: NC(CO)c1cccc(F)c1F ; "x HCl"]

Of the compound from Example 86A, 103 mg (0.38 mmol) were dissolved in 2 ml of dichloromethane and the solution was admixed at room temperature with 1.73 ml of a 4M solution of hydrogen chloride in dioxane, and stirred at room temperature for 2 hours. The mixture was concentrated on a rotary evaporator and the residue was dried in an HV. This gave 79 mg (100% of theory) of the target compound.

LC-MS [Method 4] $R_t$=0.22 min; MS [ESIpos]: m/z=173 $(M+H)^{+(free\ base)}$

Example 93A

Methyl (3RS)-3-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-3-(2-fluorophenyl)propionate

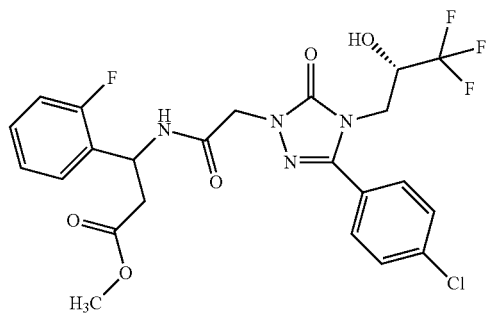 [SMILES: COC(=O)CC(NC(=O)Cn1nc(-c2ccc(Cl)cc2)n(C[C@H](O)C(F)(F)F)c1=O)c1ccccc1F]

Of the compound from Example 8A, 50 mg (0.14 mmol) were dissolved in 1 ml of DMF, admixed with 34 mg (0.18 mmol) of EDC and with 22 mg (0.16 mmol) of HOBt, and stirred at room temperature for 10 minutes. Then 35 mg (0.15 mmol) of methyl 3-amino-3-(2-fluorophenyl)propionate hydrochloride and also 20 μl (0.15 mmol) of triethylamine were added and the mixture was left with stirring at room temperature for 16 h. For work-up, it was admixed with 10 ml of water and extracted with twice 10 ml of ethyl acetate. The combined organic phases were dried over magnesium sulphate, filtered and concentrated on a rotary evaporator. The crude product was purified by preparative HPLC [Method 19]. This gave 47 mg (63% of theory) of the target compound.

LC-MS [Method 3] $R_t$=1.22 min; MS [ESIpos]: m/z=545 $(M+H)^+$

1H-NMR (400 MHz, CDCl₃): δ=2.80-2.96 (m, 2H), 3.53 and 3.58 (2s, 3H), 3.93-4.12 (m, 2H), 4.44-4.82 (m, 3H), 5.05 (t, 1H), 5.56-5.67 (m, 1H), 6.98-7.24 (m, 3H), 7.27-7.37 (m, 2H), 7.47-7.64 (m, 3H), 7.70 (d, 2H). (partial resolution of the duplicated signal set of the diastereomer mixture.)

Example 94A

{3-(4-Chlorophenyl)-5-oxo-4-[(3,3,3-trifluoro-2-hydroxypropyl]-4,5-dihydro-1H-1,2,4-triazol-1-yl}acetic acid

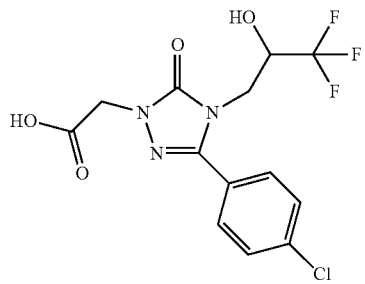 [SMILES: O=C(O)Cn1nc(-c2ccc(Cl)cc2)n(CC(O)C(F)(F)F)c1=O]

Of the compound from Example 5A, 400 mg (1.05 mmol) were reacted in the same way as for Example 8A. This gave 328 mg (85% of theory) of the title compound.

LC/MS [Method 6]: $R_t$=2.01 min; m/z=366 $(M+H)^+$.

Example 95A

Amino[3-(trifluoromethyl)phenyl]acetic acid hydrochloride

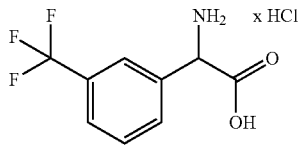 [SMILES: NC(C(=O)O)c1cccc(C(F)(F)F)c1 ; "x HCl"]

A quantity of 1.00 g (3.13 mmol) of N-tert-butoxycarbonyl-2-(3-trifluoromethylphenyl)-DL-glycine was admixed with 15.7 ml of a 4N solution of hydrogen chloride in dioxane and stirred at RT overnight. The volatile components were removed on a rotary evaporator. The residue was dried in an HV. This gave 795 mg (99% of theory) of the title compound.

LC/MS [Method 2]: $R_t$=0.79 min; m/z=220 (M+H)$^+$

Example 96A 2-(Dibenzylamino)-2-[3-(trifluoromethyl)phenyl]ethanol

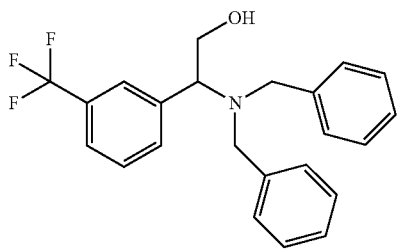 [SMILES: OCC(c1cccc(C(F)(F)F)c1)N(Cc1ccccc1)Cc1ccccc1]

A solution of 1.48 ml (12.4 mmol) of benzyl bromide in 5 ml of ethanol was added dropwise at RT to an initial-charge solution of 795 mg of the compound from Example 95A (3.11 mmol) and 2.15 g (15.5 mmol) of potassium carbonate in 20 ml of ethanol and 5 ml of water. The resulting mixture was heated at reflux overnight. After cooling to RT, the solvent was removed on a rotary evaporator. The residue was admixed with 250 ml of water and extracted three times with ethyl acetate. The combined organic phases were washed twice with saturated aqueous sodium chloride solution, dried over sodium sulphate and concentrated on a rotary evaporator. The residue (1.72 g) contains, according to LC-MS (Method 2), a mixture of N,N-dibenzylamino acid ($R_t$=2.66 min), N,N-dibenzylamino acid ethyl ester (Rt=3.21 min) and N,N-dibenzylamino acid benzyl ester (Rt=3.32 min).

This mixture was dissolved in 50 ml of diethyl ether and added under argon to a 1M solution of lithium aluminium hydride in THF (12.9 ml, 12.9 mmol) which was cooled with ice water. Then the ice bath was removed and the reaction mixture was heated at reflux for 1 h. After cooling to RT, the excess hydride was decomposed with a few drops of water. The mixture was stirred with sodium sulphate for a few minutes and filtered. The filtrate was concentrated on a rotary evaporator. Drying of the residue in an HV gave the title compound (730 mg, 28% of theory).

LC/MS [Method 2]: $R_t$=2.72 min; m/z=386 (M+H)$^+$ $^1$H NMR (DMSO-d$_6$, 400 MHz): δ=7.59-7.70 (m, 4H), 7.29-7.38 (m, 8H), 7.20-7.26 (m, 2H), 4.69 (t, 1H), 3.94-4.05 (m, 2H), 3.72-3.82 (m, 3H), 3.30 (d, 1H) (possibly 1H under the water signal at 3.32 ppm).

Example 97A 2-(Dibenzylamino)-2-[3-(trifluoromethyl)phenyl]acetaldehyde

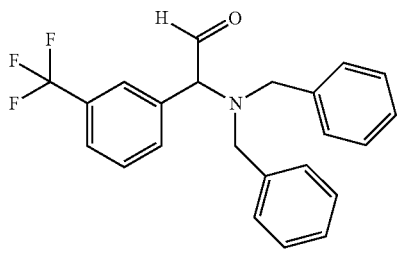 [SMILES: O=CC(c1cccc(C(F)(F)F)c1)N(Cc1ccccc1)Cc1ccccc1]

A 2M solution of oxalyl dichloride in dichloromethane was diluted under argon with 10 ml of dichloromethane and cooled to −78° C. A solution of 221 μl (3.11 mmol) of DMSO in 2 ml of dichloromethane was added dropwise thereto. After 10 min, a solution of 600 mg (1.56 mmol) of the compound from Example 96A in 10 ml of dichloromethane was added dropwise. The mixture was stirred at −78° C. for 15 min, then admixed with 868 μl (6.22 mmol) of triethylamine. After a further 10 min, the cooling bath was removed and the mixture was allowed to warm to RT, then admixed with 20 ml of water and 200 ml of dichloromethane. The aqueous phase was removed, for purification. The organic phase was washed twice with water and then with 5% strength aqueous sodium hydrogen carbonate solution, dried over sodium sulphate and concentrated on a rotary evaporator. The residue was dried in an HV. The title compound (600 mg, quant.) was reacted immediately further as the crude product.

LC/MS [Method 6]: $R_t$=3.18 min; m/z=384 (M+H)$^+$

Example 98A 3-(Dibenzylamino)-1,1,1-trifluoro-3-[3-(trifluoromethyl)phenyl]propan-2-ol

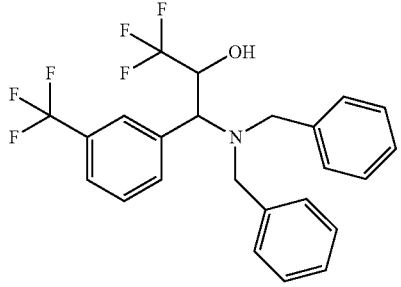 [SMILES: OC(C(c1cccc(C(F)(F)F)c1)N(Cc1ccccc1)Cc1ccccc1)C(F)(F)F]

Of the compound from Example 97A, 300 mg (0.78 mmol) were dissolved in 5 ml of THF, cooled to 0° C., and admixed with 183 μl (1.17 mmol) of (trifluoromethyl)trimethylsilane and then with 39 μl (39 μmol) of a 1M solution of tetra-n-butylammonium fluoride in THF. The cooling bath was removed and the mixture was stirred at RT overnight. Follow-

Example 99A

3-Amino-1,1,1-trifluoro-3-[3-(trifluoromethyl)phenyl]propan-2-ol

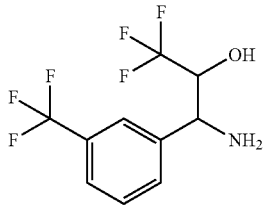 [SMILES: NC(c1cccc(C(F)(F)F)c1)C(O)C(F)(F)F]

In a continuous-flow hydrogenation apparatus (H-Cube from Thales Nano, Budapest, Model HC-2-SS), a solution of 168 mg (0.37 mmol) of the compound from Example 98A in 50 ml of methanol was hydrogenated (conditions: $Pd(OH)_2/C$ cartridge, flow rate of 1 ml/min, RT, standard hydrogen pressure). The reaction mixture was concentrated on a rotary evaporator and the residue was briefly dried in an HV. This was the title compound (93 mg, 92% of theory).

LC/MS [Method 4]: $R_t$=0.63 min+0.65 min (ratio 2:3); each m/z=274 $(M+H)^+$ $^1$H NMR (DMSO-$d_6$, 400 MHz): δ=7.79 (s, 0.4H Diast.1), 7.76 (s, 0.6H Diast.2), 7.72 (d, 0.4H Diast.1), 7.67 (d, 0.6H Diast.2), 7.50-7.64 (m, 2H), 6.40 (br. d, 1H), 4.03-4.21 (m, 2H).

Example 100A tert-Butyl {2-nitro-1-[3-(trifluoromethyl)phenyl]ethyl}-carbamate (non-racemic enantiomer mixture)

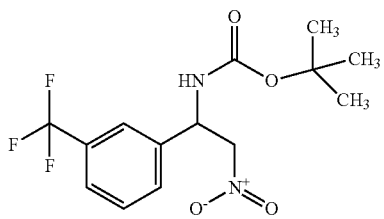 [SMILES: CC(C)(C)OC(=O)NC(C[N+](=O)[O-])c1cccc(C(F)(F)F)c1]

Under argon, 9.75 ml (56 mmol) of N,N-diisopropylethylamine were added slowly dropwise to a suspension of 20.35 g (56 mmol) of zinc(II) trifluoromethanesulphonate in 300 ml of nitromethane at RT and the mixture was stirred for 1 h thereafter. The yellow suspension was subsequently admixed with 13.9 g (84 mmol) of (1R,2S)-(−)-2-(N-methylamino)-1-phenylpropan-1-ol [(−)-N-methylephedrine] and 18.4 g of molecular sieve and stirred for 1 h thereafter, then cooled to −20° C. A dropping funnel was charged with 51.0 g (186.6 mmol) of the compound from Example 11A, with addition of 75 ml of nitromethane. The initial solution underwent spontaneous warming to about 40° C., and the formation of a precipitate began. Thereafter the entire contents of the dropping funnel were added immediately in one portion to the cooled zinc(II) trifluoromethanesulphonate/(−)-N-methylephedrine mixture (no temperature control). The reaction mixture was stirred in a cooling bath (−20° C.) for a further 5 h, and then stirred overnight as well, the temperature slowly rising to 0° C. The work-up was carried out in analogy to variant 1. The crude product was purified using a short silica gel column (eluent dichloromethane/ethanol 100:2). The product-containing fractions were combined and freed from the solvents on a rotary evaporator, and the residue was dried in an HV. The solid obtained was stirred with 200 ml of n-pentane at RT, isolated again by filtration and dried in an HV. This gave 32.4 g of the title compound (approximately 82% purity according to LC-MS, 43% of theory).

Of this product, 5 g were purified via HPLC [Method 20]. This gave 3.87 g of the title compound.

LC/MS [Method 5]: $R_t$=1.15 min; (ES neg.): m/z=333 $(M-H)^-$.

$^1$H-NMR (400 MHz, DMSO-$d_6$): δ=1.36 (s, 9H), 4.77 (dd, 1H), 4.97 (dd, 1H), 5.34-5.44 (m, 1H), 7.59-7.66 (m, 1H), 7.66-7.74 (m, 2H), 7.78 (br. s, 1H), 7.89 (br. d, 1H).

Example 101A tert-Butyl {2-amino-1-[3-(trifluoromethyl)phenyl]ethyl}carbamate (non-racemic enantiomer mixture)

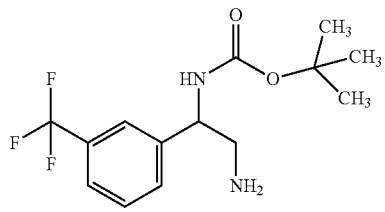 [SMILES: CC(C)(C)OC(=O)NC(CN)c1cccc(C(F)(F)F)c1]

Of the compound from Example 100A, 3.87 g (11.2 mmol) were hydrogenated in 230 ml of methanol with 5 ml of Raney nickel suspension (50% in water) at a hydrogen pressure of 3 bar for 3 h. The reaction mixture was filtered over celite and washed with methanol, and the filtrate was freed from the solvent on a rotary evaporator. The residue was dried in an HV. This gave 3.50 g (99% of theory) of the title compound.

LC/MS [Method 4]: $R_t$=0.76 min; m/z=305 $(M+H)^+$.

$^1$H-NMR (400 MHz, DMSO-$d_6$): δ=1.37 (s, 9H), 2.64-2.76 (m, 2H), 3.33 (s, 2H), 4.45-4.55 (m, 1H), 7.44 (br. d, 1H), 7.51-7.64 (m, 4H).

Example 102A tert-Butyl methyl {1-[3-(trifluoromethyl)phenyl]ethane-1,2-diyl}biscarbamate (non-racemic enantiomer mixture)

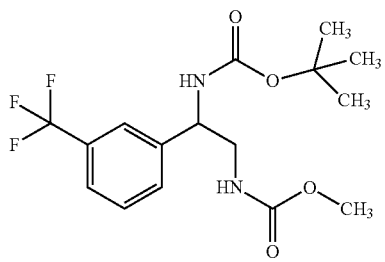 [SMILES: COC(=O)NCC(NC(=O)OC(C)(C)C)c1cccc(C(F)(F)F)c1]

Of the compound from Example 101A, 500 mg (1.64 mmol) were introduced in dichloromethane together with 320 μl (2.30 mmol) of triethylamine, with ice cooling, and 152 μl (1.97 mmol) of methyl chloroformate were added. The ice bath was removed and the mixture was stirred for a further 1 h. The solvent was removed on a rotary evaporator and the residue was purified by preparative HPLC [Method 20]. The product fractions were combined and freed from the solvents on a rotary evaporator, and the residue was dried in an HV. This gave 428 mg (72% of theory) of the title compound.

LC/MS [Method 2]: $R_t$=2.27 min; m/z=363 (M+H)$^+$.

$^1$H-NMR (400 MHz, DMSO-d$_6$): δ=1.36 (s, 9H), 3.19-3.26 (m, 2H), 3.46 (br. s, 3H), 4.64-4.76 (m, 1H), 7.18 (br. t, 1H), 7.49 (br. d, 1H), 7.53-7.65 (m, 4H).

Example 103A tert-Butyl ethyl {1-[3-(trifluoromethyl)phenyl]ethane-1,2-diyl}biscarbamate (non-racemic enantiomer mixture)

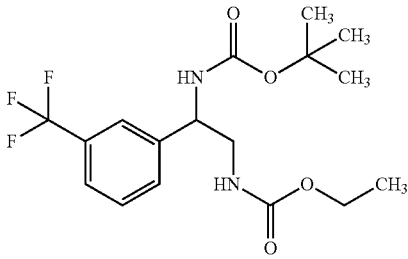 [SMILES: CCOC(=O)NCC(NC(=O)OC(C)(C)C)c1cccc(C(F)(F)F)c1]

A solution of 500 mg (1.64 mmol) of the compound from Example 101A and 321 μl (2.30 mmol) of triethylamine in 15 ml of dichloromethane was cooled to 0° C. and admixed with 189 μl (1.97 mmol) of ethyl chloroformate. The ice bath was removed and the mixture was stirred for a further 1 h. The volatile constituents were removed on a rotary evaporator and the residue was purified by preparative HPLC [Method 20]. The product fractions were combined and freed from the solvents on a rotary evaporator. The residue was dried in an HV. This gave 527 mg (85% of theory) of the title compound.

LC/MS [Method 2]: $R_t$=2.37 min; m/z=377 (M+H)$^+$.

$^1$H-NMR (400 MHz, DMSO-d$_6$): δ=1.08 (t, 3H), 1.35 (s, 9H), 3.18-3.27 (m, 2H), 3.85-3.97 (m, 2H), 4.65-4.77 (m, 1H), 7.13 (br. t, 1H), 7.48 (br. d, 1H), 7.52-7.64 (m, 4H).

Example 104A tert-Butyl {2-[(ethylcarbamoyl)amino]-1-[3-(trifluoromethyl)phenyl]ethyl}carbamate (non-racemic enantiomer mixture)

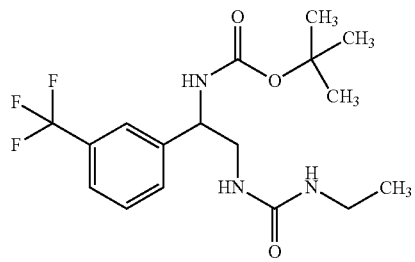 [SMILES: CCNC(=O)NCC(NC(=O)OC(C)(C)C)c1cccc(C(F)(F)F)c1]

A solution of 500 mg (1.64 mmol) of the compound from Example 101A in 15 ml of dichloromethane was admixed at 0° C. with 260 μl (3.29 mmol) of ethyl isocyanate. The ice bath was removed and the reaction mixture was stirred for a further 1 h. Then all of the volatile constituents were removed on a rotary evaporator. The residue was purified by preparative HPLC [Method 23]. The product fraction was freed from the solvent on a rotary evaporator. Drying of the residue in an HV gave 546 mg (89% of theory) of the title compound.

LC/MS [Method 2]: $R_t$=2.16 min; m/z=376 (M+H)$^+$.

$^1$H-NMR (400 MHz, DMSO-d$_6$): δ=0.95 (t, 3H), 1.35 (s, 9H), 2.91-3.04 (m, 2H), 3.08-3.19 (m, 1H), 3.21-3.31 (m, 1H), 4.57-4.66 (m, 1H), 5.88 (br. t, 1H), 5.96 (br. t, 1H), 7.48-7.64 (m, 5H).

Example 105A

2-Bromoethyl tert-butyl {1-[3-(trifluoromethyl)phenyl]ethane-1,2-diyl}biscarbamate (non-racemic enantiomer mixture)

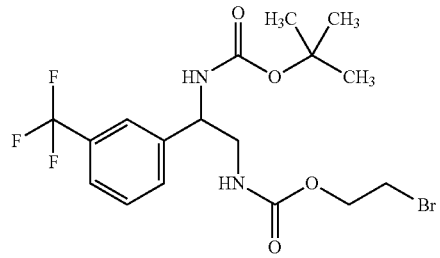 [SMILES: CC(C)(C)OC(=O)NC(CNC(=O)OCCBr)c1cccc(C(F)(F)F)c1]

A solution of 272 mg (0.89 mmol) of the compound from Example 101A and 171 μl (0.98 mmol) of N,N-diisopropylethylamine in 3 ml of acetonitrile was admixed dropwise with a solution of 106 μl (0.98 mmol) of 2-bromoethyl chloroformate in 2 ml of acetonitrile. For work-up, after 10 minutes, ethyl acetate and saturated aqueous sodium hydrogen carbonate solution were added. The organic phase was separated, washed again with saturated aqueous sodium hydrogen carbonate solution, dried over sodium sulphate and freed from the volatile constituents on a rotary evaporator. Drying of the residue in an HV gave 352 mg (82% of theory) of the title compound.

LC/MS [Method 4]: $R_t$=1.15 min; m/z=455/457 (M+H)$^+$.

$^1$H-NMR (400 MHz, DMSO-$d_6$): δ=1.36 (s, 9H), 3.25 (t, 2H), 3.56 (t, 2H), 4.09-4.28 (m, 2H), 4.66-4.79 (m, 1H), 7.39 (br. t, 1H), 7.45-7.69 (m, 5H).

Example 106A tert-Butyl {2-(2-oxo-1,3-oxazolidin-3-yl)-1-[3-(trifluoromethyl)phenyl]ethyl}carbamate (non-racemic enantiomer mixture)

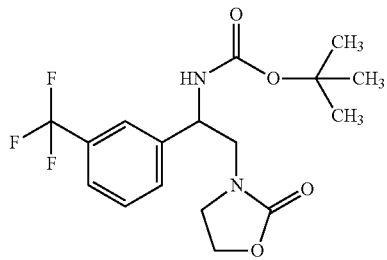 [SMILES: CC(C)(C)OC(=O)NC(CN1CCOC1=O)c1cccc(C(F)(F)F)c1]

A solution of 352 mg (0.77 mmol) of the compound from Example 105A in 10 ml of DMF was admixed with 34 mg (0.85 mmol) of sodium hydride (60% in mineral oil). The reaction mixture was stirred at RT overnight. For purification, 2 ml of 1N hydrochloric acid were added and the entire mixture was purified by preparative HPLC [Method 23]. The product fractions were combined and freed from the solvents on a rotary evaporator. Drying of the residue in an HV gave 242 mg (84% of theory) of the title compound.

LC/MS [Method 3]: $R_t$=1.19 min; m/z=275 (M+H-BOC)$^+$.
$^1$H-NMR (400 MHz, DMSO-$d_6$): δ=1.37 (s, 9H), 3.34-3.44 (m, 2H), 3.45-3.62 (m, 2H), 4.12-4.23 (m, 2H), 4.85-4.95 (m, 1H), 7.55-7.66 (m, 3H), 7.69 (d, 1H), 7.78 (br. s., 1H).

Example 107A tert-Butyl {2-(2-oxoimidazolidin-1-yl)-1-[3-(trifluoromethyl)phenyl]ethyl}carbamate (non-racemic enantiomer mixture)

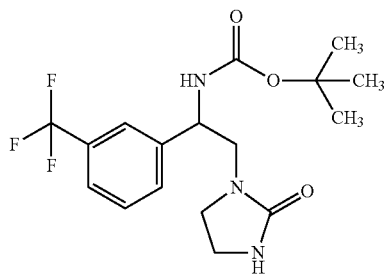 [SMILES: CC(C)(C)OC(=O)NC(CN1CCNC1=O)c1cccc(C(F)(F)F)c1]

An ice-cooled solution of 302 mg (0.99 mmol) of the compound from Example 101A in 10 ml of dichloromethane was admixed dropwise with 99 μl (1.09 mmol) of 2-bromoethyl isocyanate. After 10 minutes, the ice bath was removed and the mixture was stirred for a further 5 min. All of the volatile components were removed on a rotary evaporator. The residue was taken up in 5 ml of anhydrous THF and admixed, with ice cooling, with 44 mg of sodium hydride (60% in mineral oil, 1.09 mmol). After 2 h, 1 ml of 1M hydrochloric acid was added and the reaction mixture was freed from the solvent on a rotary evaporator. The aqueous residue was dissolved in DMSO and purified by preparative HPLC [Method 23]. The product fraction was freed from the solvents on a rotary evaporator. Drying of the residue in an HV gave 210 mg (38% of theory) of the title compound.

LC/MS [Method 4]: $R_t$=0.84+0.99 min; m/z=374 (M+H)$^+$.
1H-NMR (400 MHz, DMSO-$d_6$): δ=1.36 (br. s., 9H), 3.09-3.18 (m, 2H), 3.18-3.32 (m, 4H), 4.74-4.86 (m, 1H), 6.25-6.39 (br. s, 1H), 7.44-7.76 (m, 5H).

Example 108A tert-Butyl {2-(methylsulphinyl)-1-[2-(trifluoromethyl)phenyl]ethyl}carbamate (racemic diastereomer mixture)

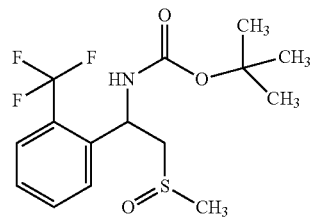 [SMILES: CS(=O)CC(NC(=O)OC(C)(C)C)c1ccccc1C(F)(F)F]

A solution of 780 μl (11.0 mmol) of dimethyl sulphoxide in 30 ml of THF was admixed slowly at −78° C. with 6.9 ml of n-butyllithium solution (1.6M in hexane, 11.0 mmol). The resulting suspension was stirred at −78° C. for 30 min and then added to a solution, cooled to −78° C. beforehand, of 1 g (3.66 mmol) of the compound from Example 15A in 30 ml of THF. The reaction mixture was stirred at −78° C. for 30 min more and then slowly warmed to RT. After 30 min at RT, it was again cooled to −20° C. and the reaction was halted by addition of 20 ml of 10% strength aqueous ammonium chloride solution. The mixture was diluted with ethyl acetate. The organic phase was separated, washed twice with water and once with saturated aqueous sodium chloride solution, dried over sodium sulphate and freed from the volatile constituents on a rotary evaporator. The residue was purified by preparative HPLC [Method 20]. The product fraction was freed from the solvents on a rotary evaporator. Drying of the residue in an HV gave 952 mg (74% of theory) of the title compound as a diastereomer mixture.

LC/MS [Method 5]: $R_t$=0.92+0.95 min; m/z=352 (M+H)$^+$.

Example 109A tert-Butyl {2-(methylsulphanyl)-1-[2-(trifluoromethyl)phenyl]ethyl}carbamate (racemate)

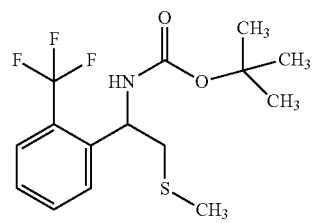 [SMILES: CSCC(NC(=O)OC(C)(C)C)c1ccccc1C(F)(F)F]

Of the compound from Example 108A, 400 mg (1.14 mmol), and 567 mg (2.16 mmol) of triphenylphosphine, were dissolved in 14 ml of tetrachloromethane. The reaction mixture was stirred overnight at reflux temperature and then freed from the solvent on a rotary evaporator. The residue was purified by preparative HPLC [Method 20]. The product fraction was freed from the solvent on a rotary evaporator. Drying in an HV gave 340 mg (85% of theory) of the title compound.

LC/MS [Method 4]: $R_t$=1.20 min; m/z=336 (M+H)$^+$.

1H-NMR (400 MHz, DMSO-d$_6$): δ=1.36 (s, 9H), 2.08 (s, 3H), 2.62 (dd, 1H), 2.71 (dd, 1H), 5.04-5.14 (m, 1H), 7.47 (t, 1H), 7.58 (br. d, 1H), 7.64-7.72 (m, 2H), 7.76 (br. d, 1H).

Example 110A tert-Butyl [(2-chlorophenyl)(phenylsulphonyl)methyl]carbamate

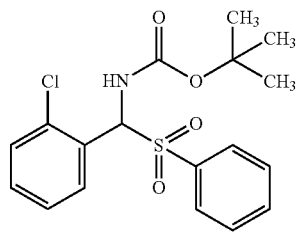 [SMILES: CC(C)(C)OC(=O)NC(c1ccccc1Cl)S(=O)(=O)c1ccccc1]

Quantities of 2.78 g (23.7 mmol) of tert-butyl carbamate and 7.79 g (47.4 mmol) of benzenesulphinic acid sodium salt were introduced in 55 ml of methanol/water 1:2 at RT and admixed with 5 g (35.6 mmol) of 2-chlorobenzaldehyde and then with 1.78 ml (47.1 mmol) of formic acid. The mixture was stirred at RT for 2 days. The white solid precipitated was filtered off with suction and washed in succession twice each with water and diethyl ether. Drying in an HV gave 5.77 g (42% of theory) of the title compound.

$^1$H-NMR (400 MHz, DMSO-d$_6$): δ=1.21 (s, 9H), 6.54 (d, 1H), 7.42-7.58 (m, 3H), 7.62-7.70 (m, 2H), 7.73-7.79 (m, 1H), 7.82 (d, 2H), 7.92-8.03 (m, 1H), 8.87 (d, 1H).

Example 111A tert-Butyl [(E)-(2-chlorophenyl)methylene]carbamate

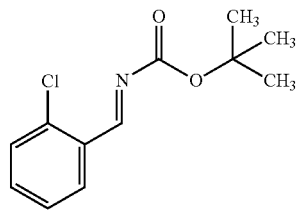 [SMILES: CC(C)(C)OC(=O)/N=C/c1ccccc1Cl]

A quantity of 12.53 g (90.7 mmol) of potassium carbonate was heated through in an HV and then cooled under an argon atmosphere. Quantities of 140 ml of anhydrous THF and 5.77 g (15.1 mmol) of the compound from Example 110A were added and the mixture was stirred under an argon atmosphere at reflux temperature for 16 h. After cooling to RT, the reaction mixture was filtered over celite. The solid was washed with a little THF. The entire filtrate was freed from the solvent on a rotary evaporator. The oily residue was dried in an HV. This gave 3.55 g (98% of theory) of the title compound.

$^1$H-NMR (400 MHz, DMSO-d$_6$): δ=1.52 (s, 9H), 7.47-7.53 (m, 1H), 7.61-7.69 (m, 2H), 8.05 (d, 1H), 9.10 (s, 1H).

Example 112A tert-Butyl [1-(2-chlorophenyl)-2-nitroethyl]carbamate (racemate)

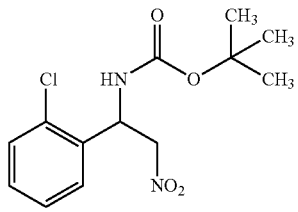 [SMILES: CC(C)(C)OC(=O)NC(C[N+](=O)[O-])c1ccccc1Cl]

A quantity of 16 ml (295.41 mmol) of nitromethane was admixed with 436 μl (2.50 mmol) of N,N-diisopropylethylamine and the yellow solution was stirred at RT for 1 h. Then 2.0 g (8.34 mmol) of the compound from Example 111A were added and the mixture was stirred overnight at RT. All of the volatile constituents were removed on a rotary evaporator. The residue was dissolved in 9 ml of isopropanol in the heat of boiling, and the solution was then cooled to 0° C. The white solid precipitated was filtered off with suction and washed with a little cold isopropanol. Drying in an HV gave 1.18 g (47% of theory) of the title compound.

The mother liquor was concentrated under reduced pressure and the residue was purified by preparative HPLC [Method 23]. The product fraction was freed from the solvents on a rotary evaporator and dried in an HV. This gave a further 0.90 g (36% of theory) of the title compound.

LC/MS [Method 2]: $R_t$=2.30 min; m/z=301 (M+H)$^+$.

$^1$H-NMR (400 MHz, DMSO-d$_6$): δ=1.35 (s, 9H), 4.62 (dd, 1H), 4.81 (dd, 1H), 5.73 (dt, 1H), 7.32-7.44 (m, 2H), 7.49 (dd, 1H), 7.54 (dd, 1H), 8.00 (d, 1H).

Example 113A tert-Butyl [2-amino-1-(2-chlorophenyl)ethyl]carbamate

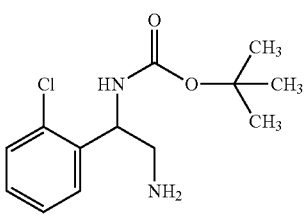 [SMILES: CC(C)(C)OC(=O)NC(CN)c1ccccc1Cl]

In the same way as for Example 33A, from 1.0 g (3.33 mmol) of the compound from Example 112A, the title compound was obtained: 993 mg (quantitative).

LC/MS [Method 4]: $R_t$=0.68 min; m/z=271 (M+H)$^+$.

$^1$H-NMR (400 MHz, DMSO-d$_6$): δ=1.36 (s, 9H), 1.65 (br. s., 2H), 2.58 (dd, 1H), 2.72 (dd, 1H), 4.79-4.87 (m, 1H), 7.24 (dt, 1H), 7.32 (t, 1H), 7.35-7.40 (m, 2H), 7.45 (br. d, 1H).

Example 114A tert-Butyl [2-(carbamoylamino)-1-(2-chlorophenyl)ethyl]carbamate

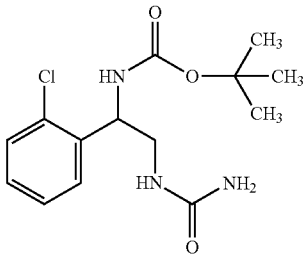 [SMILES: CC(C)(C)OC(=O)NC(CNC(N)=O)c1ccccc1Cl]

Of the compound from Example 113A, 330 mg (1.15 mmol) in 12 ml of water/methanol 1:1 were admixed at RT with 279 mg (3.44 mmol) of potassium cyanate. The mixture was heated at 40° C. for 1 h and then admixed with 1.15 ml of 1M hydrochloric acid (1.15 mmol) and stirred overnight at RT. A further 93 mg (1.14 mmol) of potassium cyanate were added and the mixture was stirred further at RT for 3 h. The entire reaction mixture was purified by preparative HPLC [Method 10]. The product fraction was freed from the solvents on a rotary evaporator. Drying of the residue in an HV gave 292 mg (80% of theory) of the title compound.

LC/MS [Method 4]: $R_t$=0.86 min; m/z=314 (M+H)$^+$.

$^1$H-NMR (400 MHz, DMSO-d$_6$): δ=1.35 (s, 9H), 3.03-3.13 (m, 1H), 3.19-3.29 (m, 1H), 4.84-4.94 (m, 1H), 5.56 (br. s, 2H), 6.01-6.08 (m, 1H), 7.26 (dt, 1H), 7.33 (t, 1H), 7.37-7.43 (m, 2H), 7.52 (br. d, 1H).

Example 115A tert-Butyl {1-(2-chlorophenyl)-2-[(methylsulphonyl)amino]ethyl}carbamate

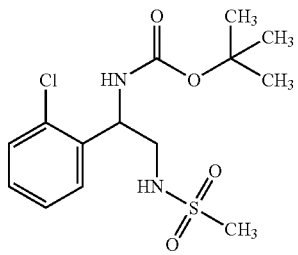 [SMILES: CC(C)(C)OC(=O)NC(CNS(C)(=O)=O)c1ccccc1Cl]

A solution of 330 mg (1.15 mmol) of the compound from Example 113A in 7 ml of pyridine was admixed at RT with 177 μl (2.29 mmol) of methanesulphonyl chloride. After 1 h the volatile constituents were removed on a rotary evaporator. The residue is purified by preparative HPLC [Method 23]. The product fraction was freed from the solvents on a rotary evaporator. Drying of the residue in an HV gave 312 mg (78% of theory) of the title compound.

LC/MS [Method 4]: $R_t$=0.96 min; m/z=349 (M+H)$^+$.

$^1$H-NMR (400 MHz, DMSO-d$_6$): δ=1.37 (s, 9H), 2.82 (s, 3H), 3.08 (ddd, 1H), 3.14-3.23 (m, 1H), 5.01-5.10 (m, 1H), 7.21 (t, 1H), 7.29 (dt, 1H), 7.35 (br. t, 1H), 7.41 (dd, 1H), 7.44 (br. d, 1H), 7.50 (dd, 1H).

Example 116A tert-Butyl {1-(2-chlorophenyl)-2-[(ethylsulphonyl)amino]ethyl}carbamate

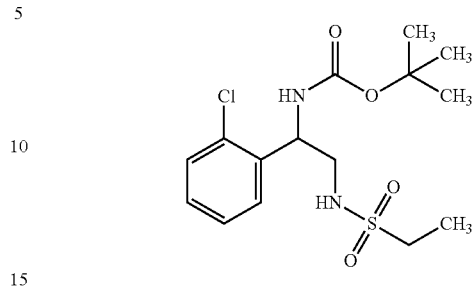

From 330 mg (1.15 mmol) of the compound from Example 113A and 217 μl (2.29 mmol) of ethanesulphonyl chloride, in the same way as for Example 115A, 263 mg (63% of theory) of the title compound were obtained.

LC/MS [Method 4]: $R_t$=1.01 min; m/z=363 (M+H)$^+$.

$^1$H-NMR (400 MHz, DMSO-d$_6$): δ=1.14 (t, 3H), 1.37 (s, 9H), 2.84-3.00 (m, 2H), 3.07 (ddd, 1H), 3.12-3.22 (m, 1H), 4.99-5.08 (m, 1H), 7.23-7.31 (m, 2H), 7.32-7.38 (m, 1H), 7.41 (dd, 1H), 7.42 (br. d, 1H), 7.49 (dd, 1H).

Example 117A tert-Butyl [1-(2-chlorophenyl)-2-(methylsulphonyl)ethyl]carbamate

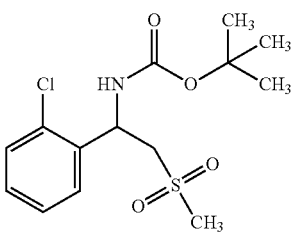 [SMILES: CC(C)(C)OC(=O)NC(CS(C)(=O)=O)c1ccccc1Cl]

A solution of 1 g (10.6 mmol) of (methylsulphonyl)methane in 30 ml of THF was cooled to −78° C. and admixed slowly with 6.65 ml of n-butyllithium solution (1.6M in hexane, 10.6 mmol). After 30 min at −78° C., the suspension obtained was added to a solution, cooled to −78° C. beforehand, of 850 mg (3.55 mmol) of the compound from Example 111A in 20 ml of THF. The reaction mixture was stirred at −78° C. for a further 30 min and then slowly warmed to RT. After 30 min, it was cooled to −20° C. again and the reaction was halted by addition of 20 ml of 10% strength aqueous ammonium chloride solution. The mixture was diluted with ethyl acetate. The organic phase was separated and washed twice with water and once with saturated aqueous sodium chloride solution. The organic phase was dried over sodium sulphate, filtered and freed from the solvent on a rotary evaporator. The residue was stirred with 10 ml of methanol/water 10:1 and the solid was filtered off with suction. The slightly yellowish solid was stirred with 20 ml of pentane/isopropanol 5:1, then filtered off with suction again. Drying in an HV gave 800 mg (55% of theory) of the title compound (82% purity according to LC/MS).

LC/MS [Method 3]: $R_t$=1.08 min; m/z=234 (M+H−BOC)$^+$.

$^1$H-NMR (400 MHz, DMSO-d$_6$): δ=1.36 (s, 9H), 3.01 (s, 3H), 3.19-3.28 (m, 1H), 3.43-3.55 (m, 1H), 5.47-5.54 (m, 1H), 7.28-7.35 (m, 1H), 7.38 (t, 1H), 7.45 (d, 1H), 7.51 (d, 1H), 7.82 (br. d, 1H).

Example 118A tert-Butyl [1-(2-chlorophenyl)-2-(methylsulphinyl)ethyl]carbamate (racemic diastereomer mixture)

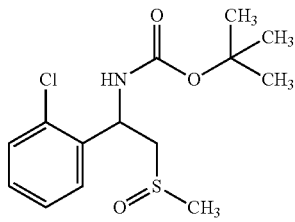 [SMILES: CS(=O)CC(NC(=O)OC(C)(C)C)c1ccccc1Cl]

In the same way as for Example 108A, from 850 mg (3.55 mmol) of the compound from Example 111A, the title compound was obtained: 697 mg (62% of theory).

LC/MS [Method 4]: $R_t$=0.87+0.88 min; m/z=318 (M+H)$^+$.
$^1$H-NMR (400 MHz, DMSO-d$_6$): δ=1.36 (s, 9H), 2.55 (br. s., "1.5H" (3H first diastereomer)), 2.64 (s, "1.5H" (3H second diastereomer)), 2.81-3.15 (m, 2H), 5.22-5.38 (m, 1H), 7.31 (br. t, 1H), 7.35-7.50 (m, 3H), 7.54 (br. d, 1H), 7.75-7.87 (m, 1H).

Example 119A tert-Butyl [1-(2-chlorophenyl)-2-(methylsulphanyl)ethyl]carbamate (racemate)

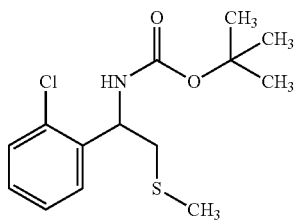 [SMILES: CSCC(NC(=O)OC(C)(C)C)c1ccccc1Cl]

In the same way as for Example 109A, 100 mg (0.32 mmol) of the compound from Example 118A were reduced. This gave 44 mg (45% of theory) of the title compound.

LC/MS [Method 5]: $R_t$=1.20 min; m/z=302 (M+H)$^+$.
$^1$H-NMR (400 MHz, DMSO-d$_6$): δ=1.37 (s, 9H), 2.11 (s, 3H), 2.59-2.72 (m, 2H), 5.05-5.17 (m, 1H), 7.27 (dt, 1H), 7.35 (t, 1H), 7.41 (dd, 1H), 7.49 (dd, 1H), 7.57 (br. d, 1H).

Example 120A tert-Butyl {2-(methylsulphonyl)-1-[2-(trifluoromethyl)phenyl]ethyl}carbamate

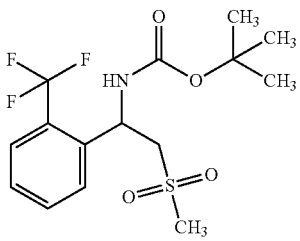 [SMILES: CC(C)(C)OC(=O)NC(CS(C)(=O)=O)c1ccccc1C(F)(F)F]

From 1.03 g (11.0 mmol) of (methylsulphonyl)methane and 1.0 g (3.7 mmol) of the compound from Example 15A, in the same way as for Example 117A, 1.11 g (82% of theory) of the title compound were obtained.

LC/MS [Method 3]: $R_t$=1.12 min; m/z=268 (M+H-BOC)$^+$.
$^1$H-NMR (400 MHz, DMSO-d$_6$): δ=1.35 (s, 9H), 2.99 (s, 3H), 3.19 (br. d, 1H), 3.58 (dd, 1H), 5.53 (br. t, 1H), 7.50 (t, 1H), 7.67-7.80 (m, 3H), 7.85 (br. d, 1H).

Example 121A tert-Butyl {2-(methylsulphonyl)-1-[3-(trifluoromethyl)phenyl]ethyl}carbamate

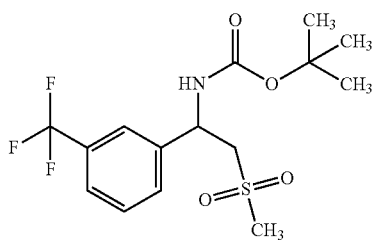 [SMILES: CC(C)(C)OC(=O)NC(CS(C)(=O)=O)c1cccc(C(F)(F)F)c1]

From 1.50 g (15.9 mmol) of (methylsulphonyl)methane and 1.45 g (5.31 mmol) of the compound from Example 11A, using the same process as for Example 117A, 535 mg (27% of theory) of the title compound were obtained.

LC/MS [Method 4]: $R_t$=1.02 min; m/z=368 (M+H)$^+$.
$^1$H-NMR (400 MHz, DMSO-d$_6$): δ=1.36 (s, 9H), 2.99 (s, 3H), 3.48-3.64 (m, 2H), 5.17 (m, 1H), 7.56-7.70 (m, 3H), 7.70-7.78 (m, 2H).

Example 122A tert-Butyl {2-(dimethylsulphamoyl)-1-[3-(trifluoromethyl)phenyl]ethyl}carbamate

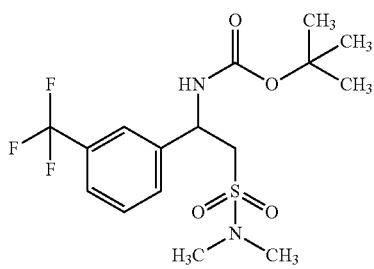 [SMILES: CN(C)S(=O)(=O)CC(NC(=O)OC(C)(C)C)c1cccc(C(F)(F)F)c1]

A solution of 676 mg (5.49 mmol) of N,N-dimethylmethanesulphonamide in 10 ml of THF was admixed slowly at −78° C. with 3.43 ml (5.49 mmol) of 1.6M n-butyllithium solution in hexane versetzt. After 30 min at −78° C., the colourless solution obtained was added to a solution, cooled to −78° C. beforehand, of 500 mg (1.83 mmol) of the compound from Example 11A in 10 ml of THF. The reaction mixture was stirred at −78° C. for 30 min more and then slowly warmed to RT. After 30 min it was cooled to −20° C. again and the reaction was halted by addition of 5 ml of 10% strength aqueous ammonium chloride solution. The mixture was diluted with ethyl acetate and then washed twice with water and once with saturated aqueous sodium chloride solution. The organic phase was dried over sodium sulphate and freed from the solvent on a rotary evaporator. The residue was purified by preparative HPLC [Method 23]. The product fraction was freed from the solvent on a rotary evaporator. Drying of the residue in an HV gave 296 mg (41% of theory) of the title compound.

LC/MS [Method 3]: $R_t$=1.28 min; m/z=297 (M+H-BOC)$^+$.

$^1$H-NMR (400 MHz, DMSO-d$_6$): δ=1.36 (s, 9H), 2.76 (s, 6H), 3.33 (dd, 1H), 3.53 (dd, 1H), 5.01-5.11 (m, 1H), 7.56-7.69 (m, 4H), 7.71 (br. s, 1H).

Example 123A tert-Butyl methyl [1-(2,3-dichlorophenyl)ethane-1,2-diyl]biscarbamate

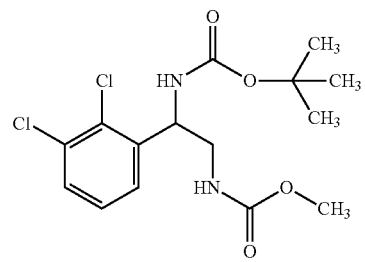 [SMILES: COC(=O)NCC(NC(=O)OC(C)(C)C)c1cccc(Cl)c1Cl]

A solution of 192 mg (0.63 mmol) of the compound from Example 40A in 5.7 ml of dichloromethane together was admixed at RT with 123 µl (0.88 mmol) of triethylamine and then with 58 µl (0.75 mmol) of methyl chloroformate. The reaction mixture was stirred at RT overnight and then all of the volatile constituents were removed on a rotary evaporator. The residue was taken up in DMSO and purified by preparative HPLC [Method 20]. The product fraction was freed from the solvents on a rotary evaporator and dried in an HV. This gave 167 mg (73% of theory) of the title compound.

LC/MS [Method 3]: R$_t$=1.22 min; m/z=263 (M+H-BOC)$^+$.

$^1$H-NMR (400 MHz, DMSO-d$_6$): δ=3.14-3.27 (m, 2H), 3.48 (s, 3H), 5.07 (br. q, 1H), 7.13-7.21 (m, 1H), 7.32-7.38 (m, 1H), 7.38-7.44 (m, 1H), 7.47 (br. d, 1H), 7.53 (dd, 1H).

Example 124A tert-Butyl ethyl [1-(2,3-dichlorophenyl)ethane-1,2-diyl]biscarbamate

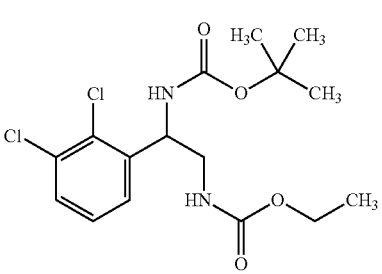 [SMILES: CCOC(=O)NCC(NC(=O)OC(C)(C)C)c1cccc(Cl)c1Cl]

From 192 mg (629 µmol) of the compound from Example 40A and 72 µl (755 µmol) of ethyl chloroformate, in the same way as for Example 123A, 184 mg (78% of theory) of the title compound were prepared.

LC/MS [Method 3]: R$_t$=1.29 min; ES$^+$: m/z=277 (M+H-BOC)$^+$. ES$^-$: m/z=375 (M-H)$^-$ $^1$H-NMR (400 MHz, DMSO-d$_6$): δ=7.31-7.57 (m, 4H), 7.12 (br. t., 1H), 5.07 (q, 1H), 3.88-3.98 (m, 2H), 3.12-3.28 (m, 2H), 1.35 (m, 9H), 1.10 (t, 3H).

Example 125A tert-Butyl [2-(carbamoylamino)-1-(2,3-dichlorophenyl)ethyl]carbamate

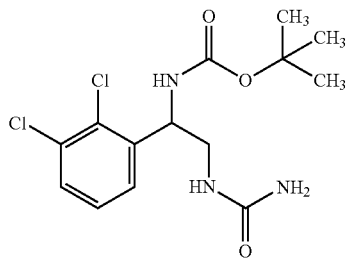 [SMILES: CC(C)(C)OC(=O)NC(CNC(N)=O)c1cccc(Cl)c1Cl]

Of the compound from Example 40A, 192 mg (0.63 mmol) were introduced in 11 ml of water/methanol 1:2 and admixed in succession at RT with 0.63 ml (0.63 mmol) of 1M hydrochloric acid and 166 mg (2.05 mmol) of potassium cyanate. The reaction mixture was stirred at RT overnight and then freed from the methanol on a rotary evaporator. The residue was taken up in DMSO and purified by preparative HPLC [Method 20]. The product fraction was concentrated on a rotary evaporator. Drying of the residue in an HV gave 177 mg (73% of theory) of the title compound.

LC/MS [Method 3]: R$_t$=1.05 min; m/z=348 (M+H)$^+$.

$^1$H-NMR (400 MHz, DMSO-d$_6$): δ=1.34 (s, 9H), 3.04-3.19 (m, 1H), 3.19-3.30 (m, 1H), 4.86-4.99 (m, 1H), 5.57 (br. s., 2H), 6.02-6.16 (br.m, 1H), 7.31-7.42 (m, 2H), 7.47-7.57 (m, 1H), 7.61 (d, 1H).

Example 126A tert-Butyl {1-(2,3-dichlorophenyl)-2-[(ethylcarbamoyl)amino]ethyl}carbamate

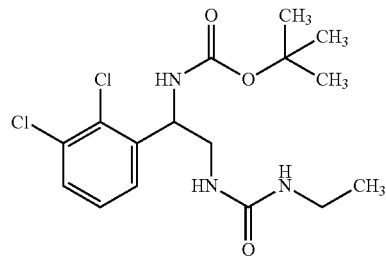 [SMILES: CCNC(=O)NCC(NC(=O)OC(C)(C)C)c1cccc(Cl)c1Cl]

A solution of 192 mg (0.63 mmol) of the compound from Example 40A in 5.7 ml of dichloromethane was admixed at RT with 100 µl (1.26 mmol) of ethyl isocyanate. The reaction mixture was stirred overnight at RT and then freed from the solvent on a rotary evaporator. The residue was taken up in DMSO and purified by preparative HPLC [Method 20]. The product fraction was freed from the solvents on a rotary evaporator. Drying of the residue in an HV gave 173 mg (73% of theory) of the title compound.

LC/MS [Method 3]: R$_t$=1.16 min; m/z=276 (M+H-BOC)$^+$.

$^1$H-NMR (400 MHz, DMSO-d$_6$): δ=0.96 (t, 3H), 1.34 (s, 9H), 2.89-3.07 (m, 2H), 3.07-3.19 (m, 1H), 3.23-3.32 (m, 2H), 4.88-4.99 (m, 1H), 5.88-6.01 (m, 2H), 7.31-7.43 (m, 2H), 7.48-7.56 (m, 1H), 7.60 (br. d, 1H).

Example 127A

3-Amino-3-[3-(trifluoromethyl)phenyl]propan-1-ol

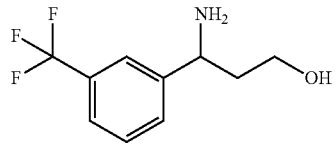 [SMILES: NC(CCO)c1cccc(C(F)(F)F)c1]

With ice cooling and under argon, 10.9 ml (10.94 mmol) of borane-tetrahydrofuran complex (1M in THF) were introduced. Then 850 mg (3.65 mmol) of 3-amino-3-[3-(trifluoromethyl)phenyl]propanoic acid were added. After 5 minutes, the cooling bath was removed and the mixture was stirred at RT overnight and for 4 h at reflux. After cooling to RT, pieces of ice were added until the evolution of gas came to an end. The mixture was rendered alkaline with 1M aqueous sodium hydroxide solution, diluted with water to a volume of approximately 150 ml, and extracted three times with dichloromethane. The combined organic phases were dried over sodium sulphate, filtered and freed from the solvent on a rotary evaporator. Drying in an HV gave 744 mg (85% of theory) of the title compound in 92% purity.

LC/MS [Method 4]: $R_t$=0.45 min; m/z=220 (M+H)$^+$.

$^1$H-NMR (400 MHz, DMSO-$d_6$): δ=7.71 (s, 1H), 7.60-7.67 (m, 1H), 7.49-7.58 (m, 2H), 4.55 (br.s, 1H), 3.97-4.04 (dd, 1H), 3.34-3.50 (m, 2H), 2.00 (br. s., 2H), 1.59-1.78 (m, 2H).

Example 128A tert-Butyl {3-hydroxy-1-[3-(trifluoromethyl)phenyl]propyl}carbamate

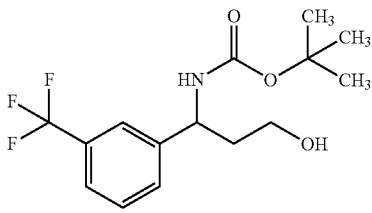 [SMILES: CC(C)(C)OC(=O)NC(CCO)c1cccc(C(F)(F)F)c1]

A solution of 744 mg (3.39 mmol) of the compound from Example 127A in 30 ml of dichloromethane was admixed with 1.56 ml (6.79 mmol) of di-tert-butyl dicarbonate and stirred at RT for 3 h. For work-up, the reaction mixture was diluted with 100 ml of ethyl acetate and washed in succession twice each with 1M hydrochloric acid, saturated aqueous sodium hydrogen carbonate solution and saturated aqueous sodium chloride solution. The organic phase was dried over sodium sulphate and freed from the solvent on a rotary evaporator. The residue was purified by preparative HPLC [Method 23]. The product fraction was freed from the solvents on a rotary evaporator and the residue was dried in an HV. This gave 870 mg (80% of theory) of the title compound.

LC/MS [Method 5]: $R_t$=1.03 min; m/z=320 (M+H)$^+$.

$^1$H-NMR (400 MHz, DMSO-$d_6$) (principal rotamer): δ=7.52-7.67 (m, 4H), 7.49 (d, 1H), 4.70 (q, 1H), 4.53 (t, 1H), 3.35-3.45 (m, 1H), 3.23-3.30 (m, 1H), 1.79-1.90 (m, 1H), 1.64-1.78 (m, 1H), 1.44 (s, 9H).

Example 129A

3-Amino-3-[3-(trifluoromethyl)phenyl]propyl carbamate

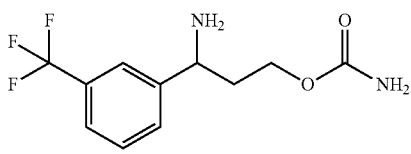 [SMILES: NC(=O)OCCC(N)c1cccc(C(F)(F)F)c1]

Of the compound from Example 128A, 827 mg (2.59 mmol) were introduced in 100 ml of acetonitrile. A solution of 676 μl (7.77 mmol) of chlorosulphonyl isocyanate in 10 ml of acetonitrile was added dropwise at −15° C. After 5 min, 50 ml of water were added and the mixture was then stirred at 60° C. overnight. The reaction mixture was admixed with saturated aqueous sodium hydrogen carbonate solution and then extracted three times with ethyl acetate. The combined organic phases were dried over sodium sulphate and freed from the solvent on a rotary evaporator. Drying of the residue in an HV gave 678 mg (quant.) of the title compound.

LC/MS [Method 2]: $R_t$=1.06 min; m/z=263 (M+H)$^+$.

$^1$H-NMR (400 MHz, DMSO-$d_6$): δ=7.72 (s, 1H), 7.64 (d, 1H), 7.51-7.61 (m, 2H), 6.43 (br. s, 2H), 3.90-4.01 (m, 2H), 3.82 (dt, 1H), 3.30 (s, 2H), 1.73-1.93 (m, 2H).

Example 130A

Ethyl amino[3-(difluoromethyl)phenyl]acetate

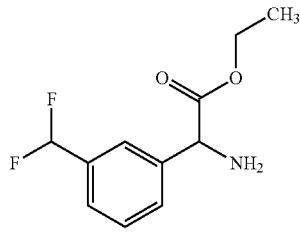 [SMILES: CCOC(=O)C(N)c1cccc(C(F)F)c1]

Quantities of 1.0 g (4.83 mmol) of 3-(difluoromethyl)phenyl bromide, 1.42 g (5.31 mmol) of ethyl N-(diphenylmethylene)glycinate, 0.19 ml (0.193 mmol) of a 1M solution of tri-tert-butylphosphane in toluene, 55 mg (0.10 mmol) of bis(dibenzylideneacetone)palladium(0), 3.08 g (14.49 mmol) of potassium phosphate and 6.04 ml (18.11 mmol) of 3M hydrochloric acid were heated under argon to 100° C. in 20 ml of degassed toluene, and stirred at this temperature overnight. A further 0.19 ml (0.193 mmol) of tri-tert-butylphosphane (1M solution in toluene) and 55 mg (0.10 mmol) of bis(dibenzylideneacetone)palladium(0) were added and the mixture was stirred at 100° C. for a further 24 h. The mixture was cooled to RT and filtered over celite. The celite was washed with a little toluene and the filtrate was freed from the solvent under reduced pressure. For elimination of the protecting group, the residue was taken up in 50 ml of acetonitrile and admixed with 15 ml of 3M hydrochloric acid. After 2 h, the acetonitrile fraction was removed on a rotary evaporator. The aqueous residue was diluted with water to a volume of approximately 150 ml and washed three times with diethyl ether. The aqueous phase was adjusted to a pH of 9 using 2M aqueous sodium carbonate solution and then extracted three times with dichloromethane. The combined organic phases were dried over sodium sulphate, filtered and freed from the solvent on a rotary evaporator. Drying in an HV gave 265 mg (6.46% of theory) of the title compound, in a purity of about 27%, which was reacted further without additional purification.

LC/MS [Method 3]: $R_t$=0.63 min; m/z=230 (M+H)$^+$.

Example 131A

Ethyl [(tert-butoxycarbonyl)amino][3-(difluoromethyl)phenyl]acetate

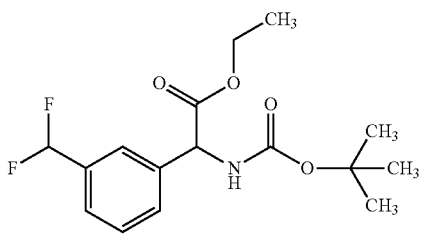 [SMILES: CCOC(=O)C(NC(=O)OC(C)(C)C)c1cccc(C(F)F)c1]

Of the compound from Example 130A, 265 mg (1.16 mmol) were stirred in 10.2 ml of dichloromethane with 505 mg (2.31 mmol) of di-tert-butyl dicarbonate at RT for 3 h. The solvent was then removed on a rotary evaporator. The residue was purified by preparative HPLC [Method 20, and again by Method 23]. The product fraction was freed from the solvent on a rotary evaporator and the residue was dried in an HV. This gave 62 mg (29% of theory) of the title compound in a purity of about 49%.

LC/MS [Method 2]: $R_t$=2.42 min; m/z=330 (M+H)$^+$.

Example 132A tert-Butyl {1-[3-(difluoromethyl)phenyl]-2-hydroxyethyl}carbamate

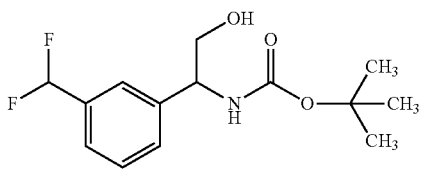 [SMILES: CC(C)(C)OC(=O)NC(CO)c1cccc(C(F)F)c1]

At RT, 11.97 mg (0.28 mmol) of lithium chloride and 10.68 mg (0.28 mmol) of sodium borohydride were stirred in 0.25 ml of ethanol for 15 min. Then the mixture was cooled to 0° C. and a solution of 62 mg (about 0.09 mmol, purity 49%) of the compound from Example 131A in 0.25 ml of tetrahydrofuran was added dropwise. The mixture was stirred overnight at RT. For work-up, it was cooled with ice-water and adjusted to a pH of 2 using 1M hydrochloric acid. The reaction mixture was purified by preparative HPLC [Method 20]. The product fraction was freed from the solvent on a rotary evaporator and dried in an HV. This gave 56 mg (about 45% purity, 93% of theory) of the title compound.

$^1$H-NMR (400 MHz, DMSO-d$_6$): δ=1.36 (br. s, 9H), 3.45-3.56 (m, 2H), 4.49-4.64 (m, 1H), 4.82 (t, 1H), 7.01 (t, $J_{H-F}$=56 Hz, 1H), 7.18-7.53 (m, 4H).

Example 133A tert-Butyl ({2-[(tert-butoxycarbonyl)amino]-2-[3-(trifluoromethyl)phenyl]ethyl}sulphamoyl)-carbamate

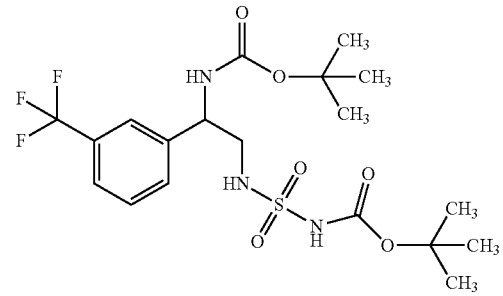 [SMILES: CC(C)(C)OC(=O)NC(CNS(=O)(=O)NC(=O)OC(C)(C)C)c1cccc(C(F)(F)F)c1]

A solution of 110 mg (1.48 mmol) of tert-butanol in 2 ml of dichloromethane was cooled to 0° C. and admixed dropwise with a solution of 129 μl (1.48 mmol) of chlorosulphonyl isocyanate in 2 ml of dichloromethane. The mixture was stirred at RT for 1 h. In a syringe, 820 μl of this solution were taken and were added dropwise to a solution of 90 mg (296 μmol) of the compound from Example 22A in 2 ml of dichloromethane. Then 103 μl of N,N-diisopropylethylamine were added and the reaction mixture was stirred further at RT for 2 h. The volatile constituents were removed on a rotary evaporator. The residue was dissolved in a little acetonitrile and admixed with 1 ml of 1M hydrochloric acid, and the solution obtained was purified by preparative HPLC [Method 23]. The product-containing fraction was freed from the solvents on a rotary evaporator and the residue was dried in an HV. This gave 111 mg (76% of theory) of the title compound.

LC/MS [Method 5]: $R_t$=1.16 min; m/z=484 (M+H)$^+$.

$^1$H-NMR (400 MHz, DMSO-d$_6$): δ=1.36 (s, 9H), 1.41 (s, 9H), 3.08-3.23 (m, 2H), 4.70-4.82 (m, 1H), 7.50 (br. d, 1H), 7.54-7.72 (m, 5H), 10.91 (br. s, 1H).

Example 134A

N-{2-Amino-2-[3-(trifluoromethyl)phenyl]ethyl}sulphuric diamide

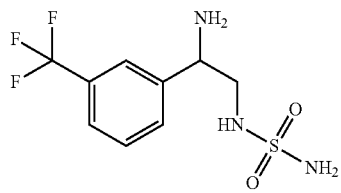 [SMILES: NC(CNS(N)(=O)=O)c1cccc(C(F)(F)F)c1]

A solution of 100 mg (0.20 mmol) of the compound from Example 133A in 2 ml of dichloromethane was admixed with 2 ml of a 4M solution of hydrogen chloride in dioxane, and the mixture was stirred at RT for 2 h. It was diluted with ethyl acetate and admixed with 10% strength aqueous sodium hydrogen carbonate solution. The alkaline aqueous phase was extracted twice with ethyl acetate. The combined organic phases were dried over sodium sulphate and freed from the solvents on a rotary evaporator. The residue was the title compound (53 mg, 92% of theory).

$^1$H-NMR (400 MHz, DMSO-d$_6$): δ=ca. 2.66 (br. s, 2H), 2.86-2.99 (m, 1H), 2.99-3.12 (m, 1H), 4.09 (dd, 1H), 6.60 (br. s, 3H), 7.52-7.64 (m, 2H), 7.68 (br. d, 1H), 7.75 (br. s, 1H).

Example 135A tert-Butyl {2-hydroxy-1-[3-(trifluoromethyl)phenyl]ethyl}methylcarbamate

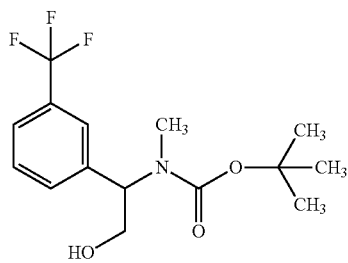 [SMILES: CN(C(=O)OC(C)(C)C)C(CO)c1cccc(C(F)(F)F)c1]

A quantity of 438 ml of borane-tetrahydrofuran complex (1M solution in THF, 438 mmol) was introduced with ice cooling. Then 35 g (110 mmol) of N-Boc-2-(3-trifluoromethylphenyl)-DL-glycine were added in portions. The reaction mixture was stirred at RT for 2 h and then cautiously admixed with pieces of ice. After the end of the evolution of gas, the solvent was removed on a rotary evaporator. The aqueous residue was admixed with saturated sodium hydrogen carbonate solution and extracted three times with ethyl acetate. The combined organic phases were dried over sodium sulphate and freed from the solvent on a rotary evaporator. The residue was taken up in acetonitrile and 2.5% strength aqueous sodium hydrogen carbonate solution. Then 25.18 ml (109.62 mmol) of di-tert-butyl dicarbonate were added and the mixture was stirred at RT for 3 h. The acetonitrile was removed on a rotary evaporator. The residue was extracted three times with ethyl acetate, dried over sodium sulphate, filtered and freed from the solvent on a rotary evaporator. The residue was again admixed with 438 ml of borane-tetrahydrofuran complex (1M solution in THF, 438 mmol) and stirred at 70° C. for 3 h. It was worked up again, and an excess of a 4N solution of hydrogen chloride in dioxane was added to the complete work-up mixture, which was stirred overnight. Thereafter the solvent was removed on a rotary evaporator. The residue was dried in an HV and then admixed once again with 400 ml of borane-tetrahydrofuran complex (1M solution in THF, 400 mmol) and stirred overnight. It was then worked up and again, as described above, reacted with 25.18 ml (109.62 mmol) of di-tert-butyl dicarbonate. The crude product obtained after work-up was purified by preparative HPLC. Drying in an HV gave 10.2 g (29% of theory) of the title compound.

LC/MS [Method 3]: R$_t$=1.24 min; m/z=220 (M+H-BOC)$^+$.

$^1$H-NMR (400 MHz, DMSO-d$_6$): δ=7.53-7.68 (m, 4H), 5.20 (br.s, 0.5H (rotamer)), 5.04 (t, 1H), 5.03 (br. s, 0.5H (rotamer)), 3.77-3.98 (m, 2H), 2.60-2.83 (br.s, 3H), 1.37 (br. s, 9H).

Example 136A tert-Butyl {2-(sulphamoyloxy)-1-[3-(trifluoromethyl)phenyl]ethyl]carbamate

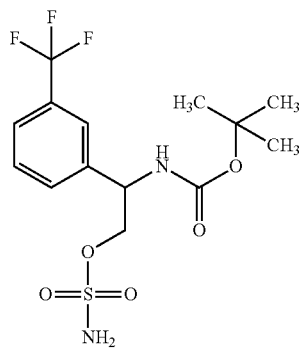 [SMILES: CC(C)(C)OC(=O)NC(COS(N)(=O)=O)c1cccc(C(F)(F)F)c1]

A quantity of 171 µl (1.97 mmol) of chlorosulphonyl isocyanate was admixed under argon at 0° C., with vigorous stirring, with 74 µl (1.97 mmol) of anhydrous formic acid. Following the addition, the reaction mixture solidified within seconds. A quantity of 2 ml of dichloromethane was added. The reaction mixture was then stirred further at 0° C. for 1 h and then RT for 8 h. Thereafter it was cooled to 0° C. again and admixed with a solution of 400 mg (1.31 mmol) of the compound from Example 59A and 159 µl (1.97 mmol) of pyridine in 2 ml of dichloromethane. The cooling bath was removed and the reaction mixture was stirred overnight at RT. For work-up, 5 ml of water and 5 ml of ethyl acetate were added. After 10 min, the mixture was diluted with 100 ml of ethyl acetate, and washed twice with water and once with saturated aqueous sodium chloride solution. The organic phase was dried over sodium sulphate and freed from the solvent on a rotary evaporator. The residue was purified by preparative HPLC [Method 10]. The product fraction was freed from the solvent on a rotary evaporator. Drying in an HV gave 260 mg (52% of theory) of the title compound.

LC/MS [Method 3]: R$_t$=1.21 min; ESIneg: m/z=383 (M–H)$^-$.

H-NMR (400 MHz, DMSO-d$_6$): δ=7.67 (s, 5H), 7.55 (s, 2H), 4.96 (d, 1H), 4.08-4.18 (m, 2H), 1.21-1.44 (m, 9H).

Example 137A

Ethyl {2-amino-2-[3-(trifluoromethyl)phenyl]ethyl}carbamate hydrochloride (non-racemic enantiomer mixture)

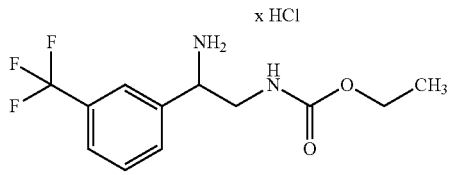 [SMILES: CCOC(=O)NCC(N)c1cccc(C(F)(F)F)c1]

A solution of 527 mg (1.40 mmol) of the compound from Example 103A in 9.6 ml of dichloromethane was admixed at RT with 9.4 ml (37 mmol) of 4M hydrogen chloride in dioxane and stirred for 1 h. Then all of the volatile constituents were removed on a rotary evaporator. Drying of the residue in an HV gave 437 mg (94% of theory) of the title compound.

LC/MS [Method 2]: $R_t$=1.31 min; m/z=277 (M+H)$^+$.

$^1$H-NMR (400 MHz, DMSO-d$_6$): δ=1.09 (t, 3H), 3.38-3.59 (m, 2H), 3.95 (q, 2H), 4.41-4.51 (m, 1H), 7.31 (br. t, 1H), 7.64-7.72 (m, 1H), 7.73-7.81 (m, 2H), 7.87 (br. s, 1H), 8.56 (br. s, 3H).

In the same way as for Example 137A, the following examples were prepared. The yields are in each case more then 94% of theory:

| Example No. | Name and Structure | Reactant No. | Analysis $^1$H-NMR (400 MHz, DMSO-d$_6$) |
|---|---|---|---|
| 138A | Methyl {2-amino-2-[3-(trifluoromethyl)phenyl]ethyl}carbamate hydrochloride (non-racemic enantiomer mixture) 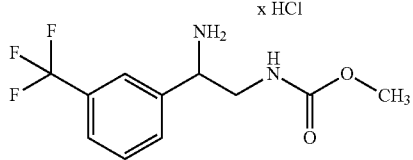 | 102A | LC/MS [Method 2]: $R_t$ = 1.16 min; m/z = 263 (M + H)$^+$. $^1$H-NMR: δ = 3.40-3.59 (m, 2H), 3.50 (s, 3H), 4.42-4.51 (m, 1H), 7.37 (br. t, 1H), 7.65-7.72 (m, 1H), 7.74-7.81 (m, 2H), 7.89 (br. s, 1H), 8.62 (br. s, 3H). |
| 139A | 1-{2-Amino-2-[3-(trifluoromethyl)phenyl]ethyl}-3-ethylurea hydrochloride (non-racemic enantiomer mixture) 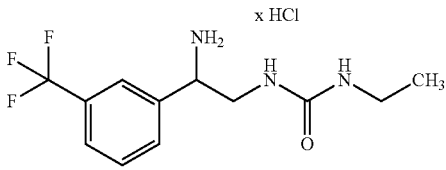 | 104A | LC/MS [Method 2]: $R_t$ = 1.18 min; m/z = 276 (M + H)$^+$. $^1$H-NMR: δ = 0.95 (t, 3H), 2.99 (q, 2H), 3.38-3.47 (m, 1H), 3.50-3.62 (m, 1H), 4.40-4.52 (m, 1H), 5.95-6.18 (br. s, 2H), 7.64-7.73 (m, 1H), 7.72-7.80 (m, 2H), 7.87 (br. s, 1H), 8.45-8.66 (br m, 3H). |
| 140A | 3-{2-Amino-2-[3-(trifluoromethyl)phenyl]ethyl}-1,3-oxazolidin-2-one hydrochloride (non-racemic enantiomer mixture) 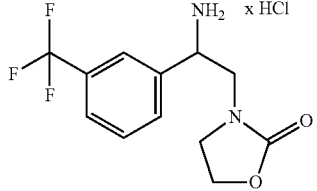 | 106A | LC/MS [Method 3]: $R_t$ = 0.56 min; m/z = 275 (M + H)$^+$. $^1$H-NMR: δ = 3.43-3.56 (m, 3H), 3.67-3.75 (m, 1H), 4.18-4.30 (m, 2H), 4.67-4.76 (m, 1H), 7.72 (t, 1H), 7.81 (br. d, 1H), 7.86 (br. d, 1H), 8.00 (br. s, 1H), 8.61 (br. s, 3H). |
| 141A | 1-{2-Amino-2-[3-(trifluoromethyl)phenyl]ethyl}imidazolidin-2-one hydrochloride (non-racemic enantiomer mixture) 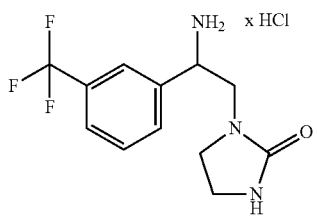 | 107A | $^1$H-NMR: δ = 3.13-3.33 (m, 4H), 3.36-3.60 (m, 2H), 4.55-4.70 (m, 1H), 6.55 (br. s, 1H), 7.66-7.73 (m, 1H), 7.75-7.81 (m, 1H), 7.82-7.89 (m, 1H), 7.98 (br. s, 1H), 8.44-8.69 (br. m, 3H). |
| 142A | 2-(Methylsulphanyl)-1-[2-(trifluoromethyl)phenyl]ethanamine hydrochloride 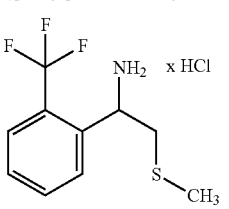 | 109A | LC/MS [Method 5]: $R_t$ = 0.61 min; m/z = 236 (M + H)$^+$. $^1$H-NMR: δ = 2.07 (s, 3H), 3.02 (dd, 1H), 3.11 (dd, 1H), 4.55 (br. t, 1H), 7.65 (t, 1H), 7.80-7.88 (m, 2H), 7.98 (d, 1H), 8.83 (br. s, 3H). |

-continued

| Example No. | Name and Structure | Reactant No. | Analysis $^1$H-NMR (400 MHz, DMSO-d$_6$) |
|---|---|---|---|
| 143A | 1-[2-Amino-2-(2-chlorophenyl)ethyl]urea hydrochloride | 114A | LC/MS [Method 2]: R$_t$ = 0.22 + 0.73 min; m/z = 214 (M + H)$^+$. $^1$H-NMR: δ = 3.35-3.45 (m, 1H), 3.48-3.58 (m, 1H), 4.65-4.75 (m, 1H), 6.30 (br. s., 1H), 7.39-7.50 (m, 2H), 7.54 (dd, 1H), 7.74 (br. d, 1H), 8.66 (br. s., 3H). (NH$_2$ presumably beneath the broad water signal (5.5-5.9 ppm)). |
| 144A | N-[2-Amino-2-(2-chlorophenyl)ethyl]-methanesulphonamide hydrochloride | 115A | $^1$H-NMR: δ = 2.91 (s, 3H), 3.35-3.49 (m, 2H), 4.70-4.77 (m, 1H), 7.42-7.53 (m, 3H), 7.56 (dd, 1H), 7.77 (dd, 1H), 8.75 (br. s., 3H). |
| 145A | N-[2-Amino-2-(2-chlorophenyl)ethyl]-ethanesulphonamide hydrochloride | 116A | $^1$H-NMR: δ = 1.14 (t, 3H), 2.90-3.05 (m, 2H), 3.35-3.49 (m, 2H), 4.73 (t, 1H), 7.42-7.54 (m, 3H), 7.56 (dd, 1H), 7.76 (dd, 1H), 8.71 (br. s., 3H). |
| 146A | 1-(2-Chlorophenyl)-2-(methylsulphonyl)-ethanamine hydrochloride | 117A | LC/MS [Method 2]: R$_t$ = 0.81 min; m/z = 234 (M + H)$^+$. $^1$H-NMR: δ = 3.01 (s, 3H), 3.85 (dd, 1H), 3.96 (dd, 1H), 5.18 (t, 1H), 7.43-7.61 (m, 3H), 7.78-7.85 (m, 1H), 8.81 (br. s, 3H). |
| 147A | 1-(2-Chlorophenyl)-2-(methylsulphanyl)-ethanamine hydrochloride | 119A | $^1$H-NMR: δ = 2.06 (s, 3H), 2.99 (dd, 1H), 3.07 (dd, 1H), 4.79 (t, 1H), 7.40-7.52 (m, 2H), 7.55 (dd, 1H), 7.76 (br. d, 1H), 8.72 (br. s, 3H). |
| 148A | 2-(Methylsulphonyl)-1-[2-(trifluoromethyl)phenyl]ethanamine hydrochloride | 120A | LC/MS [Method 5]: R$_t$ = 0.32 min; m/z = 268 (M + H)$^+$. $^1$H-NMR: δ = 3.07 (s, 3H), 3.90-4.06 (m, 2H), 4.98 (dd, 1H), 7.68 (t, 1H), 7.80-7.91 (m, 2H), 8.04 (d, 1H), 8.96 (br. s., 3H). |

-continued

| Example No. | Name and Structure | Reactant No. | Analysis ¹H-NMR (400 MHz, DMSO-d₆) |
|---|---|---|---|
| 149A | 2-(Methylsulphonyl)-1-[3-(trifluoromethyl)phenyl]ethanamine hydrochloride | 121A | LC/MS [Method 4]: $R_t$ = 0.43 min; m/z = 268 (M + H)⁺. ¹H-NMR: δ = 3.01 (s, 3H), 3.84 (dd, 1H), 4.03 (dd, 1H), 5.01 (t, 1H), 7.71 (t, 1H), 7.82 (d, 1H), 7.91 (d, 1H), 8.03 (s, 1H), 8.75 (br. s., 3H). |
| 150A | 2-Amino-N,N-dimethyl-2-[3-(trifluoromethyl)phenyl]-ethanesulphonamide hydrochloride | 122A | LC/MS [Method 4]: $R_t$ = 0.60 min; m/z = 297 (M + H)⁺. ¹H-NMR: δ = 2.72 (s, 6H), 3.73-3.88 (m, 2H), 4.87 (t, 1H), 7.70 (t, 1H), 7.80 (d, 1H), 7.92 (d, 1H), 8.03 (s, 1H), 8.74 (br. s, 3H). |
| 151A | Methyl [2-amino-2-(2,3-dichlorophenyl)ethyl]carbamate hydrochloride | 123A | LC/MS [Method 5]: $R_t$ = 0.56 min; m/z = 263 (M + H)⁺. ¹H-NMR: δ = 3.36-3.44 (m, 1H), 3.53 (s, 3H), 3.51-3.60 (m, 1H), 4.77-4.87 (m, 1H), 7.41 (br. t, 1H), 7.51 (t, 1H), 7.66-7.76 (m, 2H), 8.67 (br. s., 3H). |
| 152A | Ethyl [2-amino-2-(2,3-dichlorophenyl)ethyl]carbamate hydrochloride | 124A | LC/MS [Method 5]: $R_t$ = 0.64 min; m/z = 277 (M + H)⁺. ¹H-NMR: δ = 8.67 (br. s., 3H), 7.71 (d, 2H), 7.51 (t, 1H), 7.36 (t, 1H), 4.77-4.88 (m, 1H), 3.86-4.07 (m, 2H), 3.50-3.61 (m, 1H), 3.36-3.44 (m, 1H), 1.12 (t, 3H). |
| 153A | 1-[2-Amino-2-(2,3-dichlorophenyl)-ethyl]urea hydrochloride | 125A | LC/MS [Method 5]: $R_t$ = 0.35 min; m/z = 248 (M + H)⁺. ¹H-NMR: δ = 3.36-3.45 (m, 1H), 3.50-3.62 (m, 1H), 4.71-4.82 (m, 1H), 5.4-5.8 (very broad s, 2H), 6.23 (br. t, 1H), 7.51 (t, 1H), 7.63-7.75 (m, 2H), 8.53-8.73 (m, 3H). |

-continued

| Example No. | Name and Structure | Reactant No. | Analysis $^1$H-NMR (400 MHz, DMSO-$d_6$) |
|---|---|---|---|
| 154A | 1-[2-Amino-2-(2,3-dichlorophenyl)ethyl]-3-ethylurea hydrochloride | 126A | LC/MS [Method 5]: R$_t$ = 0.55 min; m/z = 276 (M + H)$^+$. $^1$H-NMR: δ = 0.96 (t, 3H), 2.90-3.09 (m, 2H), 3.36-3.47 (m, 1H), 3.48-3.55 (m, 1H), 4.78 (d, 1H), 6.05 (br. s., 1H), 6.13 (br. t, 1H), 7.45-7.57 (m, 1H), 7.62-7.75 (m, 2H), 8.49-8.77 (m, 3H). |
| 155A | 2-Amino-2-[3-(difluoromethyl)phenyl]ethanol hydrochloride | 132A | $^1$H-NMR: δ = 3.66-3.81 (m, 2H), 4.32-4.44 (m, 1H), 5.56 (br. s, 1H), 7.06 (t, 1H), 7.28-7.77 (m, 4H), 8.39-8.64 (m, 3H). |
| 156A | 2-(Methylamino-2-[3-(trifluoromethyl)phenyl]ethanol hydrochloride | 135A | LC/MS [Method 5]: R$_t$ = 0.41 min; m/z = 220 (M + H)$^+$. $^1$H-NMR: δ = 9.51 (br. s, 3H), 7.98 (s, 1H), 7.88 (d, 1H), 7.76-7.82 (d, 1H), 7.66-7.73 (t, 1H), 5.69 (m, 1H), 4.42 (br. s, 1 H), 3.79-3.93 (m, 2H), 3.57 (s, 1H), 2.42 (s, 3H). |
| 157A | 2-Amino-2-[3-(trifluoromethyl)phenyl]-ethyl sulphamate hydrochloride | 136A | LC/MS [Method 2]: R$_t$ = 1.07 min; m/z = 285 (M + H)$^+$. $^1$H-NMR: δ = 8.84 (br. s., 2H), 7.98 (s, 1H), 7.61-7.92 (m, 5H), 4.85 (t, 1H), 4.29-4.46 (m, 2H). |

Example 158A 5-(4-Chlorophenyl)-4-[(2S)-3,3,3-trifluoro-2-hydroxypropyl]-2,4-dihydro-3H-1,2,4-triazol-3-one

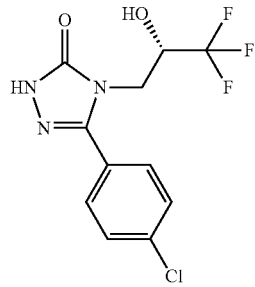 [SMILES: O=c1[nH]nc(-c2ccc(Cl)cc2)n1C[C@H](O)C(F)(F)F]

Of the compound from Example 3A, 1.08 g (3.3 mmol) were dissolved in 11 ml of N,N-dimethylacetamide. The solution was freed from atmospheric oxygen using reduced pressure, and saturated with argon. Added to this solution under argon were 21 mg (0.033 mmol) of the ruthenium complex RuCl(p-cymene)[(S,S)-Ts-DPEN)] (CAS No. 192139-90-5). Then a mixture of 0.63 ml (16.6 mmol) of formic acid and 0.27 ml (1.91 mmol) of triethylamine was added and the resulting mixture was stirred in the absence of air at RT for 48 h. For work-up, the mixture was introduced into 10 ml of 0.1N hydrochloric acid, and extracted with twice 20 ml of ethyl acetate. The combined organic phases were washed with saturated aqueous sodium hydrogen carbonate solution, dried over sodium sulphate, filtered and concentrated under reduced pressure. The crude product was purified by chromatography on silica gel (eluents: 1. cyclohexane/ethyl acetate 3:1, 2. cyclohexane/ethyl acetate 1:1). This gave 830 mg (81% of theory) of the target compound.

The enantiomeric excess was determined chromatographically by Method 27c to be 96% ee.
(S)-Enantiomer: $R_t$=5.73 min
(R)-Enantiomer: $R_t$=6.82 min

Example 159A

[(tert-Butoxycarbonyl)amino](3-chloro-2-fluorophenyl)acetic acid

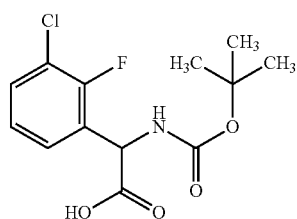 [SMILES: CC(C)(C)OC(=O)NC(C(=O)O)c1cccc(Cl)c1F]

A quantity of 5 g (24.56 mmol) of 3-chloro-2-fluoro-DL-phenylglycine was suspended in dioxane and 147 ml of 5% strength aqueous sodium hydrogen carbonate solution. Then 5.36 g (24.56 mmol) of di-tert-butyl dicarbonate were added. The suspension was stirred at RT overnight.

Ethyl acetate was added to the white suspension, these components were stirred together, and the precipitate was filtered off with suction. The mother liquor was extracted. The aqueous phase was extracted once again with ethyl acetate. The combined organic phases were dried over sodium sulphate, filtered and concentrated on a rotary evaporator. Drying in an HV gave 0.59 g (7.7% of theory) of the title compound.

The aqueous phase was acidified with 1M hydrochloric acid and extracted twice with ethyl acetate. The extracts were dried over sodium sulphate, filtered and concentrated on a rotary evaporator. Drying in an HV gave 5.05 g (65.4% of theory) of the title compound.

LC/MS [Method 2]: $R_t$=2.08 min; m/z=204 (M+H)$^+$.

Example 160A tert-Butyl [1-(3-chloro-2-fluorophenyl)-2-hydroxyethyl]carbamate

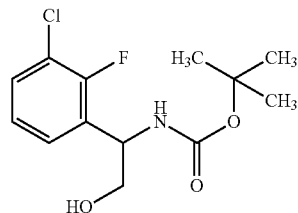 [SMILES: CC(C)(C)OC(=O)NC(CO)c1cccc(Cl)c1F]

Of the compound from Example 159A, 2 g (6.59 mmol) were dissolved under argon in 20 ml of THF. The solution was then cooled to 0° C. and 0.918 ml (6.59 mmol) of triethylamine and 0.94 ml (7.24 mmol) of isobutyl chloroformate were added dropwise. The reaction mixture was subsequently stirred at 0° C. for 1 h. Thereafter the suspension was filtered through a Seitz frit into a cooled flask, with washing with a little THF. A second flask was charged with 747 mg (19.76 mmol) of sodium borohydride in 3 ml of water, with ice cooling. With vigorous stirring, the filtrate was slowly added dropwise. After 1 h, the batch was carefully admixed with saturated aqueous sodium hydrogen carbonate solution. It was then extracted with 30 ml of ethyl acetate. The organic phase was washed again once with saturated aqueous sodium hydrogen carbonate solution and once with saturated aqueous sodium chloride solution. It was then dried over sodium sulphate, filtered and freed from the solvent on a rotary evaporator. Drying in an HV gave 1.74 g (75% of theory) of the title compound in approximately 83% purity.

LC/MS [Method 5]: $R_t$=0.99 min; m/z=290 (M+H)$^+$.
$^1$H-NMR (400 MHz, CDCl$_3$): δ=1.43 (s, 9H), 1.90-1.98 (m, 1H), 3.78-3.93 (m, 2H), 5.01-5.12 (m, 1H), 5.32-5.42 (m, 1H), 7.08 (t, 1H), 7.23 (t, 1H), 7.30-7.37 (m, 1H).

Example 161A

2-Amino-2-(3-chloro-2-fluorophenyl)ethanol hydrochloride

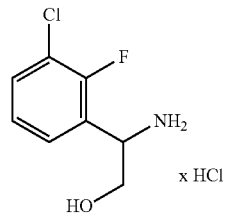 [SMILES: NC(CO)c1cccc(Cl)c1F]

Of the compound from Example 160A, 1.74 g (6.01 mmol) were introduced in 20 ml of dichloromethane. A quantity of 22 ml (88.00 mmol) of 4M hydrogen chloride in dioxane was added. After stirring at RT for 1 h, the reaction mixture was evaporated to dryness on a rotary evaporator and dried in an HV. This gave 1.38 g (88% of theory) of the title compound in approximately 87% purity.

LC/MS [Method 5]: $R_t$=0.27 min; m/z=190 (M+H)$^+$.

Example 162A

2-Amino-2-(3-chloro-2-fluorophenyl)ethyl carbamate hydrochloride

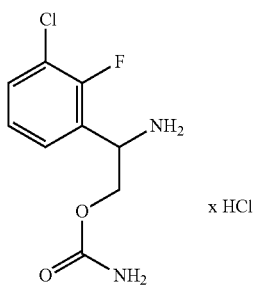 [SMILES: NC(=O)OCC(N)c1cccc(Cl)c1F]

Of the compound from Example 160A, 243 mg (0.84 mmol) were introduced in 10 ml of acetonitrile under argon. Then at −15° C. 102 μl (1.17 mmol) of chlorosulphonyl isocyanate were added dropwise. After 30 min, the reaction solution was admixed with 20 ml of water and heated at 60° C. overnight. The reaction mixture was cooled and introduced into saturated aqueous sodium hydrogen carbonate solution. It was then extracted with ethyl acetate. The organic phase was dried over sodium sulphate, filtered and freed from the solvent on a rotary evaporator. The residue was taken up in 4 ml of dichloromethane and admixed with 4 ml of a 4M solution of hydrogen chloride in dioxane. A precipitate formed immediately. After a subsequent stirring time of 10 min, the batch was freed from the solvent on a rotary evaporator. Drying in an HV gave 219 mg (77% of theory) of the title compound in 79% purity.

LC/MS [Method 5]: $R_t$=0.27 min; m/z=233 (M+H)$^+$.

Example 163A

N-Allyl-2-(2-bromo-4-chlorobenzoyl)hydrazinecarboxamide

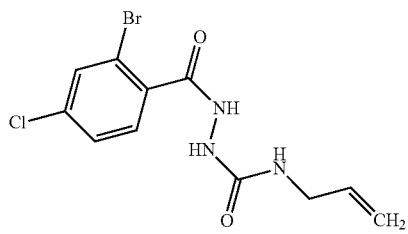 [SMILES: C=CCNC(=O)NNC(=O)c1ccc(Cl)cc1Br]

A quantity of 10.0 g (40.1 mmol) of 2-bromo-4-chlorobenzhydrazide was suspended in 100 ml of THF at 50° C. and admixed with 3.59 ml (40.9 mmol) of allyl isocyanate in solution in 50 ml of THF. Stirring was continued for 16 h at 50° C. The batch was then allowed to cool to RT and diluted with 50 ml of diethyl ether. The precipitated solid was filtered off with suction, washed with a little diethyl ether and dried in an HV. This gave 11.30 g (85% of theory) of the title compound.

LC/MS [Method 6]: $R_t$=1.81 min; m/z=332 (M+H)$^+$.

$^1$H-NMR (400 MHz, DMSO-d$_6$): δ=3.69 (t, 2H), 5.04 (d, 1H), 5.16 (d, 1H), 5.76-5.88 (m, 1H), 6.45 (t, 1H), 7.58 (s, 2H), 7.84 (s, 1H), 8.10 (s, 1H), 10.07 (s, 1H).

Example 164A

4-Allyl-5-(2-bromo-4-chlorophenyl)-2,4-dihydro-3H-1,2,4-triazol-3-one

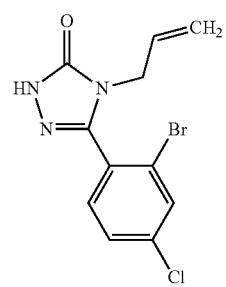 [SMILES: C=CCn1c(-c2ccc(Cl)cc2Br)n[nH]c1=O]

Of the compound from Example 163A, 11.3 g (33.98 mmol) were taken up in 61 ml (183.47 mmol) of 3M aqueous sodium hydroxide solution and heated under reflux for 36 h. The batch was then cooled, the fine precipitate was removed by filtration, and the filtrate was admixed, with ice cooling, with 28 ml (169.88 mmol) of half-concentrated hydrochloric acid to a pH of 10. The batch was filtered with suction and the product was dissolved out of the precipitate using methanol. The methanol was removed on a rotary evaporator. The residue was dried in an HV. This gave 9.78 g (69% of theory) of the title compound in 75% purity.

LC/MS [Method 2]: $R_t$=1.88 min; m/z=314 and 316 (M+H)$^+$.

$^1$H-NMR (400 MHz, CDCl$_3$): δ=4.19 (d, 2H), 4.93 (d, 1H), 5.09 (d, 1H), 5.64-5.74 (m, 1H), 7.32 (d, 1H), 7.39-7.44 (m, 1H), 7.72 (s, 1H), 9.45 (br. s., 1H).

Example 165A

Methyl [4-allyl-3-(2-bromo-4-chlorophenyl)-5-oxo-4,5-dihydro-1H-1,2,4-triazol-1-yl]acetate

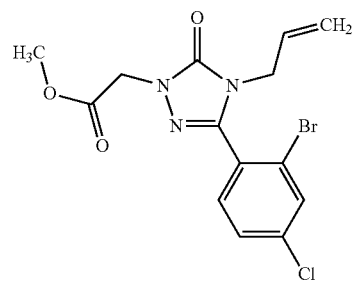 [SMILES: C=CCn1c(-c2ccc(Cl)cc2Br)nn(CC(=O)OC)c1=O]

Of the compound from Example 164A, 9.78 g (about 23.32 mmol, purity 75%) were dissolved in 75 ml of acetonitrile.

Then 3.55 g (25.65 mmol) of potassium carbonate and 2.46 ml (27.98 mmol) of methyl chloroacetate were added. The mixture was stirred under reflux for 5 hours. After cooling, it was filtered with suction. The filtrate was concentrated a little on a rotary evaporator and then diluted with 30 ml of ethyl acetate and washed with 30 ml each of 1M hydrochloric acid and of saturated aqueous sodium chloride solution. The organic phase was dried over sodium sulphate, filtered and freed from the solvent on a rotary evaporator. The residue was purified by chromatography on silica gel (elution: cyclohexane/ethyl acetate 2:1). This gave 7.1 g (79% of theory) of the title compound.

LC/MS [Method 6]: $R_f$=2.37 min; m/z=386 (M+H)$^+$.

Example 166A

[4-Allyl-3-(2-bromo-4-chlorophenyl)-5-oxo-4,5-dihydro-1H-1,2,4-triazol-1-yl]acetic acid

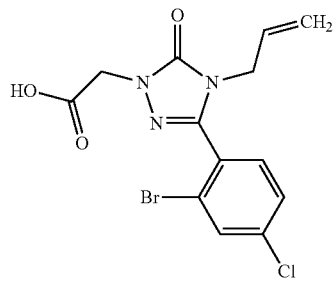 [SMILES: C=CCn1c(-c2ccc(Cl)cc2Br)nn(CC(=O)O)c1=O]

Of the compound from Example 156A, 4 g (10.35 mmol) were taken up in 30 ml of methanol and admixed with 15.5 ml (15.52 mmol) of 1M lithium hydroxide solution. The mixture was stirred at RT for 2 h. Then the solvent was removed on a rotary evaporator. The residue was diluted with 100 ml of water, washed with 20 ml of ethyl acetate and then acidified using 1M hydrochloric acid. It was then again extracted with 50 ml of ethyl acetate. The organic phase was dried over sodium sulphate, filtered, concentrated on a rotary evaporator and dried in an HV. This gave 3.61 g (94% of theory) of the title compound.

LC/MS [Method 3]: $R_f$=0.99 min; m/z=372 and 374 (M+H)$^+$.

$^1$H-NMR (400 MHz, CDCl$_3$): δ=4.21 (d, 2H), 4.72 (s, 2H), 4.94 (d, 1H), 5.09 (d, 1H), 5.63-5.76 (m, 1H), 7.31-7.43 (m, 2H), 7.71 (s, 1H).

Example 167A

2-[(5-Chloro-2-thienyl)carbonyl]-N-(2-methoxyethyl)hydrazinecarboxamide

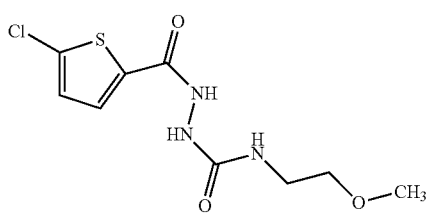 [SMILES: COCCNC(=O)NNC(=O)c1ccc(Cl)s1]

A quantity of 3.1 g (17.55 mmol) of 5-chlorothiophene-2-carbohydrazide was suspended largely finely in 30 ml of dry THF at 50° C. Then 1.81 g (17.90 mmol) of 1-isocyanato-2-methoxyethane in solution in 30 ml of THF were added dropwise. The mixture was stirred at 50° C. for 2.5 h. After cooling to RT, the solvent was removed on a rotary evaporator and the residue was admixed with diethyl ether. The crystals were filtered off with suction, washed with diethyl ether and dried in an HV. This gave 4.87 g (100% of theory) of the title compound.

$^1$H-NMR (400 MHz, DMSO-d$_6$): δ=3.14-3.21 (m, 2H), 3.28-3.36 (m, 5H), 6.52 (br. s., 1H), 7.22 (d, 1H), 7.70 (d, 1H), 7.97 (s, 1H), 10.24 (s, 1H).

Example 168A 5-(5-Chloro-2-thienyl)-4-(2-methoxyethyl)-2,4-dihydro-3H-1,2,4-triazol-3-one

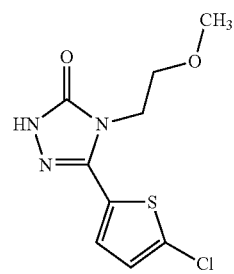 [SMILES: COCCn1c(-c2ccc(Cl)s2)n[nH]c1=O]

Of the compound from Example 167A, 4.85 g (17.46 mmol) were dissolved in 17 ml (52.39 mmol) of 3M aqueous sodium hydroxide solution and heated under reflux for 168 h. During this, after 16, 40, 64 and 88 h, 1.05 g portions (26.19 mmol, in total 104.76 mmol) of solid sodium hydroxide were added. The batch was acidified to pH 10 using 1M hydrochloric acid, and the mixture was extracted with twice 30 ml of ethyl acetate. The combined organic phases were dried over sodium sulphate, filtered, freed from the solvent on a rotary evaporator and dried in an HV. This gave 2.44 g (54% of theory) of the title compound.

$^1$H-NMR (400 MHz, DMSO-d$_6$): δ=3.20 (s, 3H), 3.53 (t, 2H), 3.92 (t, 2H), 7.24 (d, 1H), 7.51 (d, 1H), 12.04 (s, 1H).

Example 169A

Ethyl [3-(5-chloro-2-thienyl)-4-(2-methoxyethyl)-5-oxo-4,5-dihydro-1H-1,2,4-triazol-1-yl]acetate

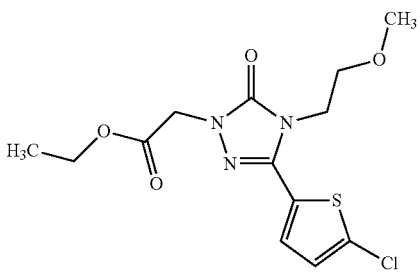 [SMILES: CCOC(=O)Cn1nc(-c2ccc(Cl)s2)n(CCOC)c1=O]

Of the compound from Example 168A, 2.4 g (9.24 mmol) were suspended with 2.55 g (18.48 mmol) of potassium carbonate in 48 ml of acetonitrile. Then 1.08 ml (10.17 mmol) of ethyl chloroacetate were added and the mixture was heated under reflux at 80° C. for 4.5 h. A further 113 mg (0.92 mmol) of ethyl chloroacetate were added, with stirring at 80° C. for 2 h. The suspension was filtered through a layer of silica gel, which was washed with ethyl acetate, and the filtrate was concentrated on a rotary evaporator and dried in an HV. This gave 3.24 g (100% of theory) of the title compound.

LC/MS [Method 6]: $R_t$=2.42 min; m/z=346 (M+H)$^+$.

$^1$H-NMR (400 MHz, DMSO-d$_6$): δ=1.21 (t, 3H), 3.30 (s, 3H), 3.55 (t, 2H), 3.99 (t, 2H), 4.15 (q, 2H), 4.65 (s, 2H), 7.27 (d, 1H), 7.58 (d, 1H).

Example 170A

[3-(5-Chloro-2-thienyl)-4-(2-methoxyethyl)-5-oxo-4,5-dihydro-1H-1,2,4-triazol-1-yl]acetic acid

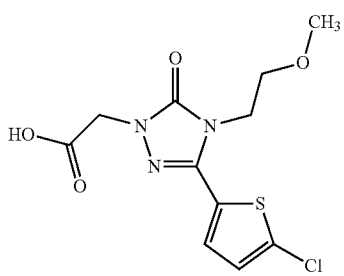 [SMILES: COCCn1c(-c2ccc(Cl)s2)nn(CC(=O)O)c1=O]

Of the compound from Example 169A, 3.2 g (9.25 mmol) were dissolved in 28 ml of methanol. Then 2.82 ml of 20% strength aqueous potassium hydroxide solution were added. The mixture was stirred at RT for 2 h. The methanol fraction was reduced to half on a rotary evaporator. The mixture was then diluted with water and extracted once with 15 ml of ethyl acetate. The aqueous phase was acidified with 920 µl of concentrated hydrochloric acid and extracted with twice 15 ml of ethyl acetate. The combined organic phases were dried over sodium sulphate, filtered and freed from the solvent on a rotary evaporator. Drying in an HV gave 2.34 g (80% of theory) of the title compound.

LC/MS [Method 6]: $R_t$=2.05 min; m/z=318 (M+H)$^+$.

$^1$H-NMR (400 MHz, DMSO-d$_6$): δ=3.20 (s, 3H), 3.55 (t, 2H), 3.99 (t, 2H), 4.53 (s, 2H), 7.27 (d, 1H), 7.58 (d, 1H), 13.14 (br. s., 1H).

Example 171A

Methyl 3-[(tert-butoxycarbonyl)amino]-3-(2-methoxyphenyl)propanoate

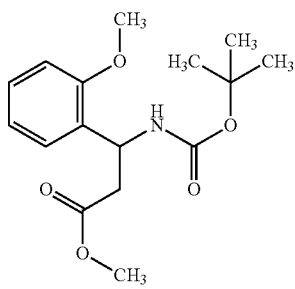 [SMILES: COC(=O)CC(NC(=O)OC(C)(C)C)c1ccccc1OC]

A quantity of 1.0 g (4.10 mmol) of methyl 3-amino-3-(2-methoxyphenyl)propanoate was suspended in 25 ml of dioxane and 27.5 ml of 5% strength aqueous sodium hydrogen carbonate solution. Then 0.89 g (4.10 mmol) of di-tert-butyl dicarbonate were added. The mixture was stirred at RT overnight. The white suspension was admixed with 50 ml of water and extracted with three times 25 ml of ethyl acetate. The combined organic phases were dried over magnesium sulphate, filtered and freed from the solvent on a rotary evaporator. This gave 1.34 g (100% of theory) of the title compound.

LC/MS [Method 4]: $R_t$=1.06 min; m/z=310 (M+H)$^+$.

Example 172A tert-Butyl [3-hydroxy-1-(2-methoxyphenyl)propyl]carbamate

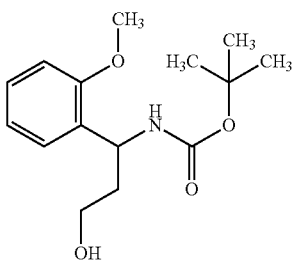 [SMILES: COc1ccccc1C(CCO)NC(=O)OC(C)(C)C]

Of the compound from Example 171A, 1.34 g (4.33 mmol) were dissolved in 10 ml of dimethoxyethane and admixed with 246 mg (6.50 mmol) of sodium borohydride and 37 mg (0.87 mmol) of lithium chloride. The mixture was heated at 85° C. for 16 h. For work-up, it was cooled to RT and cautiously admixed with 10 ml of saturated aqueous sodium potassium tartrate solution. It was extracted with three times 20 ml of ethyl acetate. The combined organic phases were dried over magnesium sulphate, filtered and freed from the solvent on a rotary evaporator. The crude product was purified by chromatography on silica gel (elution: cyclohexane/ethyl acetate 9:1, 7:3). This gave 348 mg (29% of theory) of the title compound.

LC/MS [Method 2]: $R_t$=1.90 min; m/z=282 (M+H)$^+$.

Example 173A

3-Amino-3-(2-methoxyphenyl)propan-1-ol hydrochloride

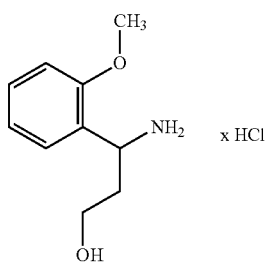

Of the compound from Example 172A, 100 mg (0.36 mmol) were dissolved in 2 ml of dichloromethane, and 1.63 ml (6.52 mmol) of a 4M solution of hydrogen chloride in dioxane were added. The yellow solution was subsequently stirred at RT for 1 h. The reaction mixture was evaporated to dryness on a rotary evaporator and dried in an HV. This gave 88 mg (100% of theory) of the title compound.

$^1$H-NMR (400 MHz, DMSO-d$_6$): δ=1.90-2.11 (m, 2H), 3.28-3.44 (m, 2H), 3.83 (s, 3H), 4.52-4.61 (m, 1H), 4.76 (br. s., 1H), 7.02 (t, 1H), 7.09 (d, 1H), 7.40 (t, 2H), 8.21 (br. s., 3H).

Example 174A

3-Amino-3-(2-methoxyphenyl)propyl carbamate hydrochloride

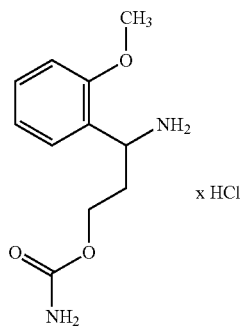 [SMILES: COc1ccccc1C(N)CCOC(N)=O]

Of the compound from Example 172A, 242 mg (0.86 mmol) were introduced in 12 ml of acetonitrile under argon, and admixed dropwise at −15° C. with 105 µl (1.20 mmol) of chlorosulphonyl isocyanate. The reaction mixture was stirred at −10° C. for 30 minutes. Then 12 ml of water were added and the mixture was stirred at 60° C. overnight. The reaction mixture was cooled, rendered basic using saturated aqueous sodium hydrogen carbonate solution and extracted with three times 10 ml of ethyl acetate. The organic phases were combined, dried over magnesium sulphate, filtered and freed from the solvent on a rotary evaporator. The residue was admixed with 6 ml of a 4M solution of hydrogen chloride in dioxane, the components were stirred together for 10 minutes, and the mixture was concentrated on a rotary evaporator. The residue was dried in an HV. This gave 186 mg (83% of theory) of the title compound.

$^1$H-NMR (400 MHz, DMSO-d$_6$): δ=2.03-2.29 (m, 2H), 3.64-3.76 (m, 2H), 3.83 (s, 3H), 4.49-4.61 (m, 1H), 6.98-7.13 (m, 2H), 7.34-7.46 (m, 2H), 8.23 (br. s., 1H), 8.35 (br. s., 2H).

Example 175A

2-Amino-2-(2,3-dichlorophenyl)ethanol

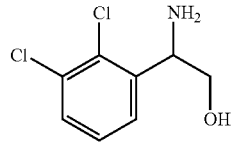 [SMILES: NC(CO)c1cccc(Cl)c1Cl]

Quantities of 1.0 g (4.54 mmol) of amino-(2,3-dichlorophenyl)acetic acid and 18.18 ml (18.18 mmol) of borane-THF complex (1M solution in THF) were stirred together at RT until the reaction was complete. For work-up, pieces of ice were added. After the end of the evolution of gas, the mixture was adjusted to a pH of 9-10 using 1M aqueous sodium hydroxide solution, and extracted three times with tert-butyl methyl ether. The combined organic phases were dried over sodium sulphate, filtered and freed from the solvent on a rotary evaporator. Drying in an HV gave 880 mg (91% of theory) of the title compound.

LC/MS [Method 5]: R$_t$=0.39 min; m/z=206 and 208 (M+H)$^+$.

Example 176A

Methyl [3-(4-chlorophenyl)-5-oxo-4-(3,3,3-trifluoropropyl)-4,5-dihydro-1H-1,2,4-triazol-1-yl]acetate

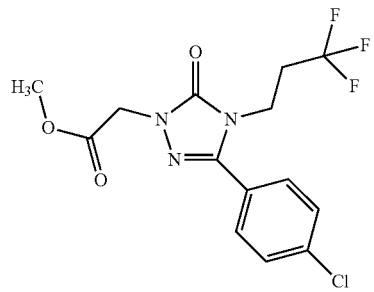 [SMILES: COC(=O)Cn1nc(-c2ccc(Cl)cc2)n(CCC(F)(F)F)c1=O]

Of the compound from Example 76A, 1.2 g (3.32 mmol), 150 mg of platinum on carbon (5%) and 150 ml of methanol were hydrogenated under standard hydrogen pressure. For work-up, the catalyst was filtered off and the filtrate was concentrated on a rotary evaporator. The crude product was purified by preparative HPLC (Method 20). The product fractions were combined and freed from the solvent on a rotary evaporator. Drying in an HV gave 890 mg (73% of theory) of the title compound.

LC/MS [Method 4]: R$_t$=1.00 min; m/z=364 (M+H)$^+$.

$^1$H-NMR (400 MHz, DMSO-d$_6$): δ=2.55-2.68 (m, 2H), 3.69 (s, 3H), 4.01 (t, 2H), 4.70 (s, 2H), 7.61-7.72 (m, 4H).

Example 177A

[3-(4-Chlorophenyl)-5-oxo-4-(3,3,3-trifluoropropyl)-4,5-dihydro-1H-1,2,4-triazol-1-yl]acetic acid

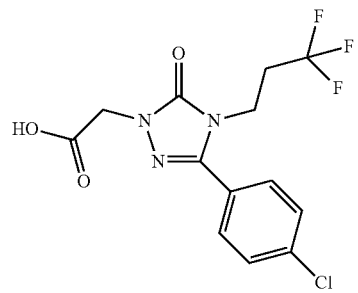 [SMILES: O=C(O)Cn1nc(-c2ccc(Cl)cc2)n(CCC(F)(F)F)c1=O]

Of the compound from Example 176A, 1.27 g (3.49 mmol), were introduced in 200 ml of methanol and 100 ml of water. Then 6.98 ml (6.98 mmol) of 1M aqueous lithium hydroxide solution were added. The mixture was stirred at RT for 2 h. For purification, 15 ml of 1N hydrochloric acid were added and the mixture was freed from methanol on a rotary evaporator. The residue was diluted with 100 ml of water and extracted three times with ethyl acetate. The combined organic phases were dried over sodium sulphate, filtered and freed from the solvent on a rotary evaporator, and dried in an HV. This gave 1.11 g (91% of theory) of the title compound.

LC/MS [Method 2]: R$_t$=1.92 min; m/z=350 (M+H)$^+$.

$^1$H-NMR (400 MHz, DMSO-d$_6$): δ=2.55-2.68 (m, 2H), 4.01 (t, 2H), 4.56 (s, 2H), 7.61-7.72 (m, 4H), 13.12 (br. s., 1H).

Example 178A tert-Butyl {2-hydroxy-1-[2-(trifluoromethyl)phenyl]ethyl}carbamate (enantiomer I)

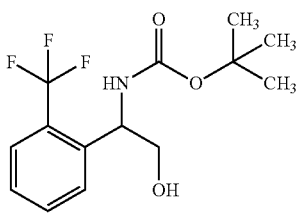 [SMILES: CC(C)(C)OC(=O)NC(CO)c1ccccc1C(F)(F)F]

Of the compound from Example 62A, 52.8 g were separated by chiral preparative HPLC [Method 33]. The first-eluting enantiomer (21 g) was obtained with 93% ee according to chiral analytical HPLC (Method 34).

Chiral analytical HPLC [Method 34]: $R_t$=1.74 min

For the last-eluting enantiomer, see Example 179A.

Example 179A tert-Butyl {2-hydroxy-1-[2-(trifluoromethyl)phenyl]ethyl}carbamate (enantiomer II)

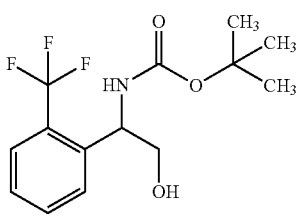 [SMILES: CC(C)(C)OC(=O)NC(CO)c1ccccc1C(F)(F)F]

Last-eluting enantiomer (18.9 g, 99.7% ee) from the separation of 52.8 g of the compound from Example 62A, by Method 33.

Chiral analytical HPLC [Method 34]: $R_t$=2.48 min.

LC/MS [Method 3]: $R_t$=1.13 min; m/z=206 (M-BOC)$^+$.

$^1$H-NMR (400 MHz, DMSO-d$_6$): δ=1.35 (s, 9H), 3.36-3.50 (m, 2H), 4.90-5.01 (m, 2H), 7.37-7.48 (m, 2H), 7.61-7.70 (m, 4H).

Further separation of the mixed fraction under the same conditions gave a further 4.0 g of the second enantiomer with 99.5% ee.

Example 180A

2-Amino-2-[2-(trifluoromethyl)phenyl]ethyl carbamate hydrochloride (enantiomer II)

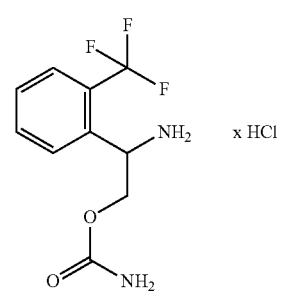 [SMILES: NC(=O)OCC(N)c1ccccc1C(F)(F)F ; "x HCl"]

Of the compound from Example 179A, 250 mg (0.82 mmol) were introduced in 9.76 ml of acetonitrile under argon. At −15° C., 100 µl (1.15 mmol) of chlorosulphonyl isocyanate were added dropwise. After 30 min, the reaction solution was admixed with 20 ml of water and heated at 60° C. overnight. The batch was cooled and introduced into saturated aqueous sodium hydrogen carbonate solution. It was extracted twice with ethyl acetate. The combined organic phases were dried over sodium sulphate, filtered and freed from the solvent on a rotary evaporator. Drying in an HV gave 220 mg (100% of theory) of the title compound.

LC/MS [Method 4]: $R_t$=0.39 min; m/z=249 (M+H)$^+$.

Example 181A

[(tert-Butoxycarbonyl)amino](2,3-dichlorophenyl)acetic acid

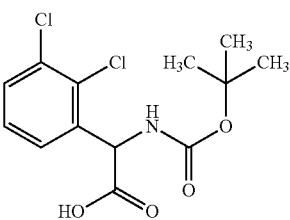

A quantity of 500 mg (2.27 mmol) of amino(2,3-dichlorophenyl)acetic acid was suspended in 5 ml of dioxane and 5% strength aqueous sodium hydrogen carbonate solution. Then 522 µl (2.27 mmol) of di-tert-butyl dicarbonate were added. The batch was stirred at RT overnight. The reaction mixture was extracted twice with ethyl acetate. The aqueous phase was acidified with 1M hydrochloric acid and extracted twice with ethyl acetate. The combined organic phases were dried over sodium sulphate, filtered and freed from the solvent on a rotary evaporator. Drying in an HV gave 703 mg (94% of theory) of the title compound.

LC/MS [Method 5]: $R_t$=1.02 min; m/z=318 and 320 (M−H)$^-$.

Example 182A tert-Butyl [1-(2,3-dichlorophenyl)-2-hydroxyethyl]carbamate

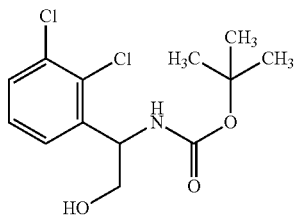 [SMILES: CC(C)(C)OC(=O)NC(CO)c1cccc(Cl)c1Cl]

Of the compound from Example 181A, 702 mg (2.19 mmol) were dissolved in 7 ml of THF under argon and cooled to 0° C. Then 306 µl (2.19 mmol) of triethylamine and 313 µl (2.41 mmol) of isobutyl chloroformate were added dropwise. The suspension was stirred at 0° C. for 1 h. It was filtered through a Seitz frit into a cooled flask, with washing with a little THF. The resulting filtrate was added slowly dropwise to a solution, cooled to 0° C., of 249 mg (6.58 mmol) of sodium borohydride in 1.5 ml of water. After 1 h, the batch was cautiously admixed with saturated aqueous sodium hydrogen carbonate solution and extracted with ethyl acetate. The organic phase was also washed once with saturated aqueous sodium hydrogen carbonate solution and once with saturated aqueous sodium chloride solution. It was dried over sodium sulphate, filtered and freed from the solvent on a rotary evaporator. Drying in an HV gave 537 mg (56% of theory) of the title compound in 70% purity.

LC/MS [Method 4]: $R_t$=1.02 min; m/z=306 and 308 (M+H)$^+$.

Example 183A

2-Amino-2-(2,3-dichlorophenyl)ethyl carbamate

Of the compound from Example 182A, 290 mg (about 0.95 mmol) were introduced in 5 ml of acetonitrile under argon. At −15° C., 115 µl (1.33 mmol) of chlorosulphonyl isocyanate were added dropwise. After 30 min, the reaction solution was admixed with 20 ml of water and heated at 60° C. overnight. The reaction mixture was cooled and introduced into saturated aqueous sodium hydrogen carbonate solution. It was extracted with twice 20 ml of ethyl acetate. The combined organic phases were dried over sodium sulphate, filtered and freed from the solvent on a rotary evaporator. Drying in an HV gave 176 mg (66% of theory) of the title compound in 89% purity.

LC/MS [Method 2]: $R_t$=1.07 min; m/z=249 (M+H)$^+$.

Example 184A

2-Amino-2-[3-(trifluoromethyl)phenyl]ethyl carbamate

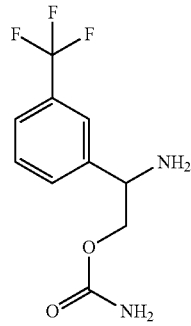 [SMILES: NC(=O)OCC(N)c1cccc(C(F)(F)F)c1]

Of the compound from Example 59A, 93 mg (0.31 mmol) were introduced in 4 ml of acetonitrile under argon. At −15° C., 37 µl (0.43 mmol) of chlorosulphonyl isocyanate were added dropwise. After 30 min, the reaction solution was admixed with 8 ml of water and heated at 60° C. overnight. The reaction mixture was cooled and introduced into saturated sodium hydrogen carbonate solution. It was extracted with twice 10 ml of ethyl acetate. The combined organic phases were dried over sodium sulphate, filtered and freed from the solvent on a rotary evaporator. Drying in an HV gave 66 mg (64% of theory) of the title compound in 73% purity.

LC/MS [Method 3]: $R_t$=0.50 min; m/z=249 (M+H)$^+$.

Example 185A

[4-(4-Chlorophenyl)-2-oxo-3-(3,3,3-trifluoro-2-hydroxypropyl)-2,3-dihydro-1H-imidazol-1-yl]acetic acid (enantiomer mixture)

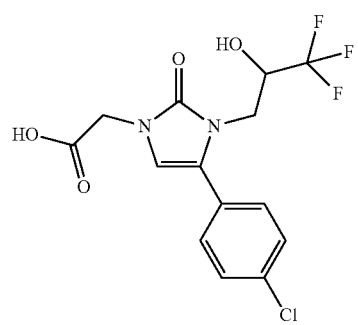 [SMILES: O=C(O)Cn1cc(-c2ccc(Cl)cc2)n(CC(O)C(F)(F)F)c1=O]

A quantity of 1.0 g (3.75 mmol) of methyl [4-(4-chlorophenyl)-2-oxo-2,3-dihydro-1H-imidazol-1-yl]acetate (prepared according to WO 2007/134862 Example 323A) was dissolved with 796 mg (4.13 mmol) of 3-bromo-1,1,1-trifluoropropan-2-ol in 50 ml of acetone, 1.47 g (4.50 mmol) of caesium carbonate were added at RT, and the mixture was heated under reflux for 16 h. For work-up, it was cooled to RT and admixed with 50 ml of water. It was neutralised by addition of 1M hydrochloric acid and extracted with three times 50 ml of ethyl acetate. The combined organic phases were dried over sodium sulphate, filtered and concentrated under reduced pressure. The crude product was purified by preparative HPLC [Method 19]. This gave 171 mg (13% of theory) of the target compound.

LC-MS [Method 3] $R_t$=1.02 min; MS [ESIpos]: m/z=365 (M+H)$^+$

Example 186A

2-[(tert-Butoxycarbonyl)amino]-2-[2-(trifluoromethyl)phenyl]ethyl ethylcarbamate (enantiomerically pure)

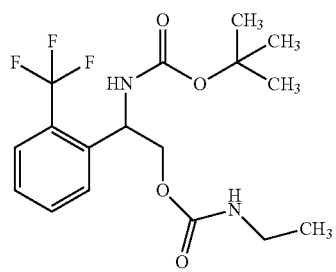 [SMILES: CCNC(=O)OCC(NC(=O)OC(C)(C)C)c1ccccc1C(F)(F)F]

A quantity of 379 µl (4.78 mmol) of ethyl isocyanate was added to a solution of 365 mg (1.20 mmol) of the compound from Example 179A and 15 mg (0.12 mmol) of 4-dimethylaminopyridine in 7 ml of pyridine. The reaction mixture was stirred at 50° C. overnight. After cooling to RT, the mixture was admixed with 0.5 ml of ammonia solution (35% in water). The volatile constituents were removed on a rotary evaporator. The residue was dissolved in a little acetonitrile and 1N hydrochloric acid, and separated by preparative HPLC [Method 20]. The product-containing fraction was freed from the solvents on a rotary evaporator and the residue was dried in an HV. This gave 380 mg (84% of theory) of the title compound.

LC-MS [Method 4] $R_t$=1.09 min; MS [ESIpos]: m/z=377 (M+H)$^+$

Example 187A

2-Amino-2-[2-(trifluoromethyl)phenyl]ethyl ethylcarbamate hydrochloride (enantiomerically pure)

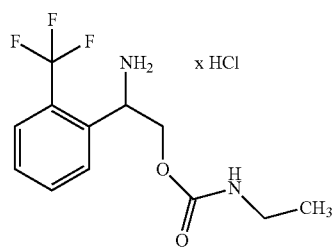 [SMILES: CCNC(=O)OCC(N)c1ccccc1C(F)(F)F ; "x HCl"]

Of the compound from Example 186A, 345 mg (0.92 mmol) were admixed with 10 ml of a 4N solution of hydrogen chloride in dioxane, and the mixture was stirred at RT for 30 min All volatile constituents were then removed on a rotary evaporator. The residue (311 mg, 100% of theory) was the title compound.

LC-MS [Method 2] $R_t$=1.20 min; MS [ESIpos]: m/z=277 (M+H)$^+$ $^1$H-NMR (500 MHz, DMSO-d$_6$): δ [ppm]=1.00 (t, 3H), 2.93-3.06 (m, 2H), 4.28 (dd, 1H), 4.38 (dd, 1H), 4.62-4.70 (m, 1H), 7.12 (br. t, 1H), 7.67 (t, 1H), 7.80-7.88 (m, 2H), 7.98 (d, 1H), 8.84 (br. s., 3H).

IMPLEMENTING EXAMPLES

Example 1

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[3-(trifluoromethyl)phenyl]ethyl}acetamide (diastereomer mixture)

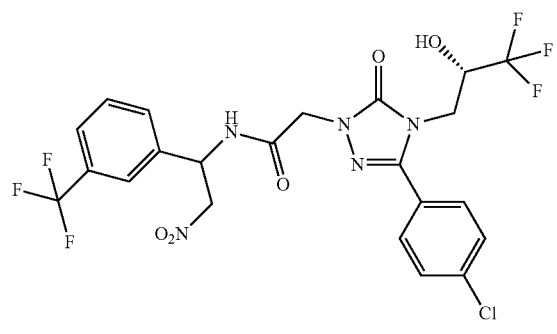 [SMILES: O=C(Cn1nc(-c2ccc(Cl)cc2)n(C[C@H](O)C(F)(F)F)c1=O)NC(C[N+](=O)[O-])c1cccc(C(F)(F)F)c1]

Of the compound from Example 8A, 337 mg (0.92 mmol) were introduced together with 274 mg (1.01 mmol, 1.1 eq.) of the compound from Example 13A, 247 mg (1.29 mmol, 1.4 eq.) of EDC and 174 mg (1.29 mmol, 1.4 eq.) of HOBt with 8 ml of DMF, and then 192 µl (1.10 mmol, 1.2 eq.) of N,N-diisopropylethylamine were added. The mixture was stirred at RT for 1 h, then purified by preparative HPLC (Method 10). This gave 445 mg (81% of theory) of the title compound.

LC-MS [Method 2]: $R_t$=2.46 min; MS [ESIpos]: m/z=582 (M+H)$^+$ $^1$H NMR (DMSO-d$_6$, 400 MHz): δ=9.07 (d, 1H), 7.83 (s, 1H), 7.66-7.79 (m, 4H), 7.56-7.66 (m, 3H), 6.925 (d, 0.5H (1H from diastereomer I)), 6.91 (d, 0.5H (1H from diastereomer II)), 5.63-5.77 (m, 1H), 5.08 (dd, 1H), 4.95 (dd, 1H), 4.53 (s, 1H (2H from diastereomer I)), 4.43-4.61 (m [AB], 1H (2H from diastereomer II)), 4.18-4.37 (m, 1H), 3.96 (br. d, 1H), 3.83 (dd, J=14.7, 9.5 Hz, 1H).

The diastereomers from Example 1 were separated by preparative chromatography on a chiral phase (Method 11a): see Example 2 and Example 3.

Example 2

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[3-(trifluoromethyl)phenyl]ethyl}acetamide (diastereomer I)

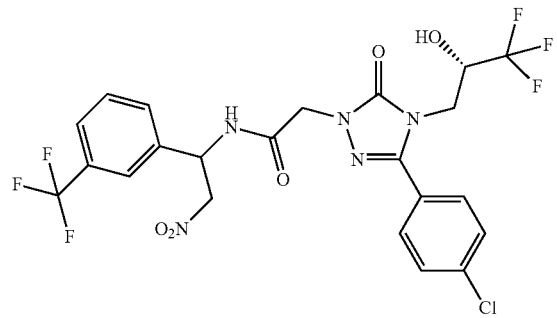 [SMILES: O=C(Cn1nc(-c2ccc(Cl)cc2)n(C[C@H](O)C(F)(F)F)c1=O)NC(C[N+](=O)[O-])c1cccc(C(F)(F)F)c1]

First-eluting diastereomer from the separation of Example 1 by Method 11a.

LC-MS [Method 2]: $R_t$=2.43 min; MS [ESIpos]: m/z=582 (M+H)$^+$

Analytical chiral HPLC [Method 12a]: $R_t$=4.40 min

Example 3

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[3-(trifluoromethyl)phenyl]ethyl}acetamide (diastereomer II)

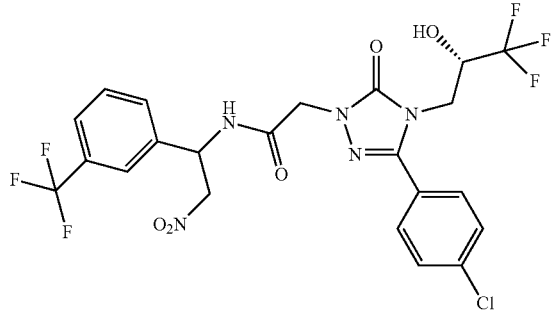 [SMILES: O=C(Cn1nc(-c2ccc(Cl)cc2)n(C[C@H](O)C(F)(F)F)c1=O)NC(C[N+](=O)[O-])c1cccc(C(F)(F)F)c1]

Last-eluting diastereomer from the separation of Example 1 by Method 11a.

LC-MS [Method 2]: $R_t$=2.44 min; MS [ESIpos]: m/z=582 (M+H)$^+$

Analytical chiral HPLC [Method 12a]: $R_t$=5.37 min.

Example 4

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[2-(trifluoromethyl)phenyl]ethyl}acetamide (diastereomer mixture)

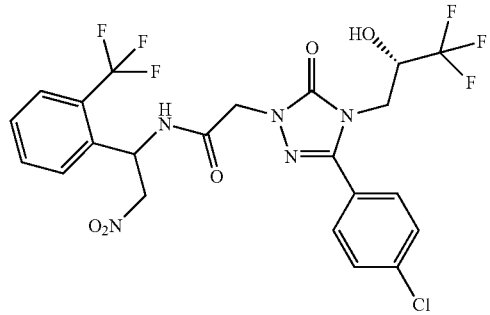 [SMILES: O=C(Cn1nc(-c2ccc(Cl)cc2)n(C[C@H](O)C(F)(F)F)c1=O)NC(C[N+](=O)[O-])c1ccccc1C(F)(F)F]

In the same way as for the preparation of Example 1, from 766 mg (2.09 mmol) of the compound from Example 8A and 656 mg (2.30 mmol) of the compound from Example 17A, 880 mg (72% of theory) of the title compound were obtained.

LC-MS [Method 5]: $R_t$=1.12 min; MS [ESIpos]: m/z=582 (M+H)$^+$

The diastereomers from Example 4 were separated by preparative chromatography on a chiral phase (Method 11b): see Example 5 and Example 6.

Example 5

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[2-(trifluoromethyl)phenyl]ethyl}acetamide (diastereomer I)

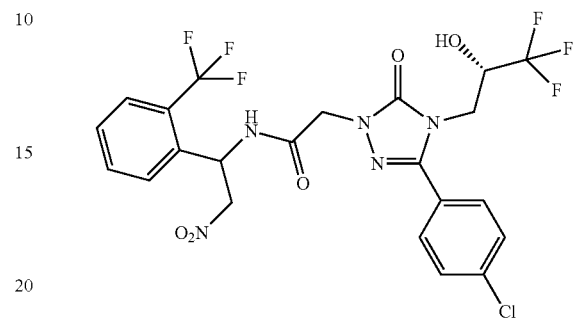

First-eluting diastereomer (419 mg) from the diastereomer separation of 880 mg of the compound from Example 4 by Method 11b.

LC-MS [Method 2]: $R_t$=2.40 min; MS [ESIpos]: m/z=582 (M+H)$^+$

Analytical chiral HPLC [Method 12a]: $R_t$=4.20 min.

$^1$H NMR (DMSO-$d_6$, 400 MHz): δ=9.20 (d, 1H), 7.82 (d, 1H), 7.80-7.71 (m, 4H), 7.63 (d, 2H), 7.58 (t, 1H), 6.92 (d, 1H), 6.02-5.94 (m, 1H), 4.92 (dd, 1H), 4.82 (dd, 1H), 4.49 (s, 2H), 4.32-4.19 (m, 1H), 3.95 (dd, 1H), 3.82 (dd, 1H).

Example 6

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-nitro-1-[2-(trifluoromethyl)phenyl]ethyl}acetamide (diastereomer II)

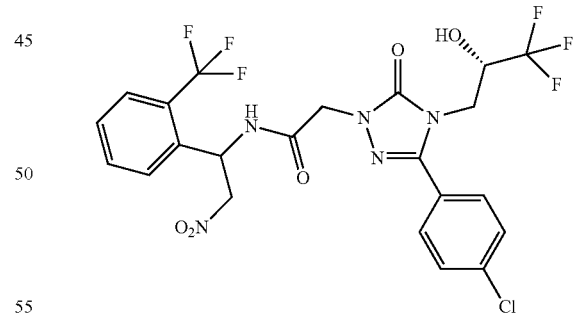

Last-eluting diastereomer (417 mg) from the diastereomer separation of 880 mg of the compound from Example 4 by Method 11b.

LC-MS [Method 2]: $R_t$=2.39 min; MS [ESIpos]: m/z=582 (M+H)$^+$

Analytical chiral HPLC [Method 12a]: $R_t$=5.64 min.

$^1$H NMR (DMSO-$d_6$, 400 MHz): δ=9.20 (d, 1H), 7.82 (d, 1H), 7.80-7.70 (m, 4H), 7.62 (d, 2H), 7.58 (t, 1H), 6.90 (d, 1H), 6.00-5.93 (m, 1H), 4.92 (dd, 1H), 4.82 (dd, 1H), 4.48 (dd [AB], 2H), 4.31-4.20 (m, 1H), 3.96 (dd, 1H), 3.82 (dd, 1H).

Example 7

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-[2,3-dichlorophenyl]-2-nitroethyl}acetamide (diastereomer mixture)

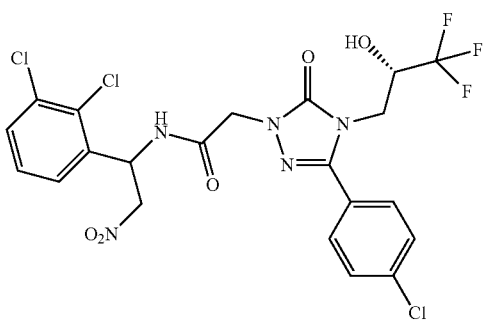 [SMILES: O=C(Cn1nc(-c2ccc(Cl)cc2)n(C[C@H](O)C(F)(F)F)c1=O)NC(C[N+](=O)[O-])c1cccc(Cl)c1Cl]

In the same way as for the preparation of Example 1, from 422 mg (1.16 mmol) of the compound from Example 8A and 363 mg (1.27 mmol) of the compound from Example 21A, 638 mg (91% of theory) of the title compound were obtained.

LC-MS [Method 5]: $R_t$=1.13 min; MS [ESIpos]: m/z=582 (M+H)$^+$

The diastereomers from Example 7 were separated by preparative chromatography on a chiral phase (Method 11c): see Example 8 and Example 9.

Example 8

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-[2,3-dichlorophenyl]-2-nitroethyl}acetamide (diastereomer I)

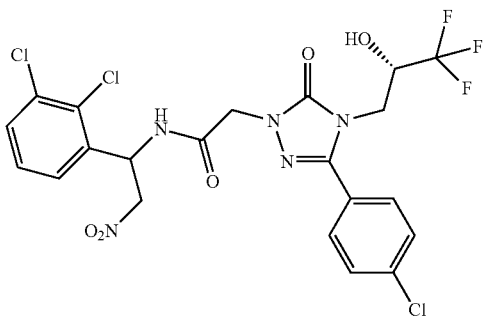 [SMILES: O=C(Cn1nc(-c2ccc(Cl)cc2)n(C[C@H](O)C(F)(F)F)c1=O)NC(C[N+](=O)[O-])c1cccc(Cl)c1Cl]

First-eluting diastereomer (181 mg) from the diastereomer separation of 630 mg of the compound from Example 7 by Method 11c.

LC-MS [Method 2]: $R_t$=2.44 min; MS [ESIpos]: m/z=582 (M+H)$^+$

Analytical chiral HPLC [Method 12b]: $R_t$=5.81 min.

$^1$H NMR (DMSO-d$_6$, 400 MHz): δ=9.22 (d, 1H), 7.74 (d, 2H), 7.67-7.61 (m, 3H), 7.55 (dd, 1H), 7.43 (t, 1H), 6.91 (d, 1H), 6.04-5.97 (m, 1H), 5.01 (dd, 1H), 4.81 (dd, 1H), 4.58-4.47 (m[AB], 2H), 4.33-4.21 (m, 1H), 3.95 (dd, 1H), 3.82 (dd, 1H).

Example 9

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-[2,3-dichlorophenyl]-2-nitroethyl}acetamide (diastereomer II)

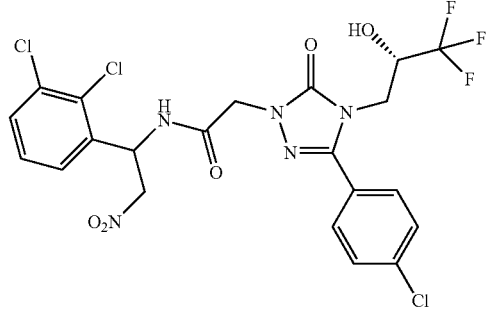 [SMILES: O=C(Cn1nc(-c2ccc(Cl)cc2)n(C[C@H](O)C(F)(F)F)c1=O)NC(C[N+](=O)[O-])c1cccc(Cl)c1Cl]

Last-eluting diastereomer (281 mg) from the diastereomer separation of 630 mg of the compound from Example 7 by Method 11c.

LC-MS [Method 2]: $R_t$=2.44 min; MS [ESIpos]: m/z=582 (M+H)$^+$

Analytical chiral HPLC [Method 12b]: $R_t$=6.66 min.

$^1$H NMR (DMSO-d$_6$, 400 MHz): δ=9.22 (d, 1H), 7.74 (d, 2H), 7.66 (d, 1H), 7.63 (d, 2H), 7.55 (dd, 1H), 7.44 (t, 1H), 6.90 (d, 1H), 6.04-5.96 (m, 1H), 5.01 (dd, 1H), 4.81 (dd, 1H), 4.58-4.47 (m[AB], 2H), 4.31-4.20 (m, 1H), 3.96 (dd, 1H), 3.82 (dd, 1H).

Example 10

N-{2-Amino-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer mixture)

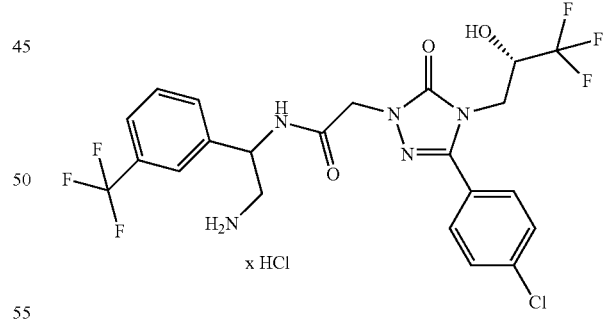

Of the compound from Example 1, 45 mg (77 μmol) and 40 mg (348 μmol) of indium powder were admixed in 0.5 ml of THF with 42 μl of conc. hydrochloric acid, and the mixture was stirred at RT for 2 h. Then the mixture was purified by preparative HPLC (Method 10). The product-containing fractions were admixed with 2 ml of 1N hydrochloric acid and concentrated on a rotary evaporator. Drying in an HV gave 21 mg (46% of theory) of the title compound as a diastereomer mixture.

LC-MS [Method 5]: $R_t$=0.85 min; MS [ESIpos]: m/z=552 (M+H)$^+$

Example 11

N-{2-Amino-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer I)

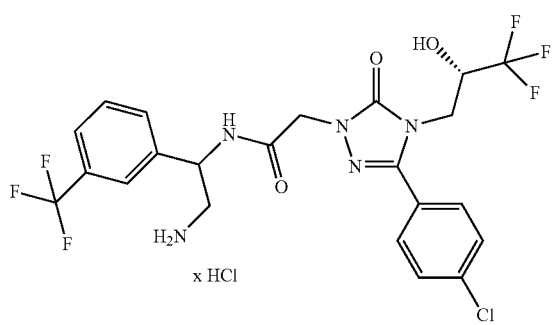 [SMILES: NCC(NC(=O)Cn1nc(-c2ccc(Cl)cc2)n(C[C@H](O)C(F)(F)F)c1=O)c1cccc(C(F)(F)F)c1]

In a continuous-flow hydrogenation apparatus (H-Cube from Thales Nano, Budapest, Model HC-2-SS) a solution of 325 mg (0.56 mmol) of the compound from Example 2 in 50 ml of methanol was hydrogenated (conditions: Raney Nickel cartridge, flow rate of 1 ml/min, 45° C., standard hydrogen pressure). The methanol was removed on a rotary evaporator and the residue was purified by preparative HPLC (Method 10). The product-containing fractions were admixed with 20 ml of 1N hydrochloric acid and concentrated on a rotary evaporator. Drying in an HV gave 266 mg (81% of theory) of the title compound.

LC-MS [Method 4]: $R_t$=0.90 min; MS [ESIpos]: m/z=552 (M+H)$^+$ $^1$H NMR (DMSO-d$_6$, 400 MHz): δ=8.99 (d, 1H), 7.99-8.21 (m, 3H), 7.67-7.80 (m, 5H), 7.57-7.67 (m, 3H), 6.89 (d, 1H), 5.18-5.28 (m, 1H), 4.50-4.67 (m [AB], 2H), 4.21-4.34 (m, 1H), 3.97 (dd, 1H), 3.83 (dd, 1H), 3.13-3.28 (m, 2H).

Example 12

N-{2-Amino-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer II)

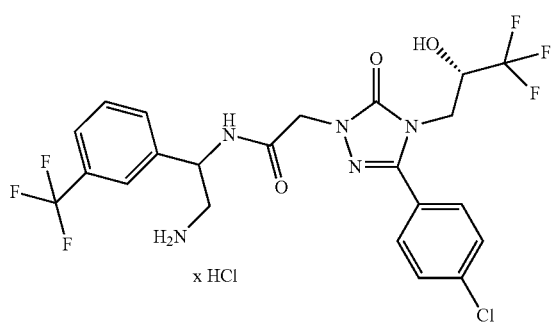 [SMILES: NCC(NC(=O)Cn1nc(-c2ccc(Cl)cc2)n(C[C@H](O)C(F)(F)F)c1=O)c1cccc(C(F)(F)F)c1]

In the same way as for Example 11, but at RT, 316 mg (0.54 mmol) of the compound from Example 3 were hydrogenated. This gave 180 mg (56% of theory) of the title compound.

LC-MS [Method 4]: $R_t$=0.89 min; MS [ESIpos]: m/z=552 (M+H)$^+$ $^1$H NMR (DMSO-d$_6$, 400 MHz): δ=9.00 (d, 1H), 8.12 (br.s, 3H), 7.66-7.81 (m, 5H), 7.57-7.66 (m, 3H), 6.94 (d, 1H), 5.20-5.29 (m, 1H), 4.50-4.66 (m [AB], 2H), 4.20-4.33 (m, 1H), 3.97 (dd, 1H), 3.83 (dd, 1H), 3.13-3.28 (m, 2H).

Example 13

N-{2-Amino-1-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer I)

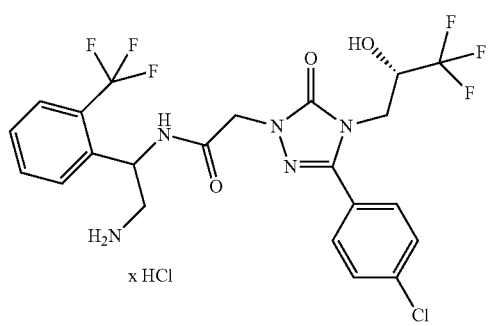 [SMILES: NCC(NC(=O)Cn1nc(-c2ccc(Cl)cc2)n(C[C@H](O)C(F)(F)F)c1=O)c1ccccc1C(F)(F)F]

In the same way as for Example 11, but at RT, 415 mg (0.71 mmol) of the compound from Example 5 in 100 ml of methanol were hydrogenated. This gave 330 mg (79% of theory) of the title compound.

LC-MS [Method 6]: $R_t$=1.57 min; MS [ESIpos]: m/z=552 (M+H)$^+$ $^1$H NMR (DMSO-d$_6$, 400 MHz): δ=9.11-9.18 (m, 1H), 8.24 (br.s, 3H), 7.87 (d, 1H), 7.71-7.78 (m, 4H), 7.60-7.65 (m, 2H), 7.55 (t, 1H), 6.93 (d, 1H), 5.44-5.53 (m, 1H), 4.66 (dd, 1H), 4.52 (d, 1H), 4.19-4.30 (m, 1H), 3.96 (dd, 1H), 3.82 (dd, 1H), 3.07-3.22 (m, 1H), 2.95-3.07 (m, 1H).

Example 14

N-{2-Amino-1-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer II)

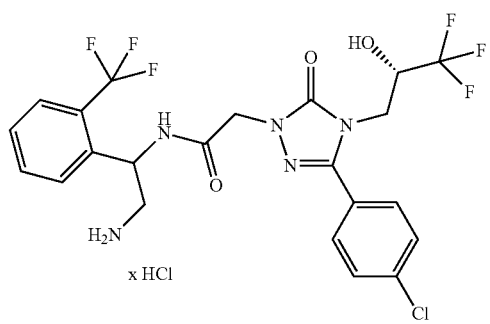 [SMILES: NCC(NC(=O)Cn1nc(-c2ccc(Cl)cc2)n(C[C@H](O)C(F)(F)F)c1=O)c1ccccc1C(F)(F)F]

In the same way as for Example 11, but at RT, 415 mg (0.71 mmol) of the compound from Example 6 in 100 ml of methanol were hydrogenated. This gave 330 mg (79% of theory) of the title compound.

LC-MS [Method 6]: $R_t$=1.56 min; MS [ESIpos]: m/z=552 (M+H)$^+$

¹H NMR (DMSO-d₆, 400 MHz): δ=9.08-9.17 (m, 1H), 8.21 (br.s, 3H), 7.86 (d, 1H), 7.70-7.78 (m, 4H), 7.62 (d, 2H), 7.53-7.59 (m, 1H), 6.88 (d, 1H), 5.44-5.52 (m, 1H), 4.67 (d, 1H), 4.51 (d, 1H), 4.20-4.32 (m, 1H), 3.96 (dd, 1H), 3.82 (dd, 1H), 3.09-3.22 (m, 1H), 2.96-3.08 (m, 1H).

Example 15

N-[2-Amino-1-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer I)

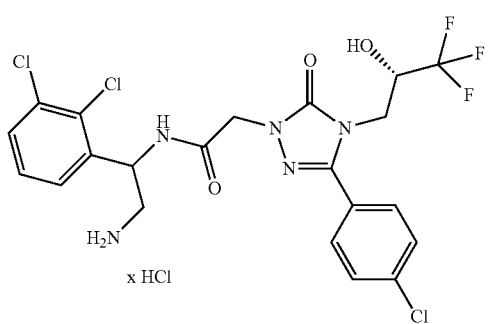 [SMILES: NCC(NC(=O)Cn1nc(-c2ccc(Cl)cc2)n(C[C@H](O)C(F)(F)F)c1=O)c1cccc(Cl)c1Cl]

In the same way as for Example 11, but at RT, 180 mg (0.31 mmol) of the compound from Example 8 in 50 ml of methanol were hydrogenated. This gave 116 mg (64% of theory) of the title compound.

LC-MS [Method 6]: $R_t$=1.61 min; MS [ESIpos]: m/z=552 (M+H)⁺

¹H NMR (DMSO-d₆, 400 MHz): δ=9.15 (d, 1H), 8.23 (br.s, 3H), 7.75 (d, 2H), 7.57-7.66 (m, 4H), 7.42 (t, 1H), 6.93 (d, 1H), 5.53 (td, 1H), 4.52-4.68 (m, 2H), 4.19-4.31 (m, 1H), 3.96 (dd, 1H), 3.83 (dd, 1H), 3.06-3.18 (m, 2H).

Example 16

N-[2-Amino-1-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide hydrochloride (diastereomer II)

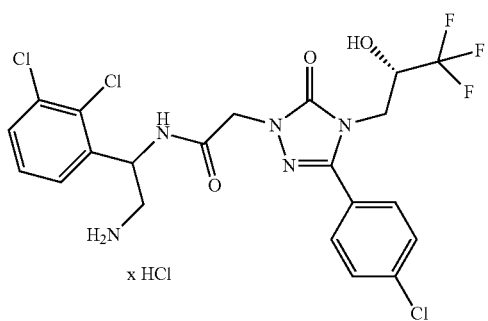 [SMILES: NCC(NC(=O)Cn1nc(-c2ccc(Cl)cc2)n(C[C@H](O)C(F)(F)F)c1=O)c1cccc(Cl)c1Cl]

In the same way as for Example 11, but at RT, 280 mg (0.48 mmol) of the compound from Example 9 in 80 ml of methanol were hydrogenated. This gave 177 mg (63% of theory) of the title compound.

LC-MS [Method 5]: $R_t$=0.84 min; MS [ESIpos]: m/z=552 (M+H)⁺

¹H NMR (DMSO-d₆, 400 MHz): δ=9.23 (d, 1H), 8.26 (br.s, 3H), 7.74 (d, 2H), 7.58-7.67 (m, 4H), 7.42 (t, 1H), 6.90 (d, 1H), 5.52 (q, 1H), 4.52-4.69 (m [AB], 2H), 4.22-4.33 (m, 1H), 3.96 (dd, 1H), 3.82 (dd, 1H), 3.08-3.18 (m, 2H).

Example 17

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(formylamino)-1-[2-(trifluoromethyl)phenyl]ethyl}acetamide (diastereomer mixture)

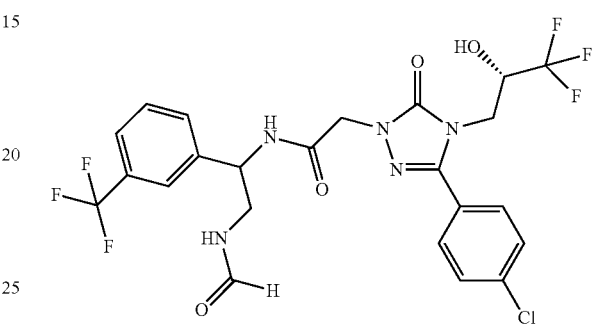

Using the method described in Example 1, from 62 mg (0.17 mmol) of the compound from Example 8A and 50 mg (0.19 mmol) of the compound from Example 24A, the title compound was obtained: 80 mg (82% of theory).

LC-MS [Method 5]: $R_t$=1.06 min; MS [ESIpos]: m/z=580 (M+H)⁺

The diastereomers from Example 17 were separated by preparative chromatography on a chiral phase (Method 17a): see Example 18 and Example 19.

Example 18

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(formylamino)-1-[3-(trifluoromethyl)phenyl]ethyl}acetamide (diastereomer I)

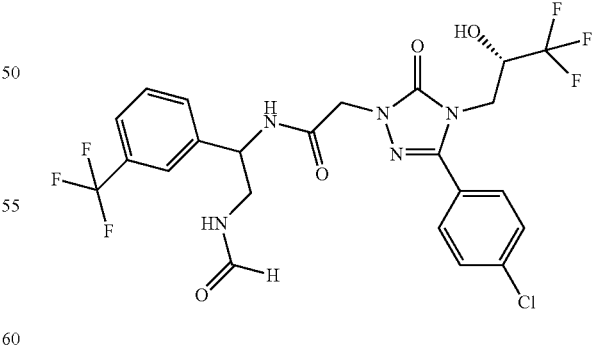

First-eluting diastereomer (28 mg) from the separation of 80 mg of the compound from Example 17 by Method 17a.

LC-MS [Method 4]: $R_t$=1.04 min; MS [ESIpos]: m/z=580 (M+H)⁺

Analytical chiral HPLC [Method 18a]: $R_t$=5.28 min

¹H NMR (DMSO-d₆, 400 MHz): δ=8.72 (d, 1H), 8.17 (t, 1H), 7.99 (s, 1H), 7.75 (d, 2H), 7.69 (s, 1H), 7.55-7.68 (m,

5H), 6.92 (d, 1H), 5.00-5.08 (m, 1H), 4.51 (s, 2H), 4.21-4.35 (m, 1H), 3.96 (dd, 1H), 3.83 (dd, 1H), 3.46-3.55 (m, 1H), 3.32-3.40 (m, 1H).

Example 19

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(formylamino)-1-[3-(trifluoromethyl)phenyl]ethyl}acetamide (diastereomer II)

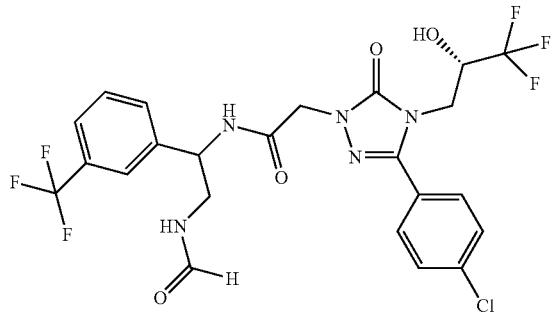 [SMILES: O=CNCC(NC(=O)Cn1nc(-c2ccc(Cl)cc2)n(C[C@H](O)C(F)(F)F)c1=O)c1cccc(C(F)(F)F)c1]

Last-eluting diastereomer (30 mg) from the separation of 80 mg of the compound from Example 17 by Method 17a.
LC-MS [Method 4]: $R_t$=1.04 min; MS [ESIpos]: m/z=580 (M+H)$^+$
Analytical chiral HPLC [Method 18a]: $R_t$=15.29 min
$^1$H NMR (DMSO-d$_6$, 400 MHz): δ=8.73 (d, 1H), 8.16 (t, 1H), 7.99 (s, 1H), 7.74 (d, 2H), 7.69 (s, 1H), 7.56-7.67 (m, 5H), 6.89 (d, 1H), 5.00-5.08 (m, 1H), 4.45-4.56 (m [AB], 2H), 4.22-4.34 (m, 1H), 3.97 (dd, 1H), 3.83 (dd, 1H), 3.47-3.55 (m, 1H), 3.32-3.40 (m, 1H).

Example 20

N-{2-(Acetylamino)-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

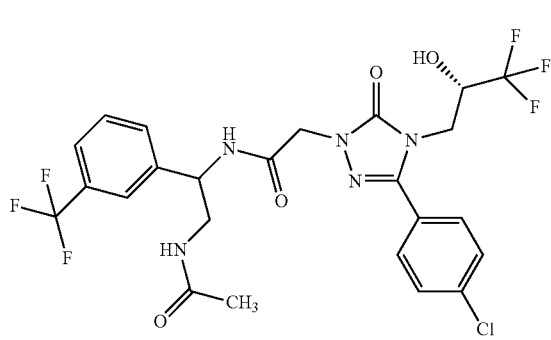 [SMILES: CC(=O)NCC(NC(=O)Cn1nc(-c2ccc(Cl)cc2)n(C[C@H](O)C(F)(F)F)c1=O)c1cccc(C(F)(F)F)c1]

Using the method described in Example 1, from 82 mg (0.22 mmol) of the compound from Example 8A and 70 mg (0.25 mmol) of the compound from Example 26A, the title compound was obtained: 110 mg (75% of theory).
LC-MS [Method 2] $R_t$=2.26/2.28 min; MS [ESIpos]: m/z=594 (M+H)$^+$
The two diastereomers were separated by preparative chromatography on a chiral phase (Method 17e): see Examples 21 and 22.

Example 21

N-{2-(Acetylamino)-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

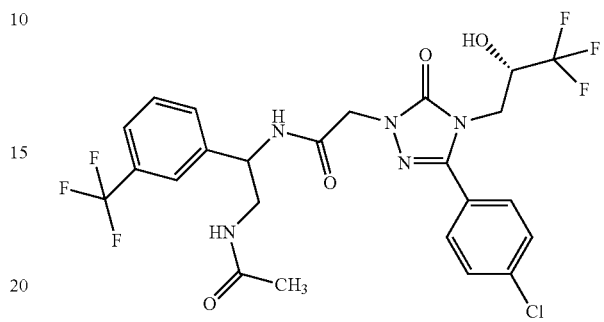

First-eluting diastereomer (42 mg) from the separation of 110 mg of the compound from Example 20 by Method 17e.
LC-MS [Method 4]: $R_t$=1.06 min; MS [ESIpos]: m/z=594 (M+H)$^+$
Analytical chiral HPLC [Method 18a]: $R_t$=4.18 min
$^1$H NMR (DMSO-d$_6$, 400 MHz): δ=8.67 (d, 1H), 8.01 (t, 1H), 7.76 (d, 2H), 7.54-7.68 (m, 6H), 6.94 (d, 1H), 4.96-5.04 (m, 1H), 4.45-4.56 (m [AB], 2H), 4.25-4.36 (m, 1H), 3.97 (dd, 1H), 3.83 (dd, 1H), 3.36-3.46 (m, 1H), 3.27-3.35 (m, 1H), 1.75 (s, 3H).

Example 22

N-{2-(Acetylamino)-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

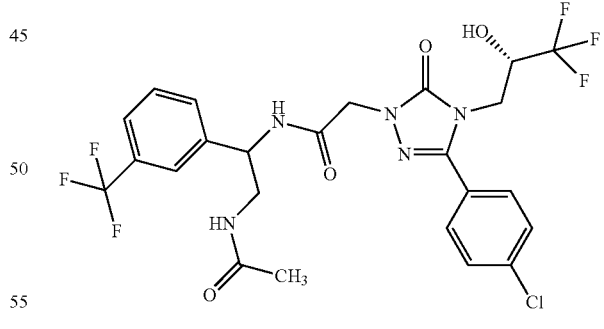

Last-eluting diastereomer (43 mg) from the separation of 110 mg of the compound from Example 20 by Method 17e.
LC-MS [Method 4]: $R_t$=1.08 min; MS [ESIpos]: m/z=594 (M+H)$^+$
Analytical chiral HPLC [Method 18a]: $R_t$=9.35 min
$^1$H NMR (DMSO-d$_6$, 400 MHz): δ=8.68 (d, 1H), 8.01 (t, 1H), 7.75 (d, 2H), 7.55-7.68 (m, 6H), 6.92 (d, 1H), 4.96-5.03 (m, 1H), 4.45-4.55 (m, 2H), 4.24-4.36 (m, 1H), 3.97 (dd, 1H), 3.83 (dd, 1H), 3.37-3.45 (m, 1H), 3.26-3.36 (m, 1H), 1.75 (s, 3H).

Example 23

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-1-[3-(trifluoromethyl)phenyl]ethyl}acetamide (diastereomer I)

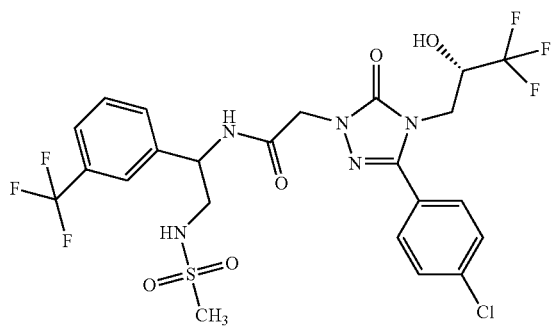 [SMILES: CS(=O)(=O)NCC(NC(=O)Cn1nc(-c2ccc(Cl)cc2)n(C[C@H](O)C(F)(F)F)c1=O)c1cccc(C(F)(F)F)c1]

A mixture of 52 mg of the compound from Example 8A (0.14 mmol) and 27 mg (0.20 mmol) of HOBt in 2 ml of DMF was introduced, admixed with 38 mg (0.20 mmol) of EDC and stirred at RT for 20 min. Then 50 mg (0.16 mmol) of the compound from Example 50A and 35 µl (0.20 mmol) of N,N-diisopropylethylamine were added and the reaction mixture was stirred further at RT overnight. The entire mixture was purified completely by preparative HPLC (Method 10). This gave 68 mg (76% of theory) of the title compound.

LC-MS [Method 2]: $R_t$=2.32 min; MS [ESIpos]: m/z=630 (M+H)$^+$ $^1$H NMR (DMSO-d$_6$, 400 MHz): δ=8.70 (d, 1H), 7.71-7.78 (m, 3H), 7.57-7.70 (m, 5H), 7.24 (t, 1H), 6.92 (d, 1H), 5.02-5.11 (m, 1H), 4.48-4.60 (m [AB], 2H), 4.23-4.34 (m, 1H), 3.96 (dd, 1H), 3.83 (dd, 1H), 3.25-3.33 (m, 2H), 2.86 (s, 3H).

Example 24

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-1-[3-(trifluoromethyl)phenyl]ethyl}acetamide (diastereomer II)

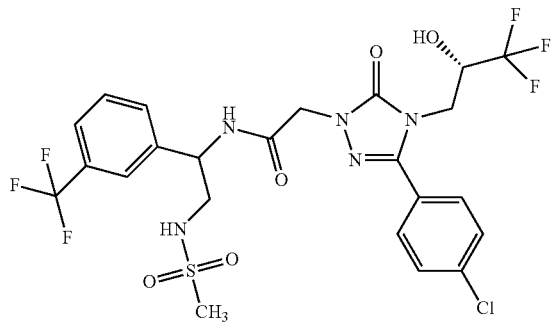 [SMILES: CS(=O)(=O)NCC(NC(=O)Cn1nc(-c2ccc(Cl)cc2)n(C[C@H](O)C(F)(F)F)c1=O)c1cccc(C(F)(F)F)c1]

A mixture of 45 mg of the compound from Example 8A (0.12 mmol) and 23 mg (0.17 mmol, 1.4 eq.) of HOBt in 1.7 ml of DMF was introduced, admixed with 33 mg (0.17 mmol, 1.4 eq.) of EDC and stirred at RT for 20 min. Then 43 mg (0.14 mmol, 1.1 eq.) of the compound from Example 47A and 30 µl (0.17 mmol, 1.4 eq.) of N,N-diisopropylethylamine were added and the reaction mixture was stirred further at RT overnight. The entire mixture was purified by preparative HPLC (Method 10). This gave 51 mg (66% of theory) of the title compound.

LC-MS [Method 2]: $R_t$=2.30 min; MS [ESIpos]: m/z=630 (M+H)$^+$ $^1$H NMR (DMSO-d$_6$, 400 MHz): δ=8.72 (d, 1H), 7.72-7.77 (m, 3H), 7.57-7.70 (m, 5H), 7.24 (t, 1H), 6.89 (d, 1H), 5.02-5.10 (m, 1H), 4.46-4.62 (m [AB], 2H), 4.22-4.32 (m, 1H), 3.97 (dd, 1H), 3.83 (dd, 1H), 3.25-3.31 (m, 2H), 2.86 (s, 3H).

Example 25

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-1-[2-(trifluoromethyl)phenyl]ethyl}acetamide (diastereomer I)

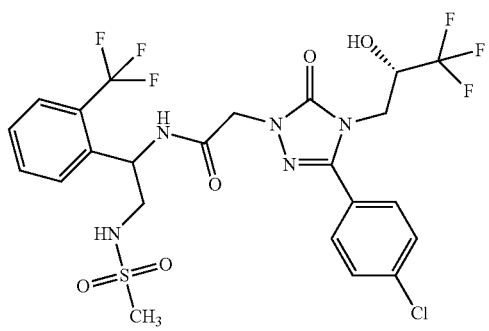 [SMILES: CS(=O)(=O)NCC(NC(=O)Cn1nc(-c2ccc(Cl)cc2)n(C[C@H](O)C(F)(F)F)c1=O)c1ccccc1C(F)(F)F]

In the same way as for Example 24, from 54 mg (0.15 mmol) of the compound from Example 8A and 52 mg (0.16 mmol) of the compound from Example 53A, the title compound was obtained: 73 mg (78% of theory).

LC-MS [Method 5]: $R_t$=1.07 min; MS [ESIpos]: m/z=630 (M+H)$^+$ $^1$H NMR (DMSO-d$_6$, 400 MHz): δ=8.75 (d, 1H), 7.68-7.80 (m, 5H), 7.62 (d, 2H), 7.51 (t, 1H), 7.41 (t, 1H), 6.93 (d, 1H), 5.30-5.38 (m, 1H), 4.61 (d, 1H), 4.47 (d, 1H), 4.22-4.33 (m, 1H), 3.95 (dd, 1H), 3.82 (dd, 1H), 3.12-3.27 (m, 2H), 2.88 (s, 3H).

Example 26

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(methylsulphonyl)amino]-1-[2-(trifluoromethyl)phenyl]ethyl}acetamide (diastereomer II)

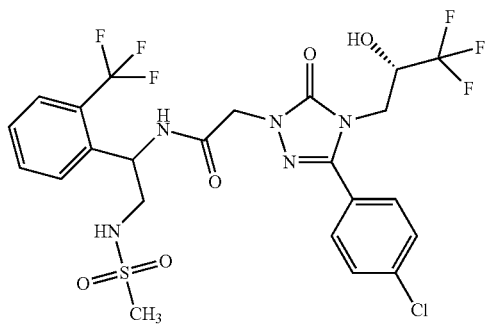 [SMILES: CS(=O)(=O)NCC(NC(=O)Cn1nc(-c2ccc(Cl)cc2)n(C[C@H](O)C(F)(F)F)c1=O)c1ccccc1C(F)(F)F]

In the same way as for Example 24, from 57 mg (0.16 mmol) of the compound from Example 8A and 55 mg (0.17 mmol) of the compound from Example 54A, the title compound was obtained: 70 mg (71% of theory).

LC-MS [Method 5]: R$_t$=1.06 min; MS [ESIpos]: m/z=630 (M+H)$^+$ $^1$H NMR (DMSO-d$_6$, 400 MHz): δ=8.76 (d, 1H), 7.70-7.80 (m, 5H), 7.61 (d, 2H), 7.52 (t, 1H), 7.41 (t, 1H), 6.89 (d, 1H), 5.29-5.37 (m, 1H), 4.62 (d, 1H), 4.46 (d, 1H), 4.21-4.34 (m, 1H), 3.96 (dd, 1H), 3.82 (dd, 1H), 3.13-3.27 (m, 2H), 2.88 (s, 3H).

Example 27

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-(2,3-dichlorophenyl)-2-[(methylsulphonyl)amino]ethyl}acetamide (diastereomer I)

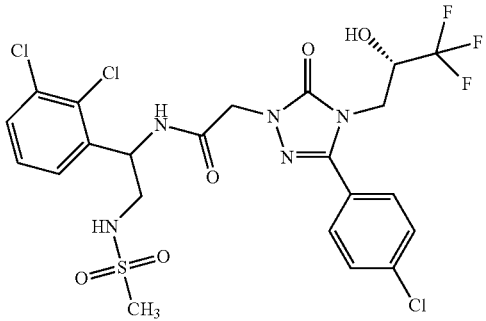 [SMILES: CS(=O)(=O)NCC(NC(=O)Cn1nc(-c2ccc(Cl)cc2)n(C[C@H](O)C(F)(F)F)c1=O)c1cccc(Cl)c1Cl]

In the same way as for Example 24, from 50 mg (0.14 mmol) of the compound from Example 8A and 48 mg (0.15 mmol) of the compound from Example 57A, the title compound was obtained: 64 mg (74% of theory).

LC-MS [Method 5]: R$_t$=1.08 min; MS [ESIpos]: m/z=630 (M+H)$^+$ $^1$H NMR (DMSO-d$_6$, 400 MHz): δ=8.76 (d, 1H), 7.74 (d, 2H), 7.62 (d, 2H), 7.59 (dd, 1H), 7.51 (dd, 1H), 7.40 (t, 1H), 7.36 (t, 1H), 6.92 (d, 1H), 5.37 (td, 1H), 4.49-4.62 (m [AB], 2H), 4.22-4.34 (m, 1H), 3.96 (dd, 1H), 3.82 (dd, 1H), 3.25-3.33 (m, 1H), 3.17 (ddd, 1H), 2.90 (s, 3H).

Example 28

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-(2,3-dichlorophenyl)-2-[(methylsulphonyl)amino]ethyl}acetamide (diastereomer II)

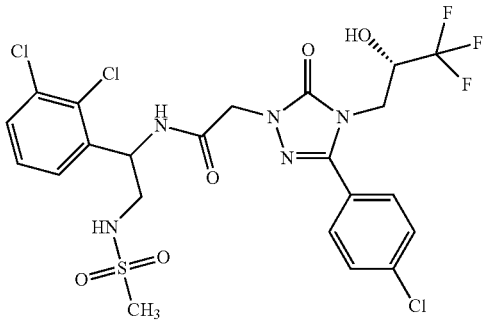 [SMILES: CS(=O)(=O)NCC(NC(=O)Cn1nc(-c2ccc(Cl)cc2)n(C[C@H](O)C(F)(F)F)c1=O)c1cccc(Cl)c1Cl]

In the same way as for Example 24, from 51 mg (0.14 mmol) of the compound from Example 8A and 49 mg (0.15 mmol) of the compound from Example 58A, the title compound was obtained: 59 mg (67% of theory).

LC-MS [Method 5]: R$_t$=1.08 min; MS [ESIpos]: m/z=630 (M+H)$^+$ $^1$H NMR (DMSO-d$_6$, 400 MHz): δ=8.77 (d, 1H), 7.74 (d, 2H), 7.58-7.64 (m, 3H), 7.51 (br.d, 1H), 7.42 (t, 1H), 7.36 (t, 1H), 6.89 (d, 1H), 5.37 (td, 1H), 4.46-4.64 (m [AB], 2H), 4.21-4.31 (m, 1H), 3.96 (dd, 1H), 3.82 (dd, 1H), 3.25-3.35 (m, 1H), 3.17 (ddd, 1H), 2.89 (s, 3H).

Example 29

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylsulphonyl)amino]-1-[3-(trifluoromethyl)phenyl]ethyl}acetamide (diastereomer I)

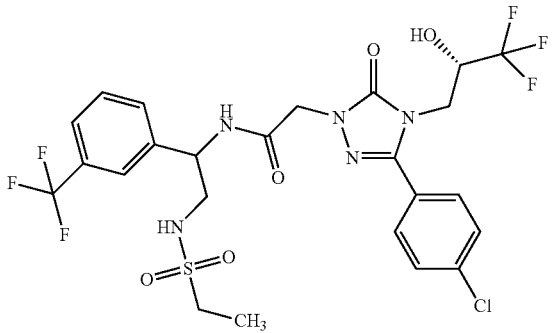 [SMILES: CCS(=O)(=O)NCC(NC(=O)Cn1nc(-c2ccc(Cl)cc2)n(C[C@H](O)C(F)(F)F)c1=O)c1cccc(C(F)(F)F)c1]

In the same way as for Example 24, from 40 mg (0.11 mmol) of the compound from Example 8A and 40 mg (0.12 mmol) of the compound from Example 48A, the title compound was obtained: 57 mg (81% of theory).

LC-MS [Method 5]: R$_t$=1.11 min; MS [ESIpos]: m/z=644 (M+H)$^+$ $^1$H NMR (DMSO-d$_6$, 400 MHz): δ=8.68 (d, 1H), 7.71-7.78 (m, 3H), 7.57-7.69 (m, 5H), 7.27 (t, 1H), 6.93 (d, 1H), 5.00-5.08 (m, 1H), 4.48-4.58 (m [AB], 2H), 4.23-4.34 (m, 1H), 3.96 (dd, 1H), 3.83 (dd, 1H), 3.27 (t, 2H), 2.94 (dd, 2H), 1.11 (t, 3H).

Example 30

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylsulphonyl)amino]-1-[3-(trifluoromethyl)phenyl]ethyl}acetamide (diastereomer II)

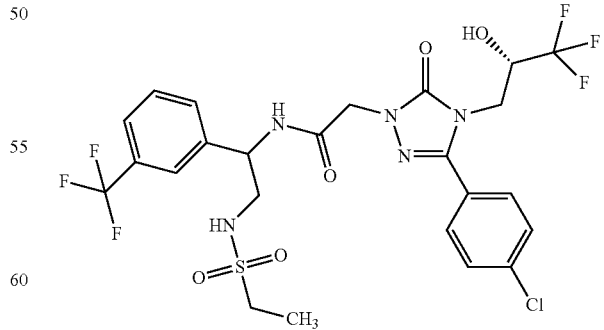

In the same way as for Example 24, from 40 mg (0.11 mmol) of the compound from Example 8A and 40 mg (0.12 mmol) of the compound from Example 49A, the title compound was obtained: 56 mg (80% of theory).

LC-MS [Method 2]: $R_t$=2.35 min; MS [ESIpos]: m/z=644 (M+H)$^+$ $^1$H NMR (DMSO-d$_6$, 400 MHz): δ=8.69 (d, 1H), 7.71-7.76 (m, 3H), 7.57-7.69 (m, 5H), 7.26 (t, 1H), 6.89 (d, 1H), 5.00-5.07 (m, 1H), 4.46-4.61 (m [AB], 2H), 4.21-4.33 (m, 1H), 3.97 (dd, 1H), 3.83 (dd, 1H), 3.27 (t, 2H), 2.90-2.98 (m, 2H), 1.10 (t, 3H).

Example 31

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylsulphonyl)amino]-1-[2-(trifluoromethyl)phenyl]ethyl}acetamide (diastereomer I)

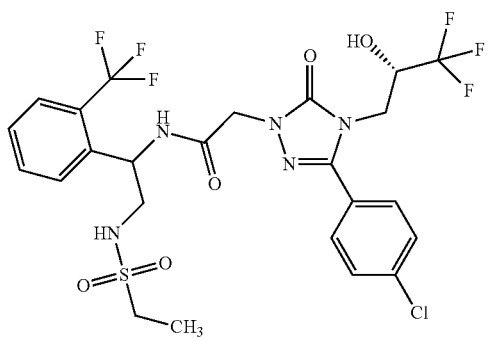 [SMILES: CCS(=O)(=O)NCC(NC(=O)Cn1nc(-c2ccc(Cl)cc2)n(C[C@H](O)C(F)(F)F)c1=O)c1ccccc1C(F)(F)F]

In the same way as for Example 24, from 40 mg (0.11 mmol) of the compound from Example 8A and 40 mg (0.12 mmol) of the compound from Example 51A, the title compound was obtained: 53 mg (75% of theory).

LC-MS [Method 5]: $R_t$=1.10 min; MS [ESIpos]: m/z=644 (M+H)$^+$ $^1$H NMR (DMSO-d$_6$, 400 MHz): δ=8.74 (d, 1H), 7.68-7.79 (m, 5H), 7.62 (d, 2H), 7.51 (t, 1H), 7.46 (t, 1H), 6.93 (d, 1H), 5.27-5.35 (m, 1H), 4.43-4.63 (m [AB], 2H), 4.22-4.34 (m, 1H), 3.95 (dd, 1H), 3.82 (dd, 1H), 3.10-3.26 (m, 2H), 2.91-3.02 (m, 2H), 1.16 (t, 3H).

Example 32

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylsulphonyl)amino]-1-[2-(trifluoromethyl)phenyl]ethyl}acetamide (diastereomer II)

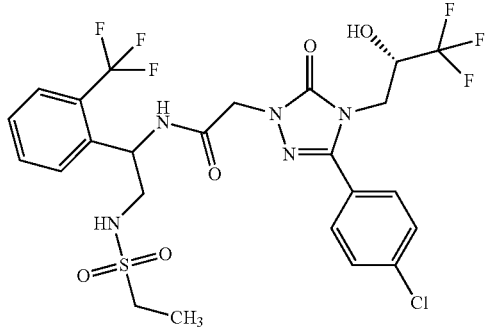 [SMILES: CCS(=O)(=O)NCC(NC(=O)Cn1nc(-c2ccc(Cl)cc2)n(C[C@H](O)C(F)(F)F)c1=O)c1ccccc1C(F)(F)F]

In the same way as for Example 24, from 40 mg (0.11 mmol) of the compound from Example 8A and 40 mg (0.12 mmol) of the compound from Example 52A, the title compound was obtained: 51 mg (72% of theory).

LC-MS [Method 2]: $R_t$=2.31 min; MS [ESIpos]: m/z=644 (M+H)$^+$ $^1$H NMR (DMSO-d$_6$, 400 MHz): δ=8.74 (d, 1H), 7.69-7.79 (m, 5H), 7.61 (d, 2H), 7.51 (t, 1H), 7.45 (t, 1H), 6.89 (d, 1H), 5.26-5.36 (m, 1H), 4.42-4.65 (m [AB], 2H), 4.20-4.32 (m, 1H), 3.96 (dd, 1H), 3.82 (dd, 1H), 3.10-3.25 (m, 2H), 2.90-3.02 (m, 2H), 1.15 (t, 3H).

Example 33

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-(2,3-dichlorophenyl)-2-[(ethylsulphonyl)amino]ethyl}acetamide (diastereomer I)

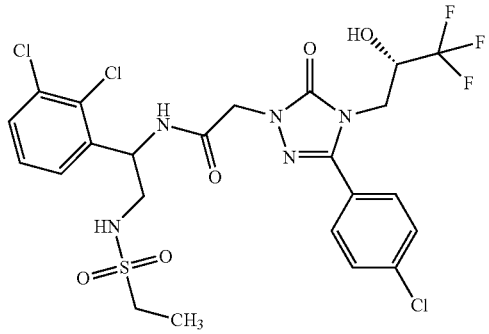 [SMILES: CCS(=O)(=O)NCC(NC(=O)Cn1nc(-c2ccc(Cl)cc2)n(C[C@H](O)C(F)(F)F)c1=O)c1cccc(Cl)c1Cl]

In the same way as for Example 24, from 40 mg (0.11 mmol) of the compound from Example 8A and 40 mg (0.12 mmol) of the compound from Example 55A, the title compound was obtained: 54 mg (77% of theory).

LC-MS [Method 2]: $R_t$=2.35 min; MS [ESIpos]: m/z=644 (M+H)$^+$ $^1$H NMR (DMSO-d$_6$, 400 MHz): δ=8.72 (d, 1H), 7.75 (d, 2H), 7.63 (d, 2H), 7.59 (dd, 1H), 7.50 (d, 1H), 7.36-7.43 (m, 2H), 6.92 (d, 1H), 5.31-5.39 (m, 1H), 4.49-4.61 (m [AB], 2H), 4.23-4.33 (m, 1H), 3.95 (dd, 1H), 3.82 (dd, 1H), 3.23-3.29 (m, 1H), 3.11-3.20 (m, 1H), 2.92-3.03 (m, 2H), 1.15 (t, 3H).

Example 34

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-(2,3-dichlorophenyl)-2-[(ethylsulphonyl)amino]ethyl}acetamide (diastereomer II)

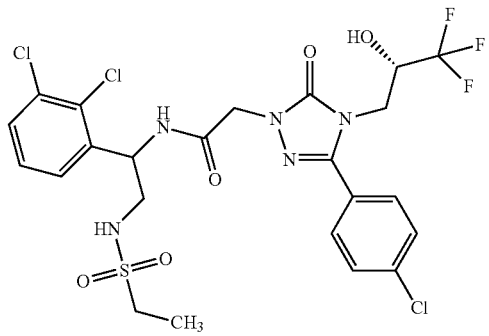 [SMILES: CCS(=O)(=O)NCC(NC(=O)Cn1nc(-c2ccc(Cl)cc2)n(C[C@H](O)C(F)(F)F)c1=O)c1cccc(Cl)c1Cl]

In the same way as for Example 24, from 40 mg (0.11 mmol) of the compound from Example 8A and 40 mg (0.12 mmol) of the compound from Example 56A, the title compound was obtained: 56 mg (80% of theory).

LC-MS [Method 2]: $R_t$=2.34 min; MS [ESIpos]: m/z=644 (M+H)$^+$ $^1$H NMR (DMSO-d$_6$, 400 MHz): δ=8.74 (d, 1H), 7.74 (d, 2H), 7.62 (d, 2H), 7.60 (dd, 1H), 7.50 (d, 1H), 7.37-7.43 (m, 2H), 6.89 (d, 1H), 5.34 (td, 1H), 4.46-4.63 (m [AB], 2H), 4.21-4.33 (m, 1H), 3.96 (dd, 1H), 3.82 (dd, 1H), 3.23-3.30 (m, 1H), 3.11-3.21 (m, 1H), 2.92-3.03 (m, 2H), 1.15 (t, 3H).

Example 35

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}acetamide (diastereomer mixture)

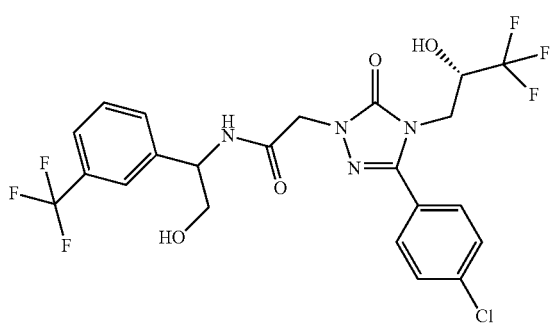 [SMILES: O=C(Cn1nc(-c2ccc(Cl)cc2)n(C[C@H](O)C(F)(F)F)c1=O)NC(CO)c1cccc(C(F)(F)F)c1]

The compound from Example 59A (300 mg, 0.98 mmol) was deprotected by stirring with a 4N solution of hydrogen chloride in dioxane for 10 min, followed by removal of the volatile components on a rotary evaporator and drying in an HV. The residue thus obtained was dissolved in 3 ml of DMF and admixed with 202 µl (1.16 mmol) of N,N-diisopropylethylamine. In a separate flask, 327 mg of the compound from Example 8A (0.89 mmol) were stirred with 257 mg (1.34 mmol) of EDC and 181 mg (1.34 mmol) of HOBt in 4.8 ml of DMF at RT for 20 min. This solution was added to the solution of the amino alcohol, and the mixture was left to react at RT for 20 min. Then 1 ml of 1N hydrochloric acid was added and the complete reaction mixture was purified by preparative HPLC (Method 10). This gave 324 mg (66% of theory) of the title compound.

LC-MS [Method 5]: $R_t$=1.07 min; MS [ESIpos]: m/z=553 (M+H)$^+$

The two diastereomers were separated by preparative chromatography on a chiral phase (Method 17b): see Examples 36 and 37.

Example 36

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}acetamide (diastereomer I)

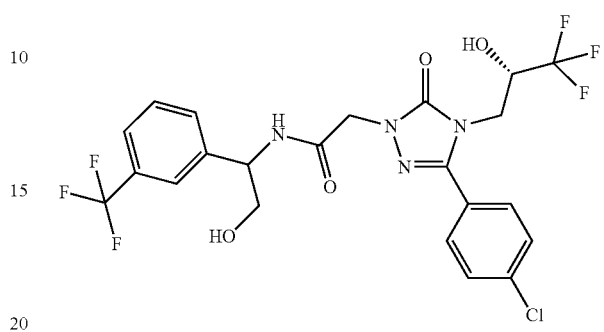

First-eluting diastereomer (147 mg) from the separation of 315 mg of the compound from Example 35 by Method 17b.

Analytical chiral HPLC [Method 18a]: $R_t$=9.82 min $^1$H NMR (DMSO-d$_6$, 400 MHz): δ=8.71 (d, 1H), 7.75 (d, 2H), 7.69 (s, 1H), 7.53-7.66 (m, 5H), 6.91 (d, 1H), 5.02 (t, 1H), 4.91-4.98 (m, 1H), 4.49-4.59 (m [AB], 2H), 4.21-4.33 (m, 1H), 3.96 (dd, 1H), 3.82 (dd, 1H), 3.62 (t, 2H).

Example 37

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}acetamide (diastereomer II)

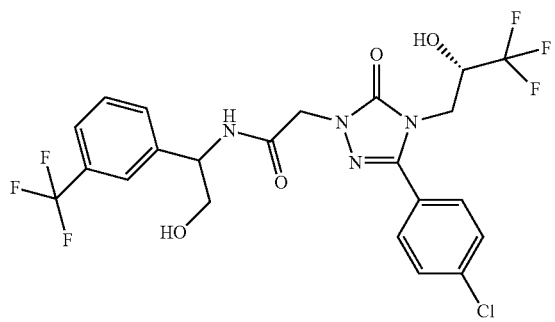 [SMILES: O=C(Cn1nc(-c2ccc(Cl)cc2)n(C[C@H](O)C(F)(F)F)c1=O)NC(CO)c1cccc(C(F)(F)F)c1]

Last-eluting diastereomer (147 mg) from the separation of 315 mg of the compound from Example 35 by Method 17b.

Analytical chiral HPLC [Method 18a]: $R_t$=13.98 min $^1$H NMR (DMSO-d$_6$, 400 MHz): δ=8.72 (d, 1H), 7.74 (d, 2H), 7.69 (s, 1H), 7.52-7.66 (m, 5H), 6.89 (d, 1H), 5.02 (t, 1H), 4.91-4.98 (m, 1H), 4.49-4.60 (m [AB], 2H), 4.21-4.33 (m, 1H), 3.96 (dd, 1H), 3.82 (dd, 1H), 3.62 (t, 2H).

Example 38

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[2-(trifluoromethyl)phenyl]ethyl}acetamide (diastereomer mixture)

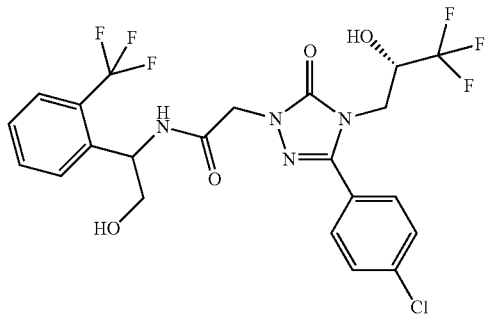 [SMILES: O=C(Cn1nc(-c2ccc(Cl)cc2)n(C[C@H](O)C(F)(F)F)c1=O)NC(CO)c1ccccc1C(F)(F)F]

Of the compound from Example 8A, 278 mg (0.76 mmol) were introduced together with 184 mg (0.76 mmol) of the compound from Example 61A, 219 mg (1.14 mmol) of EDC and 154 mg (1.14 mmol) of HOBt in 18 ml of DMF, then admixed with 265 µl (1.52 mmol) of N,N-diisopropylethylamine The mixture was stirred at RT overnight, admixed with 1 ml of 1N hydrochloric acid and then purified by preparative HPLC (Method 10). This gave 310 mg (74% of theory) of the title compound.

LC-MS [Method 4]: $R_t$=1.03 min; MS [ESIpos]: m/z=553 (M+H)$^+$

The two diastereomers were separated by preparative chromatography on a chiral phase (Method 17e): see Examples 39 and 40.

Example 39

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[2-(trifluoromethyl)phenyl]ethyl}acetamide (diastereomer I)

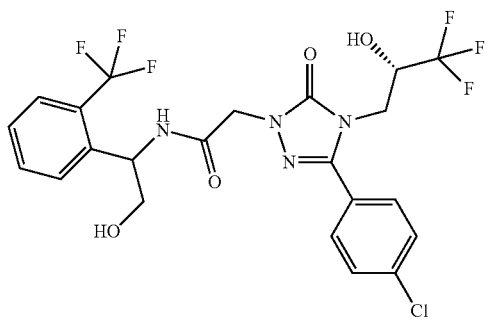 [SMILES: O=C(Cn1nc(-c2ccc(Cl)cc2)n(C[C@H](O)C(F)(F)F)c1=O)NC(CO)c1ccccc1C(F)(F)F]

First-eluting diastereomer (134 mg) from the separation of 310 mg of the compound from Example 38 by Method 17e. This product was purified to remove solvent residues by preparative HPLC (Method 10). This gave 99 mg of the title compound.

Analytical chiral HPLC [Method 18a]: $R_t$=2.12 min $^1$H NMR (DMSO-d$_6$, 400 MHz): δ=8.79 (d, 1H), 7.73 (d, 2H), 7.64-7.71 (m, 3H), 7.61 (d, 2H), 7.44-7.51 (m, 1H), 6.89 (d, 1H), 5.17-5.24 (m, 1H), 5.14 (t, 1H), 4.52 (q [AB], 2H), 4.19-4.31 (m, 1H), 3.95 (dd, 1H), 3.82 (dd, 1H), 3.54-3.62 (m, 1H), 3.44-3.53 (m, 1H).

Example 40

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[2-(trifluoromethyl)phenyl]ethyl}acetamide (diastereomer II)

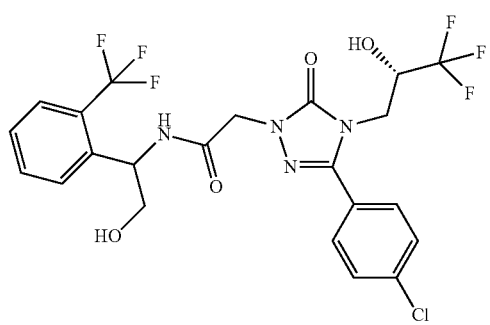 [SMILES: O=C(Cn1nc(-c2ccc(Cl)cc2)n(C[C@H](O)C(F)(F)F)c1=O)NC(CO)c1ccccc1C(F)(F)F]

Last-eluting diastereomer (156 mg) from the separation of 310 mg of the compound from Example 38 by Method 17e. This product was also purified to remove solvent residues by preparative HPLC (Method 10). This gave 128 mg of the title compound.

Analytical chiral HPLC [Method 18a]: $R_t$=5.59 min $^1$H NMR (DMSO-d$_6$, 400 MHz): δ=8.79 (d, 1H), 7.74 (d, 2H), 7.65-7.70 (m, 3H), 7.62 (d, 2H), 7.44-7.50 (m, 1H), 6.91 (d, 1H), 5.18-5.26 (m, 1H), 5.15 (t, 1H), 4.46-4.57 (m [AB], 2H), 4.20-4.33 (m, 1H), 3.95 (dd, 1H), 3.82 (dd, 1H), 3.54-3.62 (m, 1H), 3.44-3.53 (m, 1H).

Example 41

N-[1-(2-Chlorophenyl)-2-hydroxyethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

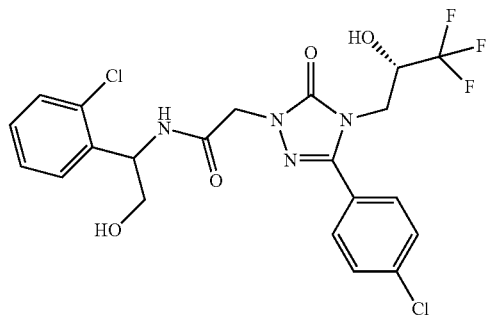 [SMILES: O=C(Cn1nc(-c2ccc(Cl)cc2)n(C[C@H](O)C(F)(F)F)c1=O)NC(CO)c1ccccc1Cl]

Of the compound from Example 8A, 355 mg (0.97 mmol), 223 mg (1.17 mmol) of EDC and 166 mg (1.17 mmol) of HOBt were stirred in 5 ml of DMF and 10 ml of acetonitrile at RT for 20 min. This solution was added dropwise to the solution of the amino alcohol from Example 66A (200 mg, 1.17 mmol) in 10 ml of acetonitrile, and the mixture was left to react at RT for 30 min. Then 1 ml of 1N hydrochloric acid was added and the complete reaction mixture was purified by preparative HPLC (Method 10). This gave 400 mg (77% of theory) of the title compound.

LC-MS [Method 3]: $R_t$=1.15 min+1.16 min; in each case MS [ESIpos]: m/z=519 (M+H)$^+$ The two diastereomers were separated by preparative chromatography on a chiral phase (Method 17f): see Examples 42 and 43.

Example 42

N-[1-(2-Chlorophenyl)-2-hydroxyethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

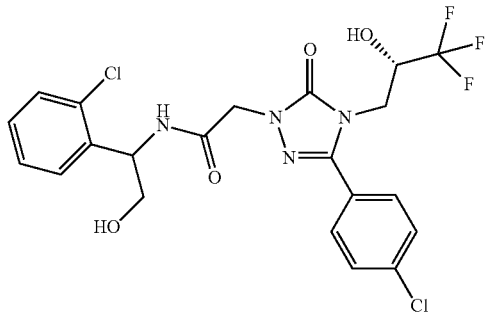 [SMILES: O=C(Cn1nc(-c2ccc(Cl)cc2)n(C[C@H](O)C(F)(F)F)c1=O)NC(CO)c1ccccc1Cl]

First-eluting diastereomer (186 mg) from the separation of 400 mg of the compound from Example 41 by Method 17f. This product was also purified to remove solvent residues by preparative HPLC (Method 10). This gave 153 mg of the title compound.

Analytical chiral HPLC [Method 18b]: $R_t$=5.30 min $^1$H NMR (DMSO-d$_6$, 400 MHz): δ=8.75 (d, 1H), 7.74 (d, 2H), 7.62 (d, 2H), 7.46 (dd, 1H), 7.41 (dd, 1H), 7.25-7.36 (m, 2H), 6.89 (d, 1H), 5.24 (td, 1H), 5.09 (t, 1H), 4.48-4.60 (m [AB], 2H), 4.20-4.32 (m, 1H), 3.96 (dd, 1H), 3.82 (dd, 1H), 3.57-3.65 (m, 1H), 3.46-3.54 (m, 1H).

Example 43

N-[1-(2-Chlorophenyl)-2-hydroxyethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

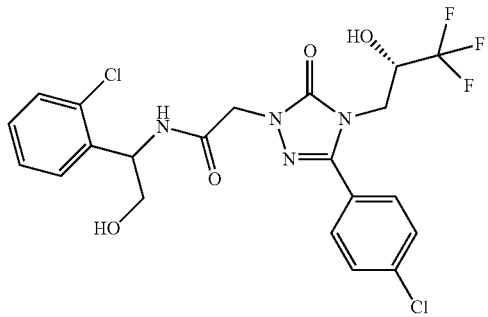 [SMILES: O=C(Cn1nc(-c2ccc(Cl)cc2)n(C[C@H](O)C(F)(F)F)c1=O)NC(CO)c1ccccc1Cl]

Last-eluting diastereomer (209 mg) from the separation of 400 mg of the compound from Example 41 by Method 17f. This product was also purified to remove solvent residues by preparative HPLC (Method 10). This gave 156 mg of the title compound.

Analytical chiral HPLC [Method 18b]: $R_t$=6.94 min $^1$H NMR (DMSO-d$_6$, 400 MHz): δ=8.74 (d, 1H), 7.75 (d, 2H), 7.63 (d, 2H), 7.46 (dd, 1H), 7.41 (dd, 1H), 7.24-7.36 (m, 2H), 6.91 (d, 1H), 5.25 (td, 1H), 5.09 (t, 1H), 4.54 (s, 2H), 4.22-4.32 (m, 1H), 3.95 (dd, 1H), 3.82 (dd, 1H), 3.57-3.65 (m, 1H), 3.45-3.54 (m, 1H).

Example 44

2-{3-(4-Chlorophenyl)-5-oxo-4-[(2S)-3,3,3-trifluoro-2-hydroxypropyl]-4,5-dihydro-1H-1,2,4-triazol-1-yl}-N-{(2R)-1-hydroxy-2-[3-(trifluoromethyl)phenyl]propan-2-yl}acetamide

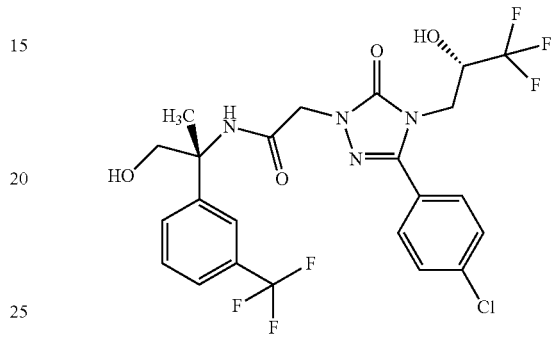

Of the compound from Example 8A, 151 mg (0.42 mmol) were stirred together with 100 mg (0.46 mmol) of the compound from Example 69A, 119 mg (0.62 mmol) of EDC and 84 mg (0.62 mmol) of HOBt in 4 ml of DMF overnight at RT, admixed with 1 ml of 1N hydrochloric acid and then purified completely by preparative HPLC (Method 10). This gave 91 mg (39% of theory) of the title compound.

LC-MS [Method 1] $R_t$=2.04 min; MS [ESIpos]: m/z=567 (M+H)$^+$ $^1$H NMR (DMSO-d$_6$, 400 MHz): δ=8.33 (s, 1H), 7.74 (d, 2H), 7.60-7.66 (m, 4H), 7.48-7.57 (m, 2H), 6.89 (d, 1H), 5.12 (t, 1H), 4.48-4.60 (m [AB], 2H), 4.20-4.32 (m, 1H), 3.95 (dd, 1H), 3.81 (dd, 1H), 3.55-3.66 (m, 2H), 1.62 (s, 3H).

Example 45

(2R)-2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]propyl carbamate

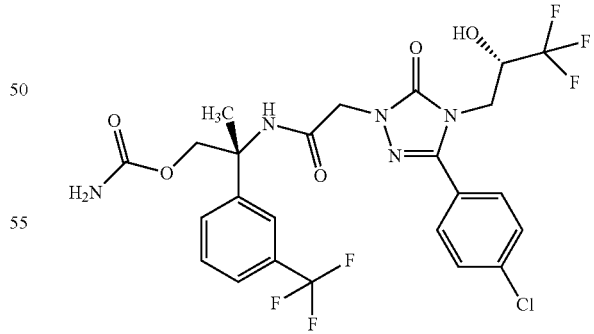

Of the compound from Example 8A, 76 mg (0.21 mmol) were introduced together with 75 mg (0.25 mmol) of the compound from Example 71A, 48 mg (0.25 mmol) of EDC, 36 mg (0.25 mmol) of HOBt in 2 ml of DMF, 73 μl (0.42 mmol) of N,N-diisopropylethylamine were added, and the mixture was stirred at RT overnight. It was admixed with 1 ml of 1N hydrochloric acid and then purified completely by preparative HPLC (Method 10). This gave 78 mg of the title compound (58% of theory).

LC-MS [Method 3] $R_t$=1.23 min; MS [ESIpos]: m/z=610 (M+H)$^+$ $^1$H NMR (DMSO-d$_6$, 400 MHz): δ=8.58 (s, 1H), 7.74 (d, 2H), 7.69 (d, 1H), 7.57-7.66 (m, 4H), 7.54 (t, 1H), 6.87 (d, 1H), 6.40-6.75 (br.s, 2H), 4.50 (s, 2H), 4.22-4.32 (m, 1H), 4.22 (d, 1H), 4.16 (d, 1H), 3.95 (dd, 1H), 3.81 (dd, 1H), 1.68 (s, 3H).

Example 46

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl carbamate (diastereomer mixture)

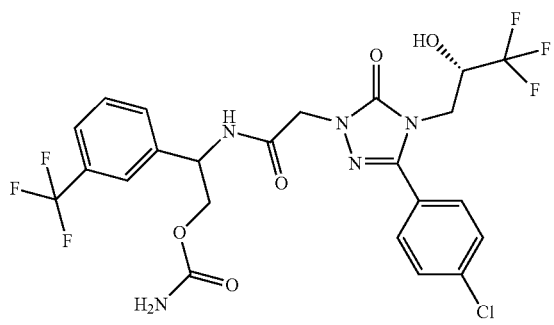 [SMILES: NC(=O)OCC(NC(=O)Cn1nc(-c2ccc(Cl)cc2)n(C[C@H](O)C(F)(F)F)c1=O)c1cccc(C(F)(F)F)c1]

Of the compound from Example 8A, 599 mg (1.64 mmol) were introduced together with 750 mg (1.96 mmol) of the compound from Example 60A, 377 mg (1.96 mmol) of EDC and 279 mg (1.96 mmol) of HOBt in 20 ml of DMF, 570 μl (3.27 mmol) of N,N-diisopropylethylamine were added and the mixture was stirred at RT overnight. It was admixed with 5 ml of 1N hydrochloric acid and then purified completely by preparative HPLC (Method 10). This gave 450 mg of the title compound (46% of theory).

LC-MS [Method 5] $R_t$=1.06 min; MS [ESIpos]: m/z=596 (M+H)$^+$

The two diastereomers were separated by preparative chromatography on a chiral phase (Method 17a): see Examples 47 and 48.

Example 47

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl carbamate (diastereomer I)

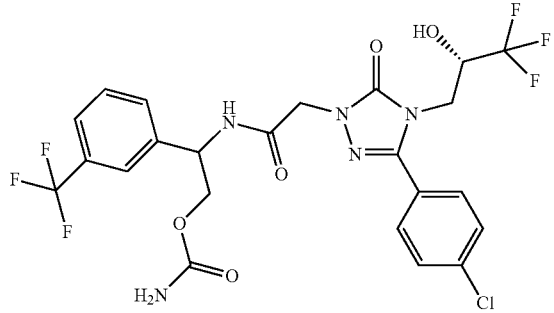 [SMILES: NC(=O)OCC(NC(=O)Cn1nc(-c2ccc(Cl)cc2)n(C[C@H](O)C(F)(F)F)c1=O)c1cccc(C(F)(F)F)c1]

First-eluting diastereomer (209 mg) from the separation of 400 mg of the compound from Example 46 by Method 17a. This product was also purified to remove solvent residues by preparative HPLC (Method 10). This gave 169 mg of the title compound.

Analytical chiral HPLC [Method 18a]: $R_t$=7.44 min $^1$H NMR (DMSO-d$_6$, 400 MHz): δ=8.88 (d, 1H), 7.70-7.78 (m, 3H), 7.56-7.70 (m, 5H), 6.92 (d, 1H), 6.39-6.79 (br.s, 2H), 5.12-5.20 (m, 1H), 4.45-4.60 (m [AB], 2H), 4.22-4.34 (m, 1H), 4.06-4.17 (m, 2H), 3.96 (dd, 1H), 3.83 (dd, 1H).

Example 48

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl carbamate (diastereomer II)

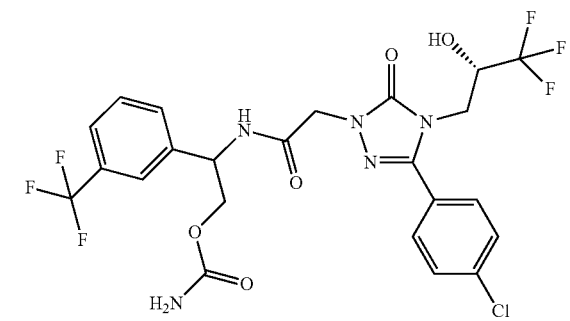 [SMILES: NC(=O)OCC(NC(=O)Cn1nc(-c2ccc(Cl)cc2)n(C[C@H](O)C(F)(F)F)c1=O)c1cccc(C(F)(F)F)c1]

Last-eluting diastereomer (190 mg) from the separation of 450 mg of the compound from Example 46 by Method 17a. This product was also purified to remove solvent residues by preparative HPLC (Method 10). This gave 167 mg of the title compound.

Analytical chiral HPLC [Method 18a]: $R_t$=17.99 min $^1$H NMR (DMSO-d$_6$, 400 MHz): δ=8.89 (d, 1H), 7.70-7.77 (m, 3H), 7.56-7.70 (m, 5H), 6.90 (d, 1H), 6.45-6.77 (br.s, 2H), 5.12-5.19 (m, 1H), 4.53 (s, 2H), 4.21-4.33 (m, 1H), 4.07-4.17 (m, 2H), 3.96 (dd, 1H), 3.83 (dd, 1H).

Example 49

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]ethyl carbamate (diastereomer mixture)

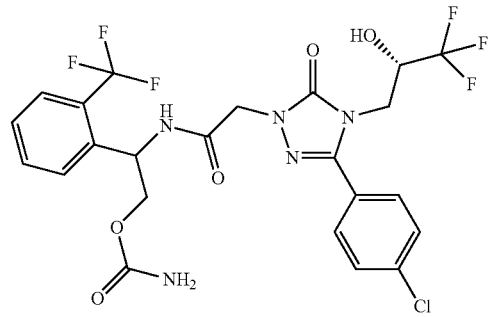 [SMILES: NC(=O)OCC(NC(=O)Cn1nc(-c2ccc(Cl)cc2)n(C[C@H](O)C(F)(F)F)c1=O)c1ccccc1C(F)(F)F]

Of the compound from Example 8A, 428 mg (1.17 mmol) were stirred together with 269 mg (1.41 mmol) of EDC and 200 mg (1.41 mmol) of HOBt in 10 ml of DMF and 40 ml of acetonitrile at RT for 10 min. This solution was added dropwise to a solution of 400 mg (1.41 mmol) of the compound from Example 63A and 408 µl (2.34 mmol) of N,N-diisopropylethylamine in 50 ml of acetonitrile, and the mixture was stirred at RT overnight. It was then admixed with 1 ml of 1N hydrochloric acid and purified completely by preparative HPLC (Method 10). This gave 580 mg of the title compound (83% of theory).

LC-MS [Method 2] $R_t$=2.24 min; MS [ESIpos]: m/z=596 (M+H)⁺

The two diastereomers were separated by preparative chromatography on a chiral phase (Method 17d): see Examples 50 and 51.

Example 50

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]ethyl carbamate (diastereomer I)

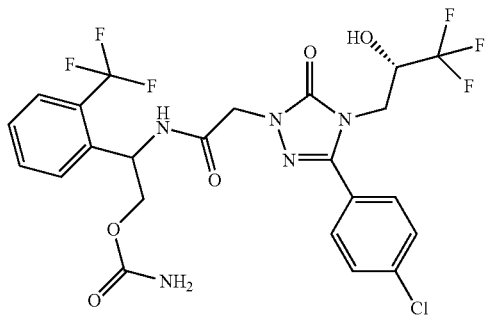 [SMILES: NC(=O)OCC(NC(=O)Cn1nc(-c2ccc(Cl)cc2)n(C[C@H](O)C(F)(F)F)c1=O)c1ccccc1C(F)(F)F]

First-eluting diastereomer (297 mg) from the separation of 580 mg of the compound from Example 49 by Method 17d. This product was also purified to remove solvent residues by preparative HPLC (Method 10). This gave 239 mg of the title compound.

Analytical chiral HPLC [Method 18c]: $R_t$=3.26 min
¹H NMR (DMSO-d₆, 400 MHz): δ=8.97 (d, 1H), 7.68-7.78 (m, 5H), 7.62 (d, 2H), 7.52 (t, 1H), 6.92 (d, 1H), 6.40-6.81 (2 br. s, 2H), 5.36-5.44 (m, 1H), 4.49 (s, 2H), 4.21-4.33 (m, 1H), 4.13 (dd, 1H), 3.91-4.01 (m, 2H), 3.81 (dd, 1H).

Example 51

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]ethyl carbamate (diastereomer II)

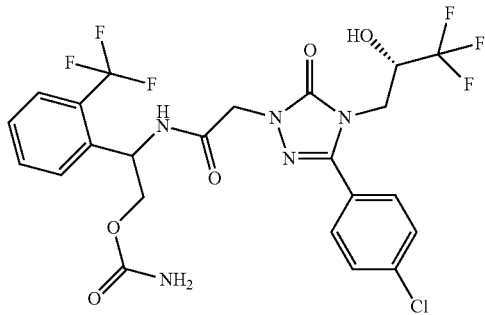 [SMILES: NC(=O)OCC(NC(=O)Cn1nc(-c2ccc(Cl)cc2)n(C[C@H](O)C(F)(F)F)c1=O)c1ccccc1C(F)(F)F]

Last-eluting diastereomer (280 mg) from the separation of 580 mg of the compound from Example 49 by Method 17d.

This product was also purified by preparative HPLC (Method 10). This gave 222 mg of the title compound.

Analytical chiral HPLC [Method 18c]: $R_t$=4.49 min
¹H NMR (DMSO-d₆, 400 MHz): δ=8.98 (d, 1H), 7.69-7.79 (m, 5H), 7.62 (d, 2H), 7.49-7.56 (m, 1H), 6.90 (d, 1H), 6.40-6.81 (2 br. s, 2H), 5.35-5.42 (m, 1H), 4.43-4.55 (m [AB], 2H), 4.19-4.32 (m, 1H), 4.13 (dd, 1H), 3.92-4.01 (m, 2H), 3.82 (dd, 1H).

Example 52

(2R)-2-(3-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate

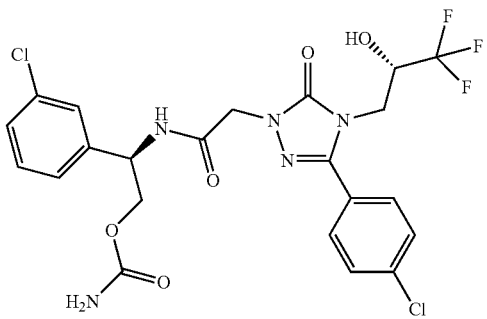 [SMILES: NC(=O)OC[C@H](NC(=O)Cn1nc(-c2ccc(Cl)cc2)n(C[C@H](O)C(F)(F)F)c1=O)c1cccc(Cl)c1]

In the same way as for Example 1, from 203 mg (0.55 mmol) of the compound from Example 8A and 153 mg (0.61 mmol) of the compound from Example 65A, 183 mg of the title compound were obtained (59% of theory).

LC-MS [Method 3] $R_t$=1.19 min; MS [ESIpos]: m/z=562 (M+H)⁺
¹H NMR (DMSO-d₆, 400 MHz): δ=8.79 (d, 1H), 7.76 (d, 2H), 7.63 (d, 2H), 7.43 (s, 1H), 7.29-7.41 (m, 3H), 6.92 (d, 1H), 6.41-6.80 (2 br. s, 2H), 5.02-5.11 (m, 1H), 4.43-4.59 (m, 2H), 4.22-4.34 (m, 1H), 4.02-4.15 (m, 2H), 3.96 (dd, 1H), 3.83 (dd, 1H).

Example 53

2-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (diastereomer mixture)

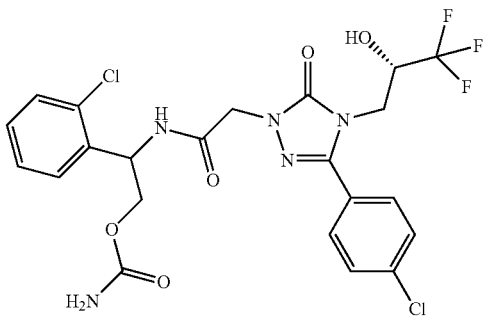 [SMILES: NC(=O)OCC(NC(=O)Cn1nc(-c2ccc(Cl)cc2)n(C[C@H](O)C(F)(F)F)c1=O)c1ccccc1Cl]

Of the compound from Example 8A, 606 mg (1.66 mmol) were stirred together with 382 mg (1.99 mmol) of EDC and 283 mg (1.99 mmol) of HOBt in 5 ml of DMF and 10 ml of acetonitrile at RT for 10 min. This solution was added dropwise to a solution of 500 mg (1.99 mmol) of the compound from Example 68A and 578 µl (3.31 mmol) of N,N-diisopropylethylamine in 10 ml of acetonitrile, and the mixture was stirred at RT for a further 30 min. It was admixed with 1 ml of

Example 54

2-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (diastereomer I)

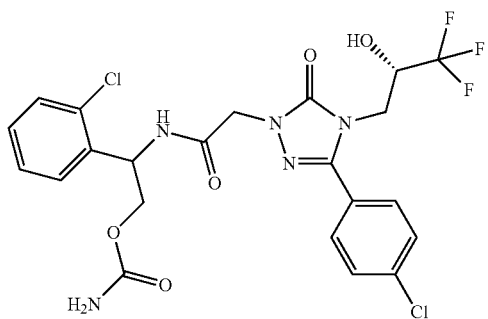 [SMILES: NC(=O)OCC(NC(=O)Cn1nc(-c2ccc(Cl)cc2)n(C[C@H](O)C(F)(F)F)c1=O)c1ccccc1Cl]

Last-eluting diastereomer (227 mg) from the separation of 443 mg of the compound from Example 53 by Method 17f. This product was also purified to remove solvent residues by preparative HPLC (Method 10). This gave 200 mg of the title compound.

Analytical chiral HPLC [Method 18b]: $R_t$=1.77 min
$^1$H NMR (DMSO-$d_6$, 400 MHz): δ=8.92 (d, 1H), 7.75 (d, 2H), 7.63 (d, 2H), 7.51 (dd, 1H), 7.44 (dd, 1H), 7.29-7.40 (m, 2H), 6.92 (d, 1H), 6.43-6.80 (2 br.s, 2H), 5.40-5.47 (m, 1H), 4.45-4.57 (m [AB], 2H), 4.21-4.32 (m, 1H), 4.00-4.12 (m, 2H), 3.96 (dd, 1H), 3.82 (dd, 1H).

Example 55

2-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]ethyl carbamate (diastereomer II)

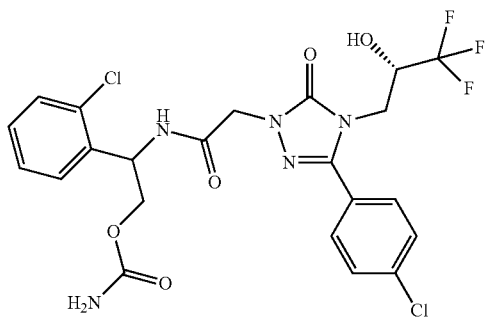 [SMILES: NC(=O)OCC(NC(=O)Cn1nc(-c2ccc(Cl)cc2)n(C[C@H](O)C(F)(F)F)c1=O)c1ccccc1Cl]

Last-eluting diastereomer (231 mg) from the separation of 443 mg of the compound from Example 53 by Method 17f. This product was also purified to remove solvent residues by preparative HPLC (Method 10). This gave 202 mg of the title compound.

Analytical chiral HPLC [Method 18b]: $R_t$=2.46 min
$^1$H NMR (DMSO-$d_6$, 400 MHz): δ=8.93 (d, 1H), 7.74 (d, 2H), 7.62 (d, 2H), 7.51 (dd, 1H), 7.45 (dd, 1H), 7.30-7.40 (m, 2H), 6.90 (d, 1H), 6.44-6.79 (2 br.s, 2H), 5.38-5.46 (m, 1H), 4.52 (s, 2H), 4.21-4.32 (m, 1H), 4.00-4.12 (m, 2H), 3.96 (dd, 1H), 3.82 (dd, 1H).

Example 56

(2R)-2-(2-Chlorophenyl)-2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]propyl carbamate

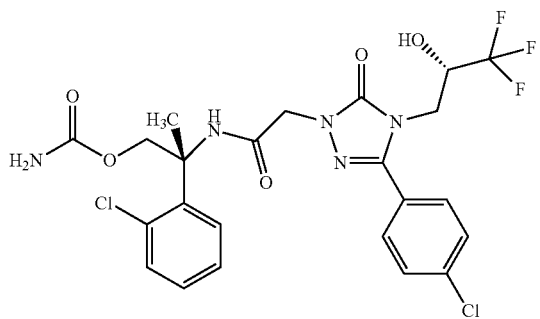 [SMILES: C[C@@](COC(N)=O)(NC(=O)Cn1nc(-c2ccc(Cl)cc2)n(C[C@H](O)C(F)(F)F)c1=O)c1ccccc1Cl]

Of the compound from Example 8A, 42 mg (0.12 mmol) were stirred together with 32 mg (approximately 90% pure, 0.13 mmol) of the compound from Example 75A, 26 mg (0.14 mmol) of EDC, 17 mg (0.14 mmol) of HOBt in 1.3 ml of DMF at RT for 1 h. The mixture was then purified completely by preparative HPLC (Method 10). This gave 42 mg of the title compound (63% of theory).

LC-MS [Method 4] $R_t$=1.01 min; MS [ESIpos]: m/z=576 (M+H)$^+$
$^1$H NMR (DMSO-$d_6$, 400 MHz): δ=8.58 (s, 1H), 7.74 (d, 2H), 7.62 (d, 2H), 7.46 (dd, 1H), 7.37 (dd, 1H), 7.22-7.32 (br. s, 2H), 6.89 (d, 1H), 6.45-6.75 (m, 2H), 4.45 (s, 2H), 4.36-4.44 (m, 2H), 4.20-4.33 (m, 1H), 3.93 (dd, 1H), 3.80 (dd, 1H), 1.74 (s, 3H).

Example 57

N-{2-(Carbamoylamino)-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

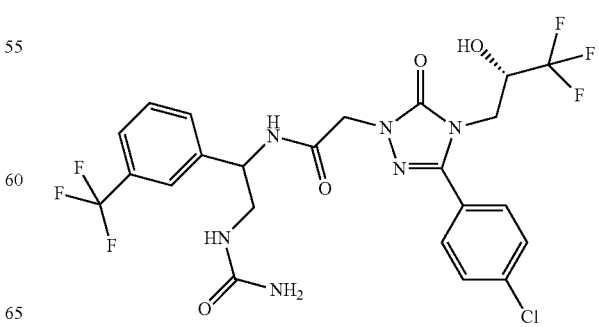

Of the compound from Example 11, 266 mg (0.45 mmol) were introduced in 6 ml of methanol/water 1:1 and admixed with potassium cyanate (110 mg, 1.36 mmol) at RT. The mixture was heated at 40° C. for 90 min. Following complete reaction, the mixture was cooled to RT and purified completely by preparative HPLC (Method 10). Drying in an HV gave 232 mg (84% of theory) of the title compound.

LC-MS [Method 4]: $R_t$=1.02 min; MS [ESIpos]: m/z=595 (M+H)$^+$ $^1$H NMR (DMSO-d$_6$, 400 MHz): δ=8.78 (d, 1H), 7.76 (d, 2H), 7.54-7.66 (m, 6H), 6.94 (d, 1H), 6.09 (t, 1H), 5.60 (s, 2H), 4.87-4.95 (m, 1H), 4.49 (s, 2H), 4.25-4.38 (m, 1H), 3.97 (dd, 1H), 3.83 (dd, 1H), 3.29-3.38 (m, 1H), 3.19-3.27 (m, 1H).

Example 58

N-{2-(Carbamoylamino)-1-[3-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

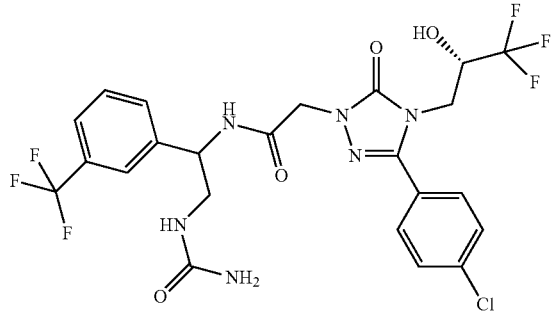 [SMILES: NC(=O)NCC(NC(=O)Cn1nc(-c2ccc(Cl)cc2)n(C[C@H](O)C(F)(F)F)c1=O)c1cccc(C(F)(F)F)c1]

Of the compound from Example 12, 180 mg (0.31 mmol) were introduced in 3 ml of methanol/water 1:1 and admixed with potassium cyanate (75 mg, 0.92 mmol) at RT. The mixture was heated at 40° C. for 90 min. The methanol was removed on a rotary evaporator and the aqueous residue was diluted with 20 ml of water. The precipitated solid was isolated by filtration, washed with a little water and dried in an HV. This gave 146 mg (76% of theory) of the title compound.

LC-MS [Method 4]: $R_t$=1.02 min; MS [ESIpos]: m/z=595 (M+H)$^+$ $^1$H NMR (DMSO-d$_6$, 400 MHz): δ=8.79 (d, 1H), 7.77 (d, 2H), 7.54-7.66 (m, 6H), 6.94 (d, 1H), 6.08 (t, 1H), 5.59 (s, 2H), 4.88-4.95 (m, 1H), 4.41-4.56 (m [AB], 2H), 4.25-4.37 (m, 1H), 3.97 (dd, 1H), 3.84 (dd, 1H), 3.29-3.38 (m, 1H), 3.16-3.27 (m, 1H).

Example 59

N-{2-(Carbamoylamino)-1-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

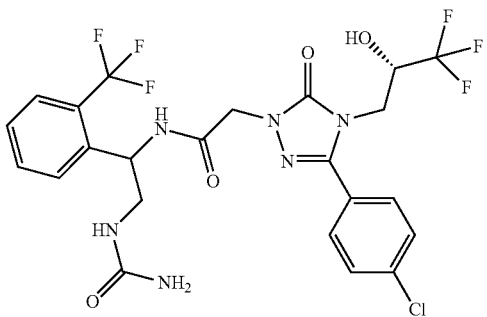

In the same way as for Example 57, from 230 mg (0.39 mmol) of the compound from Example 13, the title compound was obtained (190 mg, 79% of theory).

LC-MS [Method 3]: $R_t$=1.17 min; MS [ESIpos]: m/z=595 (M+H)$^+$ $^1$H NMR (DMSO-d$_6$, 400 MHz): δ=8.84 (d, 1H), 7.77 (d, 2H), 7.62-7.74 (m, 5H), 7.48 (t, 1H), 6.95 (d, 1H), 6.22 (t, 1H), 5.58 (s, 2H), 5.06-5.13 (m, 1H), 4.39-4.51 (m [AB], 2H), 4.25-4.37 (m, 1H), 3.97 (dd, 1H), 3.83 (dd, 1H), 3.21-3.27 (m, 2H).

Example 60

N-{2-(Carbamoylamino)-1-[2-(trifluoromethyl)phenyl]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

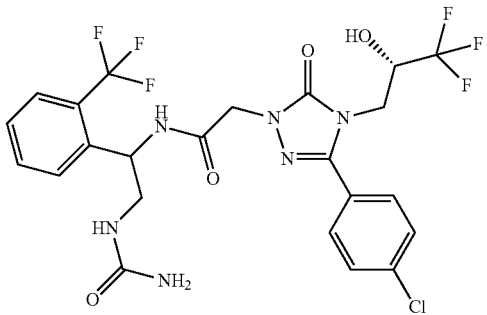 [SMILES: NC(=O)NCC(NC(=O)Cn1nc(-c2ccc(Cl)cc2)n(C[C@H](O)C(F)(F)F)c1=O)c1ccccc1C(F)(F)F]

In the same way as for Example 57, but at RT, from 50 mg (85 μmol) of the compound from Example 14, the title compound was obtained (41 mg, 81% of theory).

LC-MS [Method 2]: $R_t$=2.19 min; MS [ESIpos]: m/z=595 (M+H)$^+$ $^1$H NMR (DMSO-d$_6$, 400 MHz): δ=8.84 (d, 1H), 7.76 (d, 2H), 7.60-7.72 (m, 5H), 7.48 (t, 1H), 6.93 (d, 1H), 6.23 (t, 1H), 5.59 (s, 2H), 5.05-5.12 (m, 1H), 4.45 (s, 2H), 4.25-4.37 (m, 1H), 3.97 (dd, 1H), 3.83 (dd, 1H), 3.15-3.34 (m, 2H).

Example 61

N-[2-(Carbamoylamino)-1-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

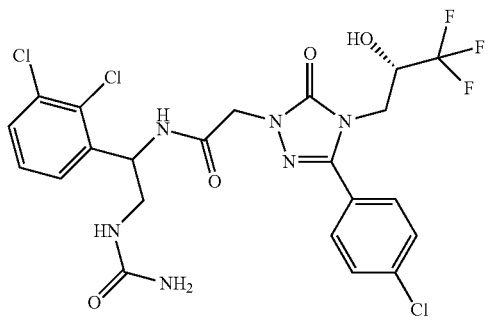

In the same way as for Example 57, from 116 mg (0.20 mmol) of the compound from Example 15, the title compound was obtained (90 mg, 77% of theory).

LC-MS [Method 3]: $R_t$=1.19 min; MS [ESIpos]: m/z=595 (M+H)$^+$ $^1$H NMR (DMSO-d$_6$, 400 MHz): δ=8.91 (d, 1H), 7.77 (d, 2H), 7.63 (d, 2H), 7.52-7.59 (m, 1H), 7.34-7.40 (m, 2H), 6.94 (d, 1H), 6.19 (t, 1H), 5.60 (s, 2H), 5.12-5.20 (m, 1H), 4.40-4.55 (q [AB], 2H), 4.25-4.37 (m, 1H), 3.97 (dd, 1H), 3.84 (dd, 1H), 3.28-3.37 (m, 1H), 3.19-3.28 (m, 1H).

Example 62

N-[2-(Carbamoylamino)-1-(2,3-dichlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

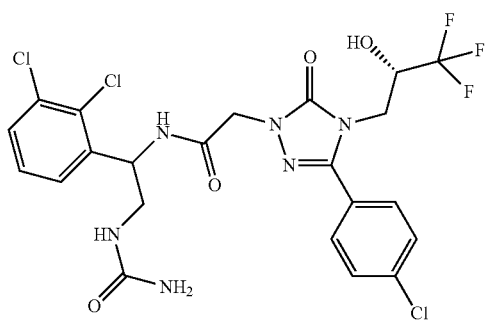 [SMILES: NC(=O)NCC(NC(=O)Cn1nc(-c2ccc(Cl)cc2)n(C[C@H](O)C(F)(F)F)c1=O)c1cccc(Cl)c1Cl]

In the same way as for Example 57, from 177 mg (0.30 mmol) of the compound from Example 16, the title compound was obtained (153 mg, 85% of theory).

LC-MS [Method 3]: $R_t$=1.20 min; MS [ESIpos]: m/z=595 (M+H)$^+$ $^1$H NMR (DMSO-d$_6$, 400 MHz): δ=8.91 (d, 1H), 7.76 (d, 2H), 7.63 (d, 2H), 7.52-7.59 (m, 1H), 7.34-7.40 (m, 2H), 6.94 (d, 1H), 6.19 (t, 1H), 5.61 (s, 2H), 5.12-5.19 (m, 1H), 4.48 (s, 2H), 4.26-4.38 (m, 1H), 3.97 (dd, 1H), 3.83 (dd, 1H), 3.29-3.38 (m, 1H), 3.18-3.27 (m, 1H).

Example 63

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-2-[3-(trifluoromethyl)phenyl]ethyl carbamate (Racemate)

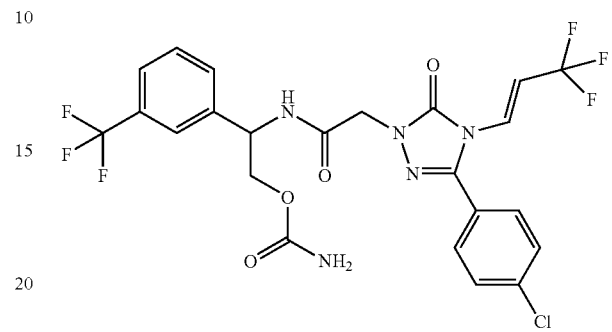

Of the compound from Example 77A, 100 mg (0.29 mmol) were introduced in 3 ml of DMF and admixed with 98.3 mg (0.35 mmol) of the compound from Example 60A, 66.1 mg (0.35 mmol) of EDC, 49 mg (0.35 mmol) of HOBt and 75 µl (0.43 mmol) of N,N-diisopropylethylamine. The mixture was stirred at RT for 30 min and then admixed with 1 ml of 1N hydrochloric acid and purified by preparative HPLC (Method 10). This gave 140 mg (84% of theory) of the title compound.

LC/MS [Method 5]: $R_t$=1.16 min; m/z=578 (M+H)$^+$ $^1$H-NMR (400 MHz, DMSO-d$_6$): δ=8.90 (d, 1H), 7.73 (s, 1H), 7.57-7.69 (m, 7H), 7.18 (dq, 1H), 6.87 (dq, 1H), 5.09-5.27 (m, 1H), 4.47-4.68 (m [AB], 2H), 3.99-4.21 (m, 2H).

The enantiomers from Example 63 were separated by preparative chromatography on a chiral phase (Method 15b): see Example 64 and Example 65.

Example 64

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-2-[3-(trifluoromethyl)phenyl]ethyl carbamate (Enantiomer I)

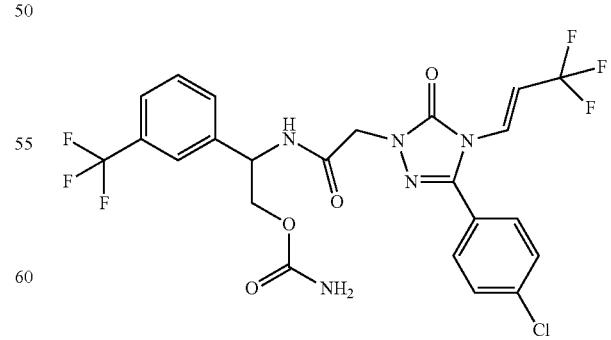

First-eluting enantiomer (64 mg) from the separation of 135 mg of the compound from Example 63 by Method 15b.

Analytical chiral HPLC [Method 16]: $R_t$=1.50 min.

Example 65

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-2-[3-(trifluoromethyl)phenyl]ethyl carbamate (Enantiomer II)

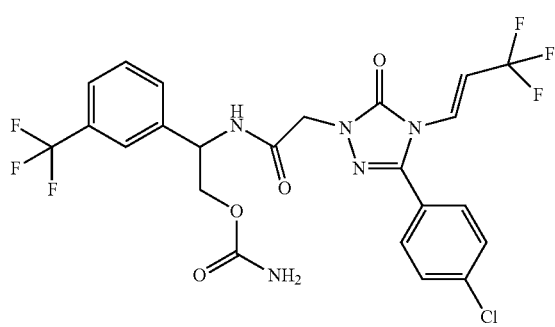 [SMILES: NC(=O)OCC(NC(=O)Cn1nc(-c2ccc(Cl)cc2)n(/C=C/C(F)(F)F)c1=O)c1cccc(C(F)(F)F)c1]

Last-eluting enantiomer (62 mg) from the separation of 135 mg of the compound from Example 63 by Method 15b.

Analytical chiral HPLC [Method 16]: $R_t$=1.90 min.

Example 66

2-{3-(4-Chlorophenyl)-5-oxo-4-[(2S)-3,3,3-trifluoro-2-hydroxypropyl]-4,5-dihydro-1H-1,2,4-triazol-1-yl}-N-{3-hydroxy-1-[3-(trifluoromethyl)phenyl]propyl}acetamide (diastereomer mixture)

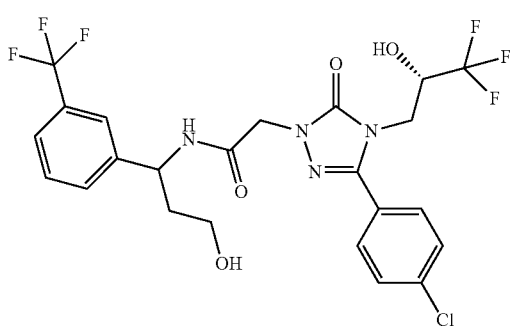 [SMILES: O=C(Cn1nc(-c2ccc(Cl)cc2)n(C[C@H](O)C(F)(F)F)c1=O)NC(CCO)c1cccc(C(F)(F)F)c1]

In the same way as for Example 24, from 100 mg (0.27 mmol) of the compound from Example 8A and 84 mg (0.33 mmol) of the compound from Example 78A, the title compound was obtained: 112 mg (72% of theory).

LC-MS [Method 3] $R_t$=1.22 min; MS [ESIpos]: m/z=567 (M+H)$^+$

The diastereomers from Example 66 were separated by preparative chromatography on a chiral phase (Method 8): see Example 67 and Example 68.

Example 67

2-{3-(4-Chlorophenyl)-5-oxo-4-[(2S)-3,3,3-trifluoro-2-hydroxypropyl]-4,5-dihydro-1H-1,2,4-triazol-1-yl}-N-{3-hydroxy-1-[3-(trifluoromethyl)phenyl]propyl}acetamide (diastereomer I)

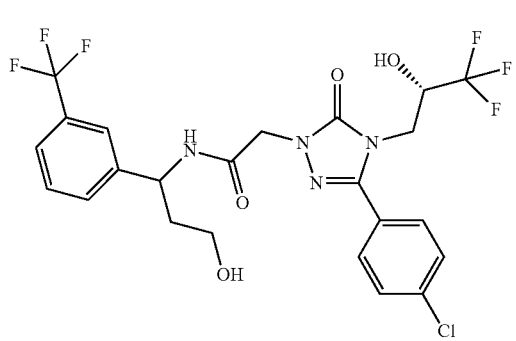 [SMILES: O=C(Cn1nc(-c2ccc(Cl)cc2)n(C[C@H](O)C(F)(F)F)c1=O)NC(CCO)c1cccc(C(F)(F)F)c1]

First-eluting diastereomer (50 mg) from the chromatographic separation of 112 mg of the compound from Example 66 by Method 8.

Analytical chiral HPLC [Method 9]: $R_t$=3.25 min $^1$H NMR (DMSO-d$_6$, 400 MHz): δ=8.71 (d, 1H), 7.73 (dd, 2H), 7.54-7.66 (m, 6H), 6.90 (d, 1H), 4.97-5.05 (m, 1H), 4.58 (t, 1H), 4.42-4.56 (m [AB], 2H), 4.21-4.33 (m, 1H), 3.96 (dd, 1H), 3.82 (dd, 1H), 3.32-3.47 (m, 2H), 1.77-1.96 (m, 2H).

Example 68

2-{3-(4-Chlorophenyl)-5-oxo-4-[(2S)-3,3,3-trifluoro-2-hydroxypropyl]-4,5-dihydro-1H-1,2,4-triazol-1-yl}-N-{3-hydroxy-1-[3-(trifluoromethyl)phenyl]propyl}acetamide (diastereomer II)

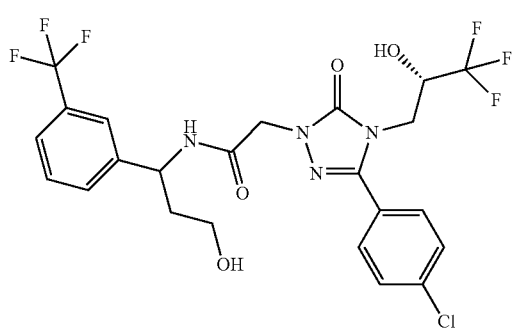 [SMILES: O=C(Cn1nc(-c2ccc(Cl)cc2)n(C[C@H](O)C(F)(F)F)c1=O)NC(CCO)c1cccc(C(F)(F)F)c1]

Last-eluting diastereomer (47 mg) from the chromatographic separation of 112 mg of the compound from Example 66 by Method 8.

Analytical chiral HPLC [Method 9]: $R_t$=4.41 min $^1$H NMR (DMSO-d$_6$, 400 MHz): δ=8.70 (d, 1H), 7.74 (dd, 2H), 7.53-7.66 (m, 6H), 6.92 (d, 1H), 4.98-5.08 (m, 1H), 4.59 (t, 1H), 4.49 (s, 2H), 4.21-4.33 (m, 1H), 3.95 (dd, 1H), 3.82 (dd, 1H), 3.32-3.47 (m, 2H), 1.77-1.96 (m, 2H).

Example 69

2-{3-(4-Chlorophenyl)-5-oxo-4-[(2S)-3,3,3-trifluoro-2-hydroxypropyl]-4,5-dihydro-1H-1,2,4-triazol-1-yl}-N-{(1S)-3-hydroxy-1-[2-(trifluoromethyl)phenyl]propyl}acetamide

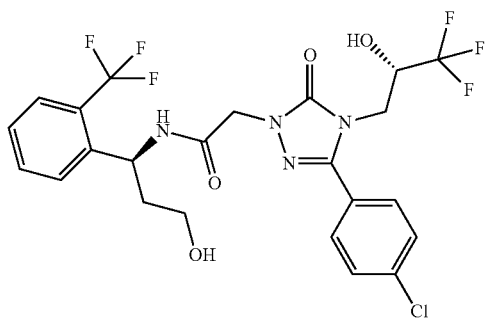 [SMILES: O=C(Cn1nc(-c2ccc(Cl)cc2)n(C[C@H](O)C(F)(F)F)c1=O)N[C@@H](CCO)c1ccccc1C(F)(F)F]

In the same way as for Example 49, from 167 mg (0.46 mmol) of the compound from Example 8A and 140 mg (0.55 mmol) of the compound from Example 80A, the title compound was obtained: 152 mg (58% of theory).

LC-MS [Method 3] $R_t$=1.21 min; MS [ESIpos]: m/z=567 (M+H)$^+$ $^1$H NMR (DMSO-d$_6$, 400 MHz): δ=8.75 (d, 1H), 7.74 (d, 2H), 7.64-7.70 (m, 3H), 7.62 (d, 2H), 7.41-7.50 (m, 1H), 6.90 (d, 1H), 5.20-5.28 (m, 1H), 4.57 (t, 1H), 4.40-4.55 (m [AB], 2H), 4.21-4.32 (m, 1H), 3.95 (dd, 1H), 3.81 (dd, 1H), 3.41-3.56 (m, 2H), 1.69-1.87 (m, 2H).

Example 70

(3S)-3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[2-(trifluoromethyl)phenyl]propyl carbamate

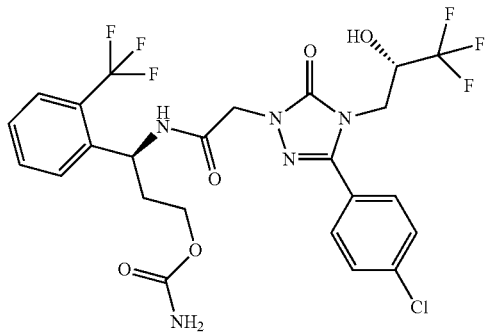 [SMILES: NC(=O)OCC[C@H](NC(=O)Cn1nc(-c2ccc(Cl)cc2)n(C[C@H](O)C(F)(F)F)c1=O)c1ccccc1C(F)(F)F]

In the same way as for Example 49, from 194 mg (0.53 mmol) of the compound from Example 8A and 190 mg (0.64 mmol) of the compound from Example 81A, the title compound was obtained: 138 mg (43% of theory).

LC-MS [Method 5] $R_t$=1.04 min; MS [ESIpos]: m/z=610 (M+H)$^+$ $^1$H NMR (DMSO-d$_6$, 400 MHz): δ=8.84 (d, 1H), 7.65-7.76 (m, 5H), 7.62 (d, 2H), 7.42-7.51 (m, 1H), 6.90 (d, 1H), 6.33-6.58 (br. s, 2H), 5.20-5.28 (m, 1H), 4.57 (t, 1H), 4.42-4.59 (m [AB], 2H), 4.01-4.08 (m, 1H), 3.86-3.99 (m, 2H), 3.82 (dd, 1H), 1.83-1.99 (m, 2H).

Example 71

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2,3-dichlorophenyl)propyl carbamate (diastereomer mixture)

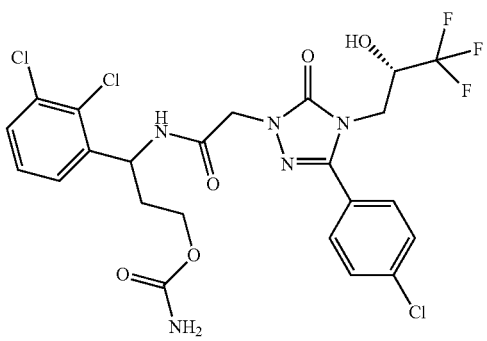

In the same way as for Example 1, from 630 mg (1.72 mmol) of the compound of Example 8A and 568 mg (1.90 mmol) of the compound from Example 88A, the title compound was obtained: 809 mg (77% of theory).

LC-MS [Method 3] $R_t$=1.22+1.23 min; MS [ESIpos]: m/z=610 (M+H)$^+$

The diastereomers from Example 71 were separated by preparative chromatography on a chiral phase (Method 13): see Example 72 and Example 73.

Example 72

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2,3-dichlorophenyl)propyl carbamate (diastereomer I)

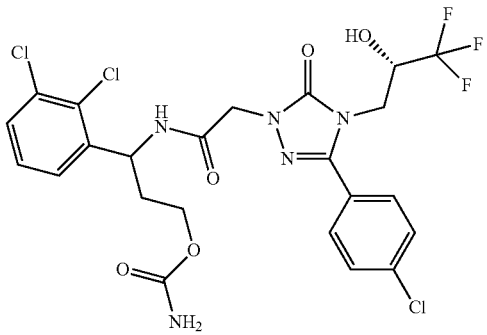 [SMILES: NC(=O)OCCC(NC(=O)Cn1nc(-c2ccc(Cl)cc2)n(C[C@H](O)C(F)(F)F)c1=O)c1cccc(Cl)c1Cl]

First-eluting diastereomer (270 mg) from the chromatographic separation of 800 mg of the compound from Example 71 by Method 13.

LC-MS [Method 5] $R_t$=1.07 min; MS [ESIpos]: m/z=610 (M+H)$^+$

Analytical chiral HPLC [Method 14]: $R_t$=5.61 min.

$^1$H NMR (DMSO-d$_6$, 400 MHz): δ=8.83-8.90 (m, 1H), 7.75 (d, 2H), 7.63 (d, 2H), 7.54 (d, 1H), 7.44 (dd, 1H), 7.37 (t, 1H), 6.91 (d, 1H), 6.32-6.70 (br. s, 2H), 5.25-5.33 (m, 1H), 4.47-4.60 (m [AB], 2H), 4.20-4.34 (m, 1H), 3.88-4.04 (m, 3H), 3.82 (dd, 1H), 1.83-2.02 (m, 2H).

Example 73

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2,3-dichlorophenyl)propyl carbamate (diastereomer II)

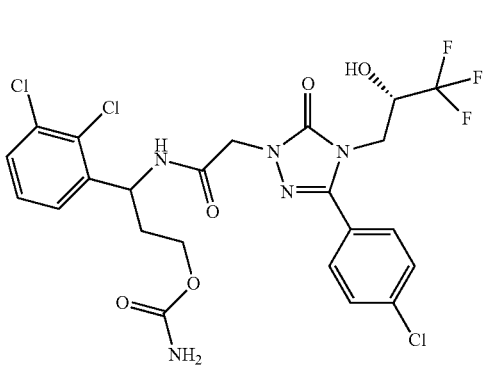 [SMILES: NC(=O)OCCC(NC(=O)Cn1nc(-c2ccc(Cl)cc2)n(C[C@H](O)C(F)(F)F)c1=O)c1cccc(Cl)c1Cl]

Last-eluting diastereomer (270 mg) from the chromatographic separation of 800 mg of the compound from Example 71 by Method 13.

LC-MS [Method 5] $R_t$=1.07 min; MS [ESIpos]: m/z=610 (M+H)$^+$

Analytical chiral HPLC [Method 14]: $R_t$=14.96 min.

$^1$H NMR (DMSO-d$_6$, 400 MHz): δ=8.87 (d, 1H), 7.74 (d, 2H), 7.62 (d, 2H), 7.55 (dd, 1H), 7.44 (dd, 1H), 7.38 (t, 1H), 6.90 (d, 1H), 6.34-6.69 (br.s, 2H), 5.24-5.32 (m, 1H), 4.44-4.62 (m [AB], 2H), 4.21-4.32 (m, 1H), 3.88-4.05 (m, 3H), 3.82 (dd, 1H), 1.83-2.02 (m, 2H)

Example 74

2-{3-(4-Chlorophenyl)-5-oxo-4-[(2S)-3,3,3-trifluoro-2-hydroxypropyl]-4,5-dihydro-1H-1,2,4-triazol-1-yl}-N-[(1R)-1-(2,3-dimethylphenyl)-2-hydroxyethyl]acetamide

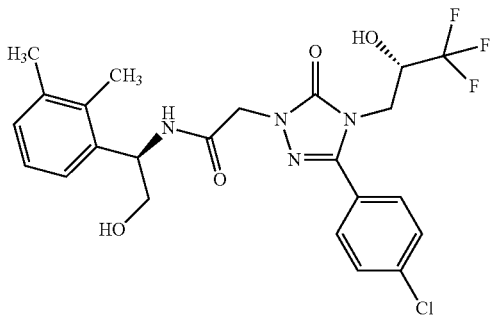 [SMILES: Cc1cccc([C@H](CO)NC(=O)Cn2nc(-c3ccc(Cl)cc3)n(C[C@H](O)C(F)(F)F)c2=O)c1C]

Of the compound from Example 8A, 50 mg (0.14 mmol), 39 mg (0.21 mmol) of EDC and 28 mg (0.21 mmol) of HOBt were stirred together in 1.2 ml of DMF at RT for 20 min, then admixed with 30 mg of (2R)-2-amino-2-(2,3-dimethylphenyl)ethanol hydrochloride (0.15 mmol) and 31 µl (0.18 mmol) of N,N-diisopropylamine. The mixture was stirred at RT for 2 h. Subsequently the complete reaction mixture was purified by preparative HPLC (Method 10). This gave 58 mg (81% of theory) of the title compound.

LC-MS [Method 5]: $R_t$=1.04 min; m/z=513 (M+H)$^+$ $^1$H NMR (DMSO-d$_6$, 400 MHz): δ=8.60 (d, 1H), 7.74 (d, 2H), 7.62 (d, 2H), 7.16 (dd, 1H), 7.01-7.08 (m, 2H), 6.89 (d, 1H), 5.08-5.16 (m, 1H), 4.94 (t, 1H), 4.41-4.56 (m [AB], 2H), 4.21-4.32 (m, 1H), 3.96 (dd, 1H), 3.82 (dd, 1H), 3.41-3.56 (m, 2H), 2.23 (s, 3H), 2.20 (s, 3H).

Example 75

2-{3-(4-Chlorophenyl)-5-oxo-4-[(2S)-3,3,3-trifluoro-2-hydroxypropyl]-4,5-dihydro-1H-1,2,4-triazol-1-yl}-N-[(1R)-1-(3-cyanophenyl)-2-hydroxyethyl]acetamide

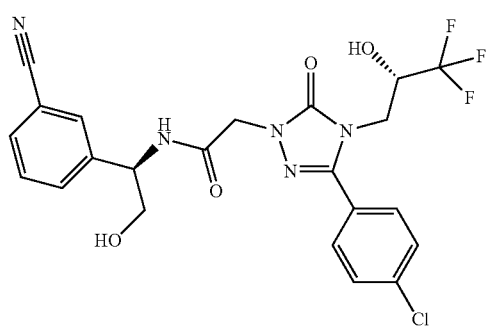 [SMILES: N#Cc1cccc([C@H](CO)NC(=O)Cn2nc(-c3ccc(Cl)cc3)n(C[C@H](O)C(F)(F)F)c2=O)c1]

In the same way as for Example 74, from 50 mg of the compound from Example 8A (0.14 mmol) and 30 mg of (2R)-2-amino-2-(3-cyanophenyl)ethanol hydrochloride (0.15 mmol), 42 mg (60% of theory) of the title compound were obtained.

LC-MS [Method 5]: $R_t$=0.95 min; m/z=510 (M+H)$^+$ $^1$H NMR (DMSO-d$_6$, 400 MHz): δ=8.68 (d, 1H), 7.79 (s, 1H), 7.70-7.77 (m, 3H), 7.68 (d, 1H), 7.62 (d, 2H), 7.54 (t, 1H), 6.90 (d, 1H), 5.03 (t, 1H), 4.87-4.94 (m, 1H), 4.56 (s, 2H), 4.22-4.33 (m, 1H), 3.97 (dd, 1H), 3.83 (dd, 1H), 3.58-3.64 (m, 2H)

Example 76

2-{3-(4-Chlorophenyl)-5-oxo-4-[(2S)-3,3,3-trifluoro-2-hydroxypropyl]-4,5-dihydro-1H-1,2,4-triazol-1-yl}-N-[(1R)-1-(3-chlorophenyl)-2-hydroxyethyl]acetamide

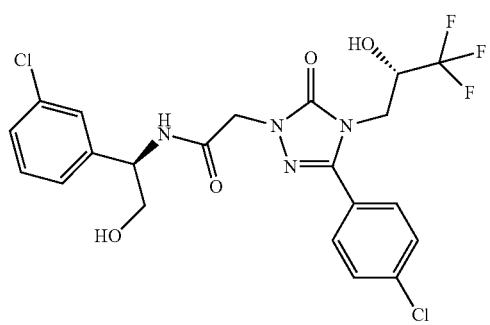 [SMILES: O=C(Cn1nc(-c2ccc(Cl)cc2)n(C[C@H](O)C(F)(F)F)c1=O)N[C@@H](CO)c1cccc(Cl)c1]

In the same way as for Example 74, from 50 mg of the compound from Example 8A (0.14 mmol) and 31 mg of (2R)-2-amino-2-(3-chlorophenyl)ethanol hydrochloride (0.15 mmol), 54 mg (76% of theory) of the title compound were obtained.

LC-MS [Method 5]: R$_t$=1.03 min; m/z=519 (M+H)$^+$ $^1$H NMR (DMSO-d$_6$, 400 MHz): δ=8.62 (d, 1H), 7.76 (d, 2H), 7.62 (d, 2H), 7.39 (s, 1H), 7.26-7.38 (m, 3H), 6.92 (d, 1H), 5.00 (t, 1H), 4.82-4.90 (m, 1H), 4.47-4.59 (m [AB], 2H), 4.21-4.35 (m, 1H), 3.96 (dd, 1H), 3.83 (dd, 1H), 3.55-3.63 (m, 2H)

Example 77

N-[(2R)-2-(2-Chlorophenyl)-1-hydroxypropan-2-yl]-2-{3-(4-chlorophenyl)-5-oxo-4-[(2S)-3,3,3-trifluoro-2-hydroxypropyl]-4,5-dihydro-1H-1,2,4-triazol-1-yl}acetamide

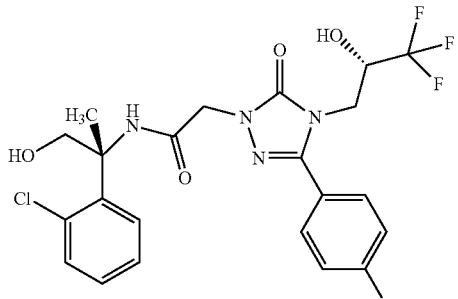

In the same way as for Example 1, from 62 mg of the compound from Example 8A (0.17 mmol) and 49 mg of the compound from Example 74A (0.19 mmol), 33 mg (36% of theory) of the title compound were obtained.

LC-MS [Method 4]: R$_t$=1.02 min; m/z=533 (M+H)$^+$ $^1$H NMR (DMSO-d$_6$, 400 MHz): δ=8.27 (s, 1H), 7.74 (d, 2H), 7.62 (d, 2H), 7.47 (dd, 1H), 7.33 (dd, 1H), 7.18-7.28 (m, 2H), 6.89 (d, 1H), 5.11 (t, 1H), 4.48 (s, 2H), 4.19-4.33 (m, 1H), 3.86-3.97 (m, 2H), 3.73-3.85 (m, 2H), 1.68 (s, 3H).

Example 78

2-{3-(4-Chlorophenyl)-5-oxo-4-[(2S)-3,3,3-trifluoro-2-hydroxypropyl]-4,5-dihydro-1H-1,2,4-triazol-1-yl}-N-{3,3,3-trifluoro-2-hydroxy-1-[3-(trifluoromethyl)phenyl]propyl}acetamide (diastereomer mixture)

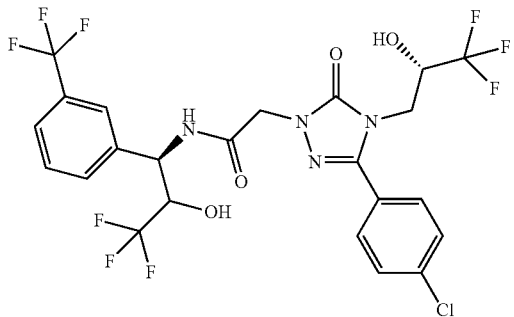 [SMILES: O=C(Cn1nc(-c2ccc(Cl)cc2)n(C[C@H](O)C(F)(F)F)c1=O)N[C@H](c1cccc(C(F)(F)F)c1)C(O)C(F)(F)F]

Of the compound from Example 8A, 113 mg (0.31 mmol), 93 mg (0.34 mmol) of the amino alcohol from Example 99A, 83 mg (0.43 mmol) of EDC and 59 mg (0.43 mmol) of HOBt were stirred together in 4.3 ml of DMF at RT for 2 h. Subsequently the reaction mixture was purified by preparative HPLC (Method 10). This gave 162 mg (80% of theory) of the title compound as a mixture of 4 diastereomers.

LC-MS [Method 5]: R$_t$=1.14 min; MS [ESIpos]: m/z=621 (M+H)$^+$ $^1$H NMR (DMSO-d$_6$, 400 MHz): δ=8.97+8.93+8.92 (3×d, 1H), 7.86+7.81 (2×s, 1H), 7.55-7.77 (m, 7H), 6.82-6.93 (5×d, 1.4H), 6.72 (d, 0.6H), 5.41 (br d, 0.4H), 5.15-5.21 (m, 0.6H), 4.42-4.66 (m, 2H), 4.20-4.40 (m, 2H), 3.92-4.01 (br d, 1H), 3.77-3.87 (2×dd, 1H).

Example 79

2-{3-(4-Chlorophenyl)-5-oxo-4-[(2S)-3,3,3-trifluoro-2-hydroxypropyl]-4,5-dihydro-1H-1,2,4-triazol-1-yl}-N-[1-(2,3-dichlorophenyl)-3-hydroxypropyl]acetamide (diastereomer mixture)

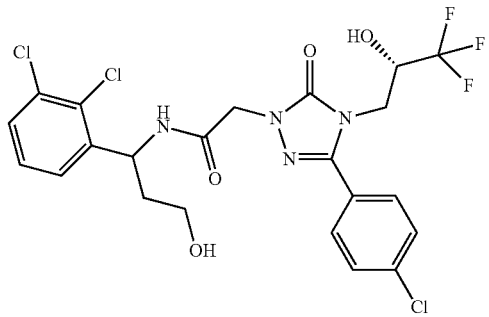 [SMILES: O=C(Cn1nc(-c2ccc(Cl)cc2)n(C[C@H](O)C(F)(F)F)c1=O)NC(CCO)c1cccc(Cl)c1Cl]

Of the compound from Example 8A, 100 mg (0.27 mmol) were dissolved in 4 ml of DMF, admixed with 68 mg (0.36 mmol) of EDC and with 44 mg (0.33 mmol) of HOBt, and stirred at room temperature for 10 minutes. Subsequently 66 mg (0.30 mmol) of the compound from Example 90A were added and the mixture was left with stirring at room temperature for 16 h. For work-up, 10 ml of water were added and the mixture was extracted with twice 10 ml of ethyl acetate. The combined organic phases were dried over sodium sulphate, filtered and concentrated on a rotary evaporator. The crude product was purified by preparative HPLC [Method 19]. This gave 44 mg (28% of theory) of the target compound.

LC-MS [Method 3] R$_t$=1.24 min; MS [ESIpos]: m/z=567/569/571 (M+H)$^+$

The diastereomer mixture from Example 79 was separated into the diastereomers by preparative HPLC on chiral phase [Method 11d]: see Examples 80 and 81.

Example 80

2-{3-(4-Chlorophenyl)-5-oxo-4-[(2S)-3,3,3-trifluoro-2-hydroxypropyl]-4,5-dihydro-1H-1,2,4-triazol-1-yl}-N-[1-(2,3-dichlorophenyl)-3-hydroxypropyl]acetamide (diastereomer I)

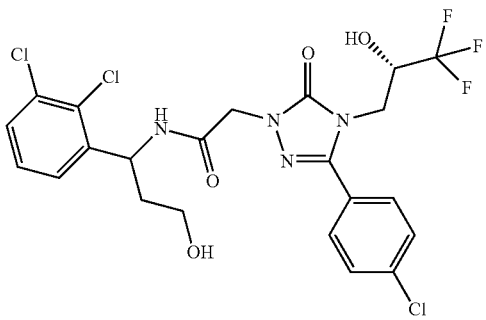 [SMILES: O=C(Cn1nc(-c2ccc(Cl)cc2)n(C[C@H](O)C(F)(F)F)c1=O)NC(CCO)c1cccc(Cl)c1Cl]

First-eluting diastereomer from the separation of Example 79.
Yield: 21 mg (14% of theory)
$R_t$=4.04 min [Method 12c]
LC-MS [Method 5] $R_t$=1.07 min; MS [ESIpos]: m/z=567/569/571 (M+H)$^+$
$^1$H-NMR (400 MHz, CDCl$_3$): δ=1.92-2.03 (m, 1H), 2.04-2.15 (m, 1H), 3.02 (br.s, 1H), 3.55-3.66 (m, 1H), 3.68-3.78 (m, 1H), 3.93-4.05 (m, 2H), 4.47-4.60 (m, 2H), 4.70 (d, 1H), 5.26 (d, 1H), 5.49 (td, 1H), 7.15-7.23 (m, 1H), 7.27-7.31 (m, 1H), 7.35-7.42 (m, 1H), 7.50 (d, 2H), 7.57-7.71 (m, 3H).

Example 81

2-{3-(4-Chlorophenyl)-5-oxo-4-[(2S)-3,3,3-trifluoro-2-hydroxypropyl]-4,5-dihydro-1H-1,2,4-triazol-1-yl}-N-[1-(2,3-dichlorophenyl)-3-hydroxypropyl]acetamide (diastereomer II)

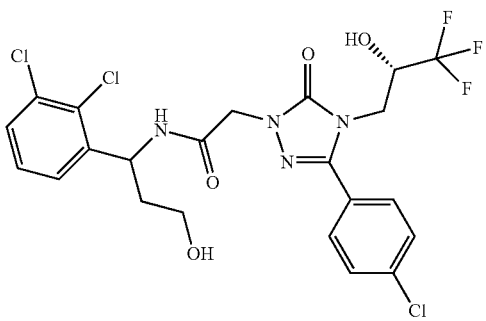 [SMILES: O=C(Cn1nc(-c2ccc(Cl)cc2)n(C[C@H](O)C(F)(F)F)c1=O)NC(CCO)c1cccc(Cl)c1Cl]

Last-eluting diastereomer from the separation of Example 79.
Yield: 20 mg (13% of theory)
$R_t$=4.84 min [Method 12c]
LC-MS [Method 5] $R_t$=1.07 min; MS [ESIpos]: m/z=567 (M+H)$^+$
$^1$H-NMR (400 MHz, CDCl$_3$): δ=1.88-2.00 (m, 1H), 2.04-2.15 (m, 1H), 3.05 (br.s, 1H), 3.54-3.68 (m, 1H), 3.70-3.81 (m, 1H), 3.91-4.06 (m, 2H), 4.51 (d, 1H), 4.54-4.62 (m, 1H), 4.69 (d, 1H), 5.22 (d, 1H), 5.49 (td, 1H), 7.10-7.23 (m, 2H), 7.37 (dd, 1H), 7.45 (d, 1H), 7.52 (d, 2H), 7.65 (d, 2H).

Example 82

N-[1-(2-Chlorophenyl)-3-hydroxypropyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

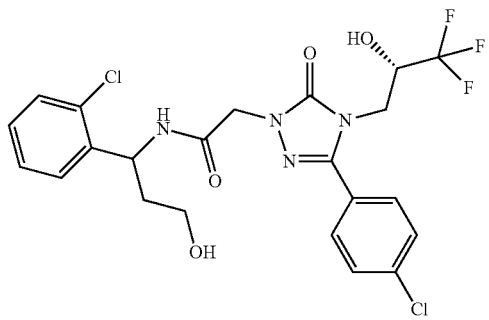 [SMILES: O=C(Cn1nc(-c2ccc(Cl)cc2)n(C[C@H](O)C(F)(F)F)c1=O)NC(CCO)c1ccccc1Cl]

Of the compound from Example 8A, 100 mg (0.27 mmol) were dissolved in 1 ml of DMF, admixed with 79 mg (0.41 mmol) of EDC and 55 mg (0.41 mmol) of HOBt and stirred at room temperature for 10 minutes. Subsequently 67 mg (0.30 mmol) of 3-amino-3-(2-chlorophenyl)propan-1-ol hydrochloride and also 63 µl (0.38 mmol) of N,N-diisopropylethylamine were added and the mixture was left with stirring at room temperature for 16 h. For work-up, 10 ml of water were added and the mixture was extracted with twice 10 ml of ethyl acetate. The combined organic phases were dried over magnesium sulphate, filtered and concentrated on a rotary evaporator. The crude product was purified by preparative HPLC [Method 19]. This gave 93 mg (64% of theory) of the target compound.
LC-MS [Method 3] $R_t$=1.16 min; MS [ESIpos]: m/z=533/535 (M+H)$^+$
The diastereomer mixture from Example 82 was separated into the diastereomers by preparative HPLC on chiral phase [Method 8a]: see Examples 83 and 84.

Example 83

N-[1-(2-Chlorophenyl)-3-hydroxypropyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

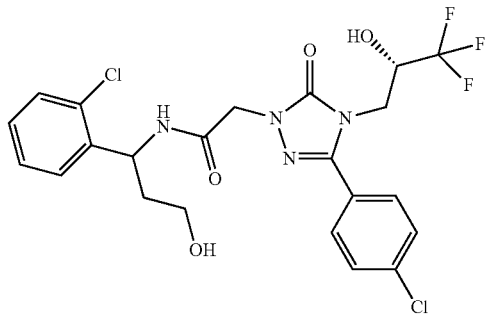 [SMILES: O=C(Cn1nc(-c2ccc(Cl)cc2)n(C[C@H](O)C(F)(F)F)c1=O)NC(CCO)c1ccccc1Cl]

First-eluting diastereomer from the separation of Example 82.
Yield: 34 mg (23% of theory)
$R_t$=2.00 min [Method 14]

LC-MS [Method 6] $R_t$=2.21 min; MS [ESIpos]: m/z=533/535 (M+H)$^+$ $^1$H-NMR (400 MHz, CDCl$_3$): δ=1.93-2.15 (m, 2H), 3.26 (br.s, 1H), 3.57-3.67 (m, 1H), 3.68-3.77 (m, 1H), 3.89-4.05 (m, 2H), 4.48-4.62 (m, 2H), 4.72 (d, 1H), 5.36-5.45 (m, 1H), 5.49 (td, 1H), 7.17-7.25 (m, 1H), 7.35 (d, 2H), 7.49 (d, 2H), 7.57 (d, 1H), 7.64 (d, 2H).

Example 84

N-[1-(2-Chlorophenyl)-3-hydroxypropyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

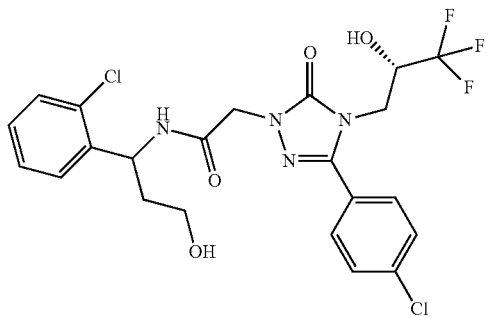 [SMILES: O=C(Cn1nc(-c2ccc(Cl)cc2)n(C[C@H](O)C(F)(F)F)c1=O)NC(CCO)c1ccccc1Cl]

Last-eluting diastereomer from the separation of Example 82.

Yield: 38 mg (26% of theory)
$R_t$=2.92 min [Method 14]
LC-MS [Method 1] $R_t$=1.86 min; MS [ESIpos]: m/z=533/535 (M+H)$^+$ $^1$H-NMR (400 MHz, CDCl$_3$): δ=1.90-2.15 (m, 2H), 3.56-3.68 (m, 1H), 3.69-3.79 (m, 1H), 3.87-4.06 (m, 2H), 4.50 (d, 1H), 4.53-4.63 (m, 1H), 4.70 (d, 1H), 5.48 (td, 1H), 7.16-7.23 (m, 2H), 7.30-7.40 (m, 2H), 7.51 (d, 2H), 7.65 (d, 2H).

Example 85

2-[3-(4-Chlorophenyl)-4-cyclopropyl-5-oxo-4,5-dihydro-1H-1,2,4-triazol-1-yl]-N-[1-(2-chlorophenyl)-3-hydroxypropyl]acetamide (Racemate)

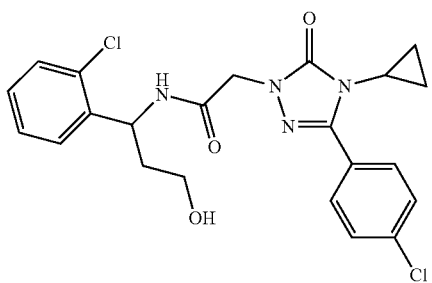 [SMILES: O=C(Cn1nc(-c2ccc(Cl)cc2)n(C2CC2)c1=O)NC(CCO)c1ccccc1Cl]

In the same way as for the compound from Example 82, 30 mg (0.10 mmol) of [3-(4-chlorophenyl)-4-cyclopropyl-5-oxo-4,5-dihydro-1H-1,2,4-triazol-1-yl]acetic acid (for preparation see WO 2007/134862, Example 88A) were reacted. This gave 14 mg (30% of theory) of the target compound.

LC-MS [Method 3] $R_t$=1.12 min; MS [ESIpos]: m/z=461/463 (M+H)$^+$ $^1$H-NMR (400 MHz, CDCl$_3$): δ=0.67-0.79 (m, 2H), 0.97-1.09 (m, 2H), 1.92-2.15 (m, 2H), 2.67 (br.s, 1H), 2.99 (tt, 1H), 3.57-3.79 (m, 2H), 4.45-4.65 (m, 2H), 5.51 (td, 1H), 7.17-7.25 (m, 2H), 7.30-7.39 (m, 2H), 7.47 (d, 2H), 7.68 (d, 2H).

Example 86

2-{3-(4-Chlorophenyl)-5-oxo-4-[(2S)-3,3,3-trifluoro-2-hydroxypropyl]-4,5-dihydro-1H-1,2,4-triazol-1-yl}-N-[3-hydroxy-1-(2-methylphenyl)propyl]acetamide (diastereomer mixture)

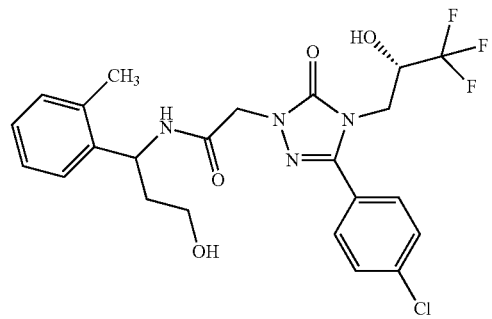 [SMILES: Cc1ccccc1C(CCO)NC(=O)Cn1nc(-c2ccc(Cl)cc2)n(C[C@H](O)C(F)(F)F)c1=O]

Of the compound from Example 8A, 250 mg (0.68 mmol) were dissolved in 5 ml of DMF, admixed with 170 mg (0.89 mmol) of EDC and with 111 mg (0.82 mmol) of HOBt and stirred at room temperature for 10 minutes. Subsequently 124 mg (0.75 mmol) of 3-amino-3-(2-methylphenyl)propan-1-ol were added and the mixture was left with stirring at room temperature for 16 h. For work-up, 10 ml of water were added and the mixture was extracted with twice 10 ml of ethyl acetate. The combined organic phases were dried over sodium sulphate, filtered and concentrated on a rotary evaporator. The crude product was purified by preparative HPLC [Method 19]. This gave 181 mg (52% of theory) of the target compound.

LC-MS [Method 1] $R_t$=1.84 and 1.86 min; MS [ESIpos]: m/z=513 (M+H)$^+$

The diastereomer mixture from Example 86 was separated into the diastereomers by preparative HPLC on chiral phase [Method 8a]: see Examples 87 and 88.

Example 87

2-{3-(4-Chlorophenyl)-5-oxo-4-[(2S)-3,3,3-trifluoro-2-hydroxypropyl]-4,5-dihydro-1H-1,2,4-triazol-1-yl}-N-[3-hydroxy-1-(2-methylphenyl)propyl]acetamide (diastereomer I)

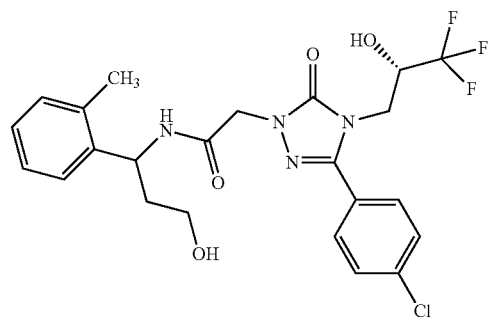 [SMILES: Cc1ccccc1C(CCO)NC(=O)Cn1nc(-c2ccc(Cl)cc2)n(C[C@H](O)C(F)(F)F)c1=O]

First-eluting diastereomer from the separation of Example 86.

Yield: 86 mg (25% of theory)
$R_t$=1.80 min [Method 14]

LC-MS [Method 6] R$_t$=2.19 min; MS [ESIpos]: m/z=513 (M+H)$^+$ $^1$H-NMR (400 MHz, DMSO-d$_6$): δ=1.65-1.91 (m, 2H), 2.32 (s, 3H), 3.33-3.48 (m, 2H), 3.81 (dd, 1H), 3.95 (dd, 1H), 4.20-4.34 (m, 1H), 4.35-4.57 (m, 3H), 5.06-5.18 (m, 1H), 6.90 (d, 1H), 7.11 (d, 2H), 7.14-7.21 (m, 1H), 7.31 (d, 1H), 7.62 (d, 2H), 7.74 (d, 2H), 8.59 (d, 1H).

Example 88

2-{3-(4-Chlorophenyl)-5-oxo-4-[(2S)-3,3,3-trifluoro-2-hydroxypropyl]-4,5-dihydro-1H-1,2,4-triazol-1-yl}-N-[3-hydroxy-1-(2-methylphenyl)propyl]acetamide (diastereomer II)

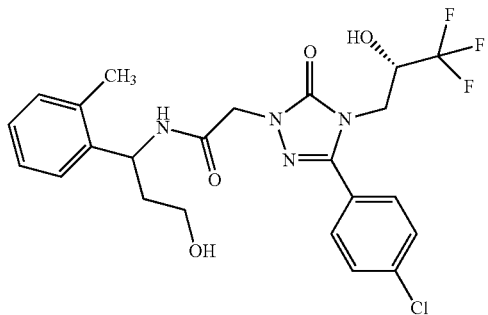 [SMILES: Cc1ccccc1C(CCO)NC(=O)Cn1nc(-c2ccc(Cl)cc2)n(C[C@H](O)C(F)(F)F)c1=O]

Last-eluting diastereomer from the separation of Example 86.

Yield: 87 mg (25% of theory)
R$_t$=2.76 min [Method 14]
LC-MS [Method 6] R$_t$=2.21 min; MS [ESIpos]: m/z=513 (M+H)$^+$ $^1$H-NMR (400 MHz, DMSO-d$_6$): δ=1.68-1.89 (m, 2H), 2.32 (s, 3H), 3.34-3.49 (m, 2H), 3.82 (dd, 1H), 3.95 (dd, 1H), 4.20-4.33 (m, 1H), 4.45 (dd, 2H), 4.53 (t, 1H), 5.08-5.18 (m, 1H), 6.91 (d, 1H), 7.11 (d, 2H), 7.14-7.20 (m, 1H), 7.31 (d, 1H), 7.59-7.65 (m, 2H), 7.74 (d, 2H), 8.58 (d, 1H).

Example 89

2-[3-(4-Chlorophenyl)-4-cyclopropyl-5-oxo-4,5-dihydro-1H-1,2,4-triazol-1-yl]-N-[3-hydroxy-1-(3-methoxyphenyl)propyl]acetamide (Racemate)

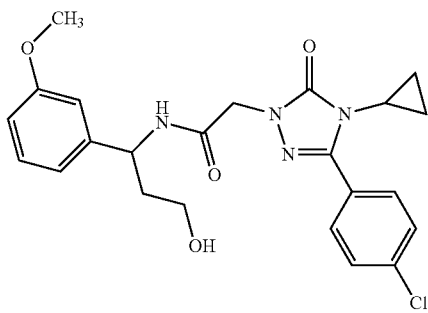 [SMILES: COc1cccc(C(CCO)NC(=O)Cn2nc(-c3ccc(Cl)cc3)n(C3CC3)c2=O)c1]

In the same way as for the compound from Example 86, 30 mg (0.10 mmol) of [3-(4-chlorophenyl)-4-cyclopropyl-5-oxo-4,5-dihydro-1H-1,2,4-triazol-1-yl]acetic acid (for preparation see WO 2007/134862, Example 88A) and 20 mg (0.11 mmol) of 3-amino-3-(3-methoxyphenyl)propan-1-ol were reacted. This gave 30 mg (63% of theory) of the target compound.

LC-MS [Method 3] R$_t$=1.08 min; MS [ESIpos]: m/z=456 (M+H)$^+$ $^1$H-NMR (400 MHz, CDCl$_3$): δ=0.69-0.80 (m, 2H), 0.97-1.08 (m, 2H), 1.78-1.90 (m, 1H), 2.05-2.17 (m, 1H), 2.86 (br.s, 1H), 2.98 (tt, 1H), 3.57-3.74 (m, 2H), 3.77 (s, 3H), 4.55 (q, 2H), 5.20 (td, 1H), 6.75-6.84 (m, 2H), 6.87 (d, 1H), 7.04 (d, 1H), 7.21-7.25 (m, 1H), 7.46 (d, 2H), 7.67 (d, 2H).

Example 90

2-{3-(4-Chlorophenyl)-5-oxo-4-[(2S)-3,3,3-trifluoro-2-hydroxypropyl]-4,5-dihydro-1H-1,2,4-triazol-1-yl}-N-(3,3,3-trifluoro-1-phenylpropyl)acetamide (diastereomer mixture)

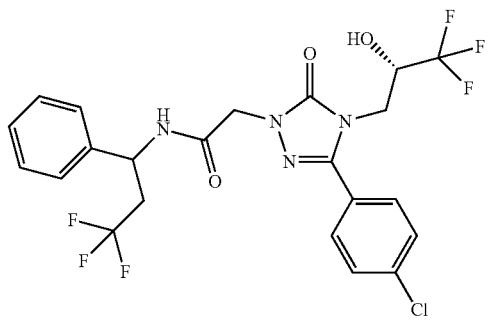 [SMILES: O=C(Cn1nc(-c2ccc(Cl)cc2)n(C[C@H](O)C(F)(F)F)c1=O)NC(CC(F)(F)F)c1ccccc1]

In the same way as for the compound from Example 86, 50 mg (0.14 mmol) of the compound from Example 8A and 28 mg (0.15 mmol) of 3,3,3-trifluoro-1-phenylpropan-1-amine were reacted. This gave 44 mg (59% of theory) of the target compound.

LC-MS [Method 3] R$_t$=1.30 min; MS [ESIpos]: m/z=537 (M+H)$^+$ $^1$H-NMR (400 MHz, CDCl$_3$): δ=2.53-2.81 (m, 2H), 3.92-4.07 (m, 2H), 4.43-4.67 (m, 4H), 5.28-5.37 (m, 1H), 6.70 (dd, 1H), 7.27-7.40 (m, 5H), 7.46-7.56 (m, 4H).

Example 91

N-[1-(3-Chlorophenyl)-3-hydroxypropyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

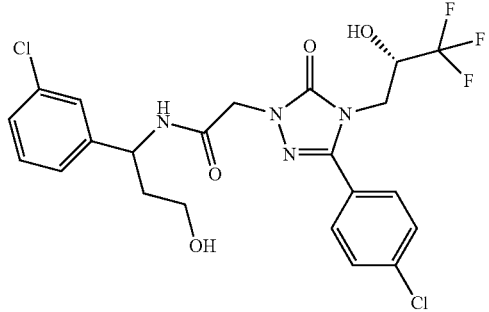 [SMILES: O=C(Cn1nc(-c2ccc(Cl)cc2)n(C[C@H](O)C(F)(F)F)c1=O)NC(CCO)c1cccc(Cl)c1]

In the same way as for the compound from Example 79, from 50 mg (0.14 mmol) of the compound from Example 8A and 28 mg (0.15 mmol) of 3-amino-3-(3-chlorophenyl)propan-1-ol, 48 mg (65% of theory) of the title compound were obtained.

LC-MS [Method 1] $R_t$=1.89 and 1.90 min; MS [ESIpos]: m/z=533 (M+H)$^+$ $^1$H-NMR (400 MHz, CDCl$_3$): δ=1.78-1.91 (m, 1H), 2.00-2.15 (m, 1H), 3.14 (br.s, 0.5H), 3.25 (br.s, 0.5H), 3.54-3.74 (m, 2H), 3.89-4.06 (m, 2H), 4.43-4.74 (m, 3H), 5.10-5.22 (m, 1H), 5.28-5.40 (m, 1H), 7.10-7.30 (m, 4.5H), 7.42 (d, 0.5H), 7.46-7.53 (m, 2H), 7.64 (m, 2H) (partial resolution of the twofold set of signals of the diastereomer mixture).

Example 92

2-{3-(4-Chlorophenyl)-5-oxo-4-[(2S)-3,3,3-trifluoro-2-hydroxypropyl]-4,5-dihydro-1H-1,2,4-triazol-1-yl}-N-[1-(2-fluorophenyl)-3-hydroxypropyl]acetamide (diastereomer mixture)

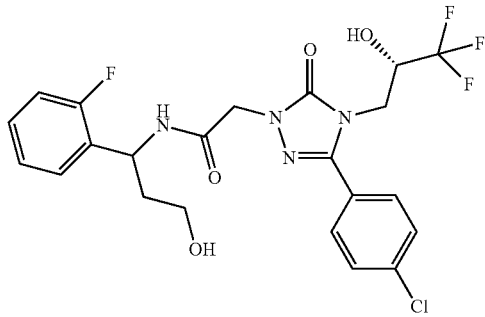 [SMILES: O=C(Cn1nc(-c2ccc(Cl)cc2)n(C[C@H](O)C(F)(F)F)c1=O)NC(CCO)c1ccccc1F]

Of the compound from Example 93A, 39 mg (0.07 mmol) were dissolved in 2 ml of 1,2-dimethoxyethane and admixed at room temperature in succession with 4.1 mg (0.11 mmol) of sodium borohydride and with 0.6 mg (0.014 mmol) of lithium chloride. Subsequently the mixture was stirred at 85° C. for 16 h. For work-up, 10 ml of saturated aqueous sodium potassium tartrate solution were added and the mixture was extracted with three times 10 ml of ethyl acetate. The combined organic phases were dried over magnesium sulphate, filtered and concentrated on a rotary evaporator. The crude product was purified by preparative HPLC [Method 19]. This gave 19 mg (49% of theory) of the target compound.

LC-MS [Method 6] $R_t$=2.13 min; MS [ESIpos]: m/z=517 (M+H)$^+$ $^1$H-NMR (400 MHz, CDCl$_3$): δ=1.92-2.11 (m, 2H), 3.55-3.76 (m, 2H), 3.89-4.07 (m, 2H), 4.43-4.77 (m, 3H), 5.31-5.44 (m, 1H), 6.98-7.15 (m, 2H), 7.17-7.39 (m, 2H), 7.46-7.54 (m, 2H), 7.59-7.68 (m, 2H).

Example 93

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2-fluorophenyl)propyl carbamate (diastereomer mixture)

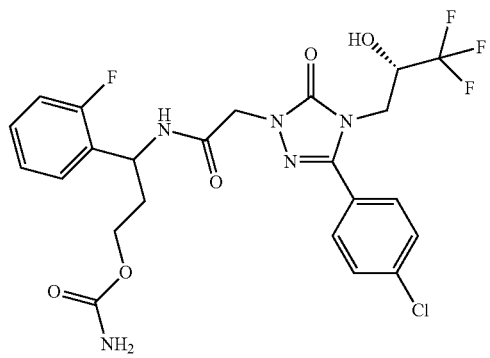 [SMILES: NC(=O)OCCC(NC(=O)Cn1nc(-c2ccc(Cl)cc2)n(C[C@H](O)C(F)(F)F)c1=O)c1ccccc1F]

Of the compound from Example 8A, 354 mg (0.97 mmol) were dissolved in 3 ml of DMF, admixed with 260 mg (1.36 mmol) of EDC and with 183 mg (1.36 mmol) of HOBt and stirred at room temperature for 10 minutes. Subsequently 265 mg (1.07 mmol) of the compound from Example 89A and also 192 µl (1.16 mmol) of N,N-diisopropylethylamine were added and the mixture was left with stirring at room temperature for 2 h. For work-up, it was diluted with 5 ml of DMF and the crude product was purified directly by preparative HPLC [Method 19]. This gave 420 mg (77% of theory) of the target compound.

LC-MS [Method 5] $R_t$=0.99 min; MS [ESIpos]: m/z=560 (M+H)$^+$ $^1$H-NMR (400 MHz, DMSO-d$_6$): δ=1.74-2.09 (m, 2H), 3.36-3.47 (m, 1H), 3.72-4.03 (m, 3H), 4.19-4.36 (m, 1H), 4.38-4.60 (m, 2H), 5.10-5.25 (m, 1H), 6.50 (br.s, 2H), 6.86-6.95 (m, 1H), 7.09-7.23 (m, 2H), 7.24-7.36 (m, 1H), 7.36-7.46 (m, 1H), 7.56-7.67 (m, 2H), 7.69-7.78 (m, 2H), 8.57-8.77 (m, 1H).

Example 94

2-{3-(4-Chlorophenyl)-5-oxo-4-[(2S)-3,3,3-trifluoro-2-hydroxypropyl]-4,5-dihydro-1H-1,2,4-triazol-1-yl}-N-(3,3,3-trifluoro-2-hydroxy-1-phenylpropyl)acetamide (diastereomer mixture)

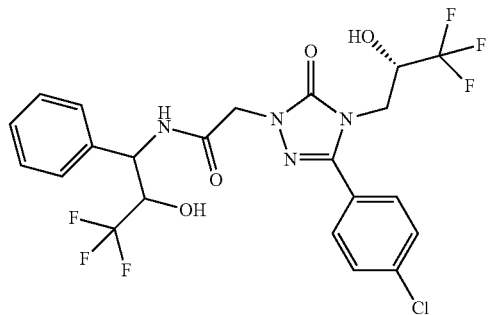 [SMILES: O=C(Cn1nc(-c2ccc(Cl)cc2)n(C[C@H](O)C(F)(F)F)c1=O)NC(c1ccccc1)C(O)C(F)(F)F]

In the same way as for the compound from Example 93, 100 mg (0.27 mmol) of the compound from Example 8A and 73 mg (0.30 mmol) of 3-amino-1,1,1-trifluoro-3-phenylpropan-2-ol hydrochloride were reacted. This gave 102 mg (63% of theory) of the target compound as a diastereomer mixture.

LC-MS [Method 2] $R_t$=2.29 min; MS [ESIpos]: m/z=552 (M+H)$^+$ $^1$H-NMR (400 MHz, CDCl$_3$): δ=3.88-4.07 (m, 2H), 4.15-4.26 (m, 1H), 4.42-4.75 (m, 5H), 4.97-5.09 (m, 1H), 5.37 (dd, 1H), 7.15-7.41 (m, 5H), 7.44-7.53 (m, 2H), 7.56-7.65 (m, 2H).

Example 95

2-{3-(4-Chlorophenyl)-5-oxo-4-[(2S)-3,3,3-trifluoro-2-hydroxypropyl]-4,5-dihydro-1H-1,2,4-triazol-1-yl}-N-[1-(2,3-difluorophenyl)-2-hydroxyethyl]acetamide (diastereomer mixture)

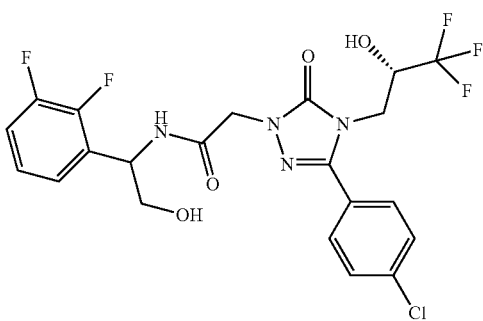 [SMILES: O=C(Cn1nc(-c2ccc(Cl)cc2)n(C[C@H](O)C(F)(F)F)c1=O)NC(CO)c1cccc(F)c1F]

Of the compound from Example 8A, 128 mg (0.33 mmol) were dissolved in 1 ml of DMF, admixed with 83 mg (0.43 mmol) of EDC and with 58 mg (0.43 mmol) of HOBt and stirred at room temperature for 10 minutes. Subsequently 79 mg (0.37 mmol) of the compound from Example 92A and also 51 μl (0.37 mmol) of triethylamine were added and the mixture was left with stirring at room temperature for 16 h. For work-up, 10 ml of water were added and the mixture was extracted with twice 10 ml of ethyl acetate. The combined organic phases were dried over sodium sulphate, filtered and concentrated on a rotary evaporator. The crude product was purified by preparative HPLC [Method 19]. This gave 118 mg (68% of theory) of the target compound.

LC-MS [Method 4] $R_t$=0.99 min; MS [ESIpos]: m/z=521 (M+H)$^+$ $^1$H-NMR (400 MHz, CDCl$_3$): δ=3.13-3.25 (m, H), 3.45-3.52 (m, H), 3.58-3.70 (m, H), 3.74-3.83 (m, H), 3.83-4.10 (m, H), 4.46-4.57 (m, H), 4.58-4.78 (m, H), 5.25 (d, H), 5.29-5.40 (m, H), 5.62 (d, H), 6.95 (d, H), 6.99-7.16 (m, H), 7.48 (dd, H), 7.54 (d, H), 7.62 (d, H), 7.68 (d, H) (partial resolution of the twofold set of signals of the diastereomer mixture).

Example 96

2-[3-(4-Chlorophenyl)-4-cyclopropyl-5-oxo-4,5-dihydro-1H-1,2,4-triazol-1-yl]-N-{2-hydroxy-1-[3-(trifluoromethyl)phenyl]ethyl}acetamide (Racemate)

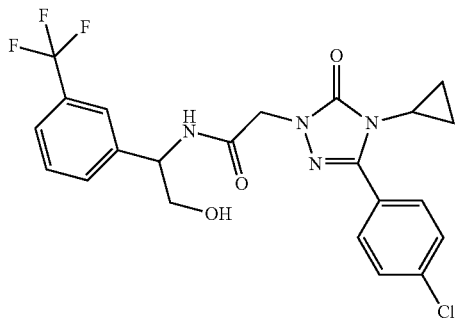 [SMILES: O=C(Cn1nc(-c2ccc(Cl)cc2)n(C2CC2)c1=O)NC(CO)c1cccc(C(F)(F)F)c1]

In the same way as for the compound from Example 95, 48 mg (0.16 mmol) of [3-(4-chlorophenyl)-4-cyclopropyl-5-oxo-4,5-dihydro-1H-1,2,4-triazol-1-yl]acetic acid (for preparation see WO 2007/134862, Example 88A) and 58 mg (0.18 mmol) of the compound from Example 91A were reacted. This gave 61 mg (77% of theory) of the target compound.

LC-MS [Method 4] $R_t$=1.02 min; MS [ESIpos]: m/z=481 (M+H)$^+$ $^1$H-NMR (400 MHz, CDCl$_3$): δ=0.72-0.82 (m, 2H), 0.99-1.09 (m, 2H), 2.36-2.45 (m, 1H), 3.00 (spt, 1H), 3.83-4.00 (m, 2H), 4.53-4.67 (m, 2H), 5.13-5.20 (m, 1H), 7.43-7.50 (m, 3H), 7.50-7.58 (m, 3H), 7.69 (d, 2H).

Example 97

Methyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer mixture)

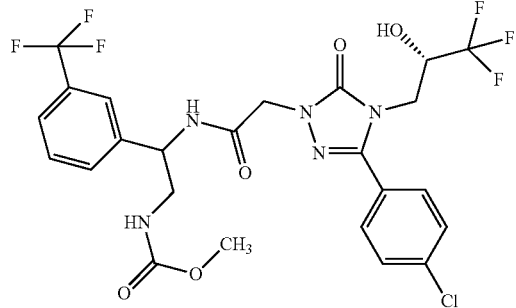 [SMILES: COC(=O)NCC(NC(=O)Cn1nc(-c2ccc(Cl)cc2)n(C[C@H](O)C(F)(F)F)c1=O)c1cccc(C(F)(F)F)c1]

Of the compound from Example 8A, 393 mg (1.07 mmol), 353 mg (1.18 mmol) of the compound from Example 138A, 247 mg (1.29 mmol) of EDC, 174 mg (1.29 mmol) of HOBt and 225 μl (1.29 mmol) of N,N-diisopropylethylamine were stirred in 13 ml of DMF at RT for one hour. The entire reaction solution was purified by preparative HPLC [Method 23]. The appropriate fraction was freed from the solvents on a rotary evaporator and the residue was dried in an HV. This gave 416 mg (64% of theory) of the title compound as a diastereomer mixture (ratio 20:78 according to analytical HPLC [Method 22]).

LC-MS [Method 5] $R_t$=1.09 min; MS [ESIpos]: m/z=610 (M+H)+

The two diastereomers were separated by preparative HPLC on a chiral phase [Method 21a]: see Example 98 and Example 99.

Example 98

Methyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer I)

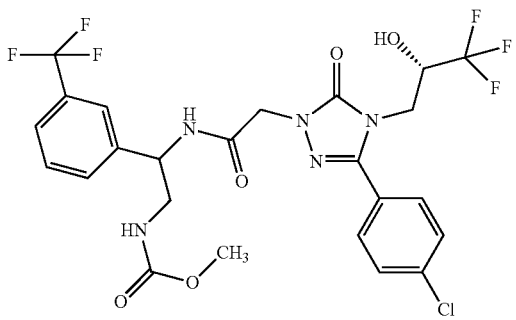 [SMILES: COC(=O)NCC(NC(=O)Cn1nc(-c2ccc(Cl)cc2)n(C[C@H](O)C(F)(F)F)c1=O)c1cccc(C(F)(F)F)c1]

First-eluting diastereomer (51 mg, d.e. >99.5%) from the chromatographic separation of 416 mg of the compound from Example 97 [Method 21a].

Chiral analytical HPLC [Method 22]: $R_t$=3.52 min

LC-MS [Method 4] $R_t$=1.11 min; MS [ESIpos]: m/z=610 (M+H)+

$^1$H NMR (400 MHz, DMSO-d$_6$): δ=3.22-3.40 (m, 2H), 3.47 (s, 3H), 3.83 (dd, 1H), 3.96 (dd, 1H), 4.22-4.35 (m, 1H), 4.51 (s, 2H), 5.02 (q, 1H), 6.91 (d, 1H), 7.26 (t, 1H), 7.54-7.65 (m, 5H), 7.66 (s, 1H), 7.75 (d, 2H), 8.68 (d, 1H).

Example 99

Methyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer II)

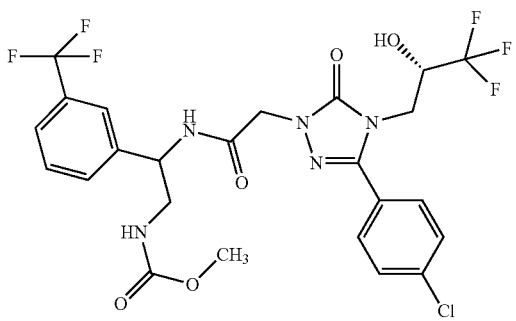 [SMILES: COC(=O)NCC(NC(=O)Cn1nc(-c2ccc(Cl)cc2)n(C[C@H](O)C(F)(F)F)c1=O)c1cccc(C(F)(F)F)c1]

Last-eluting diastereomer from the chromatographic separation of 416 mg of the compound from Example 97 by Method 21a. The resulting product (238 mg, d.e. >99.5%) was further purified by preparative HPLC [Method 20]. This gave 180 mg of the title compound.

Chiral analytical HPLC [Method 22]: $R_t$=4.81 min

LC-MS [Method 5] $R_t$=1.11 min; MS [ESIpos]: m/z=610 (M+H)+

$^1$H NMR (400 MHz, DMSO-d$_6$): δ=3.23-3.39 (m, 2H), 3.47 (s, 3H), 3.83 (dd, 1H), 3.97 (dd, 1H), 4.21-4.33 (m, 1H), 4.44-4.57 (m, 2H [AB]), 5.01 (q, 1H), 6.88 (d, 1H), 7.26 (t, 1H), 7.53-7.65 (m, 5H), 7.67 (s, 1H), 7.74 (d, 2H), 8.69 (d, 1H).

Example 100

Ethyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer mixture)

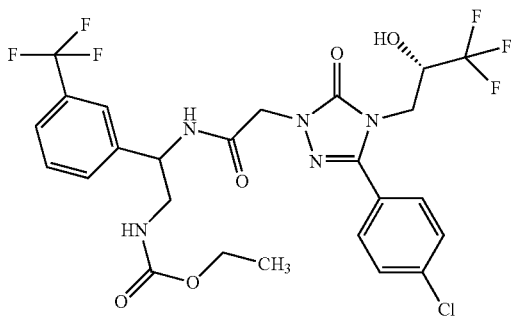 [SMILES: CCOC(=O)NCC(NC(=O)Cn1nc(-c2ccc(Cl)cc2)n(C[C@H](O)C(F)(F)F)c1=O)c1cccc(C(F)(F)F)c1]

Of the compound from Example 8A, 465 mg (1.27 mmol), 437 mg (1.40 mmol) of the compound from Example 137A, 292 mg (1.52 mmol) of EDC, 206 mg (1.52 mmol) of HOBt and 266 µl (1.52 mmol) of N,N-diisopropylethylamine were stirred in 15 ml of DMF at RT for one hour. The entire solution was purified by preparative HPLC [Method 23]. The appropriate fraction was freed from the solvents on a rotary evaporator and the residue was dried in an HV. This gave 524 mg (66% of theory) of the title compound as a diastereomer mixture (ratio 23:74).

LC-MS [Method 5] $R_t$=1.15 min; MS [ESIpos]: m/z=624 (M+H)+

The two diastereomers were separated by preparative HPLC on a chiral phase [Method 21a]: see Example 101 and Example 102.

Example 101

Ethyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer I)

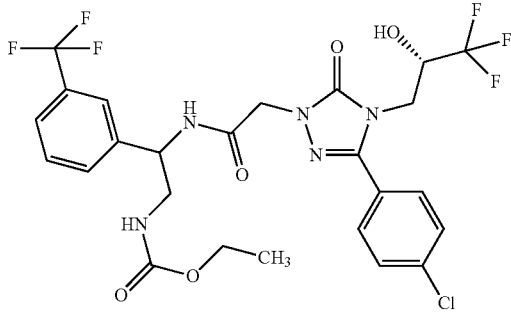 [SMILES: CCOC(=O)NCC(NC(=O)Cn1nc(-c2ccc(Cl)cc2)n(C[C@H](O)C(F)(F)F)c1=O)c1cccc(C(F)(F)F)c1]

First-eluting diastereomer (109 mg) from the chromatographic separation of 520 mg of the compound from Example 100 by Method 21a.

Chiral analytical HPLC [Method 22]: $R_t$=3.42 min

LC-MS [Method 5] $R_t$=1.15 min; MS [ESIpos]: m/z=624 (M+H)$^+$ $^1$H NMR (400 MHz, DMSO-d$_6$): δ=1.08 (t, 3H), 3.23-3.40 (m, 2H), 3.79-3.99 (m, 4H), 4.22-4.33 (m, 1H), 4.51 (s, 2H), 5.02 (q, 1H), 6.91 (d, 1H), 7.21 (t, 1H), 7.53-7.68 (m, 6H), 7.75 (d, 2H), 8.68 (d, 1H).

Example 102

Ethyl {2-[({3-(4-chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl}carbamate (diastereomer II)

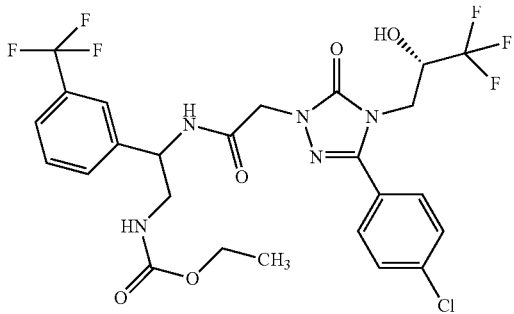

Last-eluting diastereomer from the chromatographic separation of 520 mg of the compound from Example 100 by Method 21a. The resulting product (356 mg) was further purified by preparative HPLC [Method 20]. This gave 297 mg of the title compound.

Chiral analytical HPLC [Method 22]: $R_t$=4.31 min

LC-MS [Method 5] $R_t$=1.15 min; MS [ESIpos]: m/z=624 (M+H)$^+$ $^1$H NMR (400 MHz, DMSO-d$_6$): δ=1.08 (t, 3H), 3.23-3.37 (m, 2H), 3.28-4.01 (m, 4H), 4.22-4.33 (m, 1H), 4.42-4.60 (m[AB], 2H), 5.01 (q, 1H), 6.88 (d, 1H), 7.21 (t, 1H), 7.50-7.68 (m, 6H), 7.73 (d, 2H), 8.69 (d, 1H).

Example 103

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylcarbamoyl)amino]-1-[3-(trifluoromethyl)phenyl]ethyl}acetamide (diastereomer mixture)

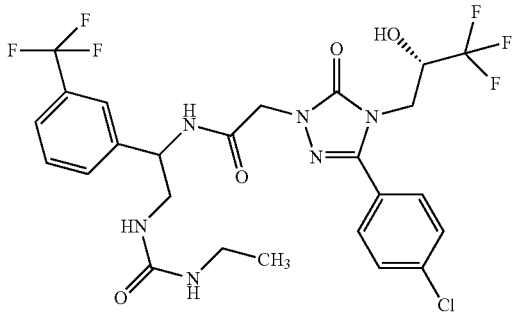 [SMILES: CCNC(=O)NCC(NC(=O)Cn1nc(-c2ccc(Cl)cc2)n(C[C@H](O)C(F)(F)F)c1=O)c1cccc(C(F)(F)F)c1]

Of the compound from Example 8A, 483 mg (1.32 mmol), 453 mg (1.45 mmol) of the compound from Example 139A, 304 mg (1.59 mmol) of EDC, 214 mg (1.59 mmol) of HOBt and 276 μl (1.59 mmol) of N,N-diisopropylethylamine were stirred in 15.5 ml of DMF at RT overnight. Since the reaction was incomplete, 0.8 mmol each of EDC, HOBt and N,N-diisopropylethylamine were added and the mixture was stirred further for 1 h. The entire solution was purified by preparative HPLC [Method 23]. The appropriate fraction was freed from the solvents on a rotary evaporator and the residue was dried in an HV. This gave 428 mg (52% of theory) of the title compound as a diastereomer mixture (ratio 3.5:1 according to NMR).

LC-MS [Method 4] $R_t$=1.09 min; MS [ESIpos]: m/z=623 (M+H)$^+$

The two diastereomers were separated by preparative HPLC on a chiral phase [Method 13a]: see Example 104 and Example 105.

Example 104

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylcarbamoyl)amino]-1-[3-(trifluoromethyl)phenyl]ethyl}acetamide (diastereomer I)

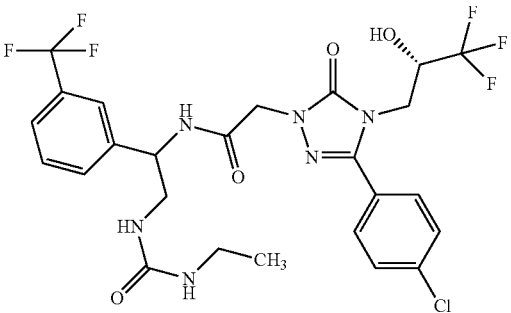 [SMILES: CCNC(=O)NCC(NC(=O)Cn1nc(-c2ccc(Cl)cc2)n(C[C@H](O)C(F)(F)F)c1=O)c1cccc(C(F)(F)F)c1]

First-eluting diastereomer (333 mg) from the chromatographic separation of 428 mg of the compound from Example 103 by Method 13a.

Chiral analytical HPLC [Method 14]: $R_t$=1.62 min $^1$H NMR (400 MHz, DMSO-d$_6$): δ=0.92 (t, 3H), 2.88-3.00 (m, 2H), 3.21-3.39 (m, 2H), 3.82 (dd, 1H), 3.97 (dd, 1H), 4.24-4.38 (m, 1H), 4.44-4.54 (m[AB], 2H), 4.87-4.98 (m, 1H), 5.95 (q, 2H), 6.91 (d, 1H), 7.53-7.66 (m, 6H), 7.76 (d, 2H), 8.79 (d, 1H).

Example 105

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-[(ethylcarbamoyl)amino]-1-[3-(trifluoromethyl)phenyl]ethyl}acetamide (diastereomer II)

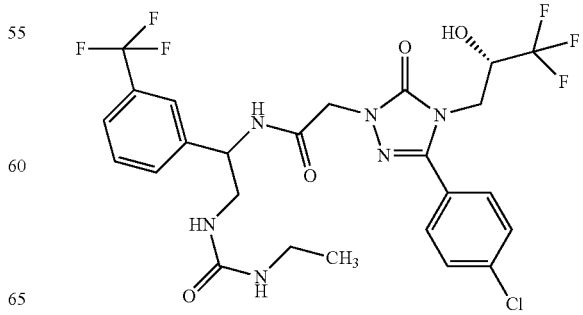

Last-eluting diastereomer (100 mg) from the chromatographic separation of 428 mg of the compound from Example 103 by Method 13a.

Chiral analytical HPLC [Method 14]: $R_t$=2.60 min

1H NMR (400 MHz, DMSO-$d_6$): δ=0.91 (t, 3H), 2.83-3.00 (m, 2H), 3.20-3.38 (m, 2H), 3.83 (dd, 1H), 3.97 (dd, 1H), 4.27-4.39 (m, 1H), 4.41-4.51 (m [AB], 2H), 4.89-4.96 (m, 1H), 5.95 (q, 2H), 6.95 (d, 1H), 7.54-7.66 (m, 6H), 7.77 (d, 2H), 8.79 (d, 1H).

Example 106

N-[2-(Carbamoylamino)-1-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

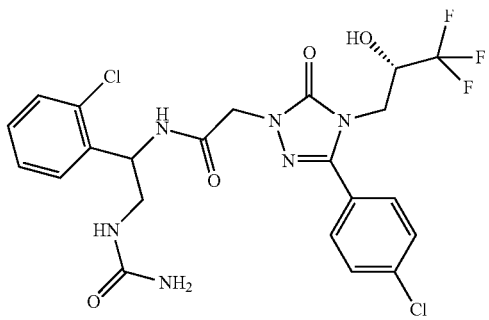 [SMILES: NC(=O)NCC(NC(=O)Cn1nc(-c2ccc(Cl)cc2)n(C[C@H](O)C(F)(F)F)c1=O)c1ccccc1Cl]

Of the compound from Example 8A, 311 mg (0.85 mmol), 279 mg (0.94 mmol) of the compound from Example 143A, 245 mg (1.28 mmol) of EDC, 173 mg (1.28 mmol) of HOBt and 193 μl (1.11 mmol) of N,N-diisopropylethylamine were stirred in 8 ml of DMF at RT for 2 h. The entire solution was purified by preparative HPLC [Method 10]. The appropriate fraction was freed from the solvents on a rotary evaporator and the residue was dried in an HV. This gave 182 mg (36% of theory) of the title compound as a diastereomer mixture.

LC-MS [Method 4] $R_t$=0.97 and 0.98 min; MS [ESIpos]: m/z=561 (M+H)$^+$

The two diastereomers were separated by preparative HPLC on a chiral phase [Method 17d]: see Example 107 and Example 108.

Example 107

N-[2-(Carbamoylamino)-1-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

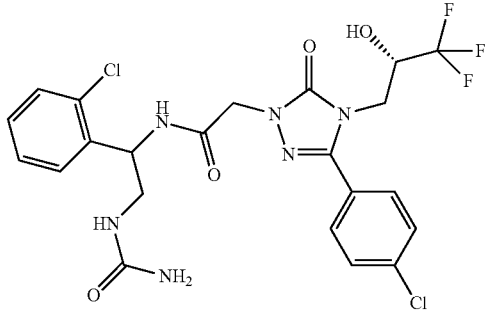 [SMILES: NC(=O)NCC(NC(=O)Cn1nc(-c2ccc(Cl)cc2)n(C[C@H](O)C(F)(F)F)c1=O)c1ccccc1Cl]

First-eluting diastereomer from the chromatographic separation of 120 mg of the compound from Example 106 by Method 17d. The resulting product was further purified by preparative HPLC [Method 10]. This gave 40 mg of the title compound.

Chiral analytical HPLC [Method 18b]: $R_t$=1.81 min.

LC-MS [Method 3] $R_t$=1.12 min; MS [ESIpos]: m/z=561 (M+H)$^+$ $^1$H NMR (400 MHz, DMSO-$d_6$): δ=3.15-3.25 (m, 1H), 3.26-3.36 (m, 1H), 3.84 (dd, 1H), 3.98 (dd, 1H), 4.24-4.37 (m, 1H), 4.39-4.55 (m[AB], 2H), 5.09-5.18 (m, 1H), 5.58 (s, 2H), 6.17 (t, 1H), 6.95 (d, 1H), 7.25-7.37 (m, 2H), 7.39-7.45 (m, 2H), 7.63 (d, 2H), 7.77 (d, 2H), 8.81 (d, 1H).

Example 108

N-[2-(Carbamoylamino)-1-(2-chlorophenyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

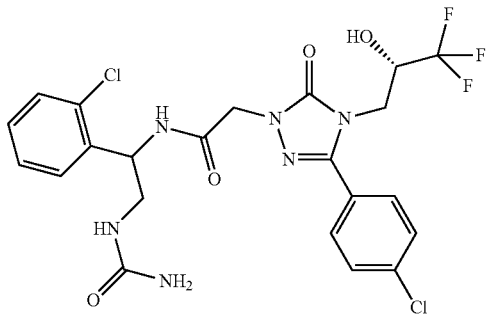 [SMILES: NC(=O)NCC(NC(=O)Cn1nc(-c2ccc(Cl)cc2)n(C[C@H](O)C(F)(F)F)c1=O)c1ccccc1Cl]

Last-eluting diastereomer from the chromatographic separation of 120 mg of the compound from Example 106 by Method 17d. The resulting product (51 mg) was further purified by preparative HPLC [Method 10]. This gave 40 mg of the title compound.

Chiral analytical HPLC [Method 18b]: $R_t$=2.77 min.

LC-MS [Method 3] $R_t$=1.13 min; MS [ESIpos]: m/z=561 (M+H)$^+$ $^1$H NMR (400 MHz, DMSO-$d_6$): δ=3.15-3.25 (m, 1H), 3.26-3.36 (m, 1H), 3.83 (dd, 1H), 3.97 (dd, 1H), 4.26-4.38 (m, 1H), 4.42-4.53 (m [AB], 2H), 5.09-5.17 (m, 1H), 5.59 (s, 2H), 6.18 (t, 1H), 6.95 (d, 1H), 7.25-7.37 (m, 2H), 7.38-7.45 (m, 2H), 7.63 (d, 2H), 7.77 (d, 2H), 8.81 (d, 1H).

Example 109

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl carbamate (diastereomer mixture)

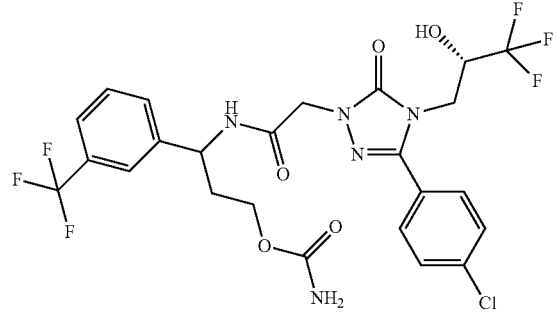 [SMILES: NC(=O)OCCC(NC(=O)Cn1nc(-c2ccc(Cl)cc2)n(C[C@H](O)C(F)(F)F)c1=O)c1cccc(C(F)(F)F)c1]

Of the compound from Example 8A, 945 mg (2.59 mmol), 743 mg (3.88 mmol) of EDC and 552 mg (3.88 mmol) of HOBt were stirred in 25 ml of DMF at RT for 20 min. The resulting solution was added dropwise to a solution of 678 mg (2.59 mmol) of the compound from Example 129A in 75 ml of acetonitrile. After 30 min at RT, the acetonitrile was removed on a rotary evaporator. The remaining solution was admixed with 1 ml of 1M hydrochloric acid and purified by preparative HPLC [Method 10]. The appropriate fraction was freed from the solvents on a rotary evaporator and the residue was dried in an HV. This gave 1.18 g (75% of theory) of the title compound.

LC-MS [Method 2] $R_t$=2.27 min; MS [ESIpos]: m/z=610 $(M+H)^+$

The two diastereomers were separated from 180 mg of the resulting compound by preparative HPLC on a chiral phase [Method 15a]: see Example 110 and Example 111.

Example 110

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl carbamate (diastereomer I)

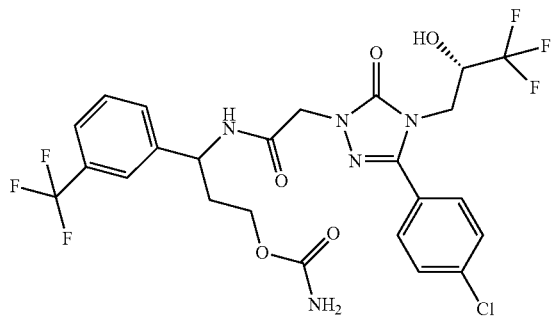 [SMILES: NC(=O)OCCC(NC(=O)Cn1nc(-c2ccc(Cl)cc2)n(C[C@H](O)C(F)(F)F)c1=O)c1cccc(C(F)(F)F)c1]

First-eluting diastereomer from the separation of 180 mg of the compound from Example 109 by Method 15a. The isolated product was further purified by preparative HPLC [Method 10]. This gave 81 mg of the title compound.

Chiral analytical HPLC [Method 16]: $R_t$=2.40 min

LC-MS [Method 5] $R_t$=1.07 min; MS [ESIpos]: m/z=610 $(M+H)^+$ $^1$H NMR (400 MHz, DMSO-$d_6$): δ=1.91-2.07 (m, 2H), 3.77-3.87 (m, 2H), 3.88-3.99 (m, 2H), 4.22-4.35 (m, 1H), 4.50 (s, 2H), 4.95-5.04 (m, 1H), 6.51 (br. s., 2H), 6.93 (d, 1H), 7.55-7.68 (m, 6H), 7.71-7.78 (m, 2H), 8.78 (d, 1H).

Example 111

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl carbamate (diastereomer II)

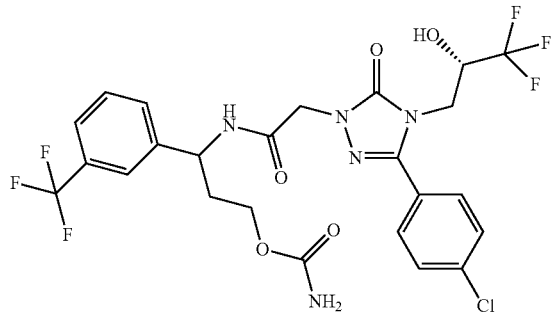 [SMILES: NC(=O)OCCC(NC(=O)Cn1nc(-c2ccc(Cl)cc2)n(C[C@H](O)C(F)(F)F)c1=O)c1cccc(C(F)(F)F)c1]

Last-eluting diastereomer from the separation of 180 mg of the compound from Example 109 by Method 15a. The isolated product was further purified by preparative HPLC [Method 10]. This gave 68 mg of the title compound.

Chiral analytical HPLC [Method 16]: $R_t$=3.28 min

LC-MS [Method 4] $R_t$=1.05 min; MS [ESIpos]: m/z=610 $(M+H)^+$ $^1$H NMR (400 MHz, DMSO-$d_6$): δ=1.90-2.07 (m, 2H), 3.76-4.03 (m, 4H), 4.20-4.34 (m, 1H), 4.41-4.60 (m [AB], 2H), 4.93-5.05 (m, 1H), 6.52 (br. s., 2H), 6.91 (d, 1H), 7.55-7.68 (m, 6H), 7.74 (d, 2H), 8.79 (d, 1H).

Example 112

2-({[3-(4-Chlorophenyl)-5-oxo-4-(3,3,3-trifluoropropyl)-4,5-dihydro-1H-1,2,4-triazol-1-yl]acetyl}amino)-2-[3-(trifluoromethyl)phenyl]ethyl carbamate (enantiomerically pure)

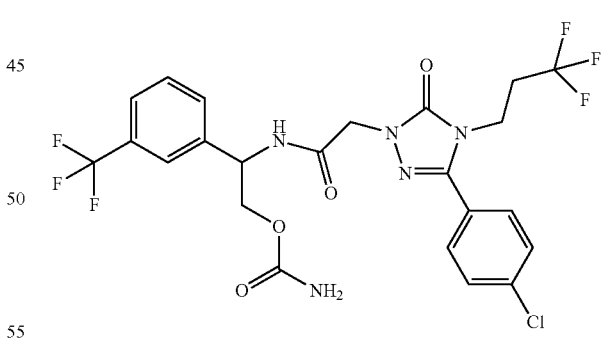

Of the compound from Example 65, 250 mg (0.43 mmol) were hydrogenated in 37 ml of methanol in the presence of platinum (5% on carbon, 104 mg) under hydrogen (pressure=1 atm) at RT overnight. Subsequently the catalyst was removed by filtration and the filtrate was purified by preparative HPLC [Method 20]. This gave 161 mg (64% of theory) of the title compound.

LC-MS [Method 2] $R_t$=2.34 min; MS [ESIpos]: m/z=580 $(M+H)^+$ $^1$H NMR (400 MHz, DMSO-$d_6$): δ=2.56-2.69 (m, 2H), 3.98 (t, 2H), 4.03-4.20 (m, 2H), 4.43-4.59 (m [AB], 2H), 5.06-5.22 (m, 1H), 6.57 (br. s., 2H), 7.55-7.75 (m, 8H), 8.85 (d, 1H).

Example 113

Methyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (racemate)

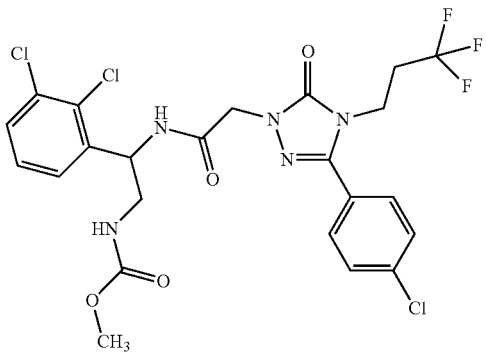 [SMILES: COC(=O)NCC(NC(=O)Cn1nc(-c2ccc(Cl)cc2)n(CCC(F)(F)F)c1=O)c1cccc(Cl)c1Cl]

Of the compound from Example 177A, 144 mg (0.41 mmol), 136 mg (0.45 mmol) of the compound from Example 151A, 94 mg (0.50 mmol) of EDC, 67 mg (0.50 mmol) of HOBt and 86 µl (0.50 mmol) of N,N-diisopropylethylamine were stirred in 4.9 ml of DMF at RT for 1 h. The entire solution was purified by preparative HPLC [Method 20]. The appropriate fraction was freed from the solvents on a rotary evaporator and the residue was dried in an HV. This gave 173 mg (70% of theory) of the title compound.

LC-MS [Method 5] $R_t$=1.15 min; MS [ESIpos]: m/z=594 (M+H)$^+$ $^1$H NMR (400 MHz, DMSO-d$_6$): δ=2.54-2.68 (m, 2H), 3.21-3.36 (m, 2H), 3.50 (s, 3H), 3.98 (t, 2H), 4.44-4.56 (m [AB], 2H), 5.31 (q, 1H), 7.31 (br. t, 1H), 7.36 (t, 1H), 7.45 (dd, 1H), 7.56 (dd, 1H), 7.61-7.69 (m, 4H), 8.67 (d, 1H).

The two enantiomers were separated by preparative HPLC on a chiral phase [Method 21b]: see Example 114 and Example 115.

Example 114

Methyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (enantiomer 1)

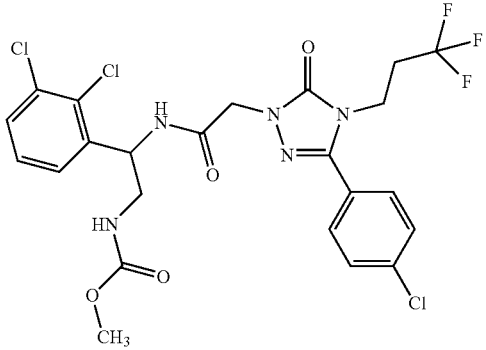 [SMILES: COC(=O)NCC(NC(=O)Cn1nc(-c2ccc(Cl)cc2)n(CCC(F)(F)F)c1=O)c1cccc(Cl)c1Cl]

First-eluting enantiomer (77 mg) from the chromatographic enantiomer separation of 173 mg of the compound from Example 113 by Method 21b. The product obtained was further purified by preparative HPLC [Method 20]. Drying in an HV gave 62 mg of the title compound as a white solid.

Chiral analytical HPLC [Method 22]: $R_t$=6.48 min.

Example 115

Methyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (enantiomer 2)

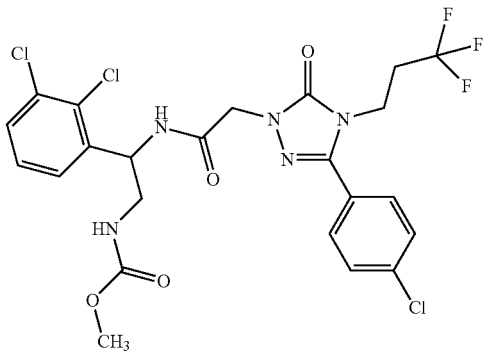 [SMILES: COC(=O)NCC(NC(=O)Cn1nc(-c2ccc(Cl)cc2)n(CCC(F)(F)F)c1=O)c1cccc(Cl)c1Cl]

Last-eluting enantiomer (71 mg) from the chromatographic enantiomer separation of 173 mg of the compound from Example 113 by Method 21b. The product obtained was further purified by preparative HPLC [Method 20]. Drying in an HV gave 60 mg of the title compound as a white solid.

Chiral analytical HPLC [Method 22]: $R_t$=11.02 min.

Example 116

Ethyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (racemate)

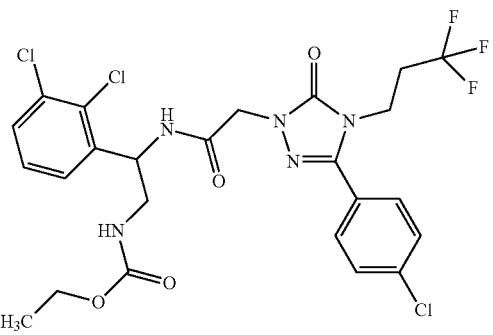 [SMILES: CCOC(=O)NCC(NC(=O)Cn1nc(-c2ccc(Cl)cc2)n(CCC(F)(F)F)c1=O)c1cccc(Cl)c1Cl]

Of the compound from Example 177A, 155 mg (0.44 mmol), 153 mg (0.49 mmol) of the compound from Example 152A, 102 mg (0.53 mmol) of EDC, 72 mg (0.53 mmol) of HOBt and 93 µl (0.53 mmol) of N,N-diisopropylethylamine were stirred in 5 ml of DMF at RT for 1 h. The reaction solution was purified by preparative HPLC [Method 20]. The product fraction was freed from the solvents on a rotary evaporator and the residue was dried in an HV. This gave 168 mg (62% of theory) of the title compound.

LC-MS [Method 5] $R_t$=1.20 min; MS [ESIpos]: m/z=608 (M+H)$^+$ $^1$H NMR (400 MHz, DMSO-d$_6$): δ=1.11 (t, 3H), 2.53-2.69 (m, 2H), 3.21-3.35 (m, 1H), 3.89-4.01 (m, 4H), 4.44-4.57 (m [AB], 2H), 5.31 (br. q, 1H), 7.26 (br. t, 1H), 7.36 (t, 1H), 7.44 (dd, 1H), 7.55 (dd, 1H), 7.60-7.68 (m, 4H), 8.67 (d, 1H).

The two enantiomers were separated by preparative HPLC on a chiral phase [Method 21b]: see Example 117 and Example 118.

Example 117

Ethyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (enantiomer 1)

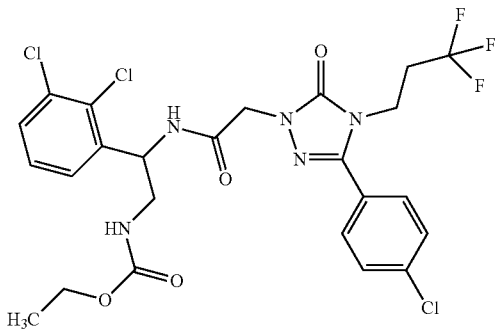 [SMILES: CCOC(=O)NCC(NC(=O)Cn1nc(-c2ccc(Cl)cc2)n(CCC(F)(F)F)c1=O)c1cccc(Cl)c1Cl]

First-eluting enantiomer (67 mg) from the chromatographic enantiomer separation of 168 mg of the compound from Example 116 by Method 21b. The product obtained was further purified by preparative HPLC [Method 20]. Drying in an HV gave 54 mg of the title compound as a white solid.

Chiral analytical HPLC [Method 22]: $R_t$=5.36 min.

Example 118

Ethyl [2-({[3-(4-chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl]carbamate (enantiomer 2)

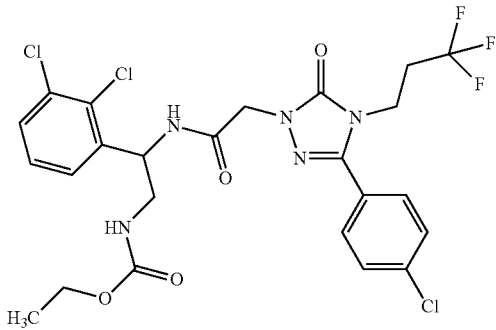 [SMILES: CCOC(=O)NCC(NC(=O)Cn1nc(-c2ccc(Cl)cc2)n(CCC(F)(F)F)c1=O)c1cccc(Cl)c1Cl]

Last-eluting enantiomer (71 mg) from the chromatographic enantiomer separation of 168 mg of the compound from Example 116 by Method 21b. The product obtained was further purified by preparative HPLC [Method 20]. Drying in an HV gave 60 mg of the title compound as a white solid.

Chiral analytical HPLC [Method 22]: $R_t$=9.85 min

Example 119

N-[2-(Carbamoylamino)-1-(2,3-dichlorophenyl)ethyl]-2-[3-(4-chlorophenyl)-5-oxo-4-(3,3,3-trifluoropropyl)-4,5-dihydro-1H-1,2,4-triazol-1-yl]acetamide (racemate)

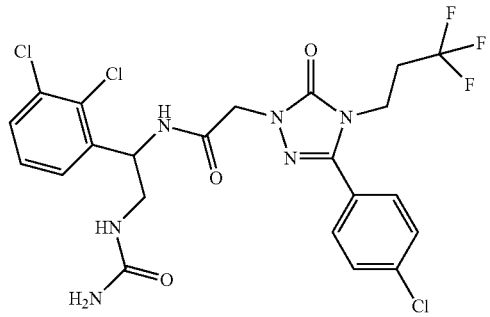 [SMILES: NC(=O)NCC(NC(=O)Cn1nc(-c2ccc(Cl)cc2)n(CCC(F)(F)F)c1=O)c1cccc(Cl)c1Cl]

Of the compound from Example 177A, 162 mg (0.46 mmol), 145 mg (0.51 mmol) of the compound from Example 153A, 107 mg (0.56 mmol) of EDC, 75 mg (0.56 mmol) of HOBt and 97 µl (0.56 mmol) of N,N-diisopropylethylamine were stirred in 5.4 ml of DMF at RT overnight. The solution was diluted with 150 ml of ethyl acetate and extracted in succession twice each with 1M hydrochloric acid and with 1M aqueous sodium hydrogen carbonate solution. The organic phase was dried over sodium sulphate and freed from the volatile components on a rotary evaporator. The residue was purified by preparative HPLC [Method 20]. The product fraction was freed from the solvents on a rotary evaporator and the residue was dried in an HV. This gave 163 mg (61% of theory) of the title compound.

LC-MS [Method 5] $R_t$=1.04 min; MS [ESIpos]: m/z=579 (M+H)$^+$ $^1$H NMR (400 MHz, DMSO-d$_6$): δ=2.56-2.72 (m, 2H), 3.17-3.37 (m, 2H), 3.98 (t, 2H), 4.40-4.52 (m [AB], 2H), 5.11-5.18 (m, 1H), 5.56 (s, 2H), 6.14 (t, 1H), 7.32-7.39 (m, 2H), 7.52-7.57 (m, 1H), 7.61-7.66 (m, 2H), 7.66-7.71 (m, 2H), 8.93 (d, 1H).

The two enantiomers were separated by preparative HPLC on a chiral phase [Method 24a]: see Example 120 and Example 121.

Example 120

N-[2-(Carbamoylamino)-1-(2,3-dichlorophenyl)ethyl]-2-[3-(4-chlorophenyl)-5-oxo-4-(3,3,3-trifluoropropyl)-4,5-dihydro-1H-1,2,4-triazol-1-yl]acetamide (enantiomer 1)

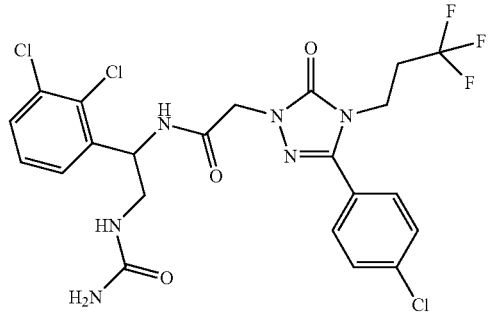 [SMILES: NC(=O)NCC(NC(=O)Cn1nc(-c2ccc(Cl)cc2)n(CCC(F)(F)F)c1=O)c1cccc(Cl)c1Cl]

First-eluting enantiomer (61 mg) from the chromatographic enantiomer separation of 160 mg of the compound from Example 119 by Method 24a. The product obtained was further purified by preparative HPLC [Method 20]. Drying in an HV gave 34 mg of the title compound.

Chiral analytical HPLC [Method 25a]: $R_t$=4.28 min.

Example 121

N-[2-(Carbamoylamino)-1-(2,3-dichlorophenyl) ethyl]-2-[3-(4-chlorophenyl)-5-oxo-4-(3,3,3-trifluoropropyl)-4,5-dihydro-1H-1,2,4-triazol-1-yl]acetamide (enantiomer 2)

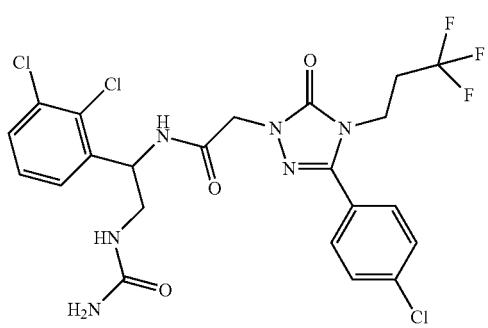 [SMILES: NC(=O)NCC(NC(=O)Cn1nc(-c2ccc(Cl)cc2)n(CCC(F)(F)F)c1=O)c1cccc(Cl)c1Cl]

Last-eluting enantiomer (81 mg) from the chromatographic enantiomer separation of 160 mg of the compound from Example 119 by Method 24a. The product obtained was further purified by preparative HPLC [Method 20]. Drying in an HV gave 39 mg of the title compound.

Chiral analytical HPLC [Method 25a]: $R_t$=9.50 min.

Example 122

2-[3-(4-Chlorophenyl)-5-oxo-4-(3,3,3-trifluoropropyl)-4,5-dihydro-1H-1,2,4-triazol-1-yl]-N-{1-(2,3-dichlorophenyl)-2-[(ethylcarbamoyl)amino]ethyl}acetamide (racemate)

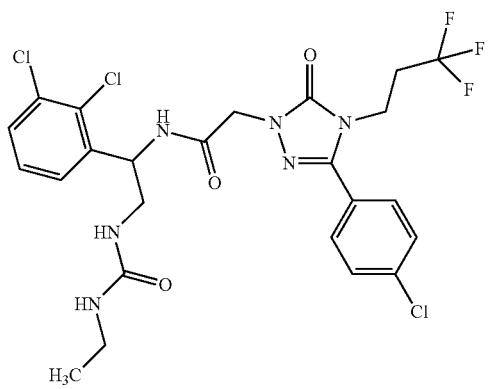 [SMILES: CCNC(=O)NCC(NC(=O)Cn1nc(-c2ccc(Cl)cc2)n(CCC(F)(F)F)c1=O)c1cccc(Cl)c1Cl]

Of the compound from Example 177A, 145 mg (0.42 mmol), 143 mg (0.46 mmol) of the compound from Example 154A, 96 mg (0.50 mmol) of EDC, 67 mg (0.50 mmol) of HOBt and 87 µl (0.50 mmol) of N,N-diisopropylethylamine were stirred in 4.9 ml of DMF at RT for 1 h. The entire solution was purified by preparative HPLC [Method 20]. The product fraction was freed from the solvents on a rotary evaporator and the residue was dried in an HV. This gave 150 mg (58% of theory) of the title compound.

LC-MS [Method 5] $R_t$=1.12 min; MS [ESIpos]: m/z=607 (M+H)$^+$ $^1$H NMR (400 MHz, DMSO-d$_6$): δ=0.92 (t, 3H), 2.57-2.71 (m, 2H), 2.86-2.99 (m, 2H), 3.19-3.38 (m, 2H), 3.98 (t, 2H), 4.40-4.53 (m [AB], 2H), 5.13-5.20 (m, 1H), 5.93 (t, 1H), 6.02 (t, 1H), 7.32-7.39 (m, 2H), 7.50-7.58 (m, 1H), 7.61-7.72 (m, 4H), 8.91 (d, 1H).

The two enantiomers were separated by preparative HPLC on a chiral phase [Method 24b]: see Example 123 and Example 124.

Example 123

2-[3-(4-Chlorophenyl)-5-oxo-4-(3,3,3-trifluoropropyl)-4,5-dihydro-1H-1,2,4-triazol-1-yl]-N-{1-(2,3-dichlorophenyl)-2-[(ethylcarbamoyl)amino]ethyl}acetamide (enantiomer 1)

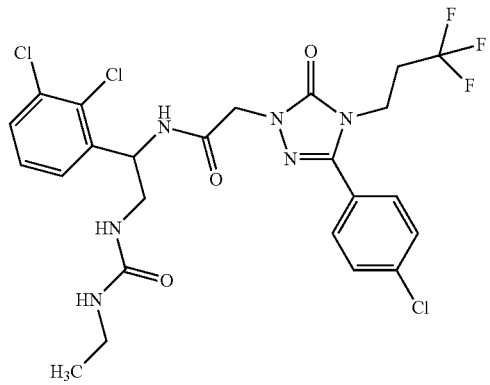 [SMILES: CCNC(=O)NCC(NC(=O)Cn1nc(-c2ccc(Cl)cc2)n(CCC(F)(F)F)c1=O)c1cccc(Cl)c1Cl]

First-eluting enantiomer from the chromatographic enantiomer separation of 160 mg of the compound from Example 122 by Method 24b. The product obtained was further purified by preparative HPLC [Method 20]. Drying in an HV gave 55 mg of the title compound.

Chiral analytical HPLC [Method 25b]: $R_t$=4.69 min.

Example 124

2-[3-(4-Chlorophenyl)-5-oxo-4-(3,3,3-trifluoropropyl)-4,5-dihydro-1H-1,2,4-triazol-1-yl]-N-{1-(2,3-dichlorophenyl)-2-[(ethylcarbamoyl)amino]ethyl}acetamide (enantiomer 2)

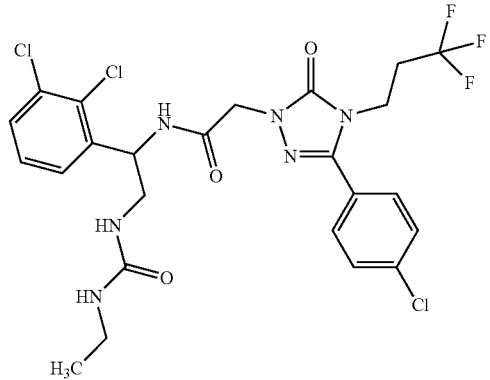 [SMILES: CCNC(=O)NCC(NC(=O)Cn1nc(-c2ccc(Cl)cc2)n(CCC(F)(F)F)c1=O)c1cccc(Cl)c1Cl]

Last-eluting enantiomer from the chromatographic enantiomer separation of 160 mg of the compound from Example 122 by Method 24b. The product obtained was further purified by preparative HPLC [Method 20]. Drying in an HV gave 51 mg of the title compound.

Chiral analytical HPLC [Method 25b]: $R_t$=9.41 min.

Example 125

N-{1-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

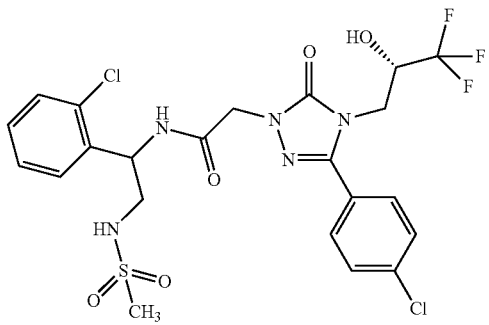 [SMILES: CS(=O)(=O)NCC(NC(=O)Cn1nc(-c2ccc(Cl)cc2)n(C[C@H](O)C(F)(F)F)c1=O)c1ccccc1Cl]

Of the compound from Example 8A, 298 mg (0.81 mmol), 304 mg (0.90 mmol) of the compound from Example 144A, 234 mg (1.22 mmol) of EDC, 165 mg (1.22 mmol) of HOBt and 184 μl (1.06 mmol) of N,N-diisopropylethylamine were stirred in 7.7 ml of DMF at RT for 2 h. The entire solution was purified by preparative HPLC [Method 10]. The product fraction was freed from the solvents on a rotary evaporator and the residue was dried in an HV. This gave 448 mg (90% of theory) of the title compound.

LC-MS [Method 4] $R_t$=1.02 min; MS [ESIpos]: m/z=596 (M+H)$^+$

The two diastereomers were separated by preparative HPLC on a chiral phase [Method 17h]: see Example 126 and Example 127.

Example 126

N-{1-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

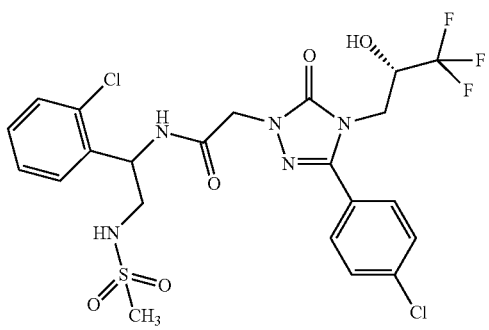 [SMILES: CS(=O)(=O)NCC(NC(=O)Cn1nc(-c2ccc(Cl)cc2)n(C[C@H](O)C(F)(F)F)c1=O)c1ccccc1Cl]

First-eluting diastereomer from the chromatographic diastereomer separation of 440 mg of the compound from Example 125 by Method 17h. The product obtained was further purified by preparative HPLC [Method 20]. Drying in an HV gave 141 mg of the title compound.

Chiral analytical HPLC [Method 18e]: $R_t$=2.81 min
LC-MS [Method 4] $R_t$=1.01 min; MS [ESIpos]: m/z=596 (M+H)$^+$ $^1$H NMR (400 MHz, DMSO-d$_6$): δ=2.87 (s, 3H), 3.11-3.20 (m, 1H), 3.25-3.35 (m, 1H), 3.82 (dd, 1H), 3.96 (dd, 1H), 4.22-4.34 (m, 1H), 4.46-4.64 (m[AB], 2H), 5.31-5.39 (m, 1H), 6.85 (d, 1H), 7.28-7.40 (m, 3H), 7.44 (d, 1H), 7.54 (d, 1H), 7.61 (d, 2H), 7.74 (d, 2H), 8.66 (d, 1H).

Example 127

N-{1-(2-Chlorophenyl)-2-[(methylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

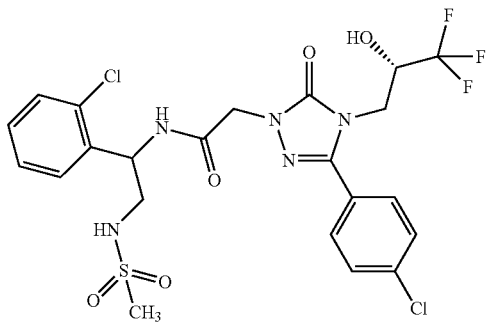 [SMILES: CS(=O)(=O)NCC(NC(=O)Cn1nc(-c2ccc(Cl)cc2)n(C[C@H](O)C(F)(F)F)c1=O)c1ccccc1Cl]

Last-eluting diastereomer from the chromatographic diastereomer separation of 440 mg of the compound from Example 125 by Method 17h. The product obtained was further purified by preparative HPLC [Method 20]. Drying in an HV gave 102 mg of the title compound.

Chiral analytical HPLC [Method 18e]: $R_t$=4.14 min
LC-MS [Method 2] $R_t$=2.20 min; MS [ESIpos]: m/z=596 (M+H)$^+$ $^1$H NMR (400 MHz, DMSO-d$_6$): δ=2.88 (s, 3H), 3.11-3.19 (m, 1H), 3.25-3.33 (m, 1H), 3.83 (dd, 1H), 3.96 (br d, 1H), 4.23-4.34 (m, 1H), 4.55 (q, 2H), 5.32-5.40 (m, 1H), 6.88 (d, 1H), 7.29-7.34 (br t, 2H), 7.37 (t, 1H), 7.44 (d, 1H), 7.54 (d, 1H), 7.62 (d, 2H), 7.75 (d, 2H), 8.65 (d, 1H).

Example 128

N-{1-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

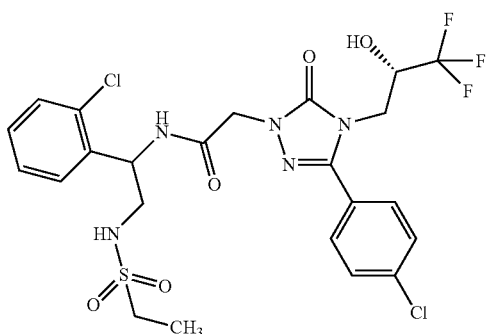

Of the compound from Example 8A, 241 mg (0.66 mmol), 249 mg (0.74 mmol) of the compound from Example 145A, 189 mg (0.99 mmol) of EDC, 133 mg (0.99 mmol) of HOBt and 149 μl (0.99 mmol) of N,N-diisopropylethylamine were stirred in 6.2 ml of DMF at RT for 2 h. The entire solution was purified by preparative HPLC [Method 10]. The product fraction was freed from the solvents on a rotary evaporator and the residue was dried in an HV. This gave 375 mg (91% of theory) of the title compound.

LC-MS [Method 4] R$_t$=1.05 min; MS [ESIpos]: m/z=610 (M+H)$^+$

The two diastereomers were separated by preparative HPLC on a chiral phase [Method 17g]: see Example 129 and Example 130.

Example 129

N-{1-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

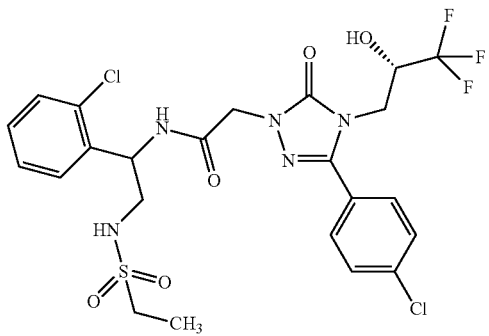 [SMILES: CCS(=O)(=O)NCC(NC(=O)Cn1nc(-c2ccc(Cl)cc2)n(C[C@H](O)C(F)(F)F)c1=O)c1ccccc1Cl]

First-eluting diastereomer from the chromatographic diastereomer separation of 370 mg of the compound from Example 128 by Method 17g. The product obtained was further purified by preparative HPLC [Method 20]. Drying in an HV gave 96 mg of the title compound as a white solid.

Chiral analytical HPLC [Method 18d]: R$_t$=3.87 min
LC-MS [Method 4] R$_t$=1.04 min; MS [ESIpos]: m/z=610 (M+H)$^+$ $^1$H NMR (400 MHz, DMSO-d$_6$): δ=1.15 (t, 3H), 2.88-3.02 (m, 2H), 3.11-3.19 (m, 1H), 3.24-3.33 (m, 1H, hidden beneath water signal), 3.82 (dd, 1H), 3.96 (dd, 1H), 4.22-4.33 (m, 1H), 4.49 (d, 1H), 4.60 (d, 1H), 5.28-5.37 (m, 1H), 6.85 (d, 1H), 7.29-7.40 (m, 3H), 7.44 (d, 1H), 7.53 (d, 1H), 7.61 (d, 2H), 7.74 (d, 2H), 8.64 (d, 1H).

Example 130

N-{1-(2-Chlorophenyl)-2-[(ethylsulphonyl)amino]ethyl}-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

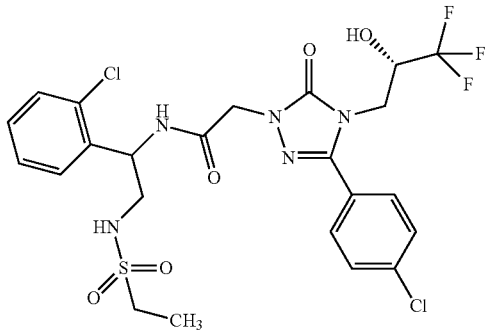 [SMILES: CCS(=O)(=O)NCC(NC(=O)Cn1nc(-c2ccc(Cl)cc2)n(C[C@H](O)C(F)(F)F)c1=O)c1ccccc1Cl]

Last-eluting diastereomer from the chromatographic diastereomer separation of 370 mg of the compound from Example 128 by Method 17g. The product obtained was further purified by preparative HPLC [Method 20]. Drying in an HV gave 134 mg of the title compound.

Chiral analytical HPLC [Method 18d]: R$_t$=5.08 min
LC-MS [Method 4] R$_t$=1.05 min; MS [ESIpos]: m/z=610 (M+H)$^+$ $^1$H NMR (400 MHz, DMSO-d$_6$): δ=1.16 (t, 3H), 2.90-3.02 (m, 2H), 3.10-3.19 (m, 1H), 3.24-3.33 (m, 1H, hidden beneath water signal), 3.83 (dd, 1H), 3.96 (br d, 1H), 4.23-4.34 (m, 1H), 4.48-4.61 (m [AB], 2H), 5.30-5.37 (m, 1H), 6.88 (d, 1H), 7.28-7.39 (m, 3H), 7.43 (d, 1H), 7.53 (d, 1H), 7.62 (d, 2H), 7.75 (d, 2H), 8.62 (d, 1H).

Example 131

N-[1-(2-Chlorophenyl)-2-(methylsulphonyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

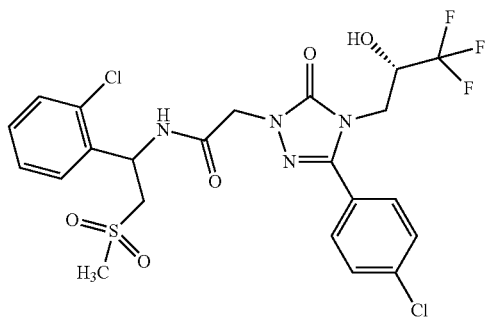 [SMILES: CS(=O)(=O)CC(NC(=O)Cn1nc(-c2ccc(Cl)cc2)n(C[C@H](O)C(F)(F)F)c1=O)c1ccccc1Cl]

Of the compound from Example 8A, 327 mg (0.89 mmol), 266 mg (0.98 mmol) of the compound from Example 146A, 206 mg (1.07 mmol) of EDC, 145 mg (1.07 mmol) of HOBt and 187 μl (1.07 mmol) of N,N-diisopropylethylamine were stirred in 10.5 ml of DMF at RT for 1 h. The entire solution was purified by preparative HPLC [Method 20]. The appropriate fraction was freed from the solvents on a rotary evaporator and the residue was dried in an HV. This gave 354 mg (68% of theory) of the title compound.

LC-MS [Method 3] R$_t$=1.16 min; MS [ESIpos]: m/z=581 (M+H)$^+$

The two diastereomers were separated by preparative HPLC on a chiral phase [Method 26a]: see Example 132 and Example 133.

Example 132

N-[1-(2-Chlorophenyl)-2-(methylsulphonyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer I)

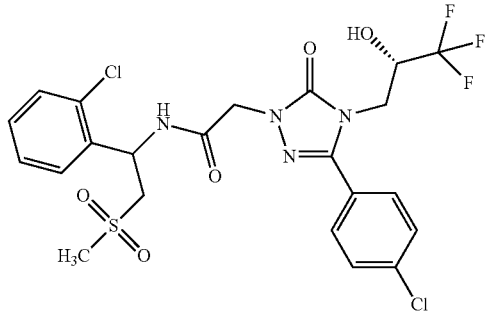 [SMILES: CS(=O)(=O)CC(NC(=O)Cn1nc(-c2ccc(Cl)cc2)n(C[C@H](O)C(F)(F)F)c1=O)c1ccccc1Cl]

First-eluting diastereomer from the chromatographic diastereomer separation of 354 mg of the compound from Example 131 by Method 26a. The product obtained (163 mg) was further purified by preparative HPLC [Method 20]. Drying in an HV gave 116 mg of the title compound.

Chiral analytical HPLC [Method 27a]: $R_t$=4.06 min

LC-MS [Method 5] $R_t$=1.03 min; MS [ESIpos]: m/z=581 (M+H)$^+$ $^1$H NMR (400 MHz, DMSO-d$_6$): δ=3.02 (s, 3H), 3.42 (m, 1H), 3.62 (dd, 1H), 3.82 (dd, 1H), 3.96 (dd, 1H), 4.20-4.33 (m, 1H), 4.51 (s, 2H), 5.72-5.80 (m, 1H), 6.89 (d, 1H), 7.31-7.42 (m, 2H), 7.47 (dd, 1H), 7.55 (dd, 1H), 7.60-7.65 (m, 2H), 7.71-7.77 (m, 2H), 9.03 (d, 1H).

Example 133

N-[1-(2-Chlorophenyl)-2-(methylsulphonyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer II)

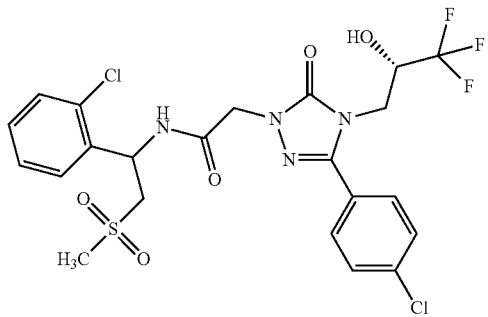 [SMILES: CS(=O)(=O)CC(NC(=O)Cn1nc(-c2ccc(Cl)cc2)n(C[C@H](O)C(F)(F)F)c1=O)c1ccccc1Cl]

Last-eluting diastereomer from the chromatographic diastereomer separation of 354 mg of the compound from Example 131 by Method 26a. The product obtained was further purified by preparative HPLC [Method 20]. Drying in an HV gave 131 mg of the title compound.

Chiral analytical HPLC [Method 27a]: $R_t$=4.71 min

LC-MS [Method 5] $R_t$=1.03 min; MS [ESIpos]: m/z=581 (M+H)$^+$ $^1$H NMR (400 MHz, DMSO-d$_6$): δ=3.02 (s, 3H), 3.42 (m, 1H), 3.62 (dd, 1H), 3.83 (dd, 1H), 3.96 (dd, 1H), 4.21-4.35 (m, 1H), 4.46-4.57 (m [AB], 2H), 5.74-5.81 (m, 1H), 6.91 (d, 1H), 7.31-7.42 (m, 2H), 7.46 (dd, 1H), 7.56 (dd, 1H), 7.60-7.66 (m, 2H), 7.72-7.78 (m, 2H), 9.03 (d, 1H).

Example 134

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[2-(trifluoromethyl)phenyl]ethyl}acetamide (diastereomer mixture)

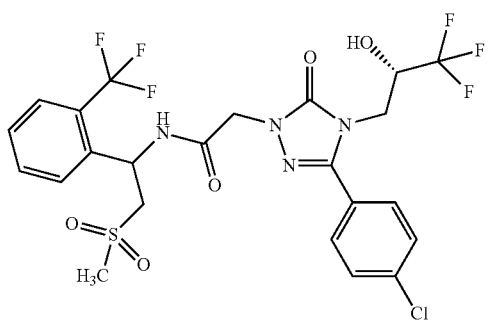 [SMILES: CS(=O)(=O)CC(NC(=O)Cn1nc(-c2ccc(Cl)cc2)n(C[C@H](O)C(F)(F)F)c1=O)c1ccccc1C(F)(F)F]

Of the compound from Example 8A, 438 mg (1.20 mmol), 400 mg (1.32 mmol) of the compound from Example 148A, 275 mg (1.44 mmol) of EDC, 194 mg (1.44 mmol) of HOBt and 250 µl (1.44 mmol) of N,N-diisopropylethylamine were stirred in 10.5 ml of DMF at RT for 1 h. The entire solution was purified by preparative HPLC [Method 20]. The appropriate fraction was freed from the solvents on a rotary evaporator and the residue was dried in an HV. This gave 594 mg (79% of theory) of the title compound.

LC-MS [Method 3] $R_t$=1.19 min; MS [ESIpos]: m/z=615 (M+H)$^+$

The two diastereomers were separated by preparative HPLC on a chiral phase [Method 11e]: see Example 135 and Example 136.

Example 135

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[2-(trifluoromethyl)phenyl]ethyl}acetamide (diastereomer I)

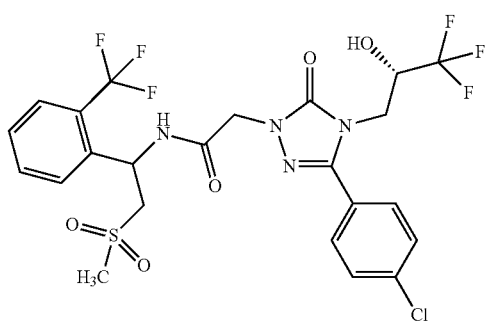 [SMILES: CS(=O)(=O)CC(NC(=O)Cn1nc(-c2ccc(Cl)cc2)n(C[C@H](O)C(F)(F)F)c1=O)c1ccccc1C(F)(F)F]

First-eluting diastereomer (245 mg) from the chromatographic diastereomer separation of 594 mg of the compound from Example 134 by Method 11e. The product obtained was admixed with 10 ml of acetonitrile and 20 ml of water and then lyophilized.

Chiral analytical HPLC [Method 12a]: $R_t$=5.11 min

LC-MS [Method 4] $R_t$=1.04 min; MS [ESIpos]: m/z=615 (M+H)$^+$ $^1$H NMR (400 MHz, DMSO-d$_6$): δ=3.01 (s, 3H), 3.36 (dd, 1H), 3.67 (dd, 1H), 3.82 (dd, 1H), 3.95 (dd, 1H), 4.21-4.33 (m, 1H), 4.48 (s, 2H), 5.74-5.84 (m, 1H), 6.92 (d, 1H), 7.53 (t, 1H), 7.59-7.65 (m, 2H), 7.70-7.82 (m, 5H), 9.08 (d, 1H).

Example 136

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[2-(trifluoromethyl)phenyl]ethyl}acetamide (diastereomer II)

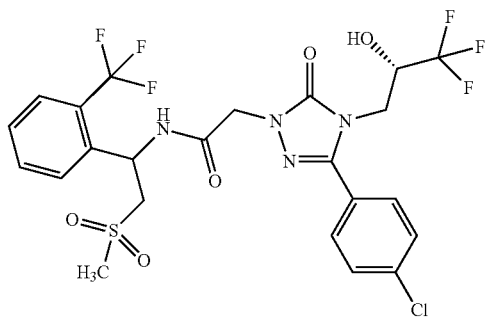 [SMILES: CS(=O)(=O)CC(NC(=O)Cn1nc(-c2ccc(Cl)cc2)n(C[C@H](O)C(F)(F)F)c1=O)c1ccccc1C(F)(F)F]

Last-eluting diastereomer (225 mg) from the chromatographic diastereomer separation of 594 mg of the compound from Example 134 by Method 11e. The product obtained was admixed with 10 ml of acetonitrile and 20 ml of water and then lyophilized.

Chiral analytical HPLC [Method 12a]: $R_t$=8.30 min

LC-MS [Method 4] $R_t$=1.03 min; MS [ESIpos]: m/z=615 (M+H)$^+$ $^1$H NMR (400 MHz, DMSO-d$_6$): δ=3.01 (s, 3H), 3.36 (dd, 1H), 3.68 (dd, 1H), 3.82 (dd, 1H), 3.96 (dd, 1H), 4.20-4.31 (m, 1H), 4.44-4.53 (m[AB], 2H), 5.73-5.82 (m, 1H), 6.89 (d, 1H), 7.53 (t, 1H), 7.59-7.64 (m, 2H), 7.70-7.82 (m, 5H), 9.08 (d, 1H).

Example 137

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[3-(trifluoromethyl)phenyl]ethyl}acetamide (diastereomer mixture)

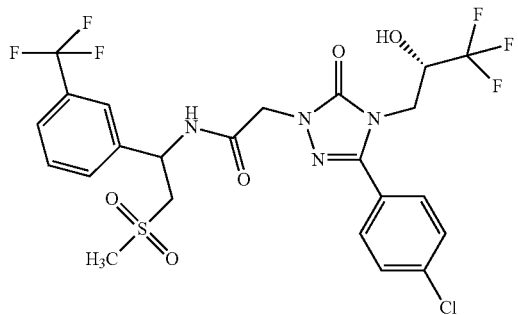 [SMILES: CS(=O)(=O)CC(NC(=O)Cn1nc(-c2ccc(Cl)cc2)n(C[C@H](O)C(F)(F)F)c1=O)c1cccc(C(F)(F)F)c1]

Of the compound from Example 8A, 416 mg (1.14 mmol), 380 mg (1.25 mmol) of the compound from Example 149A, 262 mg (1.37 mmol) of EDC, 184 mg (1.37 mmol) of HOBt and 238 µl (1.37 mmol) of N,N-diisopropylethylamine were stirred in 13.4 ml of DMF at RT for 1 h. The entire solution was purified by preparative HPLC [Method 23]. The appropriate fraction was freed from the solvents on a rotary evaporator and the residue was dried in an HV. This gave 458 mg (65% of theory) of the title compound.

LC-MS [Method 4] $R_t$=1.06 min; MS [ESIpos]: m/z=615 (M+H)$^+$

The two diastereomers were separated by preparative HPLC on a chiral phase [Method 26b]: see Example 138 and Example 139.

Example 138

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[3-(trifluoromethyl)phenyl]ethyl}acetamide (diastereomer I)

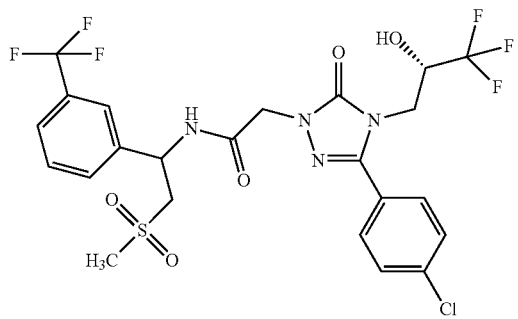 [SMILES: CS(=O)(=O)CC(NC(=O)Cn1nc(-c2ccc(Cl)cc2)n(C[C@H](O)C(F)(F)F)c1=O)c1cccc(C(F)(F)F)c1]

First-eluting diastereomer from the chromatographic diastereomer separation of 450 mg of the compound from Example 137 by Method 26b. The product obtained was further purified by preparative HPLC [Method 20]. Drying in an HV gave 151 mg of the title compound.

Chiral analytical HPLC [Method 27a]: $R_t$=3.61 min

LC-MS [Method 5] $R_t$=1.07 min; MS [ESIpos]: m/z=615 (M+H)$^+$ $^1$H NMR (400 MHz, DMSO-d$_6$): δ=2.99 (s, 3H), 3.69 (d, 2H), 3.83 (dd, 1H), 3.96 (dd, 1H), 4.21-4.31 (m, 1H), 4.45-4.55 (m [AB], 2H), 5.48 (q, 1H), 6.89 (d, 1H), 7.57-7.80 (m, 8H), 8.99 (d, 1H).

Example 139

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphonyl)-1-[3-(trifluoromethyl)phenyl]ethyl}acetamide (diastereomer II)

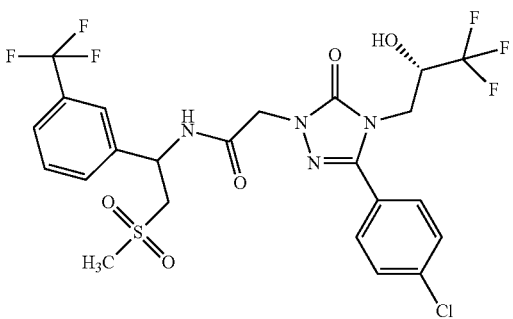 [SMILES: CS(=O)(=O)CC(NC(=O)Cn1nc(-c2ccc(Cl)cc2)n(C[C@H](O)C(F)(F)F)c1=O)c1cccc(C(F)(F)F)c1]

Last-eluting diastereomer from the chromatographic diastereomer separation of 450 mg of the compound from Example 137 by Method 26b. The product obtained was further purified by preparative HPLC [Method 20]. Drying in an HV gave 145 mg of the title compound.

Chiral analytical HPLC [Method 27a]: $R_t$=4.40 min

LC-MS [Method 5] $R_t$=1.08 min; MS [ESIpos]: m/z=615 (M+H)$^+$ $^1$H NMR (400 MHz, DMSO-d$_6$): δ=2.99 (s, 3H), 3.64-3.74 (m, 2H), 3.83 (dd, 1H), 3.96 (dd, 1H), 4.22-4.34 (m, 1H), 4.44-4.56 (m [AB], 2H), 5.45-5.53 (m, 1H), 6.91 (d, 1H), 7.57-7.80 (m, 8H), 8.98 (d, 1H).

Example 140

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(dimethylsulphamoyl)-1-[3-(trifluoromethyl)phenyl]ethyl}acetamide (diastereomer mixture)

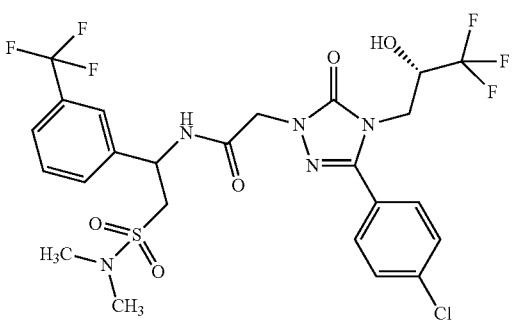 [SMILES: CN(C)S(=O)(=O)CC(NC(=O)Cn1nc(-c2ccc(Cl)cc2)n(C[C@H](O)C(F)(F)F)c1=O)c1cccc(C(F)(F)F)c1]

Of the compound from Example 8A, 221 mg (0.60 mmol), 221 mg (0.66 mmol) of the compound from Example 150A, 174 mg (0.91 mmol) of EDC, 122 mg (0.91 mmol) of HOBt and 137 µl (0.79 mmol) of N,N-diisopropylethylamine were stirred in 5.7 ml of DMF at RT for 2 h. The entire solution was purified by preparative HPLC [Method 10]. The product fraction was freed from the solvents on a rotary evaporator and the residue was dried in an HV. This gave 337 mg (87% of theory) of the title compound.

LC-MS [Method 2] R$_t$=2.41 min; MS [ESIpos]: m/z=644 (M+H)$^+$

The two diastereomers were separated by preparative HPLC on a chiral phase [Method 28]: see Example 141 and Example 142.

Example 141

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(dimethylsulphamoyl)-1-[3-(trifluoromethyl)phenyl]ethyl}acetamide (diastereomer I)

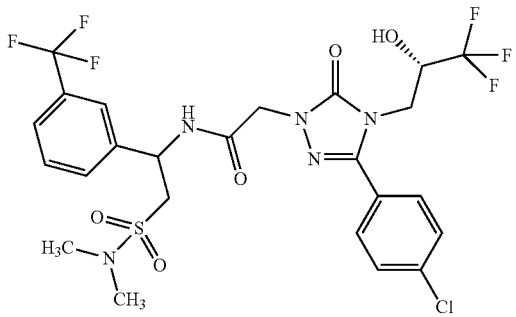 [SMILES: CN(C)S(=O)(=O)CC(NC(=O)Cn1nc(-c2ccc(Cl)cc2)n(C[C@H](O)C(F)(F)F)c1=O)c1cccc(C(F)(F)F)c1]

First-eluting diastereomer from the chromatographic diastereomer separation of 337 mg of the compound from Example 140 by Method 28. The product obtained (153 mg) was further purified by preparative HPLC [Method 20]. Drying in an HV gave 120 mg of the title compound.

Chiral analytical HPLC [Method 18d]: R$_t$=2.56 min
LC-MS [Method 5] R$_t$=1.13 min; MS [ESIpos]: m/z=644 (M+H)$^+$ $^1$H NMR (400 MHz, DMSO-d$_6$): δ=2.75 (s, 6H), 3.48-3.63 (m, 2H), 3.83 (dd, 1H), 3.97 (dd, 1H), 4.20-4.33 (m, 1H), 4.49 (s, 2H), 5.33-5.41 (m, 1H), 6.90 (d, 1H), 7.58-7.79 (m, 8H), 8.92 (d, 1H).

Example 142

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(dimethylsulphamoyl)-1-[3-(trifluoromethyl)phenyl]ethyl}acetamide (diastereomer II)

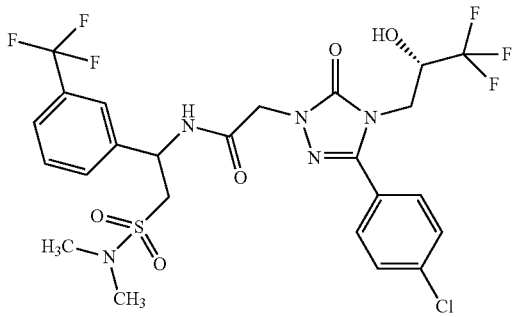 [SMILES: CN(C)S(=O)(=O)CC(NC(=O)Cn1nc(-c2ccc(Cl)cc2)n(C[C@H](O)C(F)(F)F)c1=O)c1cccc(C(F)(F)F)c1]

Last-eluting diastereomer from the chromatographic diastereomer separation of 337 mg of the compound from Example 140 by Method 28. The product obtained (160 mg) was further purified by preparative HPLC [Method 10]. Drying in an HV gave 129 mg of the title compound.

Chiral analytical HPLC [Method 18d]: R$_t$=2.56 min
LC-MS [Method 5] R$_t$=1.13 min; MS [ESIpos]: m/z=644 (M+H)$^+$ $^1$H NMR (400 MHz, DMSO-d$_6$): δ=2.76 (s, 6H), 3.48-3.63 (m, 2H), 3.83 (dd, 1H), 3.96 (dd, 1H), 4.21-4.34 (m, 1H), 4.42-4.55 (m [AB], 2H), 5.34-5.44 (m, 1H), 6.92 (d, 1H), 7.58-7.79 (m, 8H), 8.91 (d, 1H).

Example 143

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-2-[2-(trifluoromethyl)phenyl]ethyl carbamate (enantiomerically pure)

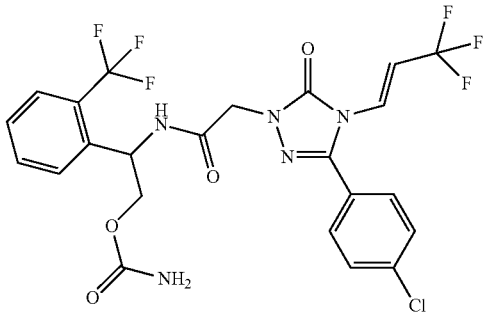 [SMILES: NC(=O)OCC(NC(=O)Cn1nc(-c2ccc(Cl)cc2)n(/C=C/C(F)(F)F)c1=O)c1ccccc1C(F)(F)F]

A solution of 135 mg (0.23 mmol) of the compound from Example 51 and 33 mg (0.27 mmol) of DMAP in 1.6 ml of pyridine was admixed dropwise with 95 µl (0.57 mmol) of trifluoromethanoic anhydride and the resulting mixture was stirred at RT for 3 days. Subsequently 2 ml of 1N hydrochloric acid were added and the volatile components were removed on a rotary evaporator.

The residue was dissolved in a little DMSO and purified by preparative HPLC [Method 10]. The product-containing fraction was freed from the solvents on a rotary evaporator and the residue was dried in an HV. This gave 118 mg (90% of theory) of the title compound.

LC-MS [Method 4] R$_t$=1.13 min; MS [ESIpos]: m/z=578 (M+H)$^+$ $^1$H NMR (400 MHz, DMSO-d$_6$): δ=3.98 (dd, 1H), 4.14 (dd, 1H), 4.48-4.58 (m [AB], 2H), 5.36-5.45 (m, 1H), 6.40-6.77 (br. s., 2H), 6.84 (dq, 1H), 7.17 (dq, 1H), 7.52 (t, 1H), 7.61-7.76 (m, 7H), 8.98 (d, 1H).

Example 144

2-({[3-(4-Chlorophenyl)-5-oxo-4-(3,3,3-trifluoropropyl)-4,5-dihydro-1H-1,2,4-triazol-1-yl]acetyl}amino)-2-[2-(trifluoromethyl)phenyl]ethyl carbamate (enantiomerically pure)

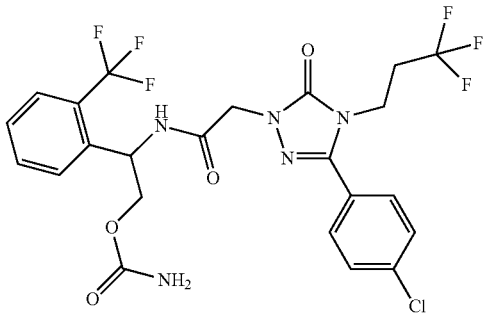 [SMILES: NC(=O)OCC(NC(=O)Cn1nc(-c2ccc(Cl)cc2)n(CCC(F)(F)F)c1=O)c1ccccc1C(F)(F)F]

A solution of 118 mg (0.20 mmol) of the compound from Example 143 in 20 ml of methanol was hydrogenated by means of a continuous-flow hydrogenation apparatus (H-Cube, Thales Nano, Budapest, Model HC-2-SS), equipped with a 5% Pt/C catalyst cartridge, at 45° C. with a flow rate of 1 ml/min under standard pressure. The methanol was removed on a rotary evaporator and the residue was purified by preparative HPLC [Method 10]. This gave 31 mg (26% of theory) of the title compound.

LC-MS [Method 2] $R_t$=2.30 min; MS [ESIpos]: m/z=580 (M+H)$^+$ $^1$H NMR (400 MHz, DMSO-d$_6$): δ=2.51-2.69 (m, 2H), 3.93-4.01 (m, 3H), 4.12 (dd, 1H), 4.48 (s, 2H), 5.34-5.42 (m, 1H), 6.40-6.78 (br. s., 2H), 7.49-7.55 (m, 1H), 7.60-7.76 (m, 7H), 8.94 (d, 1H).

Example 145

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[2-(trifluoromethyl)phenyl]ethyl ethylcarbamate (diastereomerically pure)

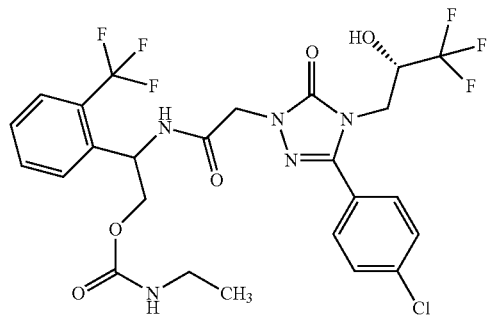 [SMILES: CCNC(=O)OCC(NC(=O)Cn1nc(-c2ccc(Cl)cc2)n(C[C@H](O)C(F)(F)F)c1=O)c1ccccc1C(F)(F)F]

Of the compound from Example 8A, 298 mg (0.81 mmol), 187 mg (0.98 mmol) of EDC and 132 mg (0.98 mmol) of HOBt were stirred in 5 ml of DMF for 10 min. The resulting solution was added dropwise to a solution of 280 mg (0.90 mmol) of the compound from Example 187A and 156 μl (0.90 mmol) of N,N-diisopropylethylamine in 10 ml of acetonitrile. The entire mixture was left with stirring at RT for 20 min, then admixed with 3 ml of 1N hydrochloric acid and purified by preparative chromatography [Method 10]. The product fraction was freed from the solvents on a rotary evaporator and the residue was dried in an HV. This gave 420 mg (83% of theory) of the title compound.

LC-MS [Method 4] $R_t$=1.11 min; MS [ESIpos]: m/z=624 (M+H)$^+$ $^1$H NMR (400 MHz, DMSO-d$_6$): δ=0.98 (t, 3H), 2.90-3.04 (m, 2H), 3.82 (dd, 1H), 3.92-4.03 (m, 2H), 4.11-4.20 (m, 1H), 4.20-4.32 (m, 1H), 4.49 (s, 2H), 5.35-5.44 (m, 1H), 6.88 (d, 1H), 7.20 (t, 1H), 7.53 (t, 1H), 7.58-7.65 (m, 2H), 7.68-7.79 (m, 5H), 8.96 (d, 1H).

Example 146

2-[({3-(4-Chlorophenyl)-5-oxo-4-[(1E)-3,3,3-trifluoroprop-1-en-1-yl]-4,5-dihydro-1H-1,2,4-triazol-1-yl}acetyl)amino]-2-[2-(trifluoromethyl)phenyl]ethyl ethylcarbamate (enantiomerically pure)

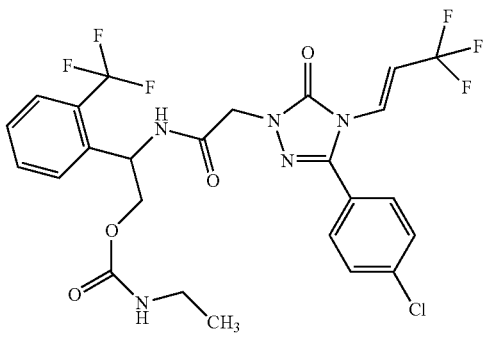 [SMILES: CCNC(=O)OCC(NC(=O)Cn1nc(-c2ccc(Cl)cc2)n(/C=C/C(F)(F)F)c1=O)c1ccccc1C(F)(F)F]

A solution of 230 mg (0.37 mmol) of the compound from Example 145 and 54 mg (0.44 mmol) of DMAP in 5 ml of pyridine was admixed dropwise with 155 μl (0.92 mmol) of trifluoromethanoic anhydride and the resulting mixture was stirred at RT overnight. Subsequently 2 ml of 1N hydrochloric acid were added and the volatile components were removed on a rotary evaporator. The residue was dissolved in a little DMSO and purified by preparative HPLC [Method 10]. The product-containing fraction was freed from the solvents on a rotary evaporator and the residue was dried in an HV. This gave 168 mg (75% of theory) of the title compound.

LC-MS [Method 4] $R_t$=1.22 min; MS [ESIpos]: m/z=606 (M+H)$^+$ $^1$H NMR (400 MHz, DMSO-d$_6$): δ=0.98 (t, 3H), 2.92-3.04 (m, 2H), 3.99 (dd, 1H), 4.13-4.20 (m, 1H), 4.48-4.59 (m[AB], 2H), 5.37-5.45 (m, 1H), 6.85 (dq, 1H), 7.17 (dq, 1H), 7.23 (t, 1H), 7.50-7.56 (m, 1H), 7.60-7.77 (m, 7H), 8.99 (d, 1H).

Example 147

2-({[3-(4-Chlorophenyl)-5-oxo-4-(3,3,3-trifluoropropyl)-4,5-dihydro-1H-1,2,4-triazol-1-yl]acetyl}amino)-2-[2-(trifluoromethyl)phenyl]ethyl ethylcarbamate (enantiomerically pure)

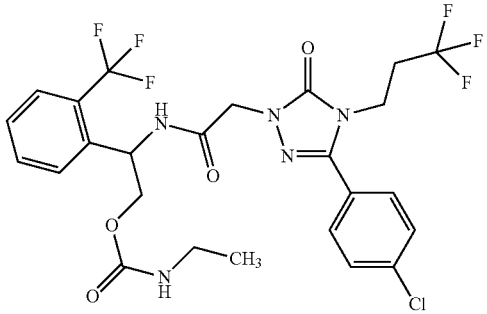 [SMILES: CCNC(=O)OCC(NC(=O)Cn1nc(-c2ccc(Cl)cc2)n(CCC(F)(F)F)c1=O)c1ccccc1C(F)(F)F]

A solution of 168 mg (0.28 mmol) of the compound from Example 146 in 30 ml of methanol was hydrogenated by means of a continuous-flow hydrogenation apparatus (H-Cube, Thales Nano, Budapest, Model HC-2-SS), equipped with a 5% Pt/C catalyst cartridge, at 70° C. with a flow rate of 1 ml/min under standard pressure. The methanol was removed on a rotary evaporator and the residue was purified by preparative HPLC [Method 20]. This gave 96 mg (55% of theory) of the title compound.

LC-MS [Method 5] $R_t$=1.16 min; MS [ESIpos]: m/z=608 (M+H)$^+$ $^1$H NMR (400 MHz, DMSO-d$_6$): δ=0.98 (t, 3H), 2.55-2.65 (m, 2H), 2.91-3.03 (m, 2H), 3.94-4.02 (m, 3H), 4.10-4.19 (m, 1H), 4.47 (s, 2H), 5.35-5.43 (m, 1H), 7.21 (t, 1H), 7.52 (t, 1H), 7.59-7.68 (m, 4H), 7.68-7.76 (m, 3H), 8.94 (d, 1H).

Example 148

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2-oxo-1,3-oxazolidin-3-yl)-1-[3-(trifluoromethyl)phenyl]ethyl}acetamide (diastereomer mixture)

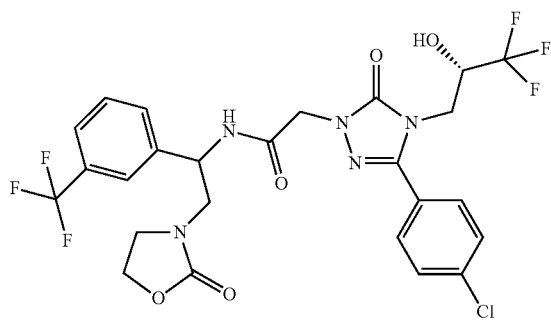 [SMILES: O=C(Cn1nc(-c2ccc(Cl)cc2)n(C[C@H](O)C(F)(F)F)c1=O)NC(CN1CCOC1=O)c1cccc(C(F)(F)F)c1]

Of the compound from Example 8A, 187 mg (0.51 mmol), 118 mg (0.61 mmol) of EDC and 87 mg (0.61 mmol) of HOBt were stirred in 5 ml of DMF for 5 min. The resulting solution was added dropwise to a solution of 175 mg (0.56 mmol) of the compound from Example 140A and 89 µl (0.51 mmol) of N,N-diisopropylethylamine in 5 ml of DMF. The entire mixture was stirred at RT for 2 h then admixed with 100 ml of 1N hydrochloric acid. Extraction was carried out with 500 ml of ethyl acetate. The organic phase was washed four times with water and once with saturated aqueous sodium chloride solution and then dried over sodium sulphate and freed from the volatile constituents on a rotary evaporator. The residue was purified by preparative chromatography [Method 10]. The product fraction was freed from the solvents on a rotary evaporator and the residue was dried in an HV. This gave 265 mg (83% of theory) of the title compound as a diastereomer mixture (ratio approximately 3:1 according to NMR, 77:23 according to chiral HPLC [Method 27a]).

LC-MS [Method 4] $R_t$=1.09 min; MS [ESIpos]: m/z=622 (M+H)$^+$

The two diastereomers were separated by preparative HPLC on a chiral phase [Method 26c]: see Example 149 and Example 150.

Example 149

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2-oxo-1,3-oxazolidin-3-yl)-1-[3-(trifluoromethyl)phenyl]ethyl}acetamide (diastereomer I)

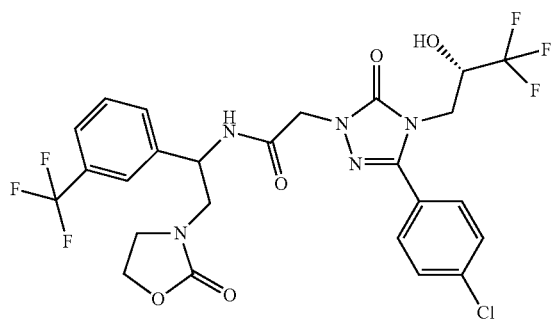 [SMILES: O=C(Cn1nc(-c2ccc(Cl)cc2)n(C[C@H](O)C(F)(F)F)c1=O)NC(CN1CCOC1=O)c1cccc(C(F)(F)F)c1]

First-eluting diastereomer from the chromatographic diastereomer separation of 265 mg of the compound from Example 148 by Method 26c. The product obtained (192 mg) was further purified by preparative HPLC [Method 20]. Drying in an HV gave 126 mg of the title compound.

Chiral analytical HPLC [Method 27a]: $R_t$=3.75 min

LC-MS [Method 4]: $R_t$=1.09 min; MS [ESIpos]: m/z=622 (M+H)$^+$ $^1$H-NMR (400 MHz, DMSO-d$_6$): δ=3.42-3.52 (m, 3H), 3.57 (q, 1H), 3.83 (dd, 1H), 3.97 (dd, 1H), 4.16 (t, 2H), 4.21-4.35 (m, 1H), 4.51 (s, 2H), 5.24 (q, 1H), 6.89 (d, 1H), 7.57-7.64 (m, 3H), 7.64-7.69 (m, 1H), 7.69-7.78 (m, 3H), 7.80 (s, 1H), 8.81 (d, 1H).

Example 150

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2-oxo-1,3-oxazolidin-3-yl)-1-[3-(trifluoromethyl)phenyl]ethyl}acetamide (diastereomer II)

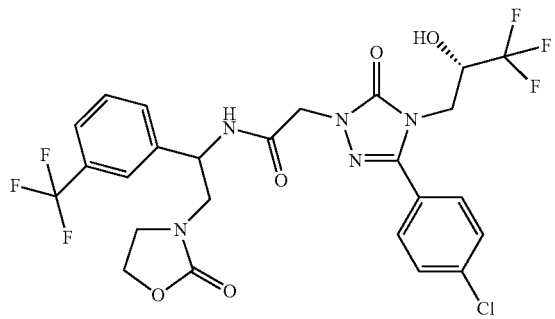 [SMILES: O=C(Cn1nc(-c2ccc(Cl)cc2)n(C[C@H](O)C(F)(F)F)c1=O)NC(CN1CCOC1=O)c1cccc(C(F)(F)F)c1]

Last-eluting diastereomer from the chromatographic diastereomer separation of 265 mg of the compound from Example 148 by Method 26c. This gave 65 mg of the title compound in approximately 90% purity.

Chiral analytical HPLC [Method 27a]: $R_t$=6.01 min

LC-MS [Method 4] $R_t$=1.08 min; MS [ESIpos]: m/z=622 (M+H)$^+$ $^1$H-NMR (400 MHz, DMSO-d$_6$): δ=3.43-3.53 (m, 3H), 3.57 (q, 1H), 3.83 (dd, 1H), 3.96 (dd, 1H), 4.17 (t, 2H), 4.22-4.33 (m, 1H), 4.43-4.58 (m, 2H), 5.24 (q, 1H), 6.90 (d, 1H), 7.57-7.69 (m, 4H), 7.69-7.78 (m, 3H), 7.80 (s, 1H), 8.80 (d, 1H).

Example 151

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2-oxoimidazolidin-1-yl)-1-[3-(trifluoromethyl)phenyl]ethyl}acetamide (diastereomer mixture)

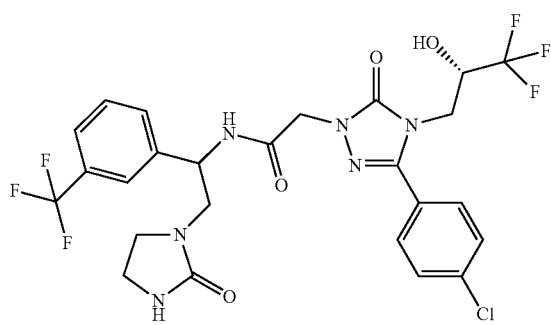 [SMILES: O=C(Cn1nc(-c2ccc(Cl)cc2)n(C[C@H](O)C(F)(F)F)c1=O)NC(CN1CCNC1=O)c1cccc(C(F)(F)F)c1]

Of the compound from Example 8A, 182 mg (0.50 mmol), 115 mg (0.60 mmol) of EDC and 85 mg (0.60 mmol) of HOBt were stirred in 5 ml of DMF for 5 min. The resulting solution was added dropwise to a solution of 170 mg (0.55 mmol) of the compound from Example 141A and 87 µl (0.50 mmol) of N,N-diisopropylethylamine in 5 ml of DMF. The entire mixture was stirred at RT for 2 h, then admixed with 100 ml of 1N hydrochloric acid. Extraction was carried out with 500 ml of ethyl acetate. The organic phase was washed four times with water and once with saturated aqueous sodium chloride solution, then dried over sodium sulphate and freed from the volatile constituents on a rotary evaporator. The residue was purified by preparative chromatography [Method 10]. The product fraction was freed from the solvents on a rotary evaporator and the residue was dried in an HV. This gave 168 mg (54% of theory) of the title compound as a diastereomer mixture (ratio 72:25 according to chiral HPLC [Method 27a]).

LC-MS [Method 4] $R_t$=1.08 min; MS [ESIpos]: m/z=621 (M+H)$^+$

The main diastereomer was isolated in pure form (see Example 152) by preparative HPLC on a chiral phase [Method 26c]. The secondary diastereomer (diastereomer 2) ($R_t$ [Method 27a]=4.66 min) was not isolated.

Example 152

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(2-oxoimidazolidin-1-yl)-1-[3-(trifluoromethyl)phenyl]ethyl}acetamide (diastereomer 1)

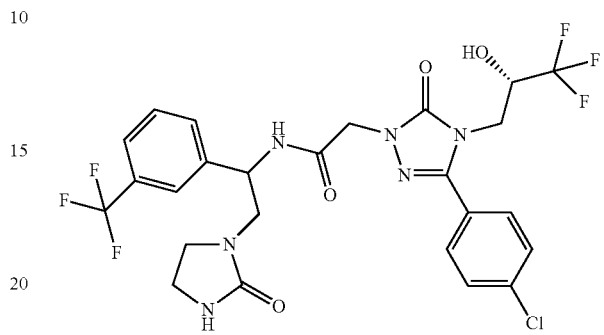

First-eluting diastereomer from the chromatographic diastereomer separation of 168 mg of the compound from Example 151 by Method 26a. Drying in an HV gave 107 mg of the title compound.

Chiral analytical HPLC [Method 27a]: $R_t$=3.87 min

LC-MS [Method 4] $R_t$=1.08 min; MS [ESIpos]: m/z=621 (M+H)$^+$ $^1$H NMR (400 MHz, DMSO-d$_6$): δ=3.07-3.19 (m, 2H), 3.20-3.43 (m, 4H), 3.82 (dd, 1H), 3.97 (m, 1H), 4.25-4.36 (m, 1H), 4.49 (s, 2H), 5.08-5.15 (m, 1H), 6.37 (s, 1H), 6.90 (d, 1H), 7.56-7.70 (m, 5H), 7.72-7.78 (m, 3H), 8.70 (d, 1H).

Example 153

N-[1-(2-Chlorophenyl)-2-(methylsulphanyl)ethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

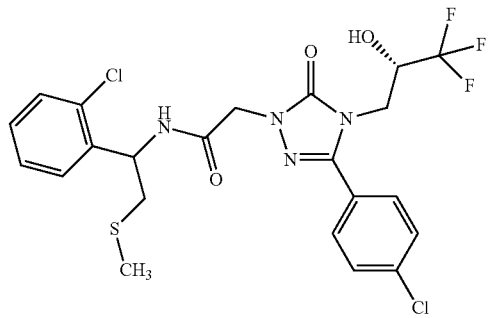 [SMILES: CSCC(NC(=O)Cn1nc(-c2ccc(Cl)cc2)n(C[C@H](O)C(F)(F)F)c1=O)c1ccccc1Cl]

Of the compound from Example 8A, 53 mg (0.14 mmol), 38 mg (0.16 mmol) of the compound from Example 147A, 33 mg (0.17 mmol) of EDC, 24 mg (0.17 mmol) of HOBt and 30 µl (0.17 mmol) of N,N-diisopropylethylamine were stirred in 1.7 ml of DMF at RT for 1 h. The solution was then acidified with 1N hydrochloric acid and the entire solution was purified by preparative HPLC [Method 20]. The product fraction was freed from the solvents on a rotary evaporator and the residue was dried in an HV. This gave 70 mg of the title compound (87% of theory).

LC-MS [Method 5] R$_t$=1.16 min; MS [ESIpos]: m/z=549 (M+H)$^+$ $^1$H NMR (400 MHz, DMSO-d$_6$): δ=2.09 (2s, 1s per diastereomer, 3H), 2.71-2.85 (m, 2H), 3.83 (dd, 1H), 3.96 (br d, 1H), 4.20-4.33 (m, 1H), 4.47-4.58 (m, 2H), 5.35-5.44 (m, 1H), 6.87-6.92 (m, interpreted as 1d per diastereomer, (6.89+6.90), 1H), 7.27-7.40 (m, 2H), 7.43 (br d, 1H), 7.52 (br d, 1H), 7.63 (2d, 2H), 7.74 (d, 2H), 8.82 (d, 1H).

Example 154

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphanyl)-1-[2-(trifluoromethyl)phenyl]ethyl}acetamide (diastereomer mixture)

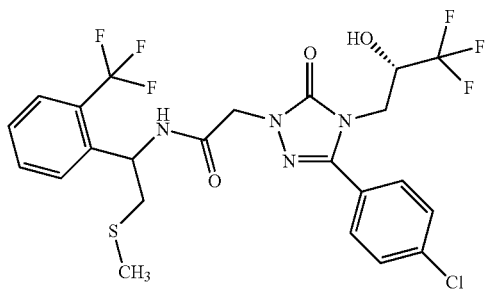 [SMILES: CSCC(NC(=O)Cn1nc(-c2ccc(Cl)cc2)n(C[C@H](O)C(F)(F)F)c1=O)c1ccccc1C(F)(F)F]

Of the compound from Example 8A, 303 mg (0.83 mmol), 248 mg (0.91 mmol) of the compound from Example 142A, 191 mg (1.00 mmol) of EDC, 135 mg (1.00 mmol) of HOBt and 173 µl (1.00 mmol) of N,N-diisopropylethylamine were stirred in 9.8 ml of DMF at RT for 1 h. The entire solution was purified by preparative HPLC [Method 20]. The appropriate fraction was freed from the solvents on a rotary evaporator and the residue was dried in an HV. This gave 362 mg (73% of theory) of the title compound.

LC-MS [Method 3] R$_t$=1.33 min; MS [ESIpos]: m/z=583 (M+H)$^+$

The two diastereomers were separated by preparative HPLC on a chiral phase [Method 29]: see Example 155 and Example 156.

Example 155

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphanyl)-1-[2-(trifluoromethyl)phenyl]ethyl}acetamide (diastereomer I)

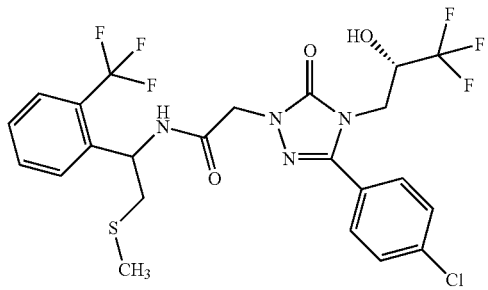 [SMILES: CSCC(NC(=O)Cn1nc(-c2ccc(Cl)cc2)n(C[C@H](O)C(F)(F)F)c1=O)c1ccccc1C(F)(F)F]

First-eluting diastereomer from the chromatographic diastereomer separation of 360 mg of the compound from Example 154 by Method 29. The resulting product (148 mg) was further purified by preparative HPLC [Method 20]. Drying in an HV gave 119 mg of the title compound.

Chiral analytical HPLC [Method 30]: R$_t$=4.40 min

LC-MS [Method 31] R$_t$=2.53 min; MS [ESIpos]: m/z=583 (M+H)$^+$ $^1$H-NMR (400 MHz, DMSO-d$_6$): δ=2.06 (s, 3H), 2.74-2.83 (m, 2H), 3.82 (dd, 1H), 3.95 (dd, 1H), 4.20-4.34 (m, 1H), 4.44-4.55 (m [AB], 2H), 5.32-5.41 (m, 1H), 6.92 (d, 1H), 7.50 (t, 1H), 7.60-7.65 (m, 2H), 7.67-7.78 (m, 5H), 8.86 (d, 1H).

Example 156

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(methylsulphanyl)-1-[2-(trifluoromethyl)phenyl]ethyl}acetamide (diastereomer II)

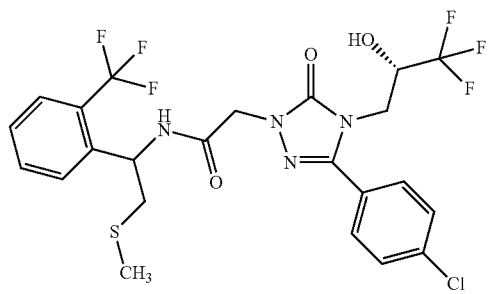 [SMILES: CSCC(NC(=O)Cn1nc(-c2ccc(Cl)cc2)n(C[C@H](O)C(F)(F)F)c1=O)c1ccccc1C(F)(F)F]

Last-eluting diastereomer from the chromatographic diastereomer separation of 360 mg of the compound from Example 154 by Method 29. The resulting product (157 mg) was further purified by preparative HPLC [Method 20]. Drying in an HV gave 108 mg of the title compound.

Chiral analytical HPLC [Method 30]: R$_t$=5.97 min

LC-MS [Method 31] R$_t$=2.54 min; MS [ESIpos]: m/z=583 (M+H)$^+$ $^1$H-NMR (400 MHz, DMSO-d$_6$): δ=2.06 (s, 3H), 2.73-2.84 (m, 2H), 3.82 (dd, 1H), 3.96 (dd, 1H), 4.20-4.32 (m, 1H), 4.43-4.56 (m [AB], 2H), 5.36 (q, 1H), 6.90 (d, 1H), 7.51 (t, 1H), 7.59-7.65 (m, 2H), 7.68-7.78 (m, 5H), 8.87 (d, 1H).

Example 157

2-{3-(4-Chlorophenyl)-5-oxo-4-[(2S)-3,3,3-trifluoro-2-hydroxypropyl]-4,5-dihydro-1H-1,2,4-triazol-1-yl}-N-{1-[3-(difluoromethyl)phenyl]-2-hydroxyethyl}acetamide (diastereomer mixture)

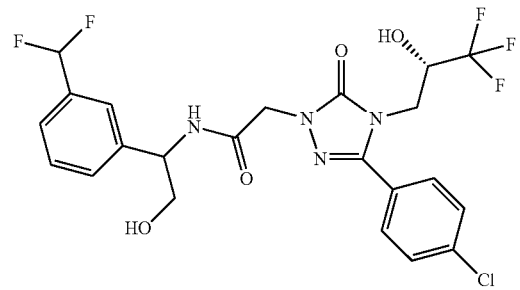 [SMILES: O=C(Cn1nc(-c2ccc(Cl)cc2)n(C[C@H](O)C(F)(F)F)c1=O)NC(CO)c1cccc(C(F)F)c1]

Of the compound from Example 8A, 53 mg (0.14 mmol), 39 mg (0.17 mmol) of the compound from Example 155A, 33 mg (0.17 mmol) of EDC, 24 mg (0.17 mmol) of HOBt and 30 μl (0.17 mmol) of N,N-diisopropylethylamine were stirred in 1.7 ml of DMF at RT overnight. On account of the partial esterification of the product with reactant 8A, 0.5 ml of 1N aqueous lithium hydroxide solution was added, and the mixture was stirred for 1 h. It was subsequently acidified with 1N hydrochloric acid and the entire solution was purified by preparative HPLC [Method 20]. The product fraction was freed from the solvents on a rotary evaporator and the residue was dried in an HV. This gave 362 mg (73% of theory) of the title compound.

LC-MS [Method 5] $R_t$=1.01 min; MS [ESIpos]: m/z=535 (M+H)$^+$ $^1$H NMR (400 MHz, DMSO-d$_6$): δ=3.61 (t, 2H), 3.83 (dd, 1H), 3.96 (dd, 1H), 4.21-4.33 (m, 1H), 4.47-4.59 (m, 2H), 4.86-4.95 (m, 1H), 4.98 (t, 1H), 6.89 (t, 1H interpreted as 1d per diastereomer), 7.00 (dt, J=3Hz, 56 Hz, 1H), 7.42-7.55 (m, 4H), 7.59-7.66 (m, 2H), 7.74 (dd, 2H, interpreted as 1d per diastereomer), 8.66 (dd, 1H, interpreted as 1d per diastereomer).

Example 158

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-[3-(trifluoromethyl)phenyl]propyl sulphamate (diastereomer mixture)

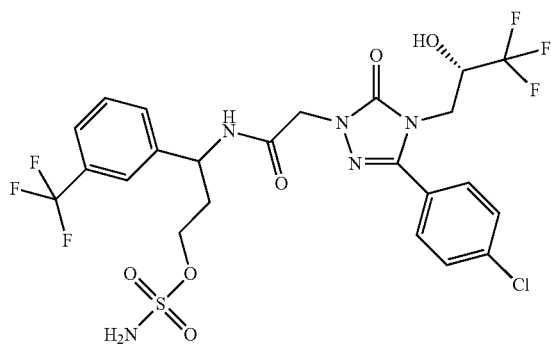 [SMILES: NS(=O)(=O)OCCC(NC(=O)Cn1nc(-c2ccc(Cl)cc2)n(C[C@H](O)C(F)(F)F)c1=O)c1cccc(C(F)(F)F)c1]

A solution of 27 mg (48 μmol) of the compound from Example 66 in 0.5 ml of dry DMF and 100 μl of triethylamine was admixed slowly dropwise with a solution of 83 mg of sulphamyl chloride in 2 ml of DMF. When a reaction check showed only 20% conversion, a further 200 mg of sulphamyl chloride in solid form were added. After 10 min, 2 ml of 1N hydrochloric acid were added and the entire reaction mixture was purified by preparative HPLC [Method 10]. The product fraction was freed from the volatile components on a rotary evaporator and the residue was dried in an HV. This gave 12 mg (36% of theory) of the title compound in approximately 92% purity.

LC-MS [Method 3] $R_t$=1.25 and 1.26 min; MS [ESIpos]: m/z=646 (M+H)$^+$ $^1$H NMR (400 MHz, DMSO-d$_6$): δ=2.12 (q, 2H), 3.82 (dd, 1H), 3.92-4.04 (m, 2H), 4.04-4.13 (m, 1H), 4.22-4.32 (m, 1H), 4.44-4.59 (m, 2H), 4.98-5.07 (m, 1H), 6.91 (t, 1H interpreted as 1d per diastereomer), 7.48 (s, 2H), 7.56-7.78 (m, 9H), 8.84 (dd, 1H, interpreted as 1d per diastereomer).

Example 159

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-[3-(trifluoromethyl)phenyl]ethyl sulphamate (diastereomer mixture)

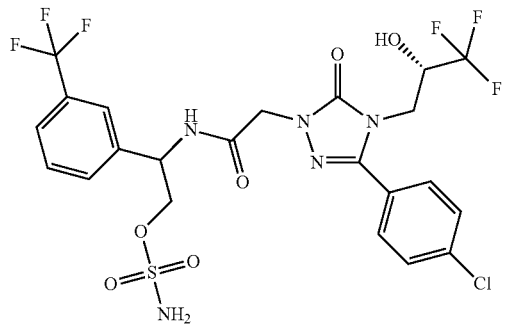 [SMILES: NS(=O)(=O)OCC(NC(=O)Cn1nc(-c2ccc(Cl)cc2)n(C[C@H](O)C(F)(F)F)c1=O)c1cccc(C(F)(F)F)c1]

Of the compound from Example 8A, 187 mg (0.51 mmol), 200 mg (approximately 90% pure, 0.56 mmol) of the compound from Example 157A, 117 mg (0.61 mmol) of EDC, 83 mg (0.61 mmol) of HOBt and 107 μl (0.61 mmol) of N,N-diisopropylethylamine were stirred in 5.9 ml of DMF at RT for 1 h. The solution was subsequently acidified with 1N hydrochloric acid and the entire solution was purified by preparative HPLC [Method 10]. The product fraction was freed from the solvents on a rotary evaporator and the residue was dried in an HV. This gave 215 mg (60% of theory) of the title compound in approximately 90% purity.

LC-MS [Method 3] $R_t$=1.26 and 1.27 min; MS [ESIpos]: m/z=632 (M+H)$^+$ $^1$H NMR (400 MHz, DMSO-d$_6$): δ=3.83 (dd, 1H), 3.97 (br d, 1H), 4.18-4.34 (m, 3H), 4.51-4.63 (m, 2H), 5.28-5.35 (m, 1H), 6.91 (t (interpreted as 1d per diastereomer, 1H), 7.53-7.83 (m, 10H), 8.95+8.97 (1d per diastereomer, 1H).

Example 160

N-[2-(Carbamoylamino)-1-(2,3-dichlorophenyl)ethyl]-2-{3-(4-chlorophenyl)-5-oxo-4-[(1E)-3,3,3-trifluoroprop-1-en-1-yl]-4,5-dihydro-1H-1,2,4-triazol-1-yl}acetamide (enantiomerically pure)

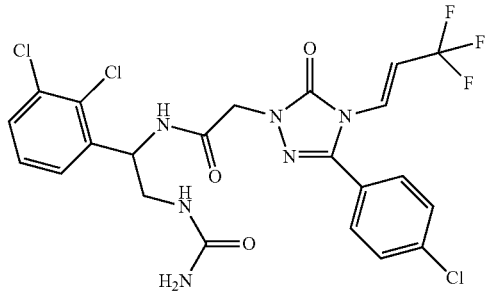 [SMILES: NC(=O)NCC(NC(=O)Cn1nc(-c2ccc(Cl)cc2)n(/C=C/C(F)(F)F)c1=O)c1cccc(Cl)c1Cl]

In the same way as for Example 146, from 110 mg (185 μmol) of the compound from Example 62, the title compound was obtained (22 mg, 21% of theory).

LC-MS [Method 3] $R_t$=1.28 min; MS [ESIpos]: m/z=577 (M+H)$^+$ $^1$H-NMR (400 MHz, DMSO-d$_6$): δ=3.19-3.38 (m, 2H), 4.45-4.60 (m, 2H), 5.14-5.23 (m, 1H), 5.54 (s, 2H), 6.14 (t, 1H), 6.85 (dq, 1H), 7.19 (dq, 1H), 7.33-7.42 (m, 2H), 7.55 (dd, 1H), 7.63-7.71 (m, 4H), 8.99 (d, 1H).

Example 161

N-{2-(Carbamoylamino)-1-[3-(trifluoromethyl)phenyl]ethyl}-2-{3-(4-chlorophenyl)-5-oxo-4-[(1E)-3,3,3-trifluoroprop-1-en-1-yl]-4,5-dihydro-1H-1,2,4-triazol-1-yl}acetamide (enantiomerically pure)

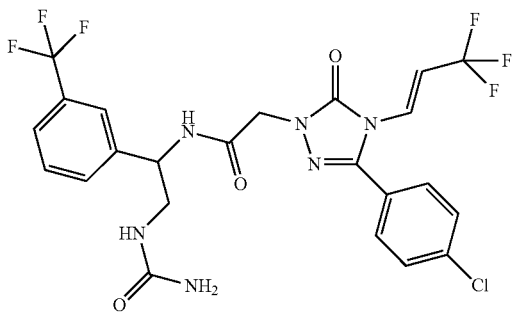 [SMILES: NC(=O)NCC(NC(=O)Cn1nc(-c2ccc(Cl)cc2)n(/C=C/C(F)(F)F)c1=O)c1cccc(C(F)(F)F)c1]

In the same way as for Example 146, from 87 mg (146 µmol) of the compound from Example 57, the title compound was obtained (15 mg, 18% of theory).

LC-MS [Method 4] R$_t$=1.09 min; MS [ESIpos]: m/z=577 (M+H)$^+$ $^1$H-NMR (400 MHz, DMSO-d$_6$): δ=3.18-3.40 (m, 2H), 4.46-4.60 (m, 2H), 4.89-4.97 (m, 1H), 5.55 (s, 2H), 6.05 (t, 1H), 6.86 (dq, 1H), 7.19 (dq, 1H), 7.54-7.69 (m, 8H), 8.86 (d, 1H).

Example 162

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-(sulphamoylamino)-1-[3-(trifluoromethyl)phenyl]ethyl}acetamide (diastereomer mixture)

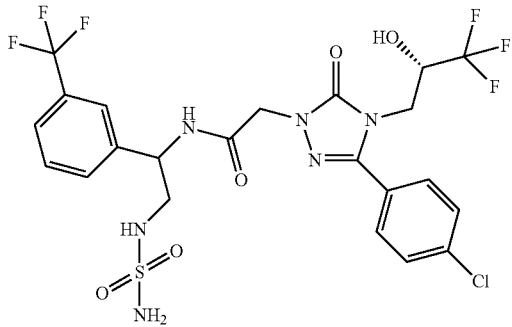 [SMILES: NS(=O)(=O)NCC(NC(=O)Cn1nc(-c2ccc(Cl)cc2)n(C[C@H](O)C(F)(F)F)c1=O)c1cccc(C(F)(F)F)c1]

Of the compound from Example 8A, 62.2 mg (0.17 mmol), 53 mg (0.19 mmol) of the compound from Example 134A, 39 mg (0.20 mmol) of EDC and 20 mg (0.20 mmol) of HOBt were stirred in 2 ml of DMF at RT overnight. Subsequently 1 ml of 1N hydrochloric acid was added and the entire solution was purified by preparative HPLC [Method 20]. The product fraction was freed from the solvents on a rotary evaporator and the residue was dried in an HV. This gave 84 mg of the title compound (78% of theory).

LC-MS [Method 5] R$_t$=1.03 min; MS [ESIpos]: m/z=631 (M+H)$^+$ $^1$H-NMR (400 MHz, DMSO-d$_6$): δ=3.20 (br. t, 1H), 3.82 (dd, 1H), 3.96 (dt, interpreted as 1 dd per diastereomer, 1H), 4.21-4.34 (m., 1H), 4.45-4.62 (m, 2H), 5.05-5.14 (m, 1H,) 6.61-6.65 (m, 2H), 6.70-6.78 (m, 1H), 6.91 (dd, interpreted as 1d per diastereomer, 2H), 7.56-7.64 (m, 5H), 7.70 (br.s, 1H), 7.74-7.78 (m, 2H), 8.62-8.70 (t, 1H, interpreted as 1d per diastereomer).

Example 163

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}-N-methylacetamide (diastereomer mixture)

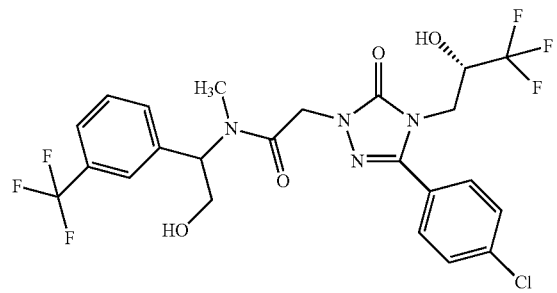 [SMILES: CN(C(=O)Cn1nc(-c2ccc(Cl)cc2)n(C[C@H](O)C(F)(F)F)c1=O)C(CO)c1cccc(C(F)(F)F)c1]

Of the compound from Example 8A, 1.87 g (5.12 mmol), 1.18 mg (6.14 mmol) of EDC and 874 mg (6.14 mmol) of HOBt were stirred in 100 ml of DMF for 5 min. The resulting solution was added dropwise to a solution of 1.44 g (5.63 mmol) of the compound from Example 156A and 892 µl (5.12 mmol) of N,N-diisopropylethylamine in 50 ml of DMF. The entire mixture was left with stirring at RT for 1 h, then admixed with 100 ml of 1N hydrochloric acid. Extraction was carried out with 500 ml of ethyl acetate. The organic phase was washed four times with water and once with saturated aqueous sodium chloride solution, then dried over sodium sulphate and freed from the volatile constituents on a rotary evaporator. The residue was purified by preparative chromatography (Method 20 and then again by Method 32). The product fraction was freed from the solvents on a rotary evaporator and the residue was dried in an HV. This gave 637 mg (22% of theory) of the title compound as a diastereomer mixture.

LC-MS [Method 4] R$_t$=1.08 min; MS [ESIpos]: m/z=567 (M+H)$^+$

The two diastereomers were separated by preparative HPLC on a chiral phase [Method 26d]: see Example 164 and Example 165.

Example 164

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}-N-methylacetamide (diastereomer I)

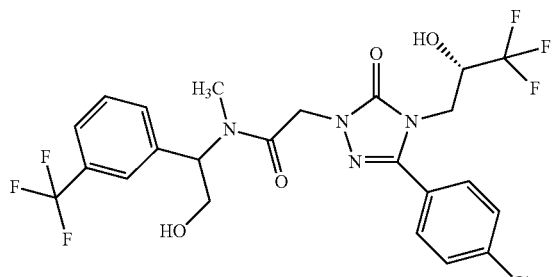

First-eluting diastereomer from the chromatographic diastereomer separation of 200 mg of the compound from Example 163 by Method 26d. The product obtained (93 mg) was further purified by preparative HPLC [Method 20]. Drying in an HV gave 80 mg of the title compound.

Chiral analytical HPLC [Method 27b]: $R_t$=4.82 min
LC-MS [Method 4] $R_t$=1.08 min; MS [ESIpos]: m/z=567 (M+H)$^+$ NMR shows two rotamers, A and B, in a ratio of about 2:1:
$^1$H NMR (400 MHz, DMSO-d$_6$): δ=2.64 (s, 3H$_B$), 2.94 (s, 3H$_A$), 3.77-4.04 (m, 4H), 4.21-4.33 (m, 1H), 4.78 (d, 1H$_A$), 4.90 (d, 1H$_B$), 4.91 (d, 1H$_A$), 5.00 (d, 1H$_B$), 5.05 (t, 1H$_A$), 5.18-5.25 (m, 1H$_B$), 5.28-5.33 (m, 1H$_B$), 5.57 (t, 1H$_A$), 6.89 (d, 1H$_A$), 6.92 (d, 1H$_B$), 7.55-7.72 (m, 6H), 7.76 (d, 2H).

Example 165

2-{3-(4-Chlorophenyl)-5-oxo-4-[(2S)-3,3,3-trifluoro-2-hydroxypropyl]-4,5-dihydro-1H-1,2,4-triazol-1-yl}-N-{2-hydroxy-1-[3-(trifluoromethyl)phenyl]ethyl}-N-methylacetamide (diastereomer II)

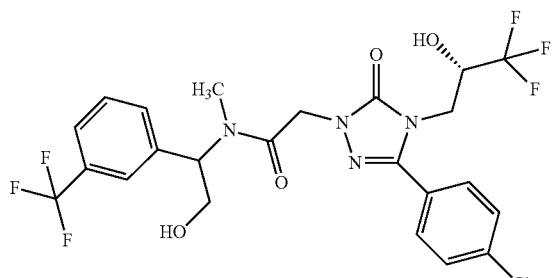

Last-eluting diastereomer from the chromatographic diastereomer separation of 200 mg of the compound from Example 163 by Method 26d. The product obtained (96 mg) was further purified by preparative HPLC [Method 20]. Drying in an HV gave 63 mg of the title compound.

Chiral analytical HPLC [Method 27b]: $R_t$=6.60 min
LC-MS [Method 4] $R_t$=2.54 min; MS [ESIpos]: m/z=567 (M+H)$^+$ NMR (in D$_6$-DMSO) shows two rotamers, A and B, in a ratio of about 2:1:
$^1$H NMR (400 MHz, DMSO-d$_6$): δ=2.63 (s, 3H$_B$), 2.94 (s, 3H$_A$), 3.81-4.03 (m, 4H), 4.21-4.33 (m, 1H), 4.78 (d, 1H$_A$), 4.91 (d, 1H$_A$), 4.90-5.03 (m [AB], 2H$_B$), 5.05 (t, 1H$_A$), 5.21 (t, 1H$_B$), 5.31 (t, 1H$_B$), 5.57 (t, 1H$_A$), 6.89 (d, 1H$_b$), 6.91 (d, 1H$_A$), 7.55-7.73 (m, 6H), 7.758 (d, 2H$_B$), 7.764 (d, 2H$_A$).

Example 166

N-[1-(3-Chloro-2-fluorophenyl)-2-hydroxyethyl]-2-{3-(4-chlorophenyl)-5-oxo-4-[(2S)-3,3,3-trifluoro-2-hydroxypropyl]-4,5-dihydro-1H-1,2,4-triazol-1-yl}acetamide (diastereomer mixture)

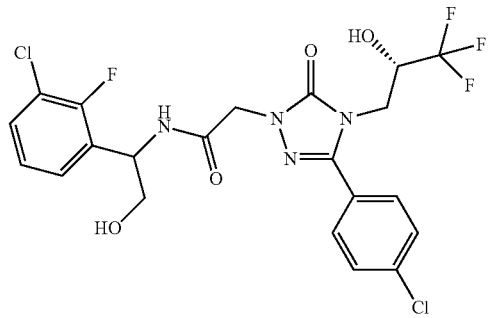 [SMILES: O=C(Cn1nc(-c2ccc(Cl)cc2)n(C[C@H](O)C(F)(F)F)c1=O)NC(CO)c1cccc(Cl)c1F]

Of the compound from Example 8A, 150 mg (0.39 mmol) were dissolved in 1 ml of DMF, admixed with 87 mg (0.51 mmol) of EDC and with 68 mg (0.51 mmol) of HOBt and stirred subsequently at room temperature for 20 minutes. Then 115 mg (0.43 mmol) of the compound from Example 161A and also 60 μl (0.43 mmol) of triethylamine were added and the mixture was left with stirring at room temperature for 16 h. For work-up, 100 μl of 1N hydrochloric acid were added and the crude product was purified directly by preparative HPLC [Method 19]. This gave 171 mg (82% of theory) of the target compound as a diastereomer mixture.

LC-MS [Method 3] $R_t$=1.18 and 1.19 min; MS [ESIpos]: m/z=537 (M+H)$^+$ $^1$H-NMR (400 MHz, CDCl$_3$): δ=3.24 and 3.48 (2m, 1H), 3.58-3.68 (m, 1H), 3.73-3.81 (2m, 1H), 3.83-4.16 (m, 3H), 4.47-4.77 (m, 3H), 5.28 and 5.62 (2d, 1H), 5.27-5.37 (m, 1H), 6.98 and 7.56 (2d, 1H), 7.01-7.10 (m, 1H), 7.12-7.22 (m, 1H), 7.29-7.37 (m, 1H), 7.46 and 7.49 (2d, 2H), 7.62 and 7.68 (2d, 2H). (Partial resolution of the two-fold set of signals of the diastereomer mixture).

The following compounds were obtained analogously:

| Example No. | Structure | Reactant; Yield [% of theory] | $^1$H-NMR (400 MHz) LC/MS: $R_t$ [Method] |
|---|---|---|---|
| 167 | | 8A; 162A 76% | (CDCl$_3$): δ = 3.93-4.19 (m, 3H), 4.36-4.84 (m, 4H), 4.84-5.00 (m, 2H), 5.36-5.48 (m, 1H), 5.74 and 6.04 (d, 1H), 7.06 and 7.61 (d, 1H), 7.08-7.24 (m, 2H), 7.30-7.40 (m, 1H), 7.53 (d, 2H), 7.70-7.79 (m, 2H). $R_t$ = 1.04 min; MS [ESIpos]: m/z = 580 (M + H)$^+$ [5] |
| 168 | 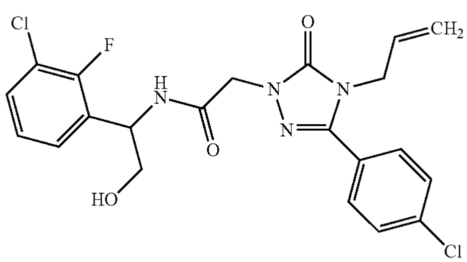 [SMILES: C=CCn1c(-c2ccc(Cl)cc2)nn(CC(=O)NC(CO)c2cccc(Cl)c2F)c1=O] | WO2007/134862 Example 218A; 161A 48% | (DMSO-d$_6$): δ = 3.60 (t, 2H), 4.33-4.40 (m, 2H), 4.48-4.58 (m, 2H), 4.95 (dd, 1H), 5.07-5.17 (m, 3H), 5.78-5.91 (m, 1H), 7.18-7.25 (m, 1H), 7.35-7.41 (m, 1H), 7.45-7.52 (m, 1H), 7.55-7.68 (m, 4H), 8.74 (d, 1H). $R_t$ = 1.00 min; MS [ESIpos]: m/z = 467 (M + H)$^+$ [4] |
| 169 | 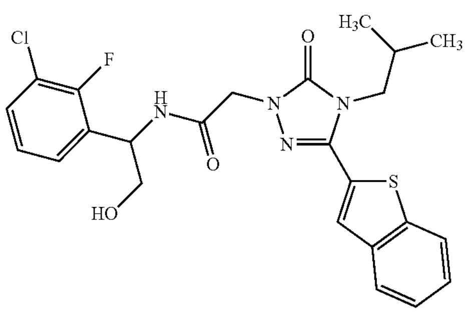 [SMILES: CC(C)Cn1c(-c2cc3ccccc3s2)nn(CC(=O)NC(CO)c2cccc(Cl)c2F)c1=O] | WO2007/134862 Example 102A; 161A 69% | (DMSO-d$_6$): δ = 0.85 (d, 6H), 1.96 (spt, 1H), 3.60 (t, 2H), 3.80 (d, 2H), 4.49-4.61 (m, 2H), 5.07-5.18 (m, 2H), 7.23 (t, 1H), 7.36-7.53 (m, 4H), 7.94-8.06 (m, 3H), 8.75 (d, 1H). $R_t$ = 1.13 min; MS [ESIpos]: m/z = 503 (M + H)+ [5] |
| 170 | 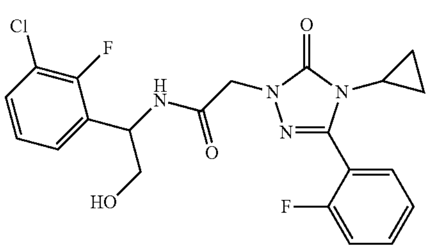 [SMILES: O=C(Cn1nc(-c2ccccc2F)n(C2CC2)c1=O)NC(CO)c1cccc(Cl)c1F] | WO2007/134862 Example 92A; 161A 53% | (DMSO-d$_6$): δ = 0.47-0.53 (m, 2H), 0.70-0.77 (m, 2H), 2.88-2.96 (m, 1H), 3.59 (t, 2H), 4.42-4.52 (m, 2H), 5.05-5.15 (m, 2H), 7.19 (t, 1H), 7.33-7.51 (m, 4H), 7.54-7.67 (m, 2H), 8.69 (d, 1H). $R_t$ = 1.03 min; MS [ESIpos]: m/z = 449 (M + H)$^+$ [3] |
| 171 | 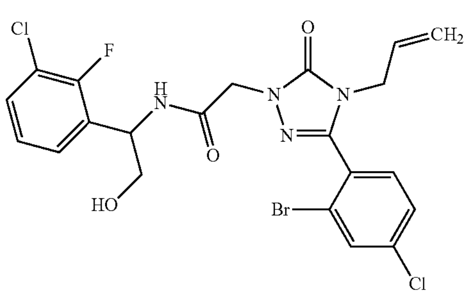 | 166A; 161A 13% | (DMSO-d$_6$): δ = 3.59 (t, 2H), 4.06-4.12 (m, 2H), 4.49-4.58 (m, 2H), 4.86 (d, 1H), 5.01 (d, 1H), 5.08-5.17 (m, 2H), 5.60-5.71 (m, 1H), 7.21 (t, 1H), 7.34-7.41 (m, 1H), 7.45-7.53 (m, 2H), 7.62 (dd, 1H), 7.99 (d, 1H), 8.70 (d, 1H). $R_t$ = 1.05 min; MS [ESIpos]: m/z = 543 (M + H)$^+$ [4] |

| Example No. | Structure | Reactant; Yield [% of theory] | ¹H-NMR (400 MHz) LC/MS: $R_t$ [Method] |
|---|---|---|---|
| 172 | 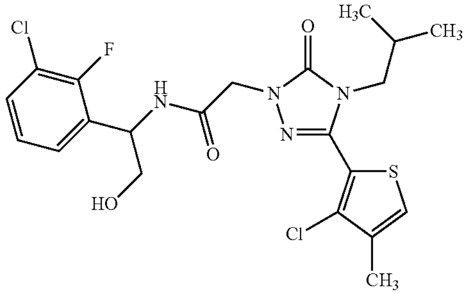 [SMILES: Cc1csc(-c2nn(CC(=O)NC(CO)c3cccc(Cl)c3F)c(=O)n2CC(C)C)c1Cl] | WO2007/134862 Example 249A; 161A 53% | (DMSO-$d_6$): δ = 0.71 (d, 6H), 1.77 (spt, 1H), 2.22 (s, 3H), 3.37-3.48 (m, 2H), 3.59 (t, 2H), 4.48-4.58 (m, 2H), 5.07-5.15 (m, 2H), 7.21 (t, 1H), 7.33-7.40 (m, 1H), 7.45-7.52 (m, 1H), 7.70 (d, 1H), 8.73 (d, 1H). $R_t$ = 2.26 min; MS [ESIpos]: m/z = 503 and 505 (M + H)⁺ [2] |
| 173 | 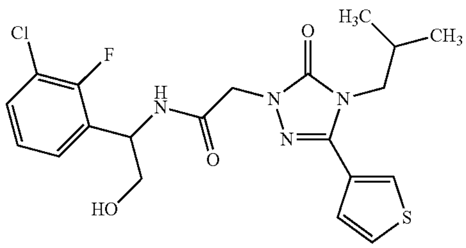 [SMILES: CC(C)Cn1c(-c2ccsc2)nn(CC(=O)NC(CO)c2cccc(Cl)c2F)c1=O] | WO2007/134862 Example 101A; 161A 55% | (DMSO-$d_6$): δ = 0.76 (d, 6H), 1.78 (spt, 1H), 3.59 (t, 2H), 3.66 (d, 2H), 4.43-4.54 (m, 2H), 5.06-5.16 (m, 2H), 7.21 (t, 1H), 7.35-7.40 (m, 1H), 7.42 (dd, 1H), 7.45-7.51 (m, 1H), 7.72 (dd, 1H), 8.02 (dd, 1H), 8.69 (d, 1H). $R_t$ = 1.11 min; MS [ESIpos]: m/z = 453 (M + H)⁺ [3] |
| 174 | 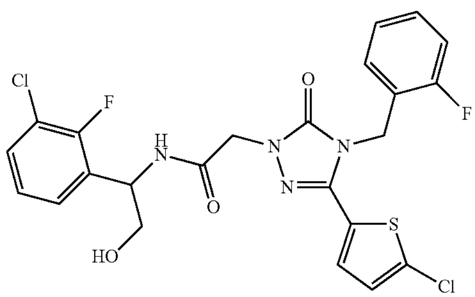 [SMILES: O=C(Cn1nc(-c2ccc(Cl)s2)n(Cc2ccccc2F)c1=O)NC(CO)c1cccc(Cl)c1F] | WO2007/134862 Example 154A; 161A 65% | (DMSO-$d_6$): δ = 3.56-3.64 (m, 2H), 4.51-4.61 (m, 2H), 5.08-5.18 (m, 4H), 7.00-7.06 (m, 1H), 7.12-7.26 (m, 5H), 7.31-7.42 (m, 2H), 7.46-7.52 (m, 1H), 8.78 (d, 1H). $R_t$ = 1.10 min; MS [ESIpos]: m/z = 538 and 540 (M + H)⁺ [4] |
| 175 | 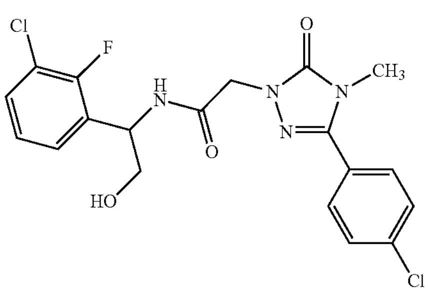 [SMILES: Cn1c(-c2ccc(Cl)cc2)nn(CC(=O)NC(CO)c2cccc(Cl)c2F)c1=O] | WO2007/134862 Example 97A; 161A 37% | (DMSO-$d_6$): δ = 3.30 (s, 3H), 3.60 (t, 2H), 4.50 (s, 2H), 5.06-5.17 (m, 2H), 7.21 (t, 1H), 7.35-7.41 (m, 1H), 7.45-7.52 (m, 1H), 7.57-7.64 (m, 2H), 7.71 (d, 2H), 8.71 (d, 1H). $R_t$ = 1.99 min; MS [ESIpos]: m/z = 439 and 441 (M + H)⁺ [2] |
| 176 | | 170A; 161A 76% | (DMSO-$d_6$): δ = 3.19 (s, 3H), 3.54 (t, 2H), 3.59 (t, 2H), 3.96 (t, 2H), 4.44-4.54 (m, 2H), 5.08-5.15 (m, 2H), 7.22 (t, 1H), 7.26 (d, 1H), 7.33-7.41 (m, 1H), 7.45-7.52 (m, 1H), 7.56 (d, 1H), 8.74 (d, 1H). $R_t$ = 2.08 min; MS [ESIpos]: m/z = 489 and 491 (M + H)⁺ [2] |

-continued

| Example No. | Structure | Reactant; Yield [% of theory] | ¹H-NMR (400 MHz) LC/MS: $R_t$ [Method] |
|---|---|---|---|
| 177 | 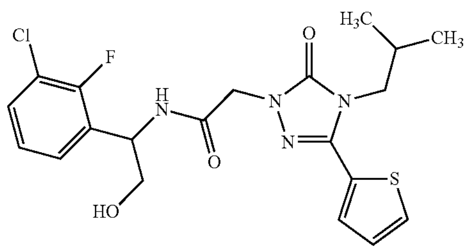 [SMILES: CC(C)Cn1c(-c2cccs2)nn(CC(=O)NC(CO)c2cccc(Cl)c2F)c1=O] | WO2007/134862 Example 99A; 161A 50% | (DMSO-$d_6$): δ = 0.81 (d, 6H), 1.87 (spt, 1H), 3.59 (t, 2H), 3.68 (d, 2H), 4.44-4.55 (m, 2H), 5.05-5.16 (m, 2H), 7.18-7.26 (m, 2H), 7.34-7.42 (m, 1H), 7.44-7.51 (m, 1H), 7.57 (d, 1H), 7.77 (d, 1H), 8.71 (d, 1H). $R_t$ = 0.99 min; MS [ESIpos]: m/z = 453 (M + H)⁺ [5] |
| 178 | 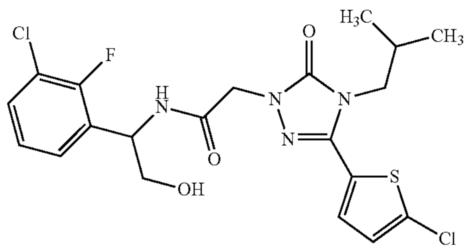 [SMILES: CC(C)Cn1c(-c2ccc(Cl)s2)nn(CC(=O)NC(CO)c2cccc(Cl)c2F)c1=O] | WO2007/134862 Example 100A; 161A 67% | (DMSO-$d_6$): δ = 0.81 (d, 6H), 1.87 (spt, 1H), 3.59 (t, 2H), 3.67 (d, 2H), 4.44-4.55 (m, 2H), 5.07-5.16 (m, 2H), 7.18-7.24 (m, 1H), 7.26 (d, 1H), 7.34-7.41 (m, 1H), 7.44-7.53 (m, 2H), 8.73 (d, 1H). $R_t$ = 1.08 min; MS [ESIpos]: m/z = 487 and 489 (M + H)⁺ [4] |
| 179 | 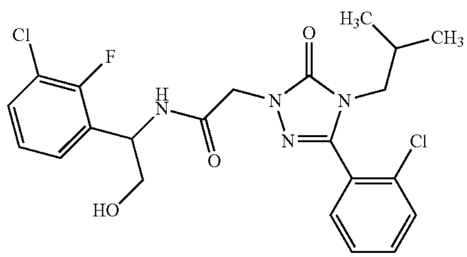 [SMILES: CC(C)Cn1c(-c2ccccc2Cl)nn(CC(=O)NC(CO)c2cccc(Cl)c2F)c1=O] | WO2007/134862 Example 89A; 161A 62% | (DMSO-$d_6$): δ = 0.66 (d, 6H), 1.66 (spt, 1H), 3.29 (d, 1H), 3.59 (t, 2H), 4.47-4.57 (m, 2H), 5.07-5.16 (m, 2H), 7.17-7.23 (m, 1H), 7.34-7.40 (m, 1H), 7.44-7.57 (m, 3H), 7.58-7.65 (m, 1H), 7.65-7.70 (m, 1H), 8.69 (d, 1H). $R_t$ = 1.04 min; MS [ESIpos]: m/z = 481 and 483 (M + H)⁺ [5] |
| 180 | 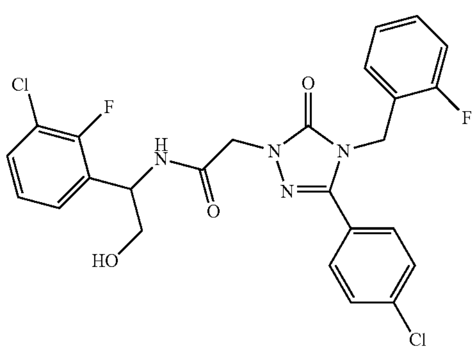 [SMILES: O=C(Cn1nc(-c2ccc(Cl)cc2)n(Cc2ccccc2F)c1=O)NC(CO)c1cccc(Cl)c1F] | WO2007/134862 Example 156A; 161A 63% | (DMSO-$d_6$): δ = 3.60 (t, 2H), 4.51-4.62 (m, 2H), 5.02 (s, 2H), 5.09-5.19 (m, 2H), 7.01-7.25 (m, 5H), 7.26-7.34 (m, 1H), 7.36-7.43 (m, 1H), 7.46-7.55 (m, 4H), 8.77 (d, 1H). $R_t$ = 1.09 min; MS [ESIpos]: m/z = 533 and 535 (M + H)⁺ [4] |
| 181 | | WO2007/134862 Example 220A; 161A 62% | (DMSO-$d_6$): δ = 0.62 (s, 9H), 3.59 (t, 2H), 3.67 (s, 2H), 4.47-4.57 (m, 2H), 5.08-5.16 (m, 2H), 7.20 (t, 1H), 7.34-7.40 (m, 1H), 7.45-7.51 (m, 1H), 7.58 (d, 2H), 7.65 (d, 2H), 8.71 (d, 1H). $R_t$ = 1.11 min; MS [ESIpos]: m/z = 495 (M + H)⁺ [4] |

| Example No. | Structure | Reactant; Yield [% of theory] | ¹H-NMR (400 MHz) LC/MS: R, [Method] |
|---|---|---|---|
| 182 | 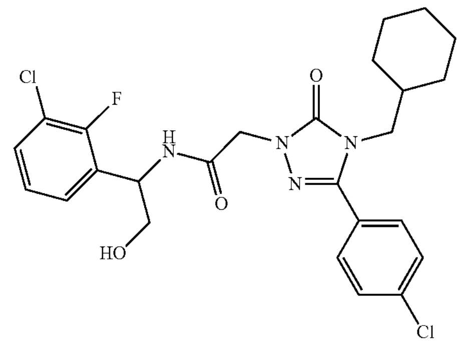 [SMILES: O=C(Cn1nc(-c2ccc(Cl)cc2)n(CC2CCCCC2)c1=O)NC(CO)c1cccc(Cl)c1F] | WO2007/134862 Example 91A, 161A 71% | (DMSO-d₆): δ = 0.66-0.80 (m, 2H), 0.91-1.09 (m, 3H), 1.33-1.61 (m, 6H), 3.55-3.66 (m, 4H), 4.45-4.56 (m, 2H), 5.07-5.16 (m, 2H), 7.20 (t, 1H), 7.34-7.40 (m, 1H), 7.44-7.52 (m, 1H), 7.60 (d, 2H), 7.66 (d, 2H), 8.72 (d, 1H). R, = 1.36 min; MS [ESIpos]: m/z = 521 and 523 (M + H)⁺ [3] |
| 183 | 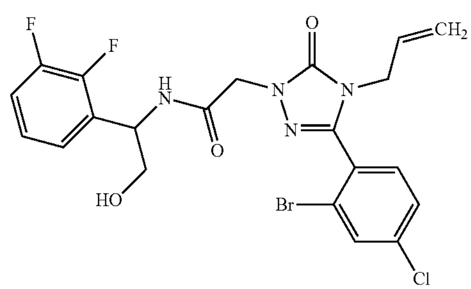 [SMILES: C=CCn1c(-c2ccc(Cl)cc2Br)nn(CC(=O)NC(CO)c2cccc(F)c2F)c1=O] | 166A; 92A 48% | (DMSO-d₆): δ = 3.60 (t, 2H), 4.10 (d, 2H), 4.48-4.59 (m, 2H), 4.86 (d, 1H), 5.01 (d, 1H), 5.07-5.19 (m, 2H), 5.60-5.71 (m, 1H), 7.13-7.26 (m, 2H), 7.32 (q, 1H), 7.50 (d, 1H), 7.62 (dd, 1H), 7.98 (d, 1H), 8.67 (d, 1H). R, = 1.16 min; MS [ESIpos]: m/z = 529 (M + H)⁺ [3] |
| 184 | 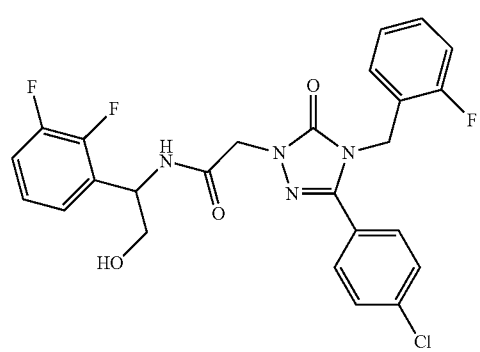 [SMILES: O=C(Cn1nc(-c2ccc(Cl)cc2)n(Cc2ccccc2F)c1=O)NC(CO)c1cccc(F)c1F] | WO2007/134862 Example 156A; 92A 70% | (DMSO-d₆): δ = 3.60 (t, 2H), 4.51-4.61 (m, 2H), 5.02 (s, 2H), 5.10 (t, 1H), 5.13-5.19 (m, 1H), 7.01-7.26 (m, 5H), 7.27-7.37 (m, 2H), 7.52 (s, 4H), 8.74 (d, 1H). R, = 1.21 min; MS [ESIpos]: m/z = 517 (M + H)⁺ [3] |
| 185 | 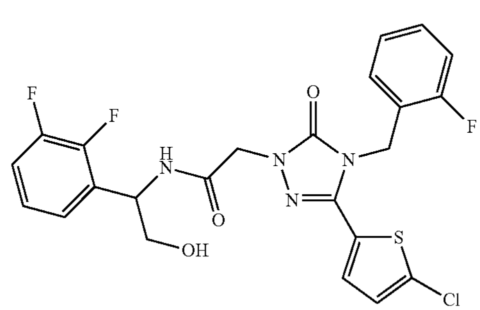 [SMILES: O=C(Cn1nc(-c2ccc(Cl)s2)n(Cc2ccccc2F)c1=O)NC(CO)c1cccc(F)c1F] | WO2007/134862 Example 154A; 92A 70% | (DMSO-d₆): δ = 3.60 (t, 2H), 4.51-4.61 (m, 2H), 5.08-5.20 (m, 4H), 7.04 (t, 1H), 7.12-7.27 (m, 6H), 7.28-7.39 (m, 2H), 8.75 (d, 1H). R, = 1.22 min; MS [ESIpos]: m/z = 523 (M + H)⁺ [3] |

-continued

| Example No. | Structure | Reactant; Yield [% of theory] | $^1$H-NMR (400 MHz) LC/MS: $R_t$ [Method] |
|---|---|---|---|
| 186 | ![structure] | WO2007/134862 Example 218A, 92A 70% | (DMSO-$d_6$): δ = 3.60 (t, 2H), 4.34-4.39 (m, 2H), 4.48-4.58 (m, 2H), 4.95 (d, 1H), 5.06-5.19 (m, 3H), 5.79-5.91 (m, 1H), 7.15-7.26 (m, 2H), 7.28-7.36 (m, 1H), 7.55-7.68 (m, 4H), 8.71 (d, 1H). $R_t$ = 0.96 min; MS [ESIpos]: m/z = 449 (M + H)$^+$ [4] |

Example 187

2-{3-(4-Chlorophenyl)-5-oxo-4-[(2S)-3,3,3-trifluoro-2-hydroxypropyl]-4,5-dihydro-1H-1,2,4-triazol-1-yl}-N-[3-hydroxy-1-(2-methoxyphenyl)propyl]acetamide (diastereomer mixture)

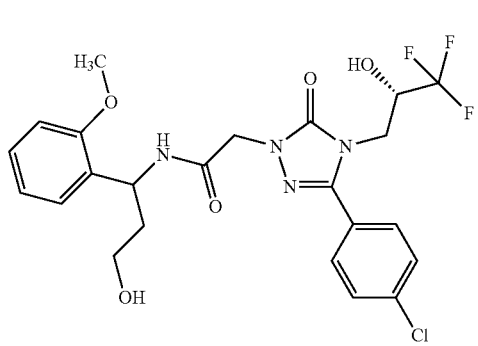 [SMILES: COc1ccccc1C(CCO)NC(=O)Cn1nc(-c2ccc(Cl)cc2)n(C[C@H](O)C(F)(F)F)c1=O]

Of the compound from Example 8A, 134 mg (0.37 mmol) were dissolved in 1 ml of DMF, admixed with 106 mg (0.55 mmol) of EDC and with 74 mg (0.55 mmol) of HOBt and subsequently stirred at room temperature for 20 minutes. Then 88 mg (0.40 mmol) of the compound from Example 172A and 85 μl (0.51 mmol) of N,N-diisopropylethylamine were added and the mixture was left with stirring at room temperature for 16 h. For work-up, 100 μl of 1N hydrochloric acid were added and the crude product was purified directly by preparative HPLC [Method 19]. This gave 77 mg (40% of theory) of the target compound as a diastereomer mixture.

LC-MS [Method 4] $R_t$=0.99 min; MS [ESIpos]: m/z=529 (M+H)$^+$ $^1$H NMR (400 MHz, DMSO-$d_6$): δ=1.70-1.87 (m, 2H), 3.35-3.45 (m, 2H), 3.78 (s, 3H), 3.80-3.86 (m, 1H), 3.92-4.01 (m, 1H), 4.22-4.33 (m, 1H), 4.40-4.56 (m, 3H), 5.16-5.26 (m, 1H), 6.86-6.99 (m, 3H), 7.16-7.31 (m, 2H), 7.59-7.68 (m, 2H), 7.71-7.79 (m, 2H), 8.42 (d, 1H). (partial resolution of the two-fold set of signals of the diastereomer mixture).

Example 188

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2-methoxyphenyl)propyl carbamate (diastereomer mixture)

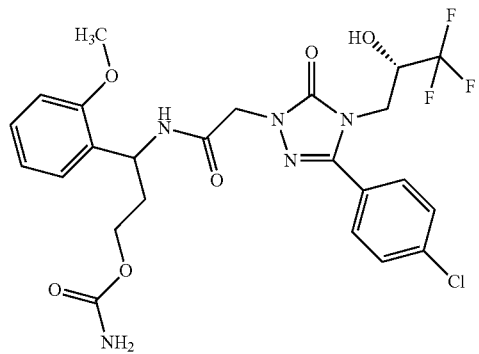 [SMILES: COc1ccccc1C(CCOC(N)=O)NC(=O)Cn1nc(-c2ccc(Cl)cc2)n(C[C@H](O)C(F)(F)F)c1=O]

Of the compound from Example 8A, 237 mg (0.65 mmol) were dissolved in 2 ml of DMF, admixed with 174 mg (0.91 mmol) of EDC and with 123 mg (0.91 mmol) of HOBt and subsequently stirred at room temperature for 20 minutes. Then 186 mg (0.71 mmol) of the compound from Example 174A and 129 μl (0.78 mmol) of N,N-diisopropylethylamine were added and the mixture was left with stirring at room temperature for 16 h. For work-up, 100 μl of 1N hydrochloric acid were added and the crude product was purified directly by preparative HPLC [Method 19]. This gave 123 mg (33% of theory) of the target compound as a diastereomer mixture.

LC-MS [Method 5] $R_t$=1.01 min; MS [ESIpos]: m/z=572 (M+H)$^+$ $^1$H NMR (400 MHz, DMSO-$d_6$): δ=1.71-1.99 (m, 2H), 3.78 (s, 3H), 3.80-4.00 (m, 4H), 4.22-4.34 (m, 1H), 4.40-4.60 (m, 2H), 5.14-5.31 (m, 1H), 6.46 (br. s., 2H), 6.85-7.01 (m, 3H), 7.16-7.33 (m, 2H), 7.59-7.67 (m, 2H), 7.69-7.80 (m, 2H), 8.38-8.54 (m, 1H). (partial resolution of the two-fold set of signals of the diastereomer mixture).

The diastereomer mixture was separated by preparative HPLC on chiral phase [Method 13a]: see Examples 189 and 190.

Example 189

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2-methoxyphenyl)propyl carbamate (diastereomer I)

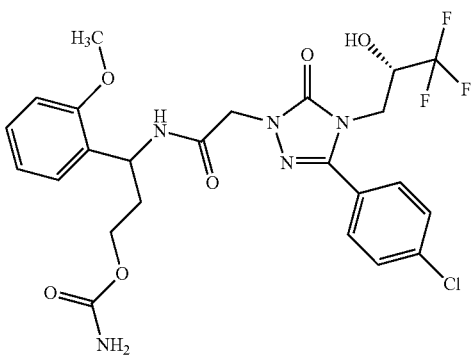 [SMILES: COc1ccccc1C(CCOC(N)=O)NC(=O)Cn1nc(-c2ccc(Cl)cc2)n(C[C@H](O)C(F)(F)F)c1=O]

First-eluting diastereomer from the separation from Example 188.
Yield: 33 mg (9% of theory)
Chiral analytical HPLC [Method 9]: $R_t$=3.46 min
LC-MS [Method 5] $R_t$=1.01 min; MS [ESIpos]: m/z=572 (M+H)$^+$
$^1$H NMR (400 MHz, DMSO-d$_6$): δ=1.81-2.00 (m, 2H), 3.79 (s, 3H), 3.81-4.07 (m, 4H), 4.22-4.35 (m, 1H), 4.44-4.56 (m, 2H), 5.17-5.29 (m, 1H), 6.47 (br. s., 2H), 6.87-7.01 (m, 3H), 7.19-7.33 (m, 2H), 7.63 (d, 2H), 7.76 (d, 2H), 8.50 (d, 1H).

Example 190

3-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-3-(2-methoxyphenyl)propyl carbamate (diastereomer II)

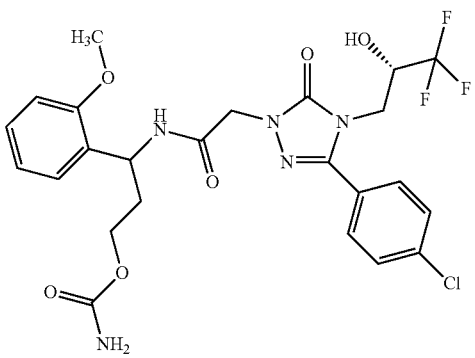 [SMILES: COc1ccccc1C(CCOC(N)=O)NC(=O)Cn1nc(-c2ccc(Cl)cc2)n(C[C@H](O)C(F)(F)F)c1=O]

Last-eluting diastereomer from the separation from Example 188.

LC-MS [Method 5] $R_t$=1.00 min; MS [ESIpos]: m/z=572 (M+H)$^+$
Chiral analytical HPLC [Method 9]: $R_t$=3.83 min
Yield: 47 mg (12% of theory)
$^1$H NMR (400 MHz, DMSO-d$_6$): δ=1.81-1.98 (m, 2H), 3.78 (s, 3H), 3.81-4.00 (m, 4H), 4.21-4.34 (m, 1H), 4.42-4.58 (m, 2H), 5.17-5.26 (m, 1H), 6.44 (br. s., 2H), 6.87-7.00 (m, 3H), 7.20-7.30 (m, 2H), 7.62 (d, 2H), 7.76 (d, 2H), 8.48 (d, 1H).

Example 191

2-({[3-(4-Chlorophenyl)-4-(2-fluorobenzyl)-5-oxo-4,5-dihydro-1H-1,2,4-triazol-1-yl]acetyl}amino)-2-[2-(trifluoromethyl)phenyl]ethyl carbamate (enantiomer II)

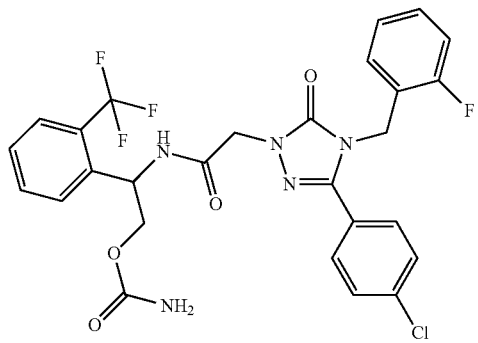 [SMILES: NC(=O)OCC(NC(=O)Cn1nc(-c2ccc(Cl)cc2)n(Cc2ccccc2F)c1=O)c1ccccc1C(F)(F)F]

A quantity of 30 mg (0.08 mmol) of [3-(4-chlorophenyl)-4-(2-fluorobenzyl)-5-oxo-4,5-dihydro-1H-1,2,4-triazol-1-yl]acetic acid (preparation according to WO2007/134862, Example 154A) was dissolved in 1 ml of DMF, and the solution was admixed with 21 mg (0.11 mmol) of EDC and with 15 mg (0.11 mmol) of HOBt and subsequently stirred at room temperature for 20 minutes. Then 23 mg (0.09 mmol) of the compound from Example 180A were added and the mixture was left with stirring at room temperature for 16 h. For work-up, 50 µl of 1N hydrochloric acid were added and the crude product was purified directly by preparative HPLC [Method 19]. This gave 34 mg (69% of theory) of the target compound.

LC-MS [Method 4] $R_t$=1.09 min; MS [ESIpos]: m/z=592 (M+H)$^+$
$^1$H NMR (400 MHz, DMSO-d$_6$): δ=3.98 (dd, 1H), 4.13 (dd, 1H), 4.47-4.57 (m, 2H), 5.01 (s, 2H), 5.37-5.44 (m, 1H), 6.59 (br. s., 2H), 7.02-7.17 (m, 3H), 7.26-7.34 (m, 1H), 7.48-7.55 (m, 5H), 7.68-7.77 (m, 3H), 8.98 (d, 1H).

The following compounds were obtained analogously:

| Example No. | Structure | Reactant; Yield [% of theory] | ¹H-NMR (400 MHz) LC/MS: $R_t$ [Method] |
|---|---|---|---|
| 192 | 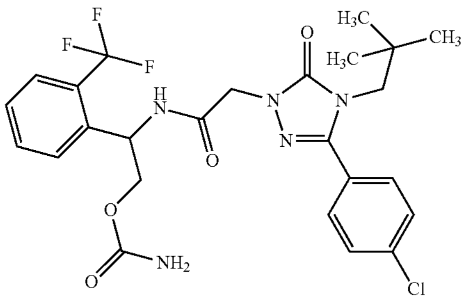 [SMILES: CC(C)(C)Cn1c(-c2ccc(Cl)cc2)nn(CC(=O)NC(COC(N)=O)c2ccccc2C(F)(F)F)c1=O] | WO2007/134862 Example 220A; 180A 60% | (DMSO-$d_6$): δ = 0.62 (s, 9H), 3.67 (s, 2H), 3.98 (dd, 1H), 4.11 (dd, 1H), 4.48 (s, 2H), 5.34-5.42 (m, 1H), 6.60 (br. s., 2H), 7.48-7.54 (m, 1H), 7.57 (d, 2H), 7.62-7.75 (m, 5H), 8.93 (d, 1H). $R_t$ = 1.11 min; MS [ESIpos]: m/z = 554 (M + H)⁺ [4] |
| 193 | | WO2007/134862 Example 221A; 180A 60% | (DMSO-$d_6$): δ = 0.93 (s, 6H), 2.67 (s, 3H), 3.77 (s, 2H), 3.97 (dd, 1H), 4.11 (dd, 1H), 4.47 (s, 2H), 5.35-5.42 (m, 1H), 6.60 (br.s., 2H), 7.48-7.57 (m, 3H), 7.62 (d, 2H), 7.66-7.75 (m, 3H), 8.93 (d, 1H). $R_t$ = 1.03 min; MS [ESIpos]: m/z = 570 (M + H)⁺ [4] |
| 194 | 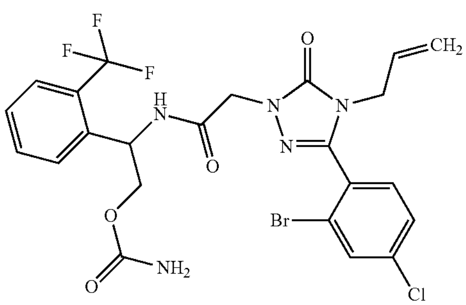 [SMILES: C=CCn1c(-c2ccc(Cl)cc2Br)nn(CC(=O)NC(COC(N)=O)c2ccccc2C(F)(F)F)c1=O] | 166A; 180A 61% | (DMSO-$d_6$): δ = 3.99 (dd, 1H), 4.07-4.15 (m, 3H), 4.49 (s, 2H), 4.82-4.90 (m, 1H), 4.98-5.03 (m, 1H), 5.36-5.44 (m, 1H), 5.59-5.70 (m, 1H), 6.57 (br.s., 2H), 7.49-7.55 (m, 2H), 7.62 (dd, 1H), 7.68-7.76 (m, 3H), 7.98 (d, 1H), 8.91 (d, 1H). $R_t$ = 1.05 min; MS [ESIpos]: m/z = 602 and 604 (M + H)⁺ [4] |
| 195 | 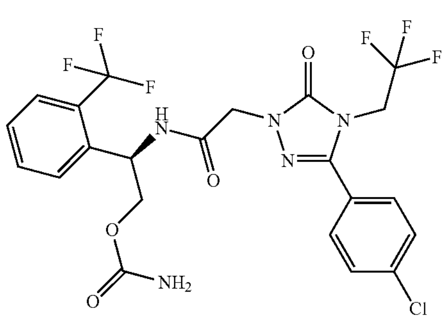 [SMILES: NC(=O)OC[C@H](NC(=O)Cn1nc(-c2ccc(Cl)cc2)n(CC(F)(F)F)c1=O)c1ccccc1C(F)(F)F] | WO2007/134862 Example 219A; 180A 72% | (DMSO-$d_6$): δ = 3.98 (dd, 1H), 4.12 (dd, 1H), 4.52 (s, 2H), 4.69 (q, 2H), 5.35-5.42 (m, 1H), 6.60 (br.s., 2H), 7.48-7.55 (m, 1H), 7.58-7.63 (m, 2H), 7.65-7.76 (m, 5H), 9.00 (d, 1H). $R_t$ = 1.04 min; MS [ESIpos]: m/z = 566 (M + H)⁺ [4] |

| Example No. | Structure | Reactant; Yield [% of theory] | $^1$H-NMR (400 MHz) LC/MS: $R_t$ [Method] |
|---|---|---|---|
| 196 | | 8A; 175A 39% | (DMSO-$d_6$): δ = 3.49-3.57 (m, 1H), 3.58-3.66 (m, 1H), 3.82 (dd, 1H), 3.91-3.99 (m, 1H), 4.23-4.28 (m, 1H), 4.47-4.61 (m, 2H), 5.09-5.14 (m, 1H), 5.22-5.30 (m, 1H), 6.88 (t, 1H), 7.32-7.39 (m, 1H), 7.41-7.45 (m, 1H), 7.52-7.57 (m, 1H), 7.60-7.64 (m, 2H), 7.71-7.76 (m, 2H), 8.78-8.83 (m, 1H). (partial resolution of the two-fold set of signals of the diastereomer mixture) $R_t$ = 1.20 min; MS [ESIpos]: m/z = 553 and 555 (M + H)$^+$ [3] |
| 197 | | 177A; 175A 51% | (DMSO-$d_6$): δ = 2.55-2.65 (m, 2H), 3.48-3.57 (m, 1H), 3.58-3.66 (m, 1H), 3.97 (t, 2H), 4.48-4.58 (m, 2H), 5.11 (t, 1H), 5.25 (td, 1H), 7.35 (t, 1H), 7.42 (dd, 1H), 7.54 (dd, 1H), 7.59-7.68 (m, 4H), 8.79 (d, 1H). $R_t$ = 1.09 min; MS [ESIpos]: m/z = 537 and 539 (M + H)$^+$ [5] |
| 198 | | 77A; 175A 45% | (DMSO-$d_6$): δ = 3.49-3.57 (m, 1H), 3.58-3.67 (m, 1H), 4.58 (s, 2H), 5.12 (t, 1H), 5.27 (td, 1H), 6.79-6.89 (m, 1H), 7.13-7.21 (m, 1H), 7.33-7.39 (m, 1H), 7.43 (dd, 1H), 7.55 (dd, 1H), 7.61-7.69 (m, 4H), 8.84 (d, 1H). $R_t$ = 1.18 min; MS [ESIpos]: m/z = 533 and 537 (M + H)$^+$ [5] |
| 199 | | 8A; 183A 45% | (DMSO-$d_6$): δ = 3.82 (dd, 1H), 3.92-3.99 (m, 1H), 4.00-4.16 (m, 2H), 4.21-4.32 (m, 1H), 4.46-4.58 (m, 2H), 5.40-5.49 (m, 1H), 6.89 (t, 1H), 7.36-7.43 (m, 1H), 7.45-7.50 (m, 1H), 7.56-7.65 (m, 3H), 7.71-7.76 (m, 2H), 8.95-9.01 (m, 1H). (partial resolution of the two-fold set of signals of the diastereomer mixture) $R_t$ = 1.20 min; MS [ESIpos]: m/z = 596 and 598 (M + H)$^+$ [3] |

| Example No. | Structure | Reactant; Yield [% of theory] | ¹H-NMR (400 MHz) LC/MS: $R_t$ [Method] |
|---|---|---|---|
| 200 | | 77A; 183A 47% | (DMSO-$d_6$): δ = 4.00-4.16 (m, 2H), 4.50-4.62 (m, 2H), 5.46 (td, 1H), 6.60 (br.s., 2H), 6.85 (sxt, 1H), 7.14-7.21 (m, 1H), 7.37-7.42 (m, 1H), 7.46-7.50 (m, 1H), 7.57-7.70 (m, 5H), 9.00 (d, 1H). $R_t$ = 1.23 min; MS [ESIpos]: m/z = 578 and 580 (M + H)⁺ [3] |
| 201 | | 177A; 183A 53% | (DMSO-$d_6$): δ = 2.52-2.68 (m, 2H), 3.97 (t, 2H), 4.02-4.15 (m, 2H), 4.46-4.55 (m, 2H), 5.40-5.47 (m, 1H), 6.40-6.80 (m br., 2H), 7.38 (t, 1H), 7.47 (dd, 1H), 7.56-7.68 (m, 5H), 8.97 (d, 1H). $R_t$ = 1.33 min; MS [ESIpos]: m/z = 580 and 582 (M + H)⁺ [3] |

Example 202

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-(2,3-dichlorophenyl)ethyl carbamate (diastereomer I)

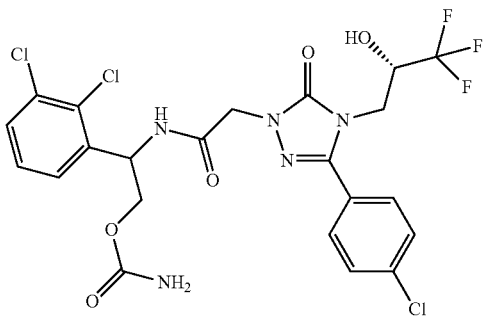 [SMILES: NC(=O)OCC(NC(=O)Cn1nc(-c2ccc(Cl)cc2)n(C[C@H](O)C(F)(F)F)c1=O)c1cccc(Cl)c1Cl]

First-eluting diastereomer from the separation of the diastereomer mixture by Method 11b from Example 199.

Yield: 43 mg (32% of theory)

Chiral analytical HPLC [Method 12a]: $R_t$=4.50 min

LC-MS [Method 4] $R_t$=1.05 min; MS [ESIpos]: m/z=596 and 598 (M+H)⁺

¹H NMR (400 MHz, DMSO-$d_6$): δ=3.82 (dd, 1H), 3.95 (dd, 1H), 4.02-4.15 (m, 2H), 4.22-4.33 (m, 1H), 4.46-4.58 (m, 2H), 5.41-5.48 (m, 1H), 6.60 (s br., 2H), 6.91 (d, 1H), 7.39 (t, 1H), 7.45-7.50 (m, 1H), 7.56-7.66 (m, 3H), 7.74 (d, 2H), 8.99 (d, 1H).

Example 203

2-[({3-(4-Chlorophenyl)-5-oxo-4-[(2S)-3,3,3-trifluoro-2-hydroxypropyl]-4,5-dihydro-1H-1,2,4-triazol-1-yl}acetyl)amino]-2-(2,3-dichlorophenyl)ethyl carbamate (diastereomer II)

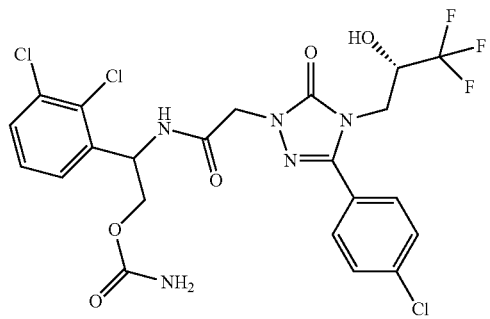 [SMILES: NC(=O)OCC(NC(=O)Cn1nc(-c2ccc(Cl)cc2)n(C[C@H](O)C(F)(F)F)c1=O)c1cccc(Cl)c1Cl]

Last-eluting diastereomer from the separation of the diastereomer mixture by Method 11b from Example 199.

Yield: 50 mg (41% of theory)

Chiral analytical HPLC [Method 12a]: $R_t$=6.55 min

LC-MS [Method 4] $R_t$=1.05 min; MS [ESIpos]: m/z=596 and 598 (M+H)⁺

¹H NMR (400 MHz, DMSO-$d_6$): δ=3.82 (dd, 1H), 3.96 (dd, 1H), 4.02-4.16 (m, 2H), 4.22-4.29 (m, 1H), 4.47-4.57 (m, 2H), 5.40-5.48 (m, 1H), 6.60 (s br., 2H), 6.89 (d, 1H), 7.40 (t, 1H), 7.46-7.50 (m, 1H), 7.57-7.65 (m, 3H), 7.74 (d, OH), 9.00 (d, 1H).

Example 204

2-({[3-(4-Chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl carbamate (enantiomer I)

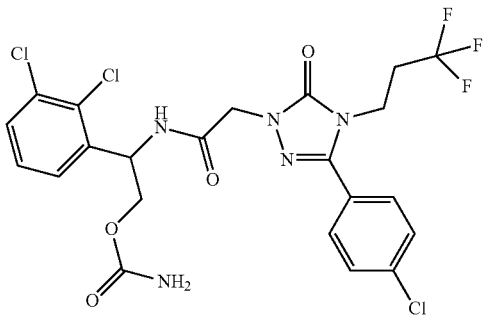 [SMILES: NC(=O)OCC(NC(=O)Cn1nc(-c2ccc(Cl)cc2)n(CCC(F)(F)F)c1=O)c1cccc(Cl)c1Cl]

First-eluting enantiomer from the separation of the enantiomer mixture by Method 25 from Example 201.

Yield: 128 mg (36% of theory)

Chiral analytical HPLC [Method 27d]: $R_t$=4.35 min

LC-MS [Method 3] $R_t$=1.24 min; MS [ESIpos]: m/z=580 and 582 (M+H)$^+$ $^1$H NMR (400 MHz, DMSO-d$_6$): δ=2.52-2.68 (m, 2H), 3.97 (t, 2H), 4.02-4.15 (m, 2H), 4.46-4.55 (m, 2H), 5.40-5.47 (m, 1H), 6.40-6.80 (m br., 2H), 7.38 (t, 1H), 7.47 (dd, 1H), 7.56-7.68 (m, 5H), 8.97 (d, 1H).

Example 205

2-({[3-(4-Chlorophenyl)-5-oxo-4-(3,3,3-trifluoropropyl)-4,5-dihydro-1H-1,2,4-triazol-1-yl]acetyl}amino)-2-(2,3-dichlorophenyl)ethyl carbamate (enantiomer II)

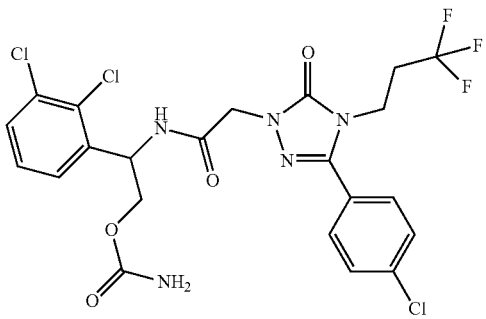 [SMILES: NC(=O)OCC(NC(=O)Cn1nc(-c2ccc(Cl)cc2)n(CCC(F)(F)F)c1=O)c1cccc(Cl)c1Cl]

Last-eluting enantiomer from the separation of the enantiomer mixture by Method 25 from Example 201.

Yield: 135 mg (40% of theory)

Chiral analytical HPLC [Method 27d]: $R_t$=5.04 min

LC-MS [Method 3] $R_t$=1.24 min; MS [ESIpos]: m/z=580 and 582 (M+H)$^+$ $^1$H NMR (400 MHz, DMSO-d$_6$): δ=2.52-2.68 (m, 2H), 3.97 (t, 2H), 4.02-4.15 (m, 2H), 4.46-4.55 (m, 2H), 5.40-5.47 (m, 1H), 6.40-6.80 (m br., 2H), 7.38 (t, 1H), 7.47 (dd, 1H), 7.56-7.68 (m, 5H), 8.97 (d, 1H).

Example 206

2-({[4-(4-Chlorophenyl)-2-oxo-3-(3,3,3-trifluoro-2-hydroxypropyl)-2,3-dihydro-1H-imidazol-1-yl]acetyl}amino)-2-[3-(trifluoromethyl)phenyl]ethyl carbamate (diastereomer mixture)

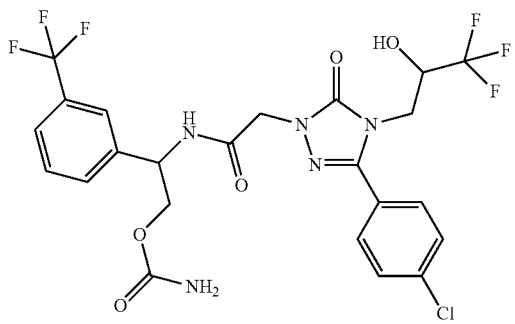 [SMILES: NC(=O)OCC(NC(=O)Cn1nc(-c2ccc(Cl)cc2)n(CC(O)C(F)(F)F)c1=O)c1cccc(C(F)(F)F)c1]

A quantity of 58 mg (0.11 mmol) of [4-(4-chlorophenyl)-2-oxo-3-(3,3,3-trifluoro-2-hydroxypropyl)-2,3-dihydro-1H-imidazol-1-yl]acetic acid from Example 184A was dissolved in 2 ml of DMF, and the solution was admixed with 28 mg (0.15 mmol) of EDC and with 20 mg (0.15 mmol) of HOBt and subsequently stirred at room temperature for 20 minutes. Then 42 mg (0.12 mmol) of the compound from Example 183A were added and the mixture was left with stirring at room temperature for 16 h. For work-up, 100 μl of 1N hydrochloric acid were added and the crude product was purified directly by preparative HPLC [Method 19]. This gave 13 mg (18% of theory) of the target compound.

LC-MS [Method 3] $R_t$=1.23 min; MS [ESIpos]: m/z=595 (M+H)$^+$ $^1$H NMR (400 MHz, DMSO-d$_6$): δ=3.74 (dd, 1H), 3.87 (dd, 1H), 4.05-4.15 (m, 2H), 4.19-4.28 (m, 1H), 4.32-4.39 (m, 2H), 5.12-5.21 (m, 1H), 6.59 (s br., 2H), 6.68-6.74 (m, 2H), 7.47-7.77 (m, 8H), 8.87 (d, 1H).

Example 207

2-({[4-(4-Chlorophenyl)-2-oxo-3-(3,3,3-trifluoro-2-hydroxypropyl)-2,3-dihydro-1H-imidazol-1-yl]acetyl}amino)-2-[2-(trifluoromethyl)phenyl]ethyl carbamate (diastereomer mixture)

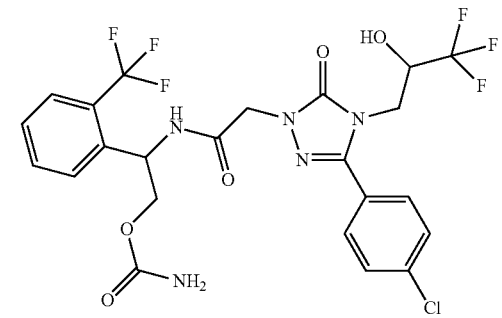 [SMILES: NC(=O)OCC(NC(=O)Cn1nc(-c2ccc(Cl)cc2)n(CC(O)C(F)(F)F)c1=O)c1ccccc1C(F)(F)F]

In the same way as for the compound from Example 206, 58 mg (0.11 mmol) of [4-(4-chlorophenyl)-2-oxo-3-(3,3,3-trifluoro-2-hydroxypropyl)-2,3-dihydro-1H-imidazol-1-yl]

acetic acid from Example 185A were reacted with 42 mg (0.12 mmol) of the compound from Example 180A. This gave 12 mg (18% of theory) of the target compound.

LC-MS [Method 5] $R_t$=1.06 min; MS [ESIpos]: m/z=595 $(M+H)^+$ $^1$H NMR (400 MHz, DMSO-d$_6$): δ=3.73 (dd, 1H), 3.86 (dd, 1H), 3.98 (dd, 1H), 4.13 (dd, 1H), 4.19-4.27 (m, 1H), 4.27-4.38 (m, 2H), 5.37-5.45 (m, 1H), 6.59 (s br., 2H), 6.68-6.74 (m, 2H), 7.47-7.56 (m, 6H), 7.69-7.77 (m, 4H), 8.95 (d, 1H).

B. EVALUATION OF THE PHARMACOLOGICAL ACTIVITY

Abbreviations

EDTA Ethylenediaminetetraacetic acid
DMEM Dulbecco's Modified Eagle Medium
FCS Foetal calf serum
HEPES 4-(2-Hydroxyethyl)-1-piperazineethanesulphonic acid
SmGM Smooth Muscle Cell Growth Media
Tris-HCl 2-Amino-2-(hydroxymethyl)-1,3-propanediol hydrochloride
UtSMC Uterine Smooth Muscle Cells The pharmacological action of the compounds of the invention can be shown in the following assays:

B-1. Cellular In Vitro Assay for Determining the Vasopressin Receptor Activity

The identification of agonists and antagonists of the V1a and V2 vasopressin receptors from humans and rats and also the quantification of the activity of the substances described here took place using recombinant cell lines. These cells derive originally from a hamster ovary epithelial cell (Chinese Hamster Ovary, CHO K1, ATCC: American Type Culture Collection, Manassas, Va. 20108, USA). The test cell lines constitutively express a modified form of the calcium-sensitive photoprotein aequorin, which, after reconstitution with the cofactor coelenterazine, emits light when there are increases in the free calcium concentration (Rizzuto R., Simpson A. W., Brini M., Pozzan T.; *Nature* 358 (1992) 325-327). In addition, the cells are stably transfected with the human or rat V1a or V2 receptors. In the case of the Gs-coupling V2 receptors, the cells are stably transfected with a further gene, which codes for the promiscuous G$_{\alpha 16}$ protein (Amatruda T. T., Steele D. A., Slepak V. Z., Simon M. I., *Proc. Nat. Acad. Sci. USA* 88 (1991), 5587-5591), either independently or as a fusion gene. The resulting vasopressin receptor test cells react to stimulation of the recombinantly expressed vasopressin receptors by intracellular release of calcium ions, which can be quantified by the resulting aequorin luminescence using a suitable luminometer (Milligan G., Marshall F., Rees S., *Trends in Pharmaco. Sci.* 17 (1996) 235-237).

Test Procedure

On the day before the assay, the cells are plated out in culture medium (DMEM, 10% FCS, 2 mM glutamine, 10 mM HEPES) in 384-well microtiter plates and kept in a cell incubator (96% humidity, 5% v/v carbon dioxide, 37° C.). On the day of the assay, the culture medium is replaced by a Tyrode solution (140 mM sodium chloride, 5 mM potassium chloride, 1 mM magnesium chloride, 2 mM calcium chloride, 20 mM glucose, 20 mM HEPES), which additionally contains the cofactor coelenterazine (50 μM), and the microtiter plate is then incubated for a further 3-4 hours. The test substances in various concentrations are placed for 10 to 20 minutes in the wells of the microtiter plate before the agonist [Arg8]-vasopressin is added, and the resulting light signal is measured immediately in the luminometer. The IC50 values are calculated using the GraphPad PRISM computer program (Version 3.02).

The table below lists representative IC$_{50}$ values for the compounds of the invention on the cell line transfected with the human V1a or V2 receptor:

TABLE 1

| Example No. | IC$_{50}$ hV1a [μM] | IC$_{50}$ hV2 [μM] |
| --- | --- | --- |
| 2 | 0.0076 | 0.0026 |
| 10 | 0.0104 | 0.0063 |
| 14 | 0.001 | 0.0089 |
| 20 | 0.0015 | 0.0063 |
| 24 | 0.0045 | 0.0013 |
| 26 | 0.0009 | 0.0032 |
| 34 | 0.003 | 0.0015 |
| 39 | 0.0014 | 0.0078 |
| 44 | 0.044 | 0.0017 |
| 45 | 0.0055 | 0.0025 |
| 48 | 0.0052 | 0.0044 |
| 51 | 0.001 | 0.0085 |
| 53 | 0.0015 | 0.0049 |
| 57 | 0.0029 | 0.0022 |
| 60 | 0.0005 | 0.0045 |
| 62 | 0.0036 | 0.001 |
| 65 | 0.0168 | 0.0168 |
| 69 | 0.0016 | 0.0097 |
| 70 | 0.0016 | 0.0099 |
| 73 | 0.0108 | 0.0016 |
| 74 | 0.0216 | 0.0024 |
| 75 | 0.513 | 0.0592 |
| 78 | 0.0211 | 0.0304 |
| 87 | 0.0038 | 0.0058 |
| 89 | 2.88 | 0.29 |
| 90 | 0.0886 | 0.231 |
| 94 | 0.251 | 0.0723 |
| 95 | 0.0573 | 0.0192 |
| 96 | 0.0713 | 0.0402 |
| 112 | 0.0024 | 0.006 |
| 115 | 0.0035 | 0.0076 |
| 121 | 0.0009 | 0.0014 |
| 126 | 0.0018 | 0.0018 |
| 136 | 0.0039 | 0.024 |
| 141 | 0.036 | 0.0048 |
| 144 | 0.0014 | 0.0139 |
| 149 | 0.002 | 0.015 |
| 152 | 0.0022 | 0.0071 |
| 156 | 0.0019 | 0.01 |
| 157 | 0.0124 | 0.0051 |
| 159 | 0.0043 | 0.0018 |
| 163 | 0.594 | 0.0077 |
| 167 | 0.003 | 0.0054 |
| 168 | 0.087 | 0.076 |
| 172 | 0.091 | 0.136 |
| 182 | 0.304 | 0.028 |
| 184 | 0.072 | 0.0266 |
| 185 | 0.055 | 0.045 |
| 188 | 0.0082 | 0.0099 |
| 191 | 0.0023 | 0.0248 |
| 203 | 0.0027 | 0.0044 |
| 207 | 0.0033 | 0.101 |

B-2. Cellular In Vitro Assay for Detecting the Action of Vasopressin V1a Receptor Antagonists on the Regulation of Pro-Fibrotic Genes The cell line H9C2 described as of cardiomyocyte type (American Type Culture Collection ATCC No. CRL-1446), isolated from rat cardiac tissue, endogenously expresses the vasopressin VIA receptor AVPR1A in high copy number, whereas the AVPR2 expression cannot be detected. For cell assays on the inhibition of the AVPR1A receptor-dependent regulation of gene expression by receptor antagonists, the procedure is as follows:

H9C2 cells are seeded in 12-well microtiter plates for cell culture, at a cell density of 100 000 cells/well, in 1.0 ml of Opti-MEM medium (Invitrogen Corp. Carlsbad Calif., USA, Cat. No. 11058-021) with 2% FCS and 1% penicillin/streptomycin solution (Invitrogen Cat. No. 10378-016), and held in a cell incubator (96% humidity, 5% v/v carbon dioxide, 37° C.). After 24 hours, sets of three wells (triplicate) are charged with vehicle solution (negative control), vasopressin solution: [Arg8]-vasopressin acetate (Sigma Cat. No. V9879) or test substances (dissolved in vehicle: water with 20% by volume ethanol) and vasopressin solution. In the cell culture, the final vasopressin concentration is 0.05 µM. The test substance solution is added to the cell culture in small volumes, and so a final concentration of 0.1% of ethanol in the cell assay is not exceeded. After an incubation time of 6 hours, the culture supernatant is drawn off under suction, the adherent cells are lysed in 250 µl of RLT buffer (Qiagen, Ratingen, Cat. No. 79216), and the RNA is isolated from this lysate using the RNeasy kit (Qiagen, Cat. No. 74104). This is followed by DNAse digestion (Invitrogen Cat. No. 18068-015), cDNA synthesis (Promaga ImProm-R Reverse Transcription System Cat. No. A3800) and RTPCR using the pPCR MasterMix RT-QP2X-03-075 from Eurogentec, Seraing, Belgium. All procedures take place in accordance with the working protocols of the test reagents' manufacturers. The primer sets for the RTPCR are selected on the basis of the mRNA gene sequences (NCBI Genbank Entrez Nucleotide Data Base) using the Primer-3Plus program with 6-FAM-TAMRA labelled probes. The RTPCR for determining the relative mRNA expression in the cells of the various assay batches is carried out using the Applied Biosystems ABI Prism 7700 Sequence Detector in 96-well or 384-well microtiter plate format in accordance with the instrument operating instructions. The relative gene expression is represented by the delta-delta Ct value [Applied Biosystems, User Bulletin No. 2 ABI Prism 7700 SDS Dec. 11, 1997 (updated 10/2001)] with reference to the level of expression of the ribosomal protein L-32 gene (Genbank Acc. No. NM_013226) and the threshold Ct value of Ct=35.

B-3. In Vivo Test for Detection of Cardiovascular Effect: Blood Pressure Measurement on Anaesthetised Rats (Vasopressin 'Challenge' Model)

In male Sprague-Dawley rats (250-350 g body weight) under ketamine/xylazine/pentobarbital injection anaesthesia, polyethylene tubes (PE-50; Intramedic®), which are prefilled with heparin-containing (500 IU/ml) isotonic sodium chloride solution, are introduced into the jugular vein and the femoral vein and then tied in. Via one venous access, with the aid of a syringe, arginine-vasopressin is injected; the test substances are administered via the second venous access. For determination of the cystolic blood pressure, a pressure catheter (Millar SPR-320 2F) is tied into the carotid artery. The arterial catheter is connected to a pressure transducer which feeds its signals to a recording computer equipped with suitable recording software. In a typical experiment the experimental animal is administered 3-4 successive bolus injections at intervals of 10-15 min with a defined amount of arginine-vasopressin (30 ng/kg) in isotonic sodium chloride solution and, when the blood pressure has reached initial levels again, the substance under test is administered as a bolus, with subsequent ongoing infusion, in a suitable solvent. After this, at defined intervals (10-15 min), the same amount of vasopressin as at the start is administered again. On the basis of the blood pressure values, a determination is made of the extent to which the test substance counteracts the hypertensive effect of the vasopressin. Control animals receive only solvent instead of the test substance.

Following intravenous administration, the compounds of the invention, in comparison to the solvent controls, bring about an inhibition in the blood pressure increase caused by arginine-vasopressin.

B-4. In Vivo Assay for Detecting the Cardiovascular Effect: Diuresis Investigations on Conscious Rats in Metabolism Cages Wistar rats (220-400 g body weight) are kept with free access to feed (Altromin) and drinking water. During the experiment, the animals are kept with free access to drinking water for 4 to 8 hours individually in metabolism cages suitable for rats of this weight class (Tecniplast Deutschland GmbH, D-82383Hohenpeißenberg). At the beginning of the experiment, the animals are administered the substance under test in a volume of 1 to 3 ml/kg body weight of a suitable solvent by means of gavage into the stomach. Control animals receive only solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per unit time is determined separately for each animal, and the concentration of the sodium and potassium ions excreted in the urine is measured by standard methods of flame photometry. To obtain a sufficient volume of urine, the animals are given a defined amount of water by gavage at the beginning of the experiment (typically 10 ml per kilogram of body weight). Before the beginning of the experiment and after the end of the experiment, the body weight of the individual animals is taken.

Following oral administration, in comparison with control animals, the compounds of the invention bring about an increased excretion of urine, which is based essentially on an increased excretion of water (aquaresis).

B-5. In Vivo Assay for Detecting the Cardiovascular Effect: Haemodynamic Investigations on Anaesthetised Dogs Male or female mongrel dogs (Mongrels, Marshall BioResources, USA) with a weight of between 20 and 30 kg are anaesthetised with pentobarbital (30 mg/kg iv, Narcoren®, Merial, Germany) for the surgical interventions and the haemodynamic and functional investigation terminii. Alcuronium chloride (Alloferin®, ICN Pharmaceuticals, Germany, 3 mg/animal iv) serves additionally as a muscle relaxant. The dogs are intubated and ventilated with an oxygen/ambient air mixture (40/60%) (about 5-6 L/min) Ventilation takes place using a ventilator from Draeger (Sulla 808) and is monitored using a carbon dioxide analyser (Engström).

The anaesthesia is maintained by continual infusion of pentobarbital (50 µg/kg/min); fentanyl is used as an analgesic (10 µg/kg/h). One alternative to pentobarbital is to use isoflurane (1-2% by volume).

In preparatory interventions, the dogs are fitted with a cardiac pacemaker.

At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with illumination, into the right ventricle.

At the same time as the implanting of the pacemaker, through retrograde advancing of a 7F biopsy forceps (Cordis) via a sheath introducer (Avanti+®; Cordis) in the fermoral artery, and after atraumatic passage through the aortic valve, there is defined lesion of the mitral valve, with monitoring by echo cardiography and illumination. Thereafter all of the accesses are removed and the dog wakes spontaneously from the anaesthesia.

After a further 7 days (i.e. 14 days before the first drug testing), the above pacemaker is activated and the heart is stimulated at a frequency of 220 beats per minute.

The actual drug testing experiments take place 14 and 28 days after the beginning of pacemaker stimulation, using the following instrumentation:

Bladder catheter for bladder relief and for measuring the flow of urine

ECG leads to the extremities (for ECG measurement)

Introduction of an NaCl-filled Fluidmedic PE-300 tube into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through the left atrium or through a port secured in the carotid artery, for measuring cardiac haemodynamics Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure Siting of a Braunüle in the cephalic vein, for infusing pentobarbital, for liquid replacement and for blood sampling (determination of the plasma levels of substance or other clinical blood values)

Siting of a Braunüle in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (Gould amplifier, Gould Instrument Systems, Valley View, USA) or Edwards Vigilance-Monitor (Edwards, Irvine, USA) and subsequently fed into the Ponemah system (DataSciences Inc, Minneapolis, USA) for evaluation. The signals are recorded continuously throughout the experimental period, and are further processed digitally by the said software, and averaged over 30 s.

C. EXEMPLARY EMBODIMENTS OF PHARMACEUTICAL COMPOSITIONS

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm

Production:
The mixture of compound of the invention, lactose and starch is granulated with a 5% strength solution (m/m) of the PVP in water. After drying, the granules are mixed with the magnesium stearate for 5 minutes. This mixture is compressed using a conventional tableting press (for tablet format see above). The guideline compressive force used for compression is 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.

A single dose of 100 mg of the compound of the invention is given by 10 ml of oral suspension.

Production:
The Rhodigel is suspended in ethanol, and the compound of the invention is added to the suspension. The water is added with stirring. Stirring is continued for about 6 h until the swelling of the Rhodigel is ended.

Solution for Oral Administration:
Composition:
500 mg of the compound of the invention, 2.5 g of polysorbate and 97 g of polyethylene glycol 400. A single dose of 100 mg of the compound of the invention is given by 20 g of oral solution.

Production:
The compound of the invention is suspended with stirring in the mixture of polyethylene glycol and polysorbate. The stirring operation continues until the compound of the invention is fully dissolved.

I.V. Solution:
The compound of the invention is dissolved at a concentration below saturation solubility in a physiologically tolerated solvent (e.g. isotonic saline solution, 5% glucose solution and/or 30% PEG 400 solution). The solution is sterile-filtered and dispensed into sterile, pyrogen-free injection containers.

The invention claimed is:
1. A compound of the formula (I)

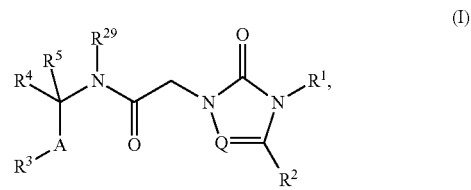

in which

A is —C($R^{6A}R^{6B}$)—* or —C($R^{6A}R^{6B}$)—C($R^{7A}R^{7B}$)—*,
where
* is the attachment site to $R^3$,
$R^{6A}$ is hydrogen, ($C_1$-$C_4$) alkyl or trifluoromethyl,
$R^{6B}$ is hydrogen or ($C_1$-$C_4$) alkyl,
$R^{7A}$ is hydrogen, ($C_1$-$C_4$) alkyl or trifluoromethyl,
$R^{7B}$ is hydrogen or ($C_1$-$C_4$) alkyl,
Q is CH or N,
$R^1$ is ($C_1$-$C_6$) alkyl, ($C_2$-$C_6$) alkenyl, ($C_2$-$C_6$) alkynyl or ($C_3$-$C_7$) cycloalkyl,
where ($C_1$-$C_6$) alkyl, ($C_2$-$C_6$) alkenyl and ($C_2$-$C_6$) alkynyl may be substituted by 1 to 3 substituents independently of one another selected from the group consisting of deuterium, halogen, cyano, oxo, hydroxyl, trifluoromethyl, ($C_3$-$C_7$) cycloalkyl, ($C_1$-$C_6$) alkoxy, trifluoromethoxy and phenyl,
in which ($C_3$-$C_7$) cycloalkyl may be substituted by 1 or 2 substituents independently of one another selected from the group consisting of ($C_1$-$C_4$) alkyl, oxo, hydroxyl, ($C_1$-$C_4$) alkoxy and amino, and
in which ($C_1$-$C_6$) alkoxy may be substituted by 1 or 2 substituents independently of one another selected from the group consisting of amino, hydroxyl, ($C_1$-$C_4$) alkoxy, hydroxycarbonyl and ($C_1$-$C_4$) alkoxycarbonyl, and
in which phenyl may be substituted by 1 to 3 substituents independently of one another selected from the group consisting of halogen, cyano, nitro, ($C_1$-$C_4$)

alkyl, trifluoromethyl, hydroxyl, hydroxymethyl, ($C_1$-$C_4$) alkoxy, trifluoromethoxy, ($C_1$-$C_4$) alkoxymethyl, hydroxycarbonyl, ($C_1$-$C_4$) alkoxycarbonyl, aminocarbonyl, mono-($C_1$-$C_4$) alkylaminocarbonyl and di-($C_1$-$C_4$) alkylaminocarbonyl, and where ($C_3$-$C_7$) cycloalkyl may be substituted by 1 or 2 substituents independently of one another selected from the group consisting of fluorine, ($C_1$-$C_4$) alkyl, ($C_1$-$C_4$) alkoxy, hydroxy, amino and oxo, $R^2$ is benzothienyl, phenyl, thienyl or furyl, where benzothienyl, phenyl, thienyl and furyl may be substituted by 1 to 3 substituents independently of one another selected from the group consisting of halogen, cyano, nitro, ($C_1$-$C_4$) alkyl, trifluoromethyl, hydroxyl, ($C_1$-$C_4$) alkoxy and trifluoromethoxy, $R^3$ is hydroxyl, trifluoromethoxy, ($C_1$-$C_4$) alkoxy, ($C_3$-$C_7$) cycloalkoxy, nitro, amino, —O—$SO_2$—$NR^{24}R^{25}$, or —$NR^{30}R^{31}$, where $R^{24}$ is hydrogen, ($C_1$-$C_4$) alkyl or ($C_3$-$C_7$) cycloalkyl,
$R^{25}$ is hydrogen, ($C_1$-$C_4$) alkyl or ($C_3$-$C_7$) cycloalkyl, or
$R^{24}$ and $R^{25}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl, ($C_1$-$C_4$) alkyl and trifluoromethyl, $R^{30}$ is hydrogen, ($C_1$-$C_4$) alkyl or ($C_3$-$C_7$) cycloalkyl,
$R^{31}$ is ($C_1$-$C_4$) alkyl or ($C_3$-$C_7$) cycloalkyl, or
$R^{30}$ and $R^{31}$ together with the nitrogen atom to which they are attached form a 4- to 7-membered heterocycle, where the 4- to 7-membered heterocycle may be substituted by 1 or 2 substituents independently of one another selected from the group consisting of fluorine, oxo, hydroxyl, ($C_1$-$C_4$) alkyl and trifluoromethyl, $R^4$ is phenyl, naphthyl or 5- to 10-membered heteroaryl, where phenyl, naphthyl and 5- to 10-membered heteroaryl may be substituted by 1 to 3 substituents independently of one another selected from the group consisting of halogen, cyano, nitro, ($C_1$-$C_4$) alkyl, difluoromethyl, trifluoromethyl, hydroxyl, ($C_1$-$C_4$) alkoxy, difluoromethoxy and trifluoromethoxy, $R^5$ is hydrogen, deuterium, trifluoromethyl or ($C_1$-$C_4$) alkyl, $R^{29}$ is hydrogen or ($C_1$-$C_4$) alkyl, or a salt thereof.

2. The compound of claim 1, in which

A is —C($R^{6A}R^{6B}$)—* or —C($R^{6A}R^{6B}$)—C($R^{7A}R^{7B}$)—*, where

* is the attachment site to $R^3$,
$R^{6A}$ is hydrogen, methyl or trifluoromethyl,
$R^{6B}$ is hydrogen or methyl,
$R^{7A}$ is hydrogen, methyl or trifluoromethyl,
$R^{7B}$ is hydrogen or methyl, Q is CH or N, $R^1$ is ($C_1$-$C_6$) alkyl, ($C_2$-$C_6$) alkenyl or ($C_3$-$C_6$) cycloalkyl, where ($C_1$-$C_6$) alkyl and ($C_2$-$C_6$) alkenyl may be substituted by 1 to 3 substituents independently of one another selected from the group consisting of fluorine, chlorine, cyano, oxo, hydroxyl, trifluoromethyl, ($C_3$-$C_6$) cycloalkyl, ($C_1$-$C_4$) alkoxy, trifluoromethoxy and phenyl, in which ($C_3$-$C_6$) cycloalkyl may be substituted by 1 or 2 substituents independently of one another selected from the group consisting of methyl, ethyl, oxo, hydroxyl, methoxy, ethoxy and amino, and in which phenyl may be substituted by a substituent selected from the group consisting of fluorine, chlorine, cyano, methyl, ethyl, trifluoromethyl, methoxy, ethoxy, trifluoromethoxy, methoxymethyl, ethoxymethyl, hydroxycarbonyl, methoxycarbonyl, ethoxycarbonyl and aminocarbonyl, and where ($C_3$-$C_6$) cycloalkyl may be substituted by 1 or 2 substituents independently of one another selected from the group consisting of fluorine, methyl, ethyl, methoxy, ethoxy, hydroxyl, amino and oxo, $R^2$ is benzothien-2-yl, phenyl or thienyl, where benzothien-2-yl, phenyl and thienyl may be substituted by 1 or 2 substituents independently of one another selected from the group consisting of fluorine, chlorine, bromine, methyl, ethyl, trifluoromethyl, hydroxyl, methoxy, ethoxy and trifluoromethoxy, $R^3$ is hydroxyl, amino, or —O—$SO_2$—$NR^{24}R^{25}$, where $R^{24}$ is hydrogen or methyl,
$R^{25}$ is hydrogen or methyl, $R^4$ is phenyl, where phenyl may be substituted by 1 to 3 substituents independently of one another selected from the group consisting of fluorine, chlorine, cyano, methyl, ethyl, difluoromethyl, trifluoromethyl, hydroxyl, methoxy, ethoxy, difluoromethoxy and trifluoromethoxy, $R^5$ is hydrogen, deuterium, trifluoromethyl, methyl or ethyl, $R^{29}$ is hydrogen or methyl, or a salt thereof.

3. The compound of claim 1, in which

A is —C($R^{6A}R^{6B}$)—* or —C($R^{6A}R^{6B}$)—C($R^{7A}R^{7B}$)—*, where

* is the attachment site to $R^3$,
$R^{6A}$ is hydrogen or trifluoromethyl,
$R^{6B}$ is hydrogen,
$R^{7A}$ is hydrogen,
$R^{7B}$ is hydrogen, Q is N, $R^1$ is ($C_2$-$C_4$) alkyl, ($C_2$-$C_4$) alkenyl or cyclopropyl, where ($C_2$-$C_4$) alkyl and ($C_2$-$C_4$) alkenyl may be substituted by 1 or 2 substituents independently of one another selected from the group consisting of fluorine, oxo, hydroxyl and trifluoromethyl, $R^2$ is phenyl, where phenyl may be substituted by a substituent selected from the group consisting of fluorine or chlorine, $R^3$ is hydroxyl, amino, $R^4$ is a group of the formula

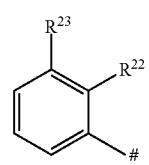

where # is the attachment site to —C($R^5$)(A$R^3$)N—,
$R^{22}$ is hydrogen, fluorine, chlorine, trifluoromethyl and methoxy, $R^{23}$ is hydrogen, fluorine, chlorine, trifluoromethyl and methoxy, where at least one of the radicals $R^{22}$ and $R^{23}$ is other than hydrogen, $R^5$ is hydrogen or methyl, $R^{29}$ is hydrogen, or a salt thereof.

4. A process for preparing a compound of claim 1, comprising

[A] coupling a compound of the formula (II)

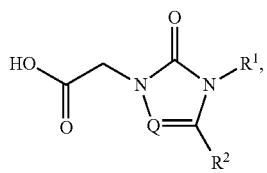

(II)

in which Q, $R^1$ and $R^2$ are each as defined in claim 1 in an inert solvent, with activation of the carboxylic acid function, to a compound of the formula (III)

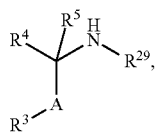

(III)

in which A, $R^3$, $R^4$, $R^5$ and $R^{29}$ are each as defined in claim 1, or

[B] reacting a compound of the formula (IV)

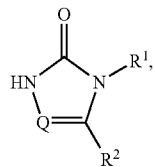

(IV)

in which Q, $R^1$ and $R^2$ are each as defined in claim 1 in an inert solvent, in the presence of a base, with a compound of the formula (V)

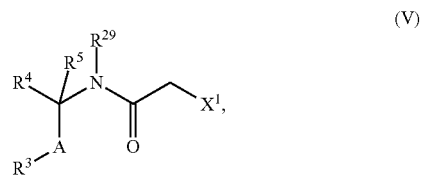

(V)

in which A, $R^3$, $R^4$, $R^5$ and $R^{29}$ are each as defined in claim 1 and $X^1$ is a leaving group, such as halogen, mesylate or tosylate, for example, and optionally converting the resulting compound of formula (I) with a (i) solvent and/or (ii) base or acid into a salt thereof.

5. A pharmaceutical composition comprising a compound of claim 1 and an inert, non-toxic, pharmaceutically suitable excipient.

6. The pharmaceutical composition of claim 5, further comprising at least one active ingredient selected from the group consisting of a diuretic, an angiotensin AII antagonist, an ACE inhibitor, a beta receptor blocker, a mineralocorticoid receptor antagonist, an organic nitrate, an NO donor, and a substance with positive inotropic activity.

7. A method for the treatment and/or prophylaxis of acute and chronic cardiac insufficiency, hypervolaemic and euvolaemic hyponatraemia, liver cirrhosis, ascites, oedemas and the syndrome of inadequate ADH secretion (SIADH) comprising administering to a human or animal in need thereof, an effective amount of at least one compound of claim 1.

8. A method for the treatment and/or prophylaxis of acute and chronic cardiac insufficiency, hypervolaemic and euvolaemic hyponatraemia, liver cirrhosis, ascites, oedemas and the syndrome of inadequate ADH secretion (SIADH), comprising administering to a human or animal in need thereof, an effective amount of at least one pharmaceutical composition of claim 5.

\* \* \* \* \*